(12) United States Patent
Vandendriessche et al.

(10) Patent No.: US 11,975,078 B2
(45) Date of Patent: *May 7, 2024

(54) MUSCLE-SPECIFIC NUCLEIC ACID REGULATORY ELEMENTS AND METHODS AND USE THEREOF

(71) Applicants: VRIJE UNIVERSITEIT BRUSSEL, Brussels (BE); VIB VZW, Ghent (BE); UNIVERSITEIT GENT, Ghent (BE)

(72) Inventors: Thierry Vandendriessche, Bierbeek (BE); Marinee Chuah, Bierbeek (BE); Pieter De Bleser, Buggenhout (BE)

(73) Assignees: Universiteit Gent, Ghent (BE); VIB VZW, Ghent (BE); VRIJE Universiteit Brussel, Brussels (BE)

(*) Notice: Subject to any disclaimer, the term of this patent is extended or adjusted under 35 U.S.C. 154(b) by 753 days.

This patent is subject to a terminal disclaimer.

(21) Appl. No.: 16/924,939

(22) Filed: Jul. 9, 2020

(65) Prior Publication Data

US 2020/0407746 A1 Dec. 31, 2020

Related U.S. Application Data

(60) Division of application No. 15/470,367, filed on Mar. 27, 2017, now Pat. No. 10,731,177, which is a continuation-in-part of application No. 15/112,795, filed as application No. PCT/EP2015/051081 on Jan. 21, 2015, now Pat. No. 11,072,801.

(30) Foreign Application Priority Data

Jan. 21, 2014 (EP) .................................. 14151960

(51) Int. Cl.
*A61K 48/00* (2006.01)
*C12N 9/26* (2006.01)
*C12N 15/85* (2006.01)
*C12N 15/86* (2006.01)
*C12N 15/864* (2006.01)

(52) U.S. Cl.
CPC ...... *A61K 48/0058* (2013.01); *A61K 48/0075* (2013.01); *C12N 9/2408* (2013.01); *C12N 15/85* (2013.01); *C12N 15/86* (2013.01); *C12N 15/8645* (2013.01); *C12N 2710/10043* (2013.01); *C12N 2750/14143* (2013.01); *C12N 2800/22* (2013.01); *C12N 2830/008* (2013.01); *C12N 2830/15* (2013.01); *C12N 2830/85* (2013.01)

(58) Field of Classification Search
CPC ............ A61K 48/0058; A61K 48/0075; C12N 9/2408; C12N 15/85; C12N 15/86; C12N 15/8645; C12N 2750/14143; C12N 2830/008
USPC .................... 514/44 R; 435/320.1, 456, 201; 536/23.2, 24.1
See application file for complete search history.

(56) References Cited

U.S. PATENT DOCUMENTS

| 10,731,177 B2* | 8/2020 | Vandendriessche ... C12N 15/86 |
| 2002/0198371 A1 | 12/2002 | Wang et al. |
| 2008/0039413 A1 | 2/2008 | Morris et al. |

FOREIGN PATENT DOCUMENTS

| CN | 103421786 | 12/2013 |
| CN | 103451284 | 12/2013 |
| WO | WO 1996/26284 | 8/1996 |
| WO | WO 2002/095006 | 11/2002 |
| WO | WO 2003/074711 | 9/2003 |
| WO | WO 2007/039699 | 4/2007 |
| WO | WO 2007/078599 | 7/2007 |
| WO | WO 2008/073303 | 6/2008 |
| WO | WO 2008/124934 | 10/2008 |
| WO | WO 2009/130208 | 10/2009 |
| WO | WO 2011/051450 | 5/2011 |

OTHER PUBLICATIONS

Milewski et al. (2004) Development, vol. 131, 829-837.*
Liu et al. (2007) PNAS, vol. 104(52), 20844-20849.*
Lim et al. (2014) Frontiers in Aging Neuroscience, vol. 6, pp. 1-14.doi:10.3389/fnagi.2104.00177.*
Doerfler et al. (2016) Mol. Ther.-Meth. & Clin. Develop., vol. 3, 15053, pp. 1-11.doi:10.1038/ mtm.2015.53.*
Sun et al. (2005) Mol. Ther., vol. 11(6), 889-898.*
Atschul et al., "Basic local alignment search tool", J Mol Bio., 215(3) 403-410 (Oct. 1990).
De Bleser et al., "A distance difference matrix approach to idenitying transcription factors that regulate differential gene expression", Genome Biol., 8(5):R83 (2007).
GenBank Accession No. HY110671, "HY110671 Riken full-length enriched human cDNA library, brain *Homo sapiens* CDNA clone H06D021N05, mRNA sequence," May 5, 2012 (1 page).
Encode project Consortium, "An integrated encyclopedia of DNA elements in the human genome", Nature, 489 (7414):57-74 (Sep. 2012).
Koo et al., "Delivery of AAV2/9-microdystrophin genes incorporating helix 1 of the coiled-coil motif in the C-terminal domain of dystrophin improves muscle pathology and restores the level of alpha1-syntrophin and alpha-dystrobrevin in skeletal muscles of mdx mice" Hum Gene Ther., 22(11):1379-88. (Nov. 2011). Epub (May 2011).

(Continued)

*Primary Examiner* — Anne Marie S Wehbe
(74) *Attorney, Agent, or Firm* — McDonnell Boehnen Hulbert & Berghoff LLP

(57) ABSTRACT

The present invention relates to nucleic acid regulatory elements that are able to enhance muscle-specific expression of genes, in particular expression in cardiac muscle and/or skeletal muscle, methods employing these regulatory elements and uses of these elements. Expression cassettes and vectors containing these nucleic acid regulatory elements are also disclosed. The present invention is particularly useful for applications using gene therapy, more particularly muscle-directed gene therapy, and for vaccination purposes.

7 Claims, 53 Drawing Sheets

Specification includes a Sequence Listing.

(56) References Cited

OTHER PUBLICATIONS

Kota et al., "Follistatin gene delivery enhances muscle growth and strength in nonhuman primates", Sci. Transl. Med., 1(6):6ra15 (Nov. 2009).
Levitt et al., "Definition of an efficient synthetic poly(A) site", Genes Dev., 3(7):1019-1025 (Jul. 1989).
Li et al., "High level desmin expression depends on a muscle-specific enhancer", J Biol. Chem., 266(10):6562-6570 (Apr. 1991).
Li et al., "Synthetic muscle promoters: activities exceeding naturally occuring regulatory sequences", Nat Biotechnol., 17(3):241-245 (Mar. 1999).
McCarty et al., "Adeno-associated virus terminal repeat (TR) mutant generates self-complementary vectors to overcome the rate-limiting step to transduction in vivo", Gene Ther., 10(26):2112-8 (Dec. 2003).
McCarty et al., "Self-complementary recombinant adeno-associated virus (scAAV) vectors promote efficient transduction independently of DNA synthesis", Gene Ther., 8(16):1248-54 (Aug. 2001).
Nathwani et al, "Sustained high-level expression of human factor IX (hFIX) after liver-targeted delivery of recombinant adeno-associated virus encoding the hFIX gene in rhesus macaques", Blood J., 100(5):1662-1669 (Sep. 2002).
Nathwani et al., "Self-complementary adeno-associated virus vectors containing a novel liver-specific human factor IX expression cassette enable highly efficient transduction of murine and nonhuman primate liver", Blood J., 107 (7):2653-2661 (Apr. 2006).
Son et al., "Database of mRNA gene expression profiles of multiple human organs", Genome Research, 15:443-450 (2005).
Su et al., "A gene atlas of the mouse and human protein-encoding transcriptomes" PNAS, 101(16):6062-6067. (Apr. 2004).
Tatusova et al., "BLAST 2 sequences, a new tool for comparing protein and nucleotide sequences", FEMS Microbiol Lett., 174(2):247-250 (May 1999).
Vandendriessche et al., "Efficacy and safety of adeno-associated viral vectors base don serotype 8 and 9 vs. entiviral vectors for hemophilia B gene therapy", J. Thromb Haemost, 5(1):16-24 (Jan. 2007). Epub (Sep. 2006).
Wang et al., "Construction and analysis of compact muscle-specific promoters for AAV vectors", Gene Ther., 15 (22):1489-1499. (Nov. 2008). Epub (Jun. 2008).
Wu et al., "Optimization of self-complementary AAV vectors for liver-directed expression results in sustained correction of hemophilia B at low vector dose", Molecular Therapy, 16(2):280-289 (Feb. 2008).
Xiao et al., "TiSGeD: a database for tissue-specific genes", Bioinformatic, 26(9):1273-1275. (May 2010). Epub (Mar. 2010).
Written Opinion issued by the International Searching Authority for International Application No. PCT/EP2015/051081; dated Jul. 1, 2015, (19 pages).
International Search Report issued by the International Searching Authority for International Application No. PCT/EP2015/051081, dated Jul. 1, 2015, (14 pages).
GenBank Accession No. FI096286, "MUGQ_CH252P470D05Sp6_CH0143_029 CHORI-252 Vervet Monkey Library Chlorocebus aethiops genomic clone CH252-470D5, genomic survey sequence," May 1, 2008 (1 page).
GenBank Accession No. AQ503558, "RPCI-11-297C4.TV RPCI-11 *Homo sapiens* genomic clone RPCI-11-297C4, genomic survey sequence," Apr. 29, 1999 [retrieved from the internet https://www.ncbi.nlm.nih.gov/nucgss/AQ503558] [retrieved on Nov. 6, 2017] (2 pages).
Katwal et al., "Adeno-associated virus serotype 9 efficiently targets ischemic skeletal muscle following systemic delivery", Gene Therapy, 20:930-938 (Mar. 2013).
GenBank: AQ703822.1 "HS_5503_B1_C10_SP6E RPCI-11 Human Male BAC Library *Homo sapiens* genomic clone Plate=1079 Col=19 Row=F, genomic survey sequence" published May 2010, one page.
GenBank: DX563003.1 "MUGQ_CH252P037A01T7_AV828_063 CHORI-252 Vervet Monkey Library Chlorocebus aethiops genomic clone CH252-37A1, genomic survey sequence" published Feb. 2014, one page.
GenBank: AC127457, "*Homo sapiens* chromosome 16 clone RP11-100F10, complete sequence," published Jan. 7, 2004, one page.
Tosolini et al. (2017) Frontiers in Molecular Neuroscience, vol. 10, Article 405, doi: 10.3389/fnmol.2017.00405, pp. 1-23.
Wang et al. (2014) Disc. Med., vol. 18(98), 151-161, author manuscript p. 1-18.
Genbank: AC024952 "*Homo sapiens* chromosome 7 clone RP11-66F23, complete sequence", published Nov. 28, 2000, one page.
Genbank: AQ471867 "CITBI-E1-2587B6, TH CITBI-E1 *Homo sapiens* genomic clone 2587B6, genomic survey sequence", published Dec. 19, 2010, one page.
Milewski et al. (2004) "Identification of minimal enhancer elements sufficient for Pax3 expression in neural crest and implication of Tead2 as a regulator of Pax3", Development 131, 829-837.
Liu et al. (2007) "An intragenic MEF2-dependent enhancer directs muscle-specific expression of microRNAs 1 and 133", PNAS, vol. 104(52), 20844-20849.
Cristiano et al., "Hepatic gene theraphy: efficient gene delivery and expression in primary hepatocytes utilizing a conjugated adenovirus-DNA complex." Proc Natl Acad Sci USA 90(24): 11548-52 (Dec. 1993).
Keyearts et al., "Bioluminescence imaging: looking beyond the light." Trends Mol Med. 18(3): 164-72 (Mar. 2012: Epub Feb. 8, 2012) PMID: 22321645.
Nathwani et al., "Adenovirus-associated virus vector-mediated gene transfer in hemophilia B." NEJM 365 (25): 2357-65 (Dec. 2011: Epub Dec. 10, 2011).
Pacak et al., "Tissue specific promoters improve specificity of AAV9 mediated transgene expression following intra-vascular gene delivery in neonatal mice." Genet Vaccines Ther. 6:13. (Sep. 2008), 5 pages.
Rudeck et al., "A compact unc45b-promoter drives muscle-specific expression in zebrafish and mouse." Genesis. 54 (8): 431-8 (Aug. 2016: Epub Jul. 9, 2016).
Yamada et al., "Phenotype correction of Fanconi anemia group A hematopoietic stem cells using lentiviral vector." Mol Ther. 8(4): 600-10 (Oct. 2003).
English language translation of Abstract of CN103451284.

\* cited by examiner

SEQ ID NO: 1

GTTCTCCTCTATAAATACCCGCTCTGGTATTTGGGGTTGGCAGCTGTTGCTGCCAGGGAGA
TGGTTGGGTTGACATGCGGCTCCTGACAAAACACAAACCCCTGGTGTGTGTGGGCGTGGGT
GGTGTGAGTAGGGGGATGAATCAGGGAGGGGCGGGGGACCCAGGGGGCAGGAGCCACACA
AAGTCTGTGCGGGGGTGGGAGCGCACATAGCAATTGGAAACTGAAAGCTTATCAGACCCTT
TCTGGAAATCAGCCCACTGTTTATAAACTTGAGGCCCCACCCTCGACAGTACCGGGGAGGA
AGAGGGCCTGCACTAGTCCAGAGGGAAACTGAGGCTCAGGGCTAGCTCGCCCATAGACATA
CATGGCAGGCAGGCT

FIG. 2B

SEQ ID NO: 2

CGTCTATAAATTCCAGGGAAGGTCTCTGATTGGCCCTGCTCATTCCCAGGCCCATTCCTTG
ACCCAGTCACTGAAGTCAGGGAGATGCAGTAATAAGACTGGCTGGAATCAGGGTCTTTAGG
GGTGGAGGGATGGGGAGGAGGCACAGCATGTCATCAAAATAAGGAAATTGCAAAAGAAAGC
TTGCAGGCTACTTTGAATGACAATGAGAAAGACGGTGCTGCCTGAGTGTGTTAAGGATCCA
CATGGTCTCCAAAATCCTCCAGGAGCATACAGTCTAGTCTGGGAGATGAGACACAAAAATA
ACCAGAACACAACAGCTTGCACTGACTCGAGGGCTGGATAAGAATATCTGGAACTCCCCCA
TCTATTTCAGAAGCTTGTCTCTTGGATGAAAATTAGACACTTAATGGGAAAGGGCTTTGAA
AAGAGTGC

FIG. 2C

SEQ ID NO: 3

AAAAAATAAAAATAAAAAATAAAAATAAATAAAGTGGATGGCTTAGAGTATCTTTTCTGTT
TAGACCTGACTAAAGCTTAGACATAATTGTTAGTTTAGGCTCTCAGGGTAAAATTTATTAC
TGTAAATCCAAAAAATCCCTTCTTCTTCTTTTTTTTTTTTTTTTGGTCCTTGAATTAAAT
GCTGTCACCTCCTTCTTGAAAGGAGAAACTATTAGTCAGATTTGAAAATCCTCTTTATCAC
CCAGGAAAATCATTTTTATGGACACTTTGTCTTTCTGTAGTCTGACTTAGAAGCAGCCTGT
TTTTGATAGGTTGAAGTTTTCATCTTGAACACAAACCCTGTTTGTGTCCCTACTCCCC
AGTTTGATGTGCCAGGCACTTTGTTCTCAAGCCCAGCAGCTGTTGTGGGATGAGGGACAT
TTTGCATGCTTAGCCAGCAGCTGCCAGAAACATTTCTAATCTGGTTTTGGCAGGAAATAGG
GCACAAGTGGAAGCCAAGTTAAAAGAAGCTGGAAAAATAAACAGAATAACTTTAGATGTCA
CT

SEQ ID NO: 4

TGCACTGTAGACTATTTATGTTTGCATATTTTTCAGGATTGTGTACAGTAAACCTTAAGTG
AATACAAAGGATCCAATTGTCCTGTAAGACTCACTTCAATTACAGATTGTGCTCAGTATTA
AACTTTGCTAGTACTTTCAGGATGCAGTCAATCAAGAGGCAGGGAAAGGTCTGTCAGCATC
CACAGCCTCCTTTTCAAATTGGACACTTAGTCTCTGGTCCGAATAATAGGTGCCCCCAGTG
TCACCTCACACAATGGGGTATACACAGTTTTTAAAAATTTATTTTCAGCTGGGCACAGTAG
CTCACACCTAAAATCCCAGCACTTTGGGAGGCTGAGGCAGGTGGATCACCTGAGGTCAGGA
GTTCAAGACCAGCCTGGCCAACGTGGCAAAATCCTGTCTCTACTAAAAATACAAAAATTAA
CCG

FIG. 2E

SEQ ID NO: 5

CAGTTTACTCACCAGGGATTCAGAGGCAGCACTGCTGAACCCTGAGCCCTTGGCACATCAG
GTTGGCTGTCAGAAGTCGGCCTTTGTACATACACAGTTCCCTTGTGAGGCCCAGCTGCGTG
TCCTAGGAGCGGGGCCTCTCTCCACAGCAGAGCTCAGCCTCTCAAGTGTATGGACAGCACG
GGTGCCTGATGGGTGGATTTAGCCATGAGTTGAAGGTGGCTTGGGGAGAATGAGAGTTCTA
GAGATAGGGAGAAGGGGTTGCCAATAGGAGAGTGGAATTCCTGAGCACCTCGTCACAGGCA
GCCGACAGAACATGAGCCGCAGGGCCCAGGCTATTTATACCTCGCCTGTCACTATCAGGGT
CCCCACAGCTCCCCCCACCTCCAGCCACACACAGCAGGTCCTTTTGCTCTTTCTGGTCCCT
TCTCTACTCCTCCCCCTCCCTACCTAA

FIG. 2F

SEQ ID NO: 6

CCCTTTCCCTGGCAGGATCTGCCCTGTGGCCCAAATGGGCATGTTGCCCAGGGGGCTCCCT
GGCACTATGGGGAAGAGTCTCTCCTTCCCCTCTTATCATCTCAGTTGAGTCAGACTTGGG
GGAGGGGGATACACAGTGTGAGTCACTGGGTACCCTTTTCCTGAGCTCAGCTTCATACCGA
GGCGATGAGGCCAAACGGGCTGGTGACAGGGACACTGAGTCAGGGGCAGGGGCCCCGGTCT
TACTCCTGGGCCTCTGGATTTGGGCCCTACATGAGGCTTTTCTATCTGTAAAGTCAAGCAA
TGGCTGGGAGGCACACACAACCCCCGCCCCCCGCAGGCTTCTCCTTCATTGGCCCGGGC
AAGGTCCTGCTTCCTCTCAGGCCGTCTCTGCACAAGCACACACTTCCCTTCCCTGTCC
ACAGGTGGACAATGCCCTGGGCTAGG

FIG. 6
FIG. 6A
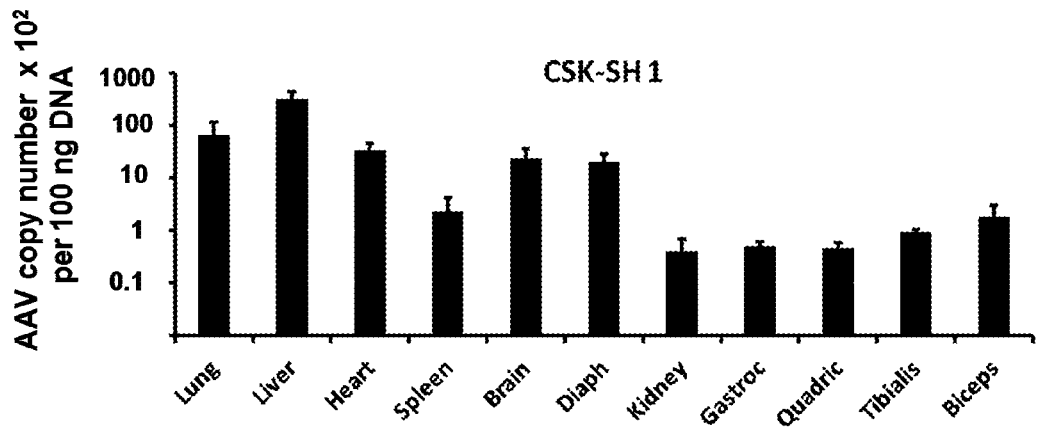
FIG. 6B
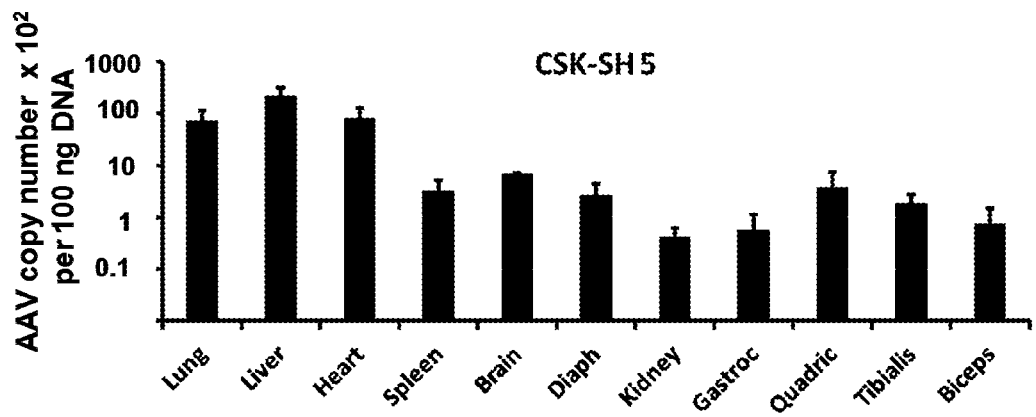

SEQ ID NO: 7

CTCACTCCCCGCCCAGGCAGCAAGGAGCCCACACCCTCATGCCCCTCAGCTTCAGCCCCCA
CCTCCAGGAGGCCCTACCCACGCTCATGACCTTGCTATTCTGGGCCTTGTGTCCTGTAGGG
AGATGGACAGGAGACAGCTGGGCTTCCAGGCCACCCAGGCGGGGGGCTAGCCGAGGGAAGC
CTGCTGGCTCTCCTGCTTGCTCTAATTTCTGGGGCTCCCCAAACCTTGGCCTCAGGAGACT
GGGGATAGGACCGGCCTTGAAAGTGGGGGAAGCTTTGGAGAGCCGGGTGCTGGGTTCTTAG
TGAGATGGCCAGTGAAGGCTGTGGTGCCCCGAGGTAAGCAGGGCCTGATCCCTCCTAATC
TTCCAGCAGCAACTGGTGCTCTGAGGCTCCCCTCCCCAGCCTGCCAGCCTTCAGGGAC
CTGCCTTCCAAAGATGGGCAGGGGAGGGGACGAGGACACCCACCCACTCCTCAGACCAGC
ATGTCTT

FIG. 7B

SEQ ID NO: 8

CCCTCCAGATGGGTTTCCTGGAATCTAGATTTCCCAGGTTCCAAAGGACACCCGAGTCTCA
TGCCTGGAACTCAGTGAGACTAATTCACCTCTCCTCTGCCCTAATCTTCATCTCCAGCCAG
AAGCCAACAGATCCCAGGGGACTGGAGCCACAGGGGCTGCACCTGTTTACCGGGTATTTTT
AGGATGGTTGATGAACACATAATACCCACCCTATAGTCAGAGAAAGACAATGCCTGCTATG
TTAATCCTGTGGCTATTATAGTCTGTCATCTCATGGGTTGGGGCAGGACACTGACCCTCTC
AGAGGCCAGAGAGAGGCCTCGCAAGCAGGAGGTTAGGGA

FIG. 7C

SEQ ID NO: 9

ATGGAGACAATCCATGAATTCCTGAGATGCTTGGCTGGTATTAGATTTTATGGGCAGCTGC
TTATTCTTAGGGCTCTGCTTCTCCAAAGACACTGAGGAAGTCCAAAGGAAACACCAGCTGG
CGAAGAGCCACCTCCAGGCCCATCTGTCCATCATCAGCCTCCAGGAATGCCAGTGTCCAGA
GGGCACCAGGTCTGCGTCTGTCTCCTGGGATGTGCCTTGTCCTTGGTGGGCATTTGGCAG
TGATCATGCCTCCCTGTCTCCCTCAGAGATCCAACTGTCCCATTGTGGGCCCTACCTTC
CAAGGCCGGTTTACACCTCCTGCCAAGCTCCGGGGCCTGCCCCAGCCTGCCTCACTGACA
AATGCCAGACCAAGGGGTCCCACGTCAGGCAAGAGGCCTCAGCCTGTGCTCTGACACCCCT
CAG

FIG. 7D

SEQ ID NO: 10

TTCTGAGTCCTCTAAGGTCCCTCACTCCCAACTCAGCCCCATGTCCTGTCAATTCCCACTC
AGTGTCTGATCTCCTTCTCCTCACCTTTCCCATCTCCGTTTGACCCAAGCTTCCTGAGCT
CTCCTCCCATTCCCCTTTTTGGAGTCCTCCTCCTCTCCCAGAACCCAGTAATAAGTGGGCT
CCTCCCTGGCCTGGACCCCGTGGTAACCCTATAAGGCGAGGCAGCTGCTGTCTGAGGCAG
GGAGGGGCTGGTGTGGGAGGCTAAGGGCAGCTGCTAAGTTTAGGGTGGCTCCTTCTCTCTT
CTTAGAGACAACAGGTGGCTGGGCCTCAGTGCCCAGAAAAGAAAATGTCTTAGAGGTATC
GGCATGGGCCTGGAGGAGGGGGACAGGGCAGGGGAGGCATCTTCCTCAGGACATCGGGT
CCTAGAGG

FIG. 7 (continued)

FIG. 7E
SEQ ID NO: 11

GACTAGGAATAAATCACATATCCTCAATCCCTGGACAACTTGTTTACTTCTAGTGTTAGTT
TTTTCTTAAAAAAAAAATTGAAATCATTCTGAGGCTGGAATACTTTGGACATGCCCAGCAG
TTCCTGGCAGTTCCCACAGAAGCATTACCTCATGACTGGAGTGGGTAAAGCATACTGTGGG
CTATGGATAAGACTGACATTAACCACAAGCATGTTTGGCAGCAGACTGGTGCTTTACAAGC
TCCATGTTCAGCAGGAGCTGCAAAGTGTTCCTCCAAACCAATATTTGTCATTCTTGGATTC
TATTTAGGAGGTCCTGTTACTCACATGTTTCAATATCAGCAGAAGCCAGTTTCCCTGTGGT
ACCGAAGTGGATCCTGATGAATTTACCCTTGTAAGTAAAAAAAATGATGTTATACCCAAAG
CTTGAAGTACGTAGTGGGGATGCCACTGAAATAATTCAGACATGCTT

FIG. 7F
SEQ ID NO: 12

GTGCTCATAGCTCCACCTTTTGTTCCTAATATGGTCTTTCCAGCTCCCTCCACCCCATCAT
TGTTCTCCTGGGGGAACACAGGGTGAGACGCTTTGATGAACTGACATCACCAGCAAAAAAA
ATATCTAGCAACAGCTGAGGCTGATTTTAGACAATGGAAAGTGGGGGAGGGAAGAGGTTCT
CCCTGACCCTGAAACTTTCCACTCATTCTGGGCAGCTCTATGGATGTTTTAAAAGAAGAGG
AAGAGGGGAGGGAAGAACATTGAAATAGAGAAGTGTACTTTGGCAATTCTAGGTTGGCAGT
TTGCATCCAGGGGGTCCTGGTTGCCTTTCAGCTTCCCGTTTCACTCTCCCCAGACTGTGT
TGAATGCTGGTCAAACTCCGTTAGTTGAGTTTTAGCTTTTGATTCCTGGTATTCAAGGAGC
TTGGGCACAGGGAAGAGGGGAGGTCACTCATGATCCTTAACAATTCTCCCAGATCCCCAGA
TCAAATTGCTGTGCTATTCTGGGAGTCTCCG

FIG. 7G
SEQ ID NO: 13

ATCGTGTGTCAGAGGTTTGTGTCAGCTTCCCAGCAAGGGAACCAGAAAGGAAAAGGAACCG
GTTCCTCATGCTTCCTAGGGGAATGCATGCATATCTGAAGAGAAGGGAATCTTATATAAGG
CTGTTTAGCTAAGGGCAGCCACCAGCCAGGTGAGCCTTACAGAAGCACAGGGCTGGGTGTC
TGCAGTTCCCTAGCAGATTAACCTGGGTCACAGTGACTCAGAGCTCCAGCATGCGAGTTCC
AGGTGTGGAACTGAGCAAGTACAGATCTGCTTTTGCTCCACTTGGGAGTATTTTCCTTCT
TAGTGAGCATGGGCAGCCTCCTGGCCAGGGAAGTCTGGCACTGTCTGGGCCTGACAGGGAA
ACCCTG

FIG. 13
FIG. 13A
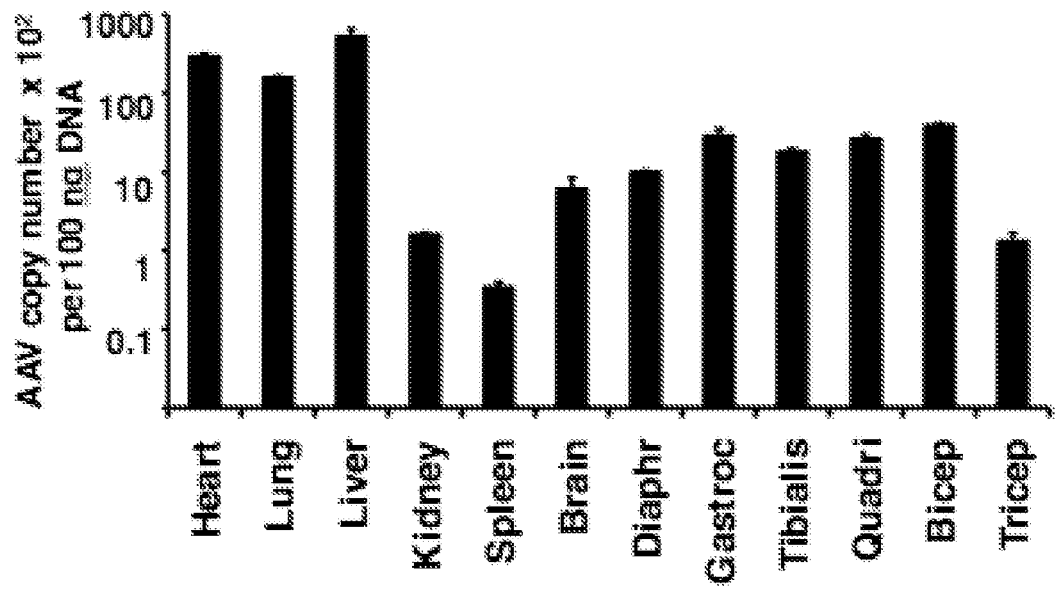
FIG. 13B
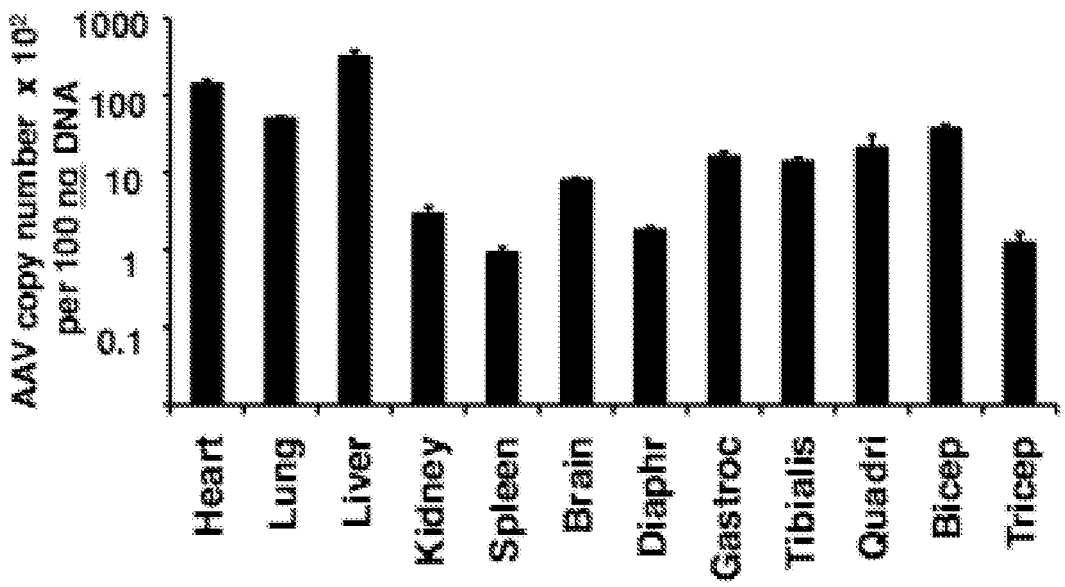

FIG. 15
FIG. 15A
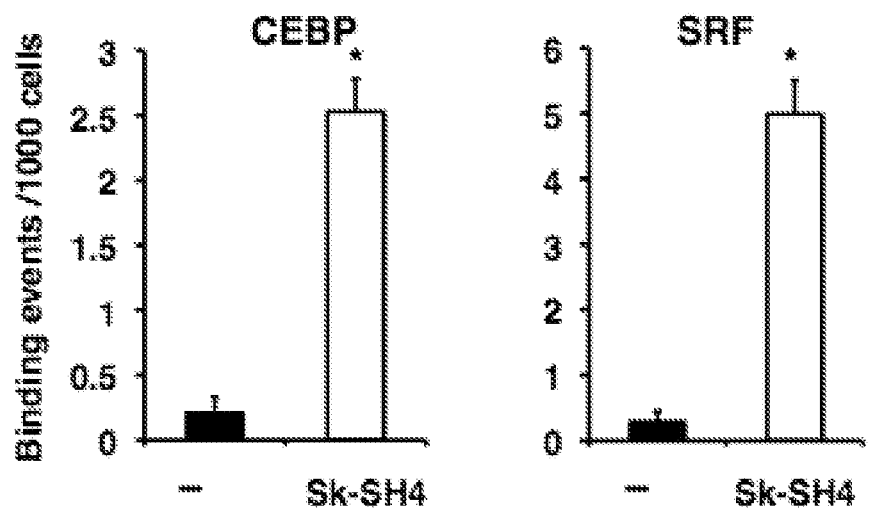
FIG. 15B
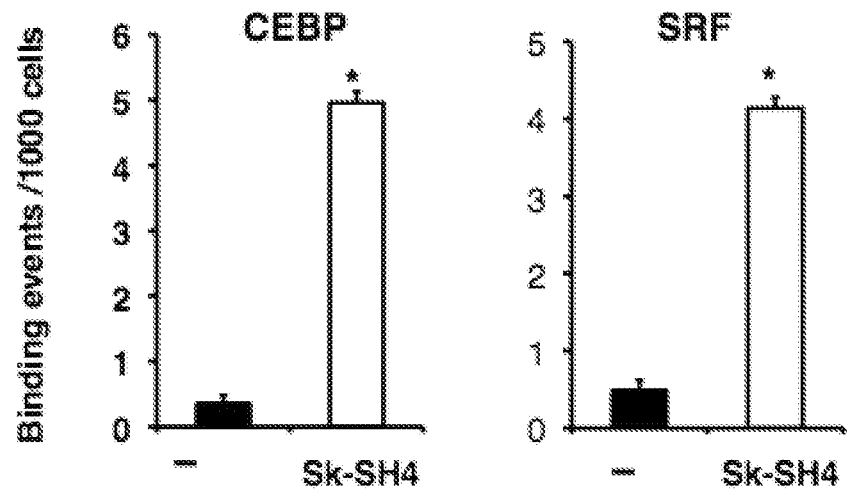

FIG. 15 (continued)
FIG. 15C
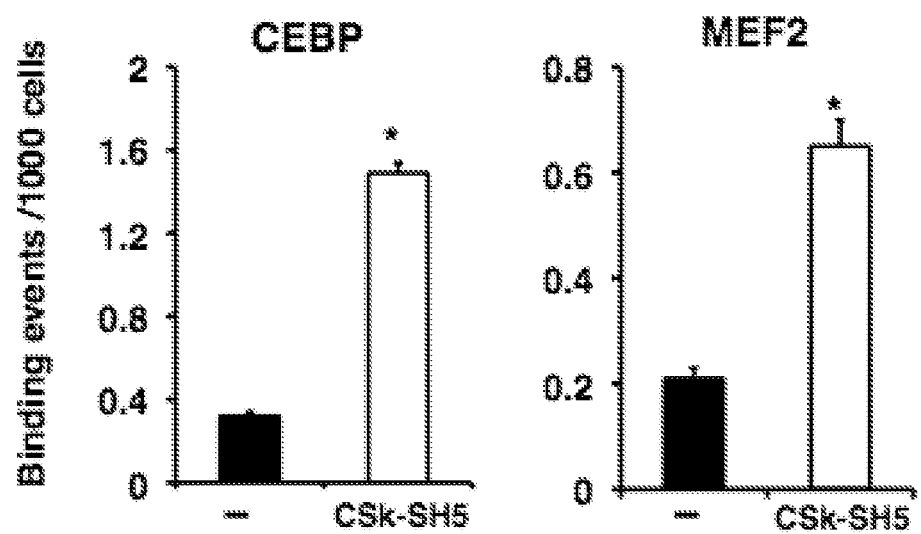
FIG. 15D
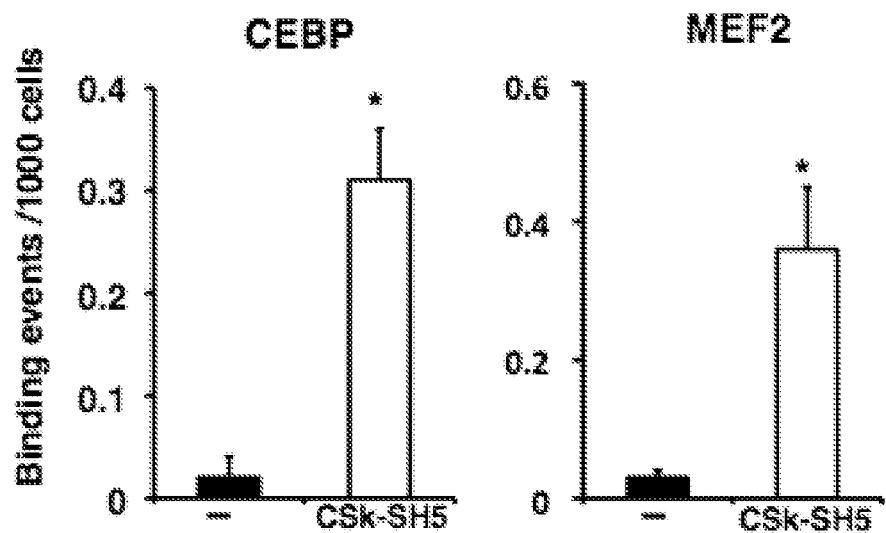

SEQ ID NO:44

CCTGCAGGCAGCTGCGCGCTCGCTCGCTCACTGAGGCCGCCCGGGCAAAGCCCGGGCGTCG
GGCGACCTTTGGTCGCCCGGCCTCAGTGAGCGAGCGAGCGCGCAGAGAGGGAGTGGCCAAC
TCCATCACTAGGGGTTCCTCGTACGTTCTGAGTCCTCTAAGGTCCCTCACTCCCAACTCAG
CCCCATGTCCTGTCAATTCCCACTCAGTGTCTGATCTCCTTCTCCTCACCTTTCCCATCTC
CCGTTTGACCCAAGCTTCCTGAGCTCTCCTCCCATTCCCCTTTTTGGAGTCCTCCTCCTCT
CCCAGAACCCAGTAATAAGTGGGCTCCTCCCTGGCCTGGACCCCGTGGTAACCCTATAAG
GCGAGGCAGCTGCTGTCTGAGGCAGGGAGGGGCTGGTGTGGGAGGCTAAGGGCAGCTGCTA
AGTTTAGGGTGGCTCCTTCTCTCTTCTTAGAGACAACAGGTGGCTGGGGCCTCAGTGCCCA
GAAAAGAAAATGTCTTAGAGGTATCGGCATGGGCCTGGAGGAGGGGGACAGGGCAGGGGG
AGGCATCTTCCTCAGGACATCGGGTCCTAGAGGGACCTTGCTTCCTAGCTGGGCCTTTCCT
TCTCCTCTATAAATACCAGCTCTGGTATTTCGCCTTGGCAGCTGTTGCTGCTAGGGAGACG
GCTGGCTTGACATGCATCTCCTGACAAAACACAAACCCGTGGTGTGAGTGGGTGTGGGCGG
TGTGAGTAGGGGGATGAATCAGAGAGGGGGCGAGGGAGACAGGGGCGCAGGAGTCAGGCAA
AGGCGATGCGGGGGTGCGACTACACGCAGTTGGAAACAGTCGTCAGAAGATTCTGGAAACT
ATCTTGCTGGCTATAAACTTGAGGGAAGCAGAAGGCCAACATTCCTCCCAAGGGAAACTGA
GGCTCAGAGTTAAAACCCAGGTATCAGTGATATGCATGTGCCCCGGCCAGGGTCACTCTCT
GACTAACCGGTACCTACCCTACAGGCCTACCTAGAGACTCTTTTGAAAGGATGGTAGAGAC
CTGTCCGGGCTTTGCCCACAGTCGTTGGAAACCTCAGCATTTTCTAGGCAACTTGTGCGAA
TAAAACACTTCGGGGGTCCTTCTTGTTCATTCCAATAACCTAAAACCTCTCCTCGGAGAAA
ATAGGGGGCCTCAAACAAACGAAATTCTCTAGCCCGCTTTCCCCAGGATAAGGCAGGCATC
CAAATGGAAAAAAGGGGCCGGCCGGGGGTCTCCTGTCAGCTCCTTGCCCTGTGAAACCCA
GCAGGCCTGCCTGTCTTCTGTCCTCTTGGGGCTGTCCAGGGGCGCAGGCCTCTTGCGGGGG
AGCTGGCCTCCCCGCCCCCTCGCCTGTGGCCGCCCTTTTCCTGGCAGGACAGAGGGATCCT
GCAGCTGTCAGGGGAGGGGCGCCGGGGGTGATGTCAGGAGGGCTACAAATAGTGCAGACA
GCTAAGGGGCTCCGTCACCCATCTTCACATCCACTCCAGCCGGCTGCCCGCCCGCTGCCTC
CTCTGTGCGTCCGCCCAGCCAGCCTCGTCCACGCCGCCACCTCTAGAAAGAGGTAAGGGTT
TAAGGGATGGTTGGTTGGTGGGGTATTAATGTTTAATTACCTGGAGCACCTGCCTGAAATC
ACTTTTTTTCAGGTTGGACGCGTGCCACCATGCTGTGGTGGGAGGAAGTGGAGGACTGCTA
CGAGAGAGAGGACGTGCAGAAGAAAACCTTCACCAAGTGGGTGAACGCCCAGTTCAGCAAG
TTCGGCAAGCAGCACATCGAGAACCTGTTCAGCGACCTGCAGGATGGCAGGAGACTGCTGG
ATCTGCTGGAGGGACTGACCGGCCAGAAGCTGCCCAAGGAGAAGGGCAGCACCAGAGTGCA
CGCCCTGAACAACGTGAACAAGGCCCTGAGAGTGCTGCAGAACAACAACGTGGACCTGGTG
AATATCGGCAGCACCGACATCGTGGACGGCAACCACAAGCTGACCCTGGGCCTGATCTGGA
ACATCATCCTGCACTGGCAGGTGAAGAACGTGATGAAGAACATCATGGCCGGCCTGCAGCA
GACCAACAGCGAGAAGATCCTGCTGAGCTGGGTGAGGCAGAGCACCAGAAACTACCCCCAG
GTGAACGTGATCAACTTCACCACCTCCTGGAGCGACGGCCTGGCCCTGAACGCCCTGATCC
ACAGCCACAGACCCGACCTGTTCGACTGGAACAGCGTGGTGTGTCAGCAGAGCGCCACCCA
GAGACTGGAGCACGCCTTCAACATCGCCAGATACCAGCTGGGCATCGAGAAGCTGCTGGAC
CCCGAGGACGTGGACACCACCTACCCCGACAAGAAAGCATCCTGATGTATATTACCTCTC
TGTTTCAGGTGCTGCCCCAGCAGGTGTCCATCGAGGCCATCCAGGAAGTGGAAATGCTGCC
CAGGCCCCCCACCGTGTCCCTGGCCCAGGGCTATGAGAGAACCAGCAGCCCCAAGCCCAGA
TTCAAGAGCACCGTGTCCCTGGCCCAGGGCTATGAGAGAACCAGCAGCCCCAAGCCCAGAT
TCAAGAGCTACGCCTACACCCAGGCCGCCTACGTGACCACCTCCGACCCCACCAGAAGCCC
CTTCCCCAGCCAGCACCTGGAGGCCCCCGAGGACAAGAGCTTCGGCAGCAGCCTGATGGAG

```
AGCGAAGTGAACCTGGACAGATACCAGACCGCCCTGGAGGAAGTGCTGTCTTGGCTGCTGT
CCGCCGAGGACACCCTGCAGGCCCAGGGCGAGATCAGCAACGACGTGGAAGTGGTGAAGGA
CCAGTTCCACACCCACGAGGGCTACATGATGGATCTGACCGCCCACCAGGGCAGAGTGGGC
AATATCCTGCAGCTGGGCAGCAAGCTGATCGGCACCGGCAAGCTGAGCGAGGACGAGGAGA
CCGAAGTGCAGGAGCAGATGAACCTGCTGAACAGCAGATGGGAGTGCCTGAGAGTGGCCAG
CATGGAGAAGCAGAGCAACCTGCACCGCGTGCTGATGGACCTGCAGAACCAGAAGCTGAAG
GAGCTGAACGACTGGCTGACCAAGACCGAGGAGCGGACCAGAAAGATGGAGGAGGAGCCCC
TGGGCCCCGACCTGGAGGACCTGAAGAGACAGGTGCAGCAGCACAAAGTGCTGCAGGAGGA
CCTGGAACAGGAGCAGGTGCGCGTGAACAGCCTGACCCACATGGTGGTCGTGGTGGACGAG
AGCAGCGGCGACCACGCCACAGCCGCCCTGGAAGAGCAGCTGAAAGTGCTGGGCGACAGAT
GGGCCAACATCTGCCGGTGGACCGAGGACAGATGGGTGCTGCTGCAGGACATCCTGCTGAA
GTGGCAGAGACTGACAGAGGAGCAGTGCCTGTTTAGCGCCTGGCTGAGCGAGAAGGAGGAC
GCCGTGAACAAGATCCACACCACCGGCTTCAAGGACCAGAACGAGATGCTGAGCAGCCTGC
AGAAGCTGGCCGTGCTGAAGGCCGATCTGGAGAAGAAAAAGCAGAGCATGGGCAAGCTGTA
CTCCCTGAAGCAGGACCTGCTGTCCACCCTGAAGAACAAGAGCGTGACCCAGAAAACCGAG
GCCTGGCTGGACAATTTCGCCCGGTGCTGGGACAATCTGGTGCAGAAACTGGAGAAGAGCA
CCGCCCAGATCAGCCAGGCCGTGACCACCACCCAGCCCAGCCTGACACAGACCACCGTGAT
GGAGACCGTGACCACAGTGACCACCAGGGAGCAGATCCTGGTGAAGCACGCCCAGGAGGAG
CTGCCCCCTCCCCCCCCTCAGAAGAAGCGGCAGATCACAGTGGACACCCTGGAGAGACTGC
AGGAGCTGCAGGAAGCCACCGACGAGCTGGACCTGAAGCTGAGACAGGCCGAAGTGATCAA
GGGCAGCTGGCAGCCTGTGGGCGATCTGCTGATCGACAGCCTGCAGGACCACCTGGAGAAA
GTGAAGGCCCTGCGGGGCGAGATCGCCCCCCTGAAGGAGAATGTGAGCCACGTGAACGACC
TGGCCAGACAGCTGACCACCCTGGGCATCCAGCTGAGCCCCTACAATCTGAGCACCCTGGA
AGATCTGAACACCCGGTGGAAACTGCTGCAGGTGGCCGTGGAGGATAGAGTGAGGCAGCTG
CACGAGGCCCACAGAGACTTCGGCCCTGCCTCCCAGCACTTCCTGAGCACCAGCGTGCAGG
GCCCCTGGGAGAGAGCCATCTCCCCCAACAAAGTGCCCTACTACATCAACCACGAGACCCA
GACCACCTGCTGGGACCACCCTAAGATGACCGAGCTGTACCAGAGCCTGGCCGACCTGAAC
AATGTGCGGTTCAGCGCCTACAGAACCGCCATGAAGCTGCGGAGACTGCAGAAGGCCCTGT
GCCTGGACCTGCTGAGCCTGAGCGCCGCCTGCGACGCCCTGGACCAGCACAACCTGAAGCA
GAACGACCAGCCCATGGACATTCTGCAGATCATCAACTGCCTGACCACCATCTACGATCGG
CTGGAGCAGGAGCACAACAACCTGGTGAACGTGCCCCTGTGCGTGGACATGTGCCTGAATT
GGCTGCTGAACGTGTACGACACCGGCAGGACCGGCAGAATCAGAGTGCTGTCCTTCAAGAC
CGGCATCATCAGCCTGTGCAAGGCCCACCTGGAGGATAAGTACCGCTACCTGTTCAAGCAG
GTGGCCAGCAGCACCGGCTTCTGCGATCAGAGGAGACTGGGCCTGCTGCTGCACGATAGCA
TCCAGATCCCTAGGCAGCTGGGCGAAGTGGCCAGCTTTGCGGCAGCAACATCGAGCCCTC
TGTGAGGAGCTGCTTCCAGTTCGCCAACAACAAGCCCGAGATCGAGGCCGCCCTGTTCCTG
GATTGGATGAGGCTGGAGCCCCAGAGCATGGTGTGGCTGCCTGTGCTGCACAGAGTGGCCG
CCGCCGAGACCGCCAAGCACCAGGCCAAGTGCAACATCTGCAAGGAGTGCCCCATCATCGG
CTTCCGGTACAGGAGCCTGAAGCACTTCAACTACGACATCTGCCAGAGCTGCTTTTTCAGC
GGCAGAGTGGCCAAGGGCCACAAGATGCACTACCCCATGGTGGAGTACTGCACCCCCACCA
CCTCCGGCGAGGATGTGAGAGACTTCGCCAAAGTGCTGAAGAATAAGTTCCGGACCAAGCG
GTACTTTGCCAAGCACCCCAGGATGGGCTACCTGCCCGTGCAGACCGTGCTGGAGGGCGAC
AACATGGAGACCGACACCATGTGATGATGACTCGAGAATAAAAGATCTTTATTTTCATTAG
ATCTGTGTGTTGGTTTTTTGTGTGAGGAACCCCTAGTGATGGAGTTGGCCACTCCCTCTCT
GCGCGCTCGCTCGCTCACTGAGGCCGGGCGACCAAAGGTCGCCCGACGCCCGGGCTTTGCC
CGGGCGGCCTCAGTGAGCGAGCGAGCGCGCAGCTGCCTGCAGGGGCGCCTGATGCGGTATT
TTCTCCTTACGCATCTGTGCGGTATTTCACACCGCATACGTCAAAGCAACCATAGTACGCG
CCCTGTAGCGGCGCATTAAGCGCGGCGGGTGTGGTGGTTACGCGCAGCGTGACCGCTACAC
TTGCCAGCGCCCTAGCGCCCGCTCCTTTCGCTTTCTTCCCTTCCTTTCTCGCCACGTTCGC
```

```
CGGCTTTCCCCGTCAAGCTCTAAATCGGGGGCTCCCTTTAGGGTTCCGATTTAGTGCTTTA
CGGCACCTCGACCCCAAAAAACTTGATTTGGGTGATGGTTCACGTAGTGGGCCATCGCCCT
GATAGACGGTTTTTCGCCCTTTGACGTTGGAGTCCACGTTCTTTAATAGTGGACTCTTGTT
CCAAACTGGAACAACACTCAACCCTATCTCGGGCTATTCTTTTGATTTATAAGGGATTTTG
CCGATTTCGGCCTATTGGTTAAAAAATGAGCTGATTTAACAAAAATTTAACGCGAATTTTA
ACAAAATATTAACGTTTACAATTTTATGGTGCACTCTCAGTACAATCTGCTCTGATGCCGC
ATAGTTAAGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTCAGAGGT
TTTCACCGTCATCACCGAAACGCGCGAGACGAAAGGGCCTCGTGATACGCCTATTTTTATA
GGTTAATGTCATGATAATAATGGTTTCTTAGACGTCAGGTGGCACTTTTCGGGGAAATGTG
CGCGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACATTT
CCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAG
CAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAG
TGATAACACTGCGGCCAACTTACTTCTGACAACGATCGGAGGACCGAAGGAGCTAACCGCT
TTTTTGCACAACATGGGGGATCATGTAACTCGCCTTGATCGTTGGGAACCGGAGCTGAATG
AAGCCATACCAAACGACGAGCGTGACACCACGATGCCTGTAGCAATGGCAACAACGTTGCG
CAAACTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACC
AAGTTTACTCATATATACTTTAGATTGATTTAAAACTTCATTTTTAATTTAAAAGGATCTA
GGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACT
GTCCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCTGGCCTTTTGCTG
GCCTTTTGCTCACATGT
```

SEQ ID NO:45

CCTGCAGGCAGCTGCGCGCTCGCTCGCTCACTGAGGCCGCCCGGGCAAAGCCCGGGCGTCG
GGCGACCTTTGGTCGCCCGGCCTCAGTGAGCGAGCGAGCGCGCAGAGAGGGAGTGGCCAAC
TCCATCACTAGGGGTTCCTCGTACGTTCTGAGTCCTCTAAGGTCCCTCACTCCCAACTCAG
CCCCATGTCCTGTCAATTCCCACTCAGTGTCTGATCTCCTTCTCCTCACCTTTCCCATCTC
CCGTTTGACCCAAGCTTCCTGAGCTCTCCTCCCATTCCCCTTTTTGGAGTCCTCCTCCTCT
CCCAGAACCCAGTAATAAGTGGGCTCCTCCCTGGCCTGGACCCCGTGGTAACCCTATAAG
GCGAGGCAGCTGCTGTCTGAGGCAGGGAGGGGCTGGTGTGGGAGGCTAAGGGCAGCTGCTA
AGTTTAGGGTGGCTCCTTCTCTCTTCTTAGAGACAACAGGTGGCTGGGGCCTCAGTGCCCA
GAAAAGAAAATGTCTTAGAGGTATCGGCATGGGCCTGGAGGAGGGGGACAGGGCAGGGGG
AGGCATCTTCCTCAGGACATCGGGTCCTAGAGGGACCTTGCTTCCTAGCTGGGCCTTTCCT
TCTCCTCTATAAATACCAGCTCTGGTATTTCGCCTTGGCAGCTGTTGCTGCTAGGGAGACG
GCTGGCTTGACATGCATCTCCTGACAAAACACAAACCCGTGGTGTGAGTGGGTGTGGGCGG
TGTGAGTAGGGGGATGAATCAGAGAGGGGGCGAGGGAGACAGGGGCGCAGGAGTCAGGCAA
AGGCGATGCGGGGGTGCGACTACACGCAGTTGGAAACAGTCGTCAGAAGATTCTGGAAACT
ATCTTGCTGGCTATAAACTTGAGGGAAGCAGAAGGCCAACATTCCTCCCAAGGGAAACTGA
GGCTCAGAGTTAAAACCCAGGTATCAGTGATATGCATGTGCCCCGGCCAGGGTCACTCTCT
GACTAACCGGTACCTACCCTACAGGCCTACCTAGAGACTCTTTTGAAAGGATGGTAGAGAC
CTGTCCGGGCTTTGCCCACAGTCGTTGGAAACCTCAGCATTTTCTAGGCAACTTGTGCGAA
TAAAACACTTCGGGGGTCCTTCTTGTTCATTCCAATAACCTAAAACCTCTCCTCGGAGAAA
ATAGGGGGCCTCAAACAAACGAAATTCTCTAGCCCGCTTTCCCCAGGATAAGGCAGGCATC
CAAATGGAAAAAAGGGGCCGGCCGGGGGTCTCCTGTCAGCTCCTTGCCCTGTGAAACCCA
GCAGGCCTGCCTGTCTTCTGTCCTCTTGGGGCTGTCCAGGGGCGCAGGCCTCTTGCGGGGG
AGCTGGCCTCCCCGCCCCCTCGCCTGTGGCCGCCCTTTTCCTGGCAGGACAGAGGGATCCT
GCAGCTGTCAGGGGAGGGGCGCCGGGGGGTGATGTCAGGAGGGCTACAAATAGTGCAGACA
GCTAAGGGGCTCCGTCACCCATCTTCACATCCACTCCAGCCGGCTGCCCGCCCGCTGCCTC
CTCTGTGCGTCCGCCCAGCCAGCCTCGTCCACGCCGCCACCTCTAGAAAGAGGTAAGGGTT
TAAGGGATGGTTGGTTGGTGGGGTATTAATGTTTAATTACCTGGAGCACCTGCCTGAAATC
ACTTTTTTTCAGGTTGGACGCGTATGGTCCGCGCGAGGCACCAGCCGGGTGGGCTTTGCCT
CCTGCTGCTGCTGCTCTGCCAGTTCATGGAGGACCGCAGTGCCCAGGCTGGGAACTGCTGG
CTCCGTCAAGCGAAGAACGGCCGCTGCCAGGTCCTGTACAAGACCGAACTGAGCAAGGAGG
AGTGCTGCAGCACCGGCCGGCTGAGCACCTCGTGGACCGAGGAGGACGTGAATGACAACAC
ACTCTTCAAGTGGATGATTTTCAACGGGGGCGCCCCCAACTGCATCCCCTGTAAAGAAACG
TGTGAGAACGTGGACTGTGGACCTGGGAAAAAATGCCGAATGAACAAGAAGAACAAACCCC
GCTGCGTCTGCGCCCCGGATTGTTCCAACATCACCTGGAAGGGTCCAGTCTGCGGGCTGGA
TGGGAAAACCTACCGCAATGAATGTGCACTCCTAAAGGCAAGATGTAAAGAGCAGCCAGAA
CTGGAAGTCCAGTACCAAGGCAGATGTAAAAAGACTTGTCGGGATGTTTTCTGTCCAGGCA
GCTCCACATGTGTGGTGGACCAGACCAATAATGCCTACTGTGTGACCTGTAATCGGATTTG
CCCAGAGCCTGCTTCCTCTGAGCAATATCTCTGTGGGAATGATGGAGTCACCTACTCCAGT
GCCTGCCACCTGAGAAAGGCTACCTGCCTGCTGGGCAGATCTATTGGATTAGCCTATGAGG
GAAAGTGTATCAAAGCAAAGTCCTGTGAAGATATCCAGTGCACTGGTGGGAAAAAATGTTT
ATGGGATTTCAAGGTTGGGAGAGGCCGGTGTTCCCTCTGTGATGAGCTGTGCCCTGACAGT
AAGTCGGATGAGCCTGTCTGTGCCAGTGACAATGCCACTTATGCCAGCGAGTGTGCCATGA
AGGAAGCTGCCTGCTCCTCAGGTGTGCTACTGGAAGTAAAGCACTCCGGATCTTGCAACTC
CATTTCGGAAGACACCGAGGAAGAGGAGGAAGATGAAGACCAGGACTACAGCTTTCCTATA

```
TCTTCTATTCTAGAGTGGGTCGAGAGGTCCGGCGGCGGAGAGGGCAGAGGAAGTCTTCTAA
CATGCGGTGACGTGGAGGAGAATCCCGGCCCAATGGAAGATGCCAAAAACATTAAGAAGGG
CCCAGCGCCATTCTACCCACTCGAAGACGGGACCGCCGGCGAGCAGCTGCACAAAGCCATG
AAGCGCTACGCCCTGGTGCCCGGCACCATCGCCTTTACCGACGCACATATCGAGGTGGACA
TTACCTACGCCGAGTACTTCGAGATGAGCGTTCGGCTGGCAGAAGCTATGAAGCGCTATGG
GCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGC
GCGAGCTGCTGAACAGCATGGGCATCAGCCAGCCCACCGTCGTATTCGTGAGCAAGAAAGG
GCTGCAAAAGATCCTCAACGTGCAAAAGAAGCTACCGATCATACAAAAGATCATCATCATG
GATAGCAAGACCGACTACCAGGGCTTCCAAAGCATGTACACCTTCGTGACTTCCCATTTGC
CACCCGGCTTCAACGAGTACGACTTCGTGCCCGAGAGCTTCGACCGGGACAAAACCATCGC
CCTGATCATGAACAGTAGTGGCAGTACCGGATTGCCCAAGGGCGTAGCCCTACCGCACCGC
ACCGCTTGTGTCCGATTCAGTCATGCCCGCGACCCCATCTTCGGCAACCAGATCATCCCCG
ACACCGCTATCCTCAGCGTGGTGCCATTTCACCACGGCTTCGGCATGTTCACCACGCTGGG
CTACTTGATCTGCGGCTTTCGGGTCGTGCTCATGTACCGCTTCGAGGAGGAGCTATTCTTG
CGCAGCTTGCAAGACTATAAGATTCAATCTGCCCTGCTGGTGCCCACACTATTTAGCTTCT
TCGCTAAGAGCACTCTCATCGACAAGTACGACCTAAGCAACTTGCACGAGATCGCCAGCGG
CGGGGCGCCGCTCAGCAAGGAGGTAGGTGAGGCCGTGGCCAAACGCTTCCACCTACCAGGC
ATCCGCCAGGGCTACGGCCTGACAGAAACAACCAGCGCCATTCTGATCACCCCCGAAGGGG
ACGACAAGCCTGGCGCAGTAGGCAAGGTGGTGCCCTTCTTCGAGGCTAAGGTGGTGGACTT
GGACACCGGTAAGACACTGGGTGTGAACCAGCGCGGCGAGCTGTGCGTCCGTGGCCCCATG
ATCATGAGCGGCTACGTTAACAACCCCGAGGCTACAAACGCTCTCATCGACAAGGACGGCT
GGCTGCACAGCGGCGACATCGCCTACTGGGACGAGGACGAGCACTTCTTCATCGTGGACCG
GCTGAAGAGCCTGATCAAATACAAGGGCTACCAGGTAGCCCCAGCCGAACTGGAGAGCATC
CTGCTGCAACACCCCAACATCTTCGACGCCGGGGTCGCCGGCCTGCCCGACGACGATGCCG
GCGAGCTGCCCGCCGCAGTCGTCGTGCTGGAACACGGTAAAACCATGACCGAGAAGGAGAT
CGTGGACTATGTGGCCAGCCAGGTTACAACCGCCAAGAAGCTGCGCGGTGGTGTTGTGTTC
GTGGACGAGGTGCCTAAAGGACTGACCGGCAAGTTGGACGCCCGCAAGATCCGCGAGATTC
TCATTAAGGCCAAGAAGGGCGGCAAGATCGCCGTGTAAAATAAAGATCTTTATTTTCATT
AGATCTGTGTGTTGGTTTTTTGTGTGAGGAACCCCTAGTGATGGAGTTGGCCACTCCCTCT
CTGCGCGCTCGCTCGCTCACTGAGGCCGGGCGACCAAAGGTCGCCCGACGCCCGGGCTTTG
CCCGGGCGGCCTCAGTGAGCGAGCGAGCGCGCAGCTGCCTGCAGGGGCGCCTGATGCGGTA
TTTTCTCCTTACGCATCTGTGCGGTATTTCACACCGCATACGTCAAAGCAACCATAGTACG
CGCCCTGTAGCGGCGCATTAAGCGCGGCGGGTGTGGTGGTTACGCGCAGCGTGACCGCTAC
ACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTT
TACGGCACCTCGACCCCAAAAAACTTGATTTGGGTGATGGTTCACGTAGTGGGCCATCGCC
CTGATAGACGGTTTTTCGCCCTTTGACGTTGGAGTCCACGTTCTTTAATAGTGGACTCTTG
TTCCAAACTGGAACAACACTCAACCCTATCTCGGCTATTCTTTTGATTTATAAGGGATTT
TGCCGATTTCGGCCTATTGGTTAAAAAATGAGCTGATTTAACAAAAATTTAACGCGAATTT
TAACAAAATATTAACGTTTACAATTTTATGGTGCACTCTCAGTACAATCTGCTCTGATGCC
GCATAGTTAAGCCAGCCCCGACACCCGCCAACACCCGCTGACGCGCCCTGACGGGCTTGTC
TGCTCCCGGCATCCGCTTACAGACAAGCTGTGACCGTCTCCGGGAGCTGCATGTGTCAGAG
GTTTTCACCGTCATCACCGAAACGCGCGAGACGAAAGGGCCTCGTGATACGCCTATTTTTA
TAGGTTAATGTCATGATAATAATGGTTTCTTAGACGTCAGGTGGCACTTTTCGGGGAAATG
TGCGCGGAACCCCTATTTGTTTATTTTTCTAAATACATTCAAATATGTATCCGCTCATGAG
ACAATAACCCTGATAAATGCTTCAATAATATTGAAAAAGGAAGAGTATGAGTATTCAACAT
TTCCGTGTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGGTTACATCGA
```

ACTGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGCCGGGCAAG
AGCAACTCGGTCGCCGCATACACTATTCTCAGAATGACTTGGTTGAGTACTCACCAGTCAC
AGAAAAGCATCTTACGGATGGCATGACAGTAAGAGAATTATGCAGTGCTGCCATAACCATG
AGTGATAACACTGCGGCCAACTTACTTCTGACAACGATCGGAGGACCGAAGGAGCTAACCG
CTTTTTTGCACAACATGGGGGATCATGTAACTCGCCTTGATCGTTGGGAACCGGAGCTGAA
TGAAGCCATACCAAACGACGAGCGTGACACCACGATGCCTGTAGCAATGGCAACAACGTTG
CGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTAT
TGCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGA
CCAAGTTTACTCATATATACTTTAGATTGATTTAAAACTTCATTTTTAATTTAAAAGGATC
TAGGTGAAGATCCTTTTTGATAATCTCATGACCAAAATCCCTTAACGTGAGTTTTCGTTCC
ACTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCAGATACCAAATA
CTGTCCTTCTAGTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCG
TGAGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCTTT
ATAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTACGGTTCCTGGCCTTTTGC
TGGCCTTTTGCTCACATGT

FIG. 18
FIG. 18A
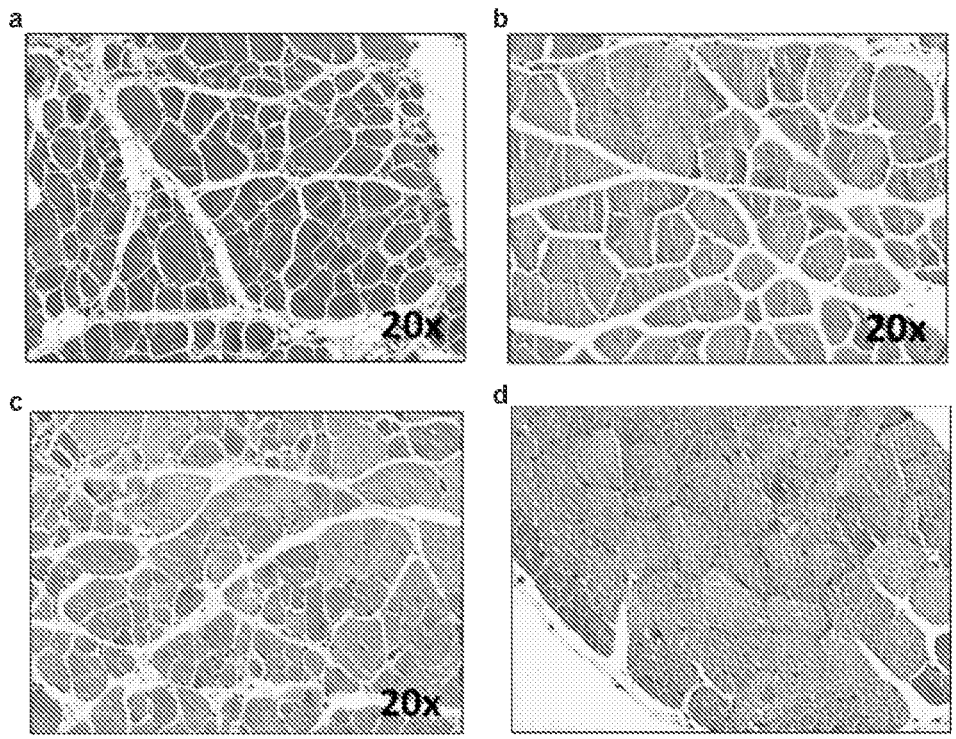
FIG. 18B
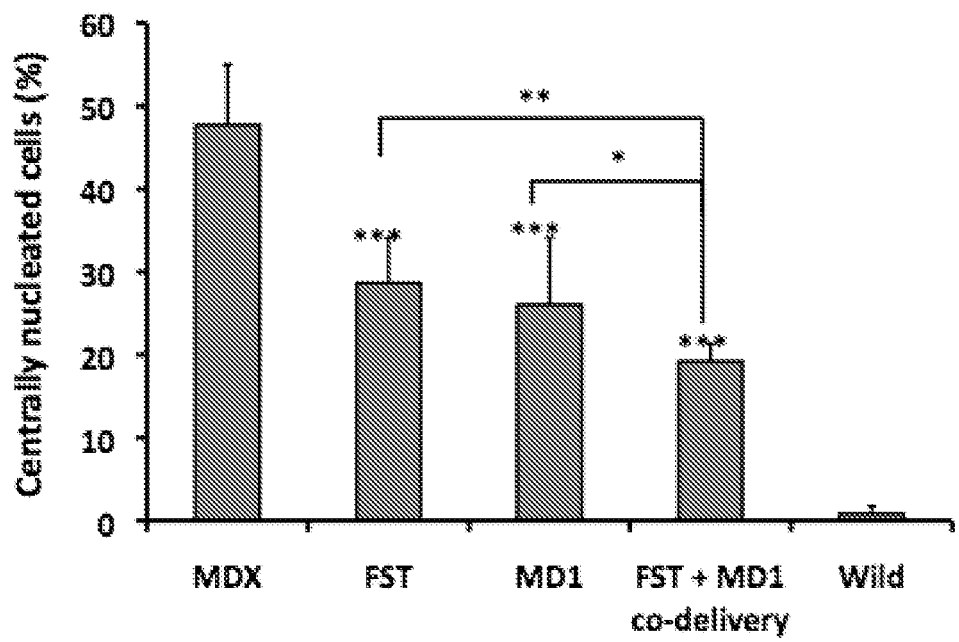

FIG. 19
FIG. 19A
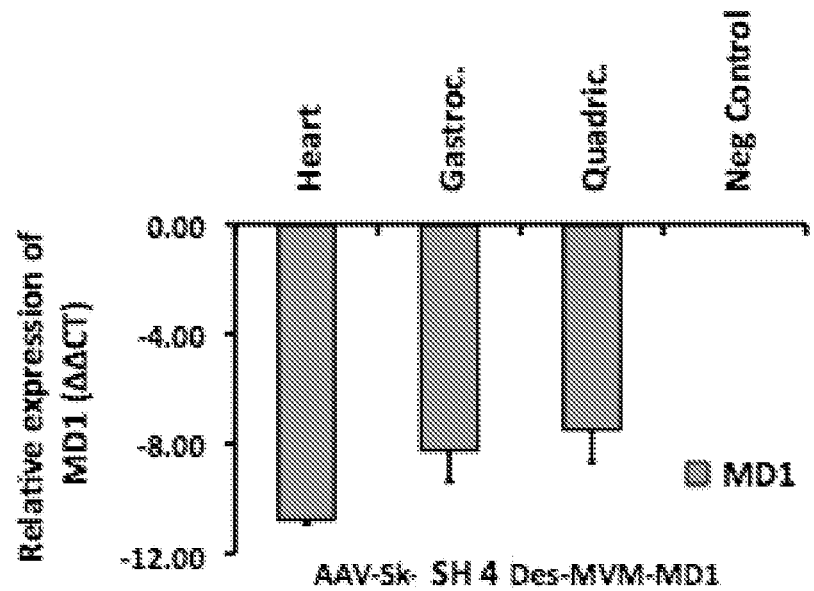
FIG. 19B
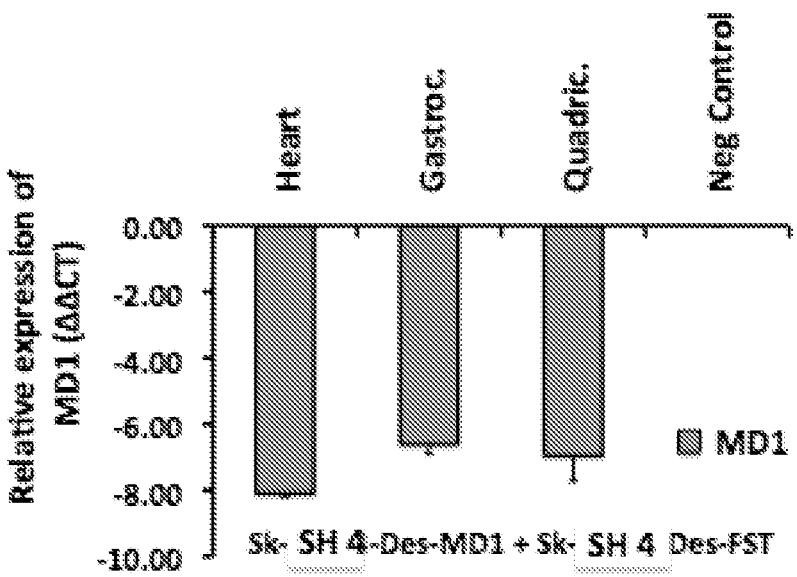

FIG. 20
FIG. 20A
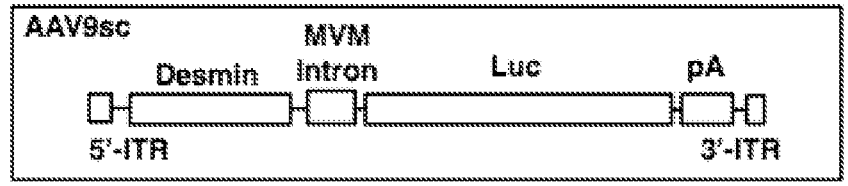
FIG. 20B
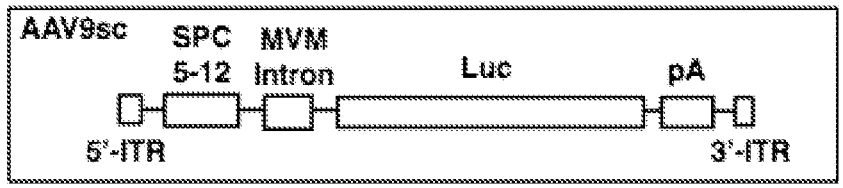
FIG. 20C
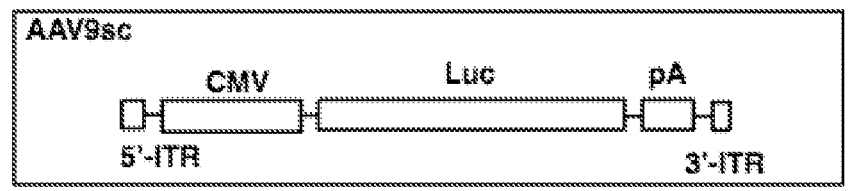
FIG. 20D
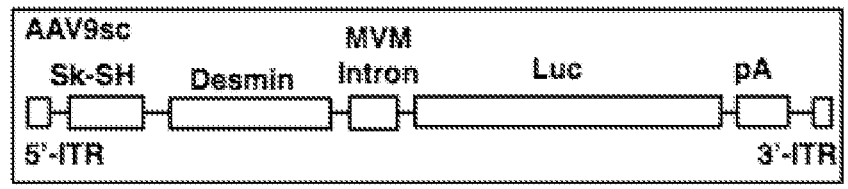
FIG. 20E
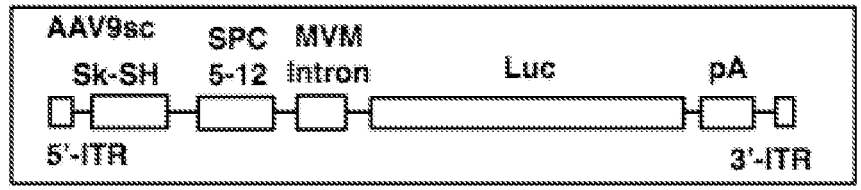

FIG. 22

FIG. 22A mouse desmin promotor (SEQ ID NO: 16)

ACCTTGCTTCCTAGCTGGGCCTTTCCTTCTCCTCTATAAATACCAGCTCTGGTATTTCGCCTTGGC
AGCTGTTGCTGCTAGGGAGACGGCTGGCTTGACATGCATCTCCTGACAAAACACAAACCCGTGGTG
TGAGTGGGTGTGGGCGGTGTGAGTAGGGGGATGAATCAGAGAGGGGCGAGGGAGACAGGGGCGCA
GGAGTCAGGCAAAGGCGATGCGGGGTGCGACTACACGCAGTTGGAAACAGTCGTCAGAAGATTCT
GGAAACTATCTTGCTGGCTATAAACTTGAGGGAAGCAGAAGGCCAACATTCCTCCCAAGGGAAACT
GAGGCTCAGAGTTAAAACCCAGGTATCAGTGATATGCATGTGCCCCGGCCAGGGTCACTCTCTGAC
TAACCGGTACCTACCCTACAGGCCTACCTAGAGACTCTTTTGAAAGGATGGTAGAGACCTGTCCGG
GCTTTGCCCACAGTCGTTGGAAACCTCAGCATTTTCTAGGCAACTTGTGCGAATAAAACACTTCGG
GGGTCCTTCTTGTTCATTCCAATAACCTAAAACCTCTCCTCGGAGAAAATAGGGGGCCTCAAACAA
ACGAAATTCTCTAGCCCGCTTTCCCCAGGATAAGGCAGGCATCCAAATGGAAAAAAAGGGGCCGGC
CGGGGGTCTCCTGTCAGCTCCTTGCCCTGTGAAACCCAGCAGGCCTGCCTGTCTTCTGTCCTCTTG
GGGCTGTCCAGGGGCGCAGGCCTCTTGCGGGGGAGCTGGCCTCCCCGCCCCCTCGCCTGTGGCCGC
CCTTTTCCTGGCAGGACAGAGGGATCCTGCAGCTGTCAGGGGAGGGGCGCCGGGGGGTGATGTCAG
GAGGGCTACAAATAGTGCAGACAGCTAAGGGGCTCCGTCACCCATCTTCACATCCACTCCAGCCGG
CTGCCCGCCCGCTGCCTCCTCTGTGCGTCCGCCCAGCCAGCCTCGTCCACGCCGCCACC

FIG. 22B human 1.0kb desmin promotor (SEQ ID NO: 47)

TGTACAACGCGTTACGCCTCAGGTACCCCTGCCCCCCACAGCTCCTCTCCTGTGCCTTGTTTCCC
AGCCATGCGTTCTCCTCTATAAATACCCGCTCTGGTATTTGGGGTTGGCAGCTGTTGCTGCCAGGG
AGATGGTTGGGTTGACATGCGGCTCCTGACAAAACACAAACCCCTGGTGTGTGTGGGCGTGGGTGG
TGTGAGTAGGGGGATGAATCAGGGAGGGGCGGGGGACCCAGGGGGCAGGAGCCACACAAAGTCTG
TGCGGGGTGGGAGCGCACATAGCAATTGGAAACTGAAAGCTTATCAGACCCTTTCTGGAAATCAG
CCCACTGTTTATAAACTTGAGGCCCCACCCTCGACAGTACCGGGGAGGAAGAGGGCCTGCACTAGT
CCAGAGGGAAACTGAGGCTCAGGGCTAGCTCGCCCATAGACATACATGGCAGGCAGGCTTTGGCCA
GGATCCCTCCGCCTGCCAGGCGTCTCCCTGCCCTCCCTTCCTGCCTAGAGACCCCCACCCTCAAGC
CTGGCTGGTCTTTGCCTGAGACCCAAACCTCTTCGACTTCAAGAGAATATTTAGGAACAAGGTGGT
TTAGGGCCTTTCCTGGGAACAGGCCTTGACCCTTTAAGAAATGACCCAAAGTCTCTCCTTGACCAA
AAAGGGGACCCTCAAACTAAAGGGAAGCCTCTCTTCTGCTGTCTCCCCTGACCCCACTCCCCCCCA
CCCCAGGACGAGGAGATAACCAGGGCTGAAAGAGGCCCGCCTGGGGCTGCAGACATGCTTGCTGC
CTGCCCTGGCGAAGGATTGGCAGGCTTGCCCGTCACAGGACCCCGCTGGCTGACTCAGGGGCGCA
GGCCTCTTGCGGGGAGCTGGCCTCCCCGCCCCACGGCCACGGGCCGCCCTTTCCTGGCAGGACA
GCGGGATCTTGCAGCTGTCAGGGGAGGGAGGCGGGGCTGATGTCAGGAGGGATACAAATAGTGC
CGACGGCTGGGGCCCTGTCTCCCCTCGCCGCATCCACTCTCCGGCCGGCCGCCTGCCCGCCGCCT
CCTCCGTGCGCCCGCCAGCCTCGCCCGCGCCGTCACCTCTAGA

FIG. 22 (continued)

FIG. 22C human 1.4kb desmin promotor (SEQ ID NO: 48)

```
ACACACCTACTAGTAACCCCTCCAGCTGGTGATGGCAGGTCTAGGGTAGGACCAGTGACTGGCTCC
TAATCGAGCACTCTATTTTCAGGGTTTGCATTCCAAAAGGGTCAGGTCCAAGAGGGACCTGGAGTG
CCAAGTGGAGGTGTAGAGGCACGGCCAGTACCCATGGAGAATGGTGGATGTCCTTAGGGGTTAGCA
AGTGCCGTGTGCTAAGGAGGGGGCTTTGGAGGTTGGGCAGGCCCTCTGTGGGGCTCCATTTTTGTG
GGGGTGGGGGCTGGAGCATTATAGGGGGTGGGAAGTGATTGGGGCTGTCACCCTAGCCTTCCTTAT
CTGACGCCCACCCATGCCTCCTCAGGTACCCCCTGCCCCCCACAGCTCCTCTCCTGTGCCTTGTTT
CCCAGCCATGCGTTCTCCTCTATAAATACCCGCTCTGGTATTTGGGGTTGGCAGCTGTTGCTGCCA
GGGAGATGGTTGGGTTGACATGCGGCTCCTGACAAAACACAAACCCCTGGTGTGTGGGCGTGGG
TGGTGTGAGTAGGGGATGAATCAGGGAGGGGCGGGGGACCCAGGGGGCAGGAGCCACACAAAGT
CTGTGCGGGGGTGGGAGCGCACATAGCAATTGGAAACTGAAAGCTTATCAGACCCTTTCTGGAAAT
CAGCCCACTGTTTATAAACTTGAGGCCCCACCCTCGACAGTACCGGGGAGGAAGAGGGCCTGCACT
AGTCCAGAGGGAAACTGAGGCTCAGGGCTAGCTCGCCCATAGACATACATGGCAGGCAGGCTTTGG
CCAGGATCCCTCCGCCTGCCAGGCGTCTCCCTGCCCTCCCTTCCTGCCTAGAGACCCCCACCCTCA
AGCCTGGCTGGTCTTTGCCTGAGACCCAAACCTCTTCGACTTCAAGAGAATATTTAGGAACAAGGT
GGTTTAGGGCCTTTCCTGGGAACAGGCCTTGACCCTTTAAGAAATGACCCAAAGTCTCTCCTTGAC
CAAAAAGGGGACCCTCAAACTAAAGGGAAGCCTCTCTTCTGCTGTCTCCCCTGACCCCACTCCCCC
CCACCCCAGGACGAGGAGATAACCAGGGCTGAAAGAGGCCCGCCTGGGGGCTGCAGACATGCTTGC
TGCCTGCCCTGGCGAAGGATTGGCAGGCTTGCCCGTCACAGGACCCCCGCTGGCTGACTCAGGGGC
GCAGGCCTCTTGCGGGGGAGCTGGCCTCCCCGCCCCCACGGCCACGGGCCGCCCTTTCCTGGCAGG
ACAGCGGGATCTTGCAGCTGTCAGGGGAGGGGAGGCGGGGGCTGATGTCAGGAGGGATACAAATAG
TGCCGACGGCTGGGGGCCCTGTCTCCCCTCGCCGCATCCACTCTCCGGCCGGCCGCCTGCCCGCCG
CCTCCTCCGTGCGCCCGCCAGCCTCGCCCGCGCCGTCACC
```

FIG. 22D SPc5-12 promoter (SEQ ID NO: 48)

```
TGGCCACCGCCTTCGGCACCATCCTCACGACACCCAAATATGGCGACGGGTGAGGAATGGTGGGGA
GTTATTTTTAGAGCGGTGAGGAAGGTGGGCAGGCAGCAGGTGTTGGCGCTCTAAAAATAACTCCCG
GGAGTTATTTTTAGAGCGGAGGAATGGTGGACACCCAAATATGGCGACGGTTCCTCACCCGTCGCC
ATATTTGGGTGTCCGCCCTCGGCCGGGGCCGCATTCCTGGGGGCCGGGCGGTGCTCCCGCCCGCCT
CGATAAAAGGCTCCGGGGCCGGCGGCGGCCCACGAGCTACCCGGAGGAGCGGGAGGCGCCAAGCTC
TAGA
```

FIG. 23
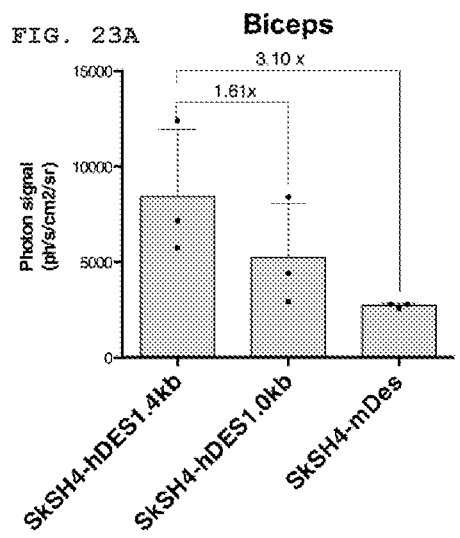
FIG. 23A
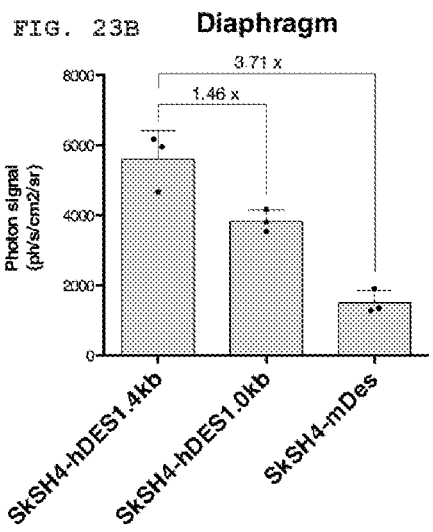
FIG. 23B
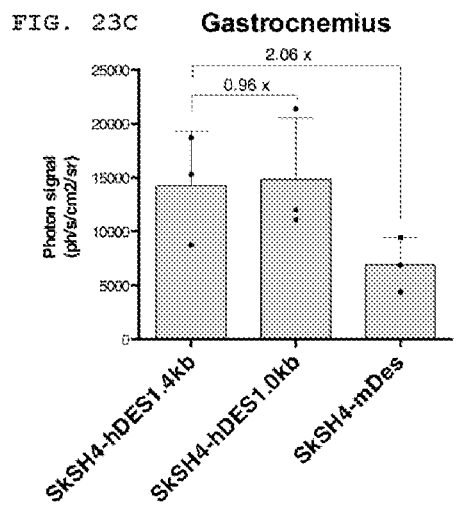
FIG. 23C
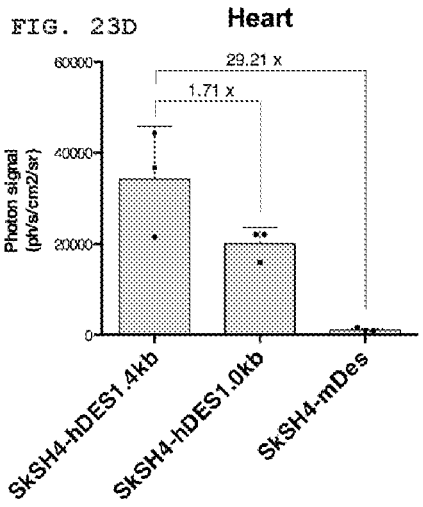
FIG. 23D FIG. 23 (continued)
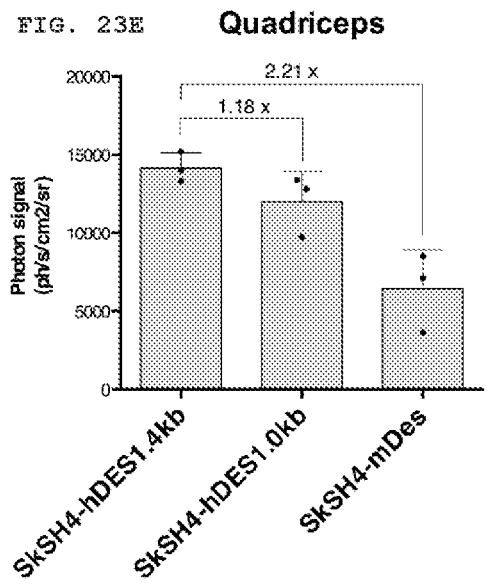
FIG. 23E Quadriceps
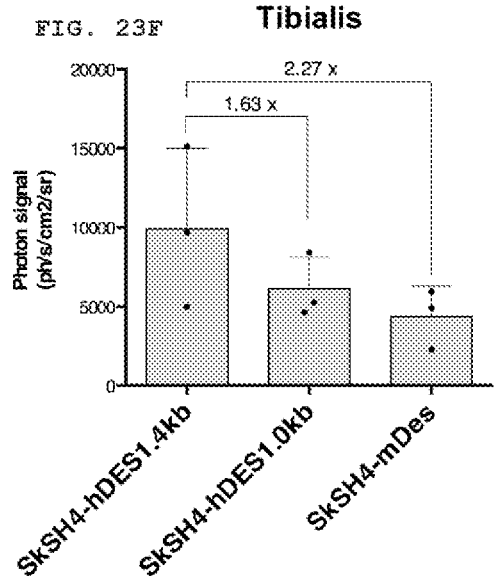
FIG. 23F Tibialis
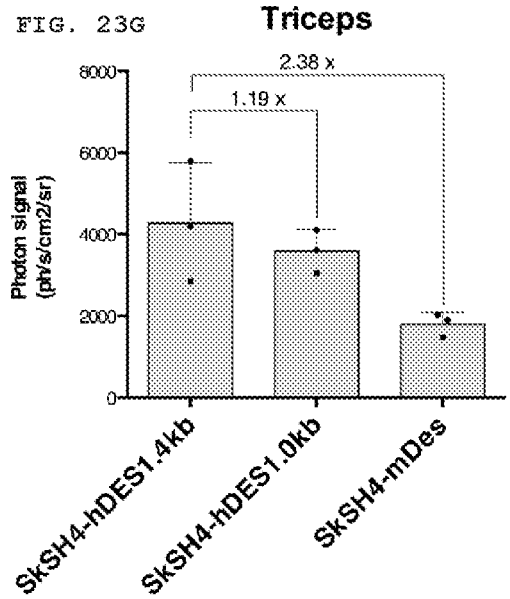
FIG. 23G Triceps

FIG. 24

FIG. 24A human GAA sequence (SEQ ID NO: 49)

ATGGGAGTGAGGCACCCGCCCTGCTCCCACCGGCTCCTGGCCGTCTGCGCCCTCGTGTCCTTGGCAACCGCTG
CACTCCTGGGGCACATCCTACTCCATGATTTCCTGCTGGTTCCCCGAGAGCTGAGTGGCTCCTCCCCAGTCCT
GGAGGAGACTCACCCAGCTCACCAGCAGGGAGCCAGCAGACCAGGGCCCCGGGATGCCCAGGCACACCCGGC
CGTCCCAGAGCAGTGCCCACACAGTGCGACGTCCCCCCCAACAGCCGCTTCGATTGCGCCCCTGACAAGGCCA
TCACCCAGGAACAGTGCGAGGCCCGCGGCTGTTGCTACATCCCTGCAAAGCAGGGGCTGCAGGGAGCCCAGAT
GGGGCAGCCCTGGTGCTTCTTCCCACCCAGCTACCCCAGCTACAAGCTGGAGAACCTGAGCTCCTCTGAAATG
GGCTACACGGCCACCCTGACCCGTACCACCCCCACCTTCTTCCCCAAGGACATCCTGACCCTGCGGCTGGACG
TGATGATGGAGACTGAGAACCGCCTCCACTTCACGATCAAAGATCCAGCTAACAGGCGCTACGAGGTGCCCTT
GGAGACCCCGCATGTCCACAGCCGGGCACCGTCCCCACTCTACAGCGTGGAGTTCTCCGAGGAGCCCTTCGGG
GTGATCGTGCGCCGGCAGCTGGACGGCCGCGTGCTGCTGAACACGACGGTGGCGCCCCTGTTCTTTGCGGACC
AGTTCCTTCAGCTGTCCACCTCGCTGCCCTCGCAGTATATCACAGGCCTCGCCGAGCACCTCAGTCCCCTGAT
GCTCAGCACCAGCTGGACCAGGATCACCCTGTGGAACCGGGACCTTGCGCCCACGCCCGGTGCGAACCTCTAC
GGGTCTCACCCTTTCTACCTGGCGCTGGAGGACGGCGGGTCGGCACACGGGGTGTTCCTGCTAAACAGCAATG
CCATGGATGTGGTCCTGCAGCCGAGCCCTGCCCTTAGCTGGAGGTCGACAGGTGGGATCCTGGATGTCTACAT
CTTCCTGGGCCCAGAGCCCAAGAGCGTGGTGCAGCAGTACCTGGACGTTGTGGGATACCCGTTCATGCCGCCA
TACTGGGGCCTGGGCTTCCACCTGTGCCGCTGGGGCTACTCCTCCACCGCTATCACCCGCCAGGTGGTGGAGA
ACATGACCAGGGCCCACTTCCCCCTGGACGTCCAGTGGAACGACCTGGACTACATGGACTCCCGGAGGGACTT
CACGTTCAACAAGGATGGCTTCCGGGACTTCCCGGCCATGGTGCAGGAGCTGCACCAGGGCGGCCGGCGCTAC
ATGATGATCGTGGATCCTGCCATCAGCAGCTCGGGCCCTGCCGGGAGCTACAGGCCCTACGACGAGGGTCTGC
GGAGGGGGGTTTTCATCACCAACGAGACCGGCCAGCCGCTGATTGGGAAGGTATGGCCCGGGTCCACTGCCTT
CCCCGACTTCACCAACCCCACAGCCCTGGCCTGGTGGAGGACATGGTGGCTGAGTTCCATGACCAGGTGCCC
TTCGACGGCATGTGGATTGACATGAACGAGCCTTCCAACTTCATCAGGGGCTCTGAGGACGGCTGCCCCAACA
ATGAGCTGGAGAACCCACCCTACGTGCCTGGGGTGGTTGGGGGGACCCTCCAGGCGGCCACCATCTGTGCCTC
CAGCCACCAGTTTCTCTCCACACACTACAACCTGCACAACCTCTACGGCCTGACCGAAGCCATCGCCTCCCAC
AGGGCGCTGGTGAAGGCTCGGGGGACACGCCCATTTGTGATCTCCCGCTCGACCTTTGCTGGCCACGGCCGAT
ACGCCGGCCACTGGACGGGGACGTGTGGAGCTCCTGGGAGCAGCTCGCCTCCTCCGTGCCAGAAATCCTGCA
GTTTAACCTGCTGGGGGTGCCTCTGGTCGGGGCCGACGTCTGCGGCTTCCTGGGCAACACCTCAGAGGAGCTG
TGTGTGCGCTGGACCCAGCTGGGGGCCTTCTACCCCTTCATGCGGAACCACAACAGCCTGCTCAGTCTGCCCC
AGGAGCCGTACAGCTTCAGCGAGCCGGCCCAGCAGGCCATGAGGAAGGCCCTCACCCTGCGCTACGCACTCCT
CCCCCACCTCTACACACTGTTCCACCAGGCCCACGTCGCGGGGGAGACCGTGGCCCGGCCCCTCTTCCTGGAG
TTCCCCAAGGACTCTAGCACCTGGACTGTGGACCACCAGCTCCTGTGGGGGGAGGCCCTGCTCATCACCCCAG
TGCTCCAGGCCGGGAAGGCCGAAGTGACTGGCTACTTCCCCTTGGGCACATGGTACGACCTGCAGACGGTGCC
AGTAGAGGCCCTTGGCAGCCTCCCACCCCCACCTGCAGCTCCCCGTGAGCCAGCCATCCACAGCGAGGGGCAG
TGGGTGACGCTGCCGGCCCCCCTGGACACCATCAACGTCCACCTCCGGGCTGGGTACATCATCCCCCTGCAGG
GCCCTGGCCTCACAACCACAGAGTCCCGCCAGCAGCCATGGCCCTGGCTGTGGCCCTGACCAAGGGTGGGGA
GGCCCGAGGGGAGCTGTTCTGGGACGATGGAGAGAGCCTGGAAGTGCTGGAGCGAGGGGCCTACACACAGGTC
ATCTTCCTGGCCAGGAATAACACGATCGTGAATGAGCTGGTACGTGTGACCAGTGAGGGAGCTGGCCTGCAGC
TGCAGAAGGTGACTGTCCTGGGCGTGGCCACGGCGCCCCAGCAGGTCCTCTCCAACGGTGTCCCTGTCTCCAA
CTTCACCTACAGCCCCGACACCAAGGTCCTGGACATCTGTGTCTCGCTGTTGATGGGAGAGCAGTTTCTCGTC
AGCTGGTGTTAG

FIG. 24 (continued)

FIG. 24B human GAAco sequence (SEQ ID NO: 50)

```
ATGGGCGTCAGACATCCTCCATGTTCTCACAGACTGCTGGCCGTGTGTGCTCTGGTGTCTCTTGCTACAGCTG
CCCTGCTGGGACATATCCTGCTGCACGATTTTCTGCTGGTGCCCAGAGAGCTGTCTGGCAGCTCTCCTGTGCT
GGAAGAAACACACCCTGCACATCAGCAGGGCGCCTCTAGACCTGGACCTAGAGATGCTCAAGCCCATCCTGGC
AGACCTAGAGCCGTGCCTACACAGTGTGACGTGCCACCTAACAGCAGATTCGACTGCGCCCCTGACAAGGCCA
TCACACAAGAGCAGTGTGAAGCCAGAGGCTGCTGCTACATTCCTGCCAAACAAGGACTGCAGGGCGCTCAGAT
GGGACAGCCTTGGTGCTTCTTCCCACCATCTTACCCCAGCTACAAGCTGGAAAACCTGAGCAGCAGCGAGATG
GGCTACACCGCCACACTGACCAGAACCACACCTACATTCTTCCCAAAGGACATCCTGACACTGCGGCTGGACG
TGATGATGGAAACCGAGAACCGGCTGCACTTCACCATCAAGGACCCCGCCAATAGAAGATACGAGGTGCCCCT
GGAAACCCCTCACGTGCACTCTAGAGCCCCATCTCCACTGTACAGCGTGGAATTCAGCGAGGAACCCTTTGGC
GTGATCGTGCGGAGACAGCTGGATGGCAGAGTGCTGCTGAATACCACAGTGGCCCCTCTGTTCTTCGCCGACC
AGTTTCTGCAGCTGAGCACAAGCCTGCCTAGCCAGTATATCACAGGCCTGGCCGAACACCTGTCTCCACTGAT
GCTGAGCACCAGCTGGACCAGAATCACCCTGTGGAACAGAGATCTGGCCCCTACACCTGGCGCCAATCTGTAC
GGCTCTCACCCTTTTTATCTGGCCCTGGAAGATGGCGGAAGCGCCCACGGTGTCTTTCTGCTGAACAGCAACG
CCATGGACGTGGTGCTGCAACCATCTCCTGCTCTGTCTTGGAGAAGCACCGGCGGCATCCTGGACGTGTACAT
CTTTCTGGGACCCGAGCCTAAGAGCGTGGTGCAGCAGTATCTGGATGTCGTGGGCTACCCCTTCATGCCTCCT
TATTGGGGCCTGGGCTTCCACCTGTGTAGATGGGGATACAGCTCCACCGCCATCACCAGACAGGTGGTGGAAA
ACATGACCCGGGCTCACTTCCCACTGGATGTGCAGTGGAACGACCTGGACTACATGGACTCCAGACGGGACTT
CACCTTTAACAAGGACGGCTTCAGAGACTTCCCCGCCATGGTGCAAGAACTGCATCAAGGCGGCAGACGGTAC
ATGATGATCGTGGATCCTGCCATCTCTTCTAGCGGCCCTGCCGGAAGCTACAGACCTTATGATGAGGGCCTGA
GAAGAGGCGTGTTCATCACCAATGAGACAGGCCAGCCTCTGATCGGCAAAGTGTGGCCTGGAAGCACCGCCTT
TCCAGACTTCACCAATCCAACCGCTCTGGCTTGGTGGGAAGATATGGTGGCCGAGTTCCACGATCAGGTGCCC
TTCGATGGCATGTGGATCGACATGAACGAGCCCAGCAACTTCATCAGGGGCAGCGAGGATGGCTGCCCCAACA
ACGAACTGGAAAATCCTCCTTACGTGCCAGGCGTTGTCGGAGGAACACTGCAGGCCGCCACAATTTGTGCCAG
CAGCCATCAGTTTCTGAGCACCCACTACAACCTGCACAACCTGTACGGCCTGACCGAGGCCATTGCCTCTCAT
AGAGCCCTGGTTAAGGCCAGAGGCACCCGGCCTTTTGTGATCAGCAGAAGCACATTTGCCGGCCACGGCAGAT
ATGCCGGACATTGGACAGGGGACGTTTGGTCTAGTTGGGAGCAGCTGGCCTCTAGCGTGCCCGAGATCCTGCA
GTTTAATCTGCTGGGAGTGCCCCTCGTGGGAGCCGATGTTTGTGGATTTCTGGGCAACACCTCCGAGGAACTG
TGCGTCAGATGGACACAGCTGGGCGCCTTCTATCCCTTCATGAGAAACCACAACAGCCTGCTGAGCCTGCCTC
AAGAGCCTTACAGCTTTAGCGAACCCGCACAGCAGGCCATGAGAAAGGCCCTGACTCTGAGATACGCTCTGCT
GCCCCACCTGTACACCCTGTTTCATCAAGCTCATGTGGCCGGCGAGACAGTGGCCAGACCACTGTTTCTGGAA
TTCCCCAAGGACAGCAGCACCTGGACAGTGGATCATCAGCTGCTCTGGGGAGAAGCCCTGCTCATTACACCTG
TGCTGCAGGCTGGCAAGGCCGAAGTGACAGGATACTTTCCCCTCGGCACTTGGTACGACCTGCAGACAGTTCC
TGTGGAAGCTCTGGGATCTCTGCCTCCACCTCCTGCTGCTCCTAGAGAGCCTGCCATTCACTCTGAAGGCCAG
TGGGTTACACTGCCCGCTCCACTGGACACCATCAATGTGCACCTGAGAGCCGGCTACATCATCCCTCTGCAAG
GCCCTGGACTGACCACAACCGAAAGCAGACAGCAGCCAATGGCTCTGGCCGTGGCTCTGACAAAAGGCGGAGA
AGCTAGAGGCGAACTGTTCTGGGATGACGGCGAGAGCCTGGAAGTGCTGGAACGGGGAGCCTACACACAAGTG
ATCTTTCTCGCCCGGAACAACACCATCGTGAACGAACTCGTCAGAGTGACCAGTGAAGGTGCCGGACTGCAGC
TCCAGAAAGTGACAGTGCTTGGAGTGGCCACAGCACCCCAGCAGGTTTTGTCTAATGGCGTGCCCGTGTCCAA
CTTCACATACAGCCCTGACACCAAGGTGCTGGACATCTGTGTGTCTCTGCTGATGGGCGAGCAGTTCCTGGTG
TCCTGGTGTTGA
```

FIG. 24 (continued)

FIG. 24C human MTM1 sequence (SEQ ID NO: 51)

```
ATGGCTTCTGCATCAACTTCTAAATATAATTCACACTCCTTGGAGAATGAGTCTATTAAGAGGACGTCTCGAG
ATGGAGTCAATCGAGATCTCACTGAGGCTGTTCCTCGACTTCCAGGAGAAACACTAATCACTGACAAAGAAGT
TATTTACATATGTCCTTTCAATGGCCCCATTAAGGGAAGAGTTTACATCACAAATTATCGTCTTTATTTAAGA
AGTTTGGAAACGGATTCTTCTCTAATACTTGATGTTCCTCTGGGTGTGATCTCGAGAATTGAAAAAATGGGAG
GCGCGACAAGTAGAGGAGAAAATTCCTATGGTCTAGATATTACTTGTAAAGACATGAGAAACCTGAGGTTCGC
TTTGAAACAGGAAGGCCACAGCAGAAGAGATATGTTTGAGATCCTCACGAGATACGCGTTTCCCCTGGCTCAC
AGTCTGCCATTATTTGCATTTTTAAATGAAGAAAAGTTTAACGTGGATGGATGGACAGTTTACAATCCAGTGG
AAGAATACAGGAGGCAGGGCTTGCCCAATCACCATTGGAGAATAACTTTTATTAATAAGTGCTATGAGCTCTG
TGACACTTACCCTGCTCTTTTGGTGGTTCCGTATCGTGCCTCAGATGATGACCTCCGGAGAGTTGCAACTTTT
AGGTCCCGAAATCGAATTCCAGTGCTGTCATGGATTCATCCAGAAAATAAGACGGTCATTGTGCGTTGCAGTC
AGCCTCTTGTCGGTATGAGTGGGAAACGAAATAAAGATGATGAGAAATATCTCGATGTTATCAGGGAGACTAA
TAAACAAATTTCTAAACTCACCATTTATGATGCAAGACCCAGCGTAAATGCAGTGGCCAACAAGGCAACAGGA
GGAGGATATGAAAGTGATGATGCATATCATAACGCCGAACTTTTCTTCTTAGACATTCATAATATTCATGTTA
TGCGGGAATCTTTAAAAAAAGTGAAGGACATTGTTTATCCTAATGTAGAAGAATCTCATTGGTTGTCCAGTTT
GGAGTCTACTCATTGGTTAGAACATATCAAGCTCGTTTTGACAGGAGCCATTCAAGTAGCAGACAAAGTTTCT
TCAGGGAAGAGTTCAGTGCTTGTGCATTGCAGTGACGGATGGGACAGGACTGCTCAGCTGACATCCTTGGCCA
TGCTGATGTTGGATAGCTTCTATAGGAGCATTGAAGGGTTCGAAATACTGGTACAAAAAAAATGGATAAGTTT
TGGACATAAATTTGCATCTCGAATAGGTCATGGTGATAAAAACCACACCGATGCTGACCGTTCTCCTATTTTT
CTCCAGTTTATTGATTGTGTGTGGCAAATGTCAAAACAGTTCCCTACAGCTTTTGAATTCAATGAACAATTTT
TGATTATAATTTTGGATCATCTGTATAGTTGCCGATTTGGTACTTTCTTATTCAACTGTGAATCTGCTCGAGA
AAGACAGAAGGTTACAGAAAGGACTGTTTCTTTATGGTCACTGATAAACAGTAATAAAGAAAAATTCAAAAAC
CCCTTCTATACTAAAGAAATCAATCGAGTTTTATATCCAGTTGCCAGTATGCGTCACTTGGAACTCTGGGTGA
ATTACTACATTAGATGGAACCCCAGGATCAAGCAACAACAGCCGAATCCAGTGGAGCAGCGTTACATGGAGCT
CTTAGCCTTACGCGACGAATACATAAAGCGGCTTGAGGAACTGCAGCTCGCCAACTCTGCCAAGCTTTCTGAT
CCCCCAACTTCACCTTCCAGTCCTTCGCAAATGATGCCCCATGTGCAAACTCACTTCTGA
```

FIG. 24 (continued)

FIG. 24D human MTM1co sequence (SEQ ID NO: 52)

ATGGCCAGCGCCAGCACAAGCAAGTACAACAGCCACAGCCTGGAAAACGAGAGCATCAAGCGGACCAGCAGAG
ATGGCGTGAACAGAGATCTGACCGAGGCCGTTCCTAGACTGCCTGGCGAGACACTGATCACCGACAAAGAAGT
GATCTACATCTGCCCCTTCAACGGCCCCATCAAGGGAAGAGTGTACATCACCAACTACCGGCTGTACCTGCGG
TCCCTGGAAACCGATAGCAGCCTGATTCTGGATGTGCCCCTGGGCGTGATCAGCCGGATTGAAAAAATGGGCG
GAGCCACCTCCAGAGGCGAGAATAGCTATGGCCTGGATATCACATGCAAGGACATGCGGAACCTGAGATTCGC
CCTGAAGCAAGAGGGCCACAGCAGACGGGACATGTTCGAGATCCTGACCAGATACGCCTTTCCTCTGGCTCAC
TCTCTGCCCCTGTTCGCCTTCCTGAACGAAGAGAAGTTCAACGTGGACGGCTGGACCGTGTACAACCCCGTGG
AAGAGTATAGACGGCAGGGACTGCCCAATCACCACTGGCGGATCACCTTCATCAACAAGTGCTACGAGCTGTG
CGACACATACCCCGCACTGCTGGTGGTGCCTTACAGAGCCTCTGACGACGATCTGAGAAGAGTGGCCACCTTT
CGGAGCCGGAACAGAATCCCTGTGCTGAGCTGGATTCACCCCGAGAACAAGACCGTGATCGTGCGGTGTTCTC
AGCCTCTCGTGGGCATGAGCGGCAAGAGAAACAAGGACGACGAGAAGTACCTGGACGTGATCCGCGAGACAAA
CAAGCAGATCAGCAAGCTGACCATCTACGACGCCAGACCTTCTGTGAACGCCGTGGCCAACAAAGCCACAGGC
GGCGGATATGAGTCCGACGATGCCTATCACAACGCCGAGCTGTTCTTCCTGGACATTCACAACATCCATGTGA
TGCGCGAGAGCCTGAAGAAAGTGAAGGACATCGTGTACCCCAATGTGGAAGAGAGCCACTGGCTGTCTAGCCT
GGAATCCACACACTGGCTGGAACACATCAAGCTGGTGCTGACAGGCGCCATCCAGGTGGCAGACAAAGTGTCT
AGCGGCAAGTCTAGCGTGCTGGTGCACTGTAGCGACGGATGGGATAGAACAGCCCAGCTGACATCCCTGGCCA
TGCTGATGCTGGACAGCTTCTACAGATCCATCGAGGGCTTTGAGATCCTGGTGCAGAAGAAGTGGATCAGCTT
CGGCCACAAGTTCGCCTCTAGAATCGGACACGGCGACAAGAACCACACCGACGCCGATAGAAGCCCCATCTTC
CTGCAGTTCATCGACTGCGTGTGGCAGATGTCCAAGCAGTTCCCTACCGCCTTCGAGTTCAACGAGCAGTTCC
TGATCATCATCCTGGACCACCTGTACTCTTGCAGATTCGGCACCTTCCTGTTCAACTGCGAGAGCGCCAGAGA
ACGGCAGAAAGTGACCGAGAGAACCGTGTCTCTGTGGTCCCTGATCAACAGCAACAAAGAGAAATTCAAGAAC
CCCTTCTACACCAAAGAAATCAACCGGGTGCTGTACCCCGTGGCCAGCATGAGACATCTGGAACTGTGGGTCA
ACTACTACATCCGGTGGAACCCCAGAATCAAGCAGCAGCAGCCCAATCCTGTGGAACAGCGGTATATGGAACT
GCTGGCCCTGCGGGACGAGTACATCAAGAGACTGGAAGAACTGCAGCTGGCCAACAGCGCCAAGCTGAGCGAT
CCTCCTACAAGCCCTAGCAGCCCCTCTCAGATGATGCCCCATGTGCAGACCCACTTTTGA

FIG. 27
FIG. 27A    SkSH4-hDES1.4kb vs SkSH4-SPc5-12
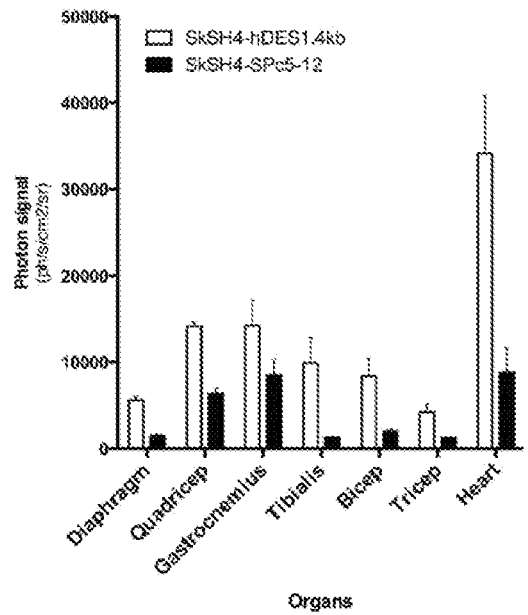
FIG. 27B    SkSH4-mDes vs CSkSH5-mDes
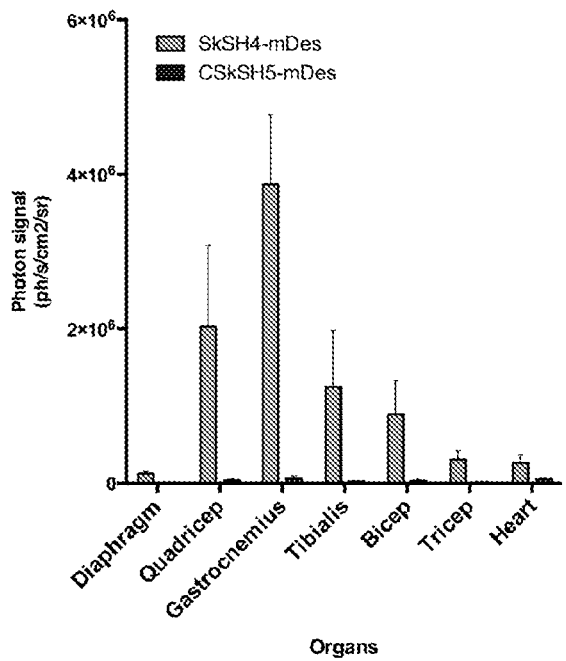

FIG. 27 (continued)
FIG. 27C
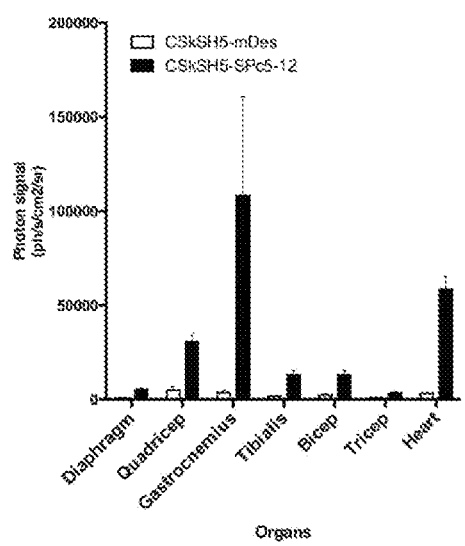
FIG. 27D
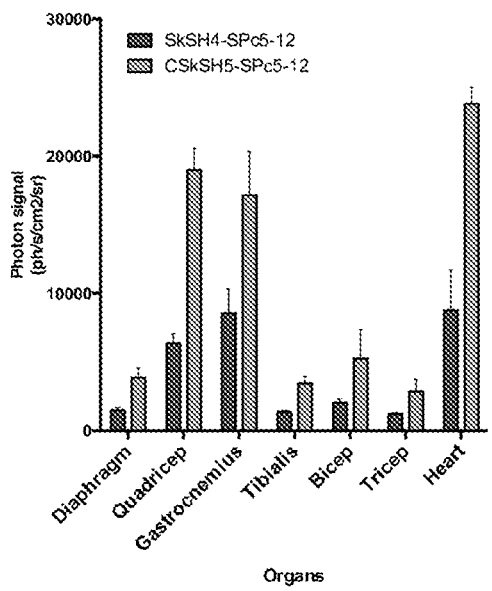

SEQUENCE LISTING

```
<160> NUMBER OF SEQ ID NOS: 70

<210> SEQ ID NO 1
<211> LENGTH: 381
<212> TYPE: DNA
<213> ORGANISM: Artificial
<220> FEATURE:
<223> OTHER INFORMATION: Heart and skeletal muscle-specific regulatory
      element 1 (CSk-SH1)

<400> SEQUENCE: 1
gttctcctct ataaataccc gctctggtat ttggggttgg cagctgttgc tgccagggag      60
atggttgggt tgacatgcgg ctcctgacaa aacacaaacc cctggtgtgt gtgggcgtgg     120
gtggtgtgag taggggatg aatcaggag ggggcgggg acccaggggg caggagccac       180
acaaagtctg tgcgggggtg ggagcgcaca tagcaattgg aaactgaaag cttatcagac     240
cctttctgga aatcagccca ctgtttataa acttgaggcc ccaccctcga cagtaccggg     300
gaggaagagg gcctgcacta gtccagaggg aaactgaggc tcagggctag ctcgcccata    360
gacatacatg gcaggcaggc t                                              381

<210> SEQ ID NO 2
<211> LENGTH: 435
<212> TYPE: DNA
<213> ORGANISM: Artificial
<220> FEATURE:
<223> OTHER INFORMATION: Heart and skeletal muscle-specific regulatory
      element 2 (CSk-SH2)

<400> SEQUENCE: 2
cgtctataaa ttccagggaa ggtctctgat tggccctgct cattcccagg cccattcctt      60
gacccagtca ctgaagtcag ggagatgcag taataagact ggctggaatc agggtctttta   120 ggggtggagg gatggggagg aggcacagca tgtcatcaaa ataaggaaat tgcaaaagaa    180
agcttgcagg ctactttgaa tgacaatgag aaagacggtg ctgcctgagt gtgttaagga    240
tccacatggt ctccaaaatc ctccaggagc atacagtcta gtctgggaga tgagacacaa    300
```

```
aaataaccag aacacaacag cttgcactga ctcgagggct ggataagaat atctggaact    360
cccccatcta tttcagaagc ttgtctcttg gatgaaaatt agacacttaa tgggaagggg    420
ctttgaaaag agtgc                                                     435

<210> SEQ ID NO 3
<211> LENGTH: 551
<212> TYPE: DNA
<213> ORGANISM: Artificial
<220> FEATURE:
<223> OTHER INFORMATION: Heart and skeletal muscle-specific regulatory
      element 3 (CSk-SH3)

<400> SEQUENCE: 3
aaaaaataaa aataaaaaat aaaaataaat aaagtggatg gcttagagta tcttttctgt     60
ttagacctga ctaaagctta gacataattg ttagtttagg ctctcagggt aaaatttatt    120
actgtaaatc caaaaaatcc cttcttcttc tttttttttt tttttttggt ccttgaatta    180
aatgctgtca cctccttctt gaaggagaaa actattagtc agatttgaaa atcctcttta    240
tcacccagga aaatcatttt tatggacact ttgtctttct gtagtctgac ttagaagcag    300 cctgttttg ataggttgaa gttttcatct tgaacacaaa ccctgtttgt gtgtcccta     360 ctccccagtt tgatgtgcca ggcactttgt tctcaagccc agcagctgtt gtgggatgag    420
gggacatttt gcatgcttag ccagcagctg ccagaaacat ttctaatctg gttttggcag    480
gaaatagggc acaagtggaa gccaagttaa agaagctgg aaaaataaac agaataactt    540
tagatgtcac t                                                         551

<210> SEQ ID NO 4
<211> LENGTH: 430
<212> TYPE: DNA
<213> ORGANISM: Artificial
<220> FEATURE:
<223> OTHER INFORMATION: Heart and skeletal muscle-specific regulatory
      element 4 (CSk-SH4)

<400> SEQUENCE: 4
tgcactgtag actatttatg tttgcatatt tttcaggatt gtgtacagta aaccttaagt     60
gaatacaaag gatccaattg tcctgtaaga ctcacttcaa ttacagattg tgctcagtat    120
taaactttgc tagtactttc aggatgcagt caatcaagag gcaggaaaag gtctgtcagc    180
atccacagcc tccttttcaa attggacact tagtctctgg tccgaataat aggtgccccc    240
agtgtcacct cacacaatgg ggtatacaca gttttttaaaa atttatttc agctgggcac    300 agtagctcac acctaaaatc ccagcacttt gggaggctga ggcaggtgga tcacctgagg    360
tcaggagttc aagaccagcc tggccaacgt ggcaaaatcc tgtctctact aaaaatacaa    420
aaattaaccg                                                           430

<210> SEQ ID NO 5
<211> LENGTH: 454
<212> TYPE: DNA
<213> ORGANISM: Artificial
<220> FEATURE:
<223> OTHER INFORMATION: Heart and skeletal muscle-specific regulatory
      element 5 (CSk-SH5)

<400> SEQUENCE: 5
cagtttactc accagggatt cagaggcagc actgctgaac cctgagccct tggcacatca     60
ggttggctgt cagaagtcgg cctttgtaca tacacagttc ccttgtgagg cccagctgcg    120
```

```
tgtcctagga gcggggcctc tctccacagc agagctcagc ctctcaagtg tatggacagc      180
acgggtgcct gatgggtgga tttagccatg agttgaaggt ggcttgggga gaatgagagt      240
tctagagata gggagaaggg gttgccaata ggagagtgga attcctgagc acctcgtcac      300
aggcagccga cagaacatga gccgcagggc ccaggctatt tatacctcgc ctgtcactat      360
cagggtcccc acagctcccc ccacctccag ccacacacag caggtccttt tgctctttct      420
ggtcccttct ctactcctcc ccctccctac ctaa                                  454

<210> SEQ ID NO 6
<211> LENGTH: 453
<212> TYPE: DNA
<213> ORGANISM: Artificial
<220> FEATURE:
<223> OTHER INFORMATION: Heart and skeletal muscle-specific regulatory
      element 6 (CSk-SH6)

<400> SEQUENCE: 6
ccctttccct ggcaggatct gccctgtggc ccaaatgggc atgttgccca gggggctccc      60
tggcactatg ggggaagagt ctctccttcc cctcttatca tctcagttga gtcagacttg     120
ggggaggggg atacacagtg tgagtcactg ggtacccttt tcctgagctc agcttcatac     180
cgaggcgatg aggccaaacg ggctggtgac agggacactg agtcaggggc aggggccccg     240
gtcttactcc tgggcctctg gatttgggcc ctacatgagg cttttctatc tgtaaagtca     300
agcaatggct gggaggcaca cacaaccccc cgcccccccg caggcttctc cttcattggc     360
ccgggcaagg tccctgcttc ctctcaggcc gtctctgcac aagcacacac acttcccttc     420
cctgtccaca ggtggacaat gccctgggct agg                                  453

<210> SEQ ID NO 7
<211> LENGTH: 495
<212> TYPE: DNA
<213> ORGANISM: Artificial
<220> FEATURE:
<223> OTHER INFORMATION: Skeletal muscle-specific regulatory element 1
      (Sk-SH1)

<400> SEQUENCE: 7
ctcactcccc gcccaggcag caaggagccc acaccctcat gcccctcagc ttcagccccc      60
acctccagga ggccctaccc acgctcatga ccttgctatt ctgggccttg tgtcctgtag     120
ggagatggac aggagacagc tgggcttcca ggccacccag gcggggggct agccgaggga     180
agcctgctgg ctctcctgct tgctctaatt tctggggctc cccaaacctt ggcctcagga     240
gactggggat aggaccggcc ttgaaagtgg gggaagcttt ggagagccgg gtgctgggtt     300
cttagtgaga tggccagtga aggctgtggt gccccgaggt aagcagggcc tgatcccctc     360
ctaatcttcc agcagcaact ggtgctctga ggctccccct ccccagccc tgccagcctt      420 cagggacctg ccttccaaag atgggcaggg gaggggacg aggacaccca cccactcctc      480
agaccagcat gtctt                                                      495

<210> SEQ ID NO 8
<211> LENGTH: 344
<212> TYPE: DNA
<213> ORGANISM: Artificial
<220> FEATURE:
<223> OTHER INFORMATION: Skeletal muscle-specific regulatory element 2
      (Sk-SH2)

<400> SEQUENCE: 8
```

```
ccctccagat gggtttcctg gaatctagat ttcccaggtt ccaaaggaca cccgagtctc     60
atgcctggaa ctcagtgaga ctaattcacc tctcctctgc cctaatcttc atctccagcc    120
agaagccaac agatcccagg ggactggagc cacaggggct gcacctgttt accgggtatt    180
tttaggatgg ttgatgaaca cataataccc accctatagt cagagaaaga caatgcctgc    240
tatgttaatc ctgtggctat tatagtctgt catctcatgg gttggggcag gacactgacc    300
ctctcagagg ccagagagag gcctcgcaag caggaggtta ggga                    344
```

<210> SEQ ID NO 9
<211> LENGTH: 430
<212> TYPE: DNA
<213> ORGANISM: Artificial
<220> FEATURE:
<223> OTHER INFORMATION: Skeletal muscle-specific regulatory element 3
    (Sk-SH3)

<400> SEQUENCE: 9

```
atggagacaa tccatgaatt cctgagatgc ttggctggta ttagatttta tgggcagctg     60
cttattctta gggctctgct tctccaaaga cactgaggaa gtccaaagga acaccagct    120 ggcgaagagc cacctccagg cccatctgtc catcatcagc ctccaggaat gccagtgtcc    180
agagggcacc aggtctgcgt ctgtctccct gggatgtgcc ttgtccttgg tgggcatttg    240
gcagtgatca tgcctccctg tctccctcag agatccaact gtccccattg tggggcccta    300
ccttccaagg ccggtttaca cctcctgcca agctccgggg cctgccccca gctgcctca    360 ctgacaaatg ccagaccaag gggtcccacg tcaggcaaga ggcctcagcc tgtgctctga    420
cacccctcag                                                           430
```

<210> SEQ ID NO 10
<211> LENGTH: 435
<212> TYPE: DNA
<213> ORGANISM: Artificial
<220> FEATURE:
<223> OTHER INFORMATION: Skeletal muscle-specific regulatory element 4
    (Sk-SH4)

<400> SEQUENCE: 10

```
ttctgagtcc tctaaggtcc ctcactccca actcagcccc atgtcctgtc aattcccact     60
cagtgtctga tctccttctc ctcacctttc ccatctcccg tttgacccaa gcttcctgag    120
ctctcctccc attccccttt ttggagtcct cctcctctcc cagaacccag taataagtgg    180
gctcctccct ggcctggacc cccgtggtaa ccctataagg cgaggcagct gctgtctgag    240
gcagggaggg gctggtgtgg gaggctaagg gcagctgcta agtttagggt ggctccttct    300
ctcttcttag agacaacagg tggctgggc ctcagtgccc agaaaagaaa atgtcttaga    360
ggtatcggca tgggcctgga ggaggggga cagggcaggg ggaggcatct tcctcaggac    420
atcgggtcct agagg                                                    435
```

<210> SEQ ID NO 11
<211> LENGTH: 474
<212> TYPE: DNA
<213> ORGANISM: Artificial
<220> FEATURE:
<223> OTHER INFORMATION: Skeletal muscle-specific regulatory element 5
    (Sk-SH5)

<400> SEQUENCE: 11

```
gactaggaat aaatcacata tcctcaatcc ctggacaact tgtttacttc tagtgttagt     60
```

```
tttttcttaa aaaaaaaatt gaaatcattc tgaggctgga atactttgga catgcccagc    120
agttcctggc agttcccaca gaagcattac ctcatgactg gagtgggtaa agcatactgt    180
gggctatgga taagactgac attaaccaca agcatgtttg gcagcagact ggtgctttac    240
aagctccatg ttcagcagga gctgcaaagt gttcctccaa accaatattt gtcattcttg    300
gattctattt aggaggtcct gttactcaca tgtttcaata tcagcagaag ccagtttccc    360
tgtggtaccg aagtggatcc tgatgaattt accettgtaa gtaaaaaaaa tgatgttata    420
cccaaagctt gaagtacgta gtgggatgc cactgaaata attcagacat gctt           474
```

<210> SEQ ID NO 12
<211> LENGTH: 519
<212> TYPE: DNA
<213> ORGANISM: Artificial
<220> FEATURE:
<223> OTHER INFORMATION: Skeletal muscle-specific regulatory element 6
    (Sk-SH6)

<400> SEQUENCE: 12

```
gtgctcatag ctccaccttt tgttcctaat atggtctttc cagctccctc caccccatca    60
ttgttctcct gggggaacac agggtgagac gctttgatga actgacatca ccagcaaaaa   120
aaatatctag caacagctga ggctgatttt agacaatgga aagtggggga gggaagaggt   180
tctccctgac cctgaaactt tccactcatt ctgggcagct ctatggatgt tttaaaagaa   240
gaggaagagg ggagggaaga acattgaaat agagaagtgt actttggcaa ttctaggttg   300 gcagttttgca tccaggggt cctggttgcc tttcagcttc ccgtttcact ctcccccaga   360
ctgtgttgaa tgctggtcaa actccgttag ttgagtttta gcttttgatt cctggtattc   420
aaggagcttg ggcacaggga agaggggagg tcactcatga tccttaacaa ttctcccaga   480
tccccagatc aaattgctgt gctattctgg gagtctccg                           519
```

<210> SEQ ID NO 13
<211> LENGTH: 372
<212> TYPE: DNA
<213> ORGANISM: Artificial
<220> FEATURE:
<223> OTHER INFORMATION: Skeletal muscle-specific regulatory element 7
    (Sk-SH7)

<400> SEQUENCE: 13

```
atcgtgtgtc agaggtttgt gtcagcttcc cagcaaggga accagaaagg aaaaggaacc    60
ggttcctcat gcttcctagg ggaatgcatg catatctgaa gagaagggaa tcttatataa   120
ggctgtttag ctaagggcag ccaccagcca ggtgagcctt acagaagcac agggctgggt   180
gtctgcagtt ccctagcaga ttaacctggg tcacagtgac tcagagctcc agcatgcgag   240
ttccaggtgt ggaactgagc aagtacagat ctgcttttgc tccacttggg agtatttttc   300
cttcttagtg agcatgggca gcctcctggc cagggaagtc tggcactgtc tgggcctgac   360
agggaaaccc tg                                                       372
```

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14

```
cccaccgtcg tattcgtgag                                                20
```

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15

```
tcagggcgat ggttttgtcc c                                            21
```

<210> SEQ ID NO 16
<211> LENGTH: 983
<212> TYPE: DNA
<213> ORGANISM: Artificial
<220> FEATURE:
<223> OTHER INFORMATION: Desmin promoter

<400> SEQUENCE: 16

```
accttgcttc ctagctgggc ctttccttct cctctataaa taccagctct ggtatttcgc    60
cttggcagct gttgctgcta gggagacggc tggcttgaca tgcatctcct gacaaaacac   120
aaacccgtgg tgtgagtggg tgtgggcggt gtgagtaggg ggatgaatca gagagggggc   180
gagggagaca ggggcgcagg agtcaggcaa aggcgatgcg ggggtgcgac tacacgcagt   240
tggaaacagt cgtcagaaga ttctggaaac tatcttgctg gctataaact tgagggaagc   300
agaaggccaa cattcctccc aagggaaact gaggctcaga gttaaaaccc aggtatcagt   360
gatatgcatg tgccccggcc agggtcactc tctgactaac cggtacctac cctacaggcc   420
tacctagaga ctcttttgaa aggatggtag agacctgtcc gggctttgcc cacagtcgtt   480
ggaaacctca gcattttcta ggcaacttgt gcgaataaaa acttcggggg gtccttcttg   540
ttcattccaa taacctaaaa cctctcctcg gagaaaatag ggggcctcaa acaaacgaaa   600
ttctctagcc cgcttttcccc aggataaggc aggcatccaa atggaaaaaa aggggccggc   660
cgggggtctc ctgtcagctc cttgccctgt gaaacccagc aggcctgcct gtcttctgtc   720
ctcttgggc tgtccagggg cgcaggcctc ttgcggggga gctggcctcc ccgccccctc   780
gcctgtggcc gcccttttcc tggcaggaca gagggatcct gcagctgtca ggggaggggc   840
gccgggggt gatgtcagga gggctacaaa tagtgcagac agctaagggg ctccgtcacc   900
catcttcaca tccactccag ccggctgccc gcccgctgcc tcctctgtgc gtccgcccag   960
ccagcctcgt ccacgccgcc acc                                          983
```

<210> SEQ ID NO 17
<211> LENGTH: 1000
<212> TYPE: DNA
<213> ORGANISM: Artificial
<220> FEATURE:
<223> OTHER INFORMATION: Fragment of DES regulatory element

<400> SEQUENCE: 17

```
ccaaaagggt caggtccaag agggacctgg agtgccaagt ggaggtgtag aggcacggcc    60
agtacccatg gagaatggtg gatgtccttg ggggttagca agtgccgtgt gctaaggagg   120
gggcttttgga ggttgggcag gccctctgtg gggctccatt tttgtggggg tggggctgg   180
agcattatag ggggtgggaa gtgattgggg ctgtcaccct agccttcctt atctgacgcc   240
cacccatgcc tcctcaggta cccctgccc ccacagctc ctctcctgtg ccttgtttcc    300
cagccatgcg ttctcctcta taaatacccg ctctggtatt tggggttggc agctgttgct   360
```

| | |
|---|---|
| gccagggaga tggttgggtt gacatgcggc tcctgacaaa acacaaaccc ctggtgtgtg | 420 |
| tgggcgtggg tggtgtgagt aggggatga atcagggagg gggcggggga cccagggggc | 480 |
| aggagccaca caaagtctgt gcggggtgg gagcgcacat agcaattgga aactgaaagc | 540 |
| ttatcagacc ctttctggaa atcagcccac tgtttataaa cttgaggccc caccctcgac | 600 |
| agtaccgggg aggaagaggg cctgcactag tccagaggga aactgaggct cagggctagc | 660 |
| tcgcccatag acatacatgg caggcaggct ttggccagga tccctccgcc tgccaggcgt | 720 |
| ctccctgccc tccttcctg cctagagacc cccaccctca agcctggctg gtctttgcct | 780 |
| gagacccaaa cctcttcgac ttcaagaaa tatttaggaa caaggtggtt tagggccttt | 840 |
| cctgggaaca ggccttgacc ctttaagaaa tgacccaaag tctctccttg accaaaaagg | 900 |
| ggaccctcaa actaagggga agcctctctt ctgctgtctc ccctgacccc actcccccc | 960 |
| accccaggac gaggagataa ccagggctga agaggcccg | 1000 |

<210> SEQ ID NO 18
<211> LENGTH: 1000
<212> TYPE: DNA
<213> ORGANISM: Artificial
<220> FEATURE:
<223> OTHER INFORMATION: Fragment of DES regulatory element

<400> SEQUENCE: 18

| | |
|---|---|
| aatctggttc tttgggctgt aagtgatcaa agcaatacca agtgccttaa attaaaaaaa | 60 |
| aaaaaaaaaa aaaaaacgga aagtttgttg gcccaaggcc aggaaggaca gtgtgggagc | 120 |
| tcaactcaca aagttgaggg aagcactgca ggaaccaagg ggctggcctg ctcctcctct | 180 |
| ccagcctcct ctgcttctta catattgacc tctctttctt cctactcccc caggggcag | 240 |
| gaaacatggc ttccacaggt tccagttgaa gaatcccagt tccgtctata aattccaggg | 300 |
| aaggtctctg attggccctg ctcattccca ggcccattcc ttgacccagt cactgaagtc | 360 |
| agggagatgc agtaataaga ctggctgaa tcagggtctt tagggtggga gggatgggga | 420 |
| ggaggcacag catgtcatca aaataaggaa attgcaaaag aaagcttgca ggctactttg | 480 |
| aatgacaatg agaaagacgg tgctgcctga gtgtgttaag gatccacatg gtctccaaaa | 540 |
| tcctccagga gcatacagtc tagtctggga gatgagacac aaaaataacc agaacacaac | 600 |
| agcttgcact gactcgaggg ctggataaga atatctggaa ctcccccatc tatttcagaa | 660 |
| gcttgtctct tggatgaaaa ttagacactt aatgggaaag ggctttgaaa agagtgcagt | 720 |
| aacaaagccc cctttacaat ttacccggca cattcacacc catcctgagg ccaaagccac | 780 |
| aggctgtgag gtctcactgt ctcagcttcc tgagctataa aatgggaatg atgctagtgt | 840 |
| ctacctccta gggttggaga attggggggtc atgggtgtga agtgctcagc agcttggccc | 900 |
| acactaggtg gtcagtacat gtaaggtatt attgttgcta catacattag tagggcctgg | 960 |
| gcctctttaa acctttatag ggtagcatgg caaggctaac | 1000 |

<210> SEQ ID NO 19
<211> LENGTH: 1000
<212> TYPE: DNA
<213> ORGANISM: Artificial
<220> FEATURE:
<223> OTHER INFORMATION: Fragment of ACTN2 regulatory element

<400> SEQUENCE: 19

| | |
|---|---|
| cagatggatc acctgaagtc aggagtttaa gaccagtctg gccaacatgg caaaaccccg | 60 |
| tctctactaa aaatacaaaa atcagctagg tgtggtggca ggcacctgta ttcctagcta | 120 |

```
ctagggtggt tgaggcggga gaatcacttg aactcgggag gcggagattg cggtgagctg      180
agatcatgcc actgcactcc agcctggaag caagactccg tctcaaaaaa taaaaataaa      240
aaataaaaat aaataaagtg gatggcttag agtatctttt ctgtttagac ctgactaaag      300
cttagacata attgttagtt taggctctca gggtaaaatt tattactgta aatccaaaaa      360
atcccttctt cttcttttt tttttttttt tggtccttga attaaatgct gtcacctcct       420
tcttgaaagg agaaactatt agtcagattt gaaaatcctc tttatcaccc aggaaaatca      480 ttttttatgga cactttgtct ttctgtagtc tgacttagaa gcagcctgtt tttgataggt     540
tgaagttttc atcttgaaca caaaccctgt ttgtgtgtcc cctactcccc agtttgatgt      600
gccaggcact tgttctcaa gcccagcagc tgttgtggga tgaggggaca ttttgcatgc       660
ttagccagca gctgccagaa acatttctaa tctggttttg gcaggaaata gggcacaagt      720
ggaagccaag ttaaagaag ctggaaaaat aaacagaata actttagatg tcacttaata       780
tatggtccat tttcagccga agatttgccc tagtaatttg ttaatatgac tggactgtga     840
tcccttccaa aggcagggtt gaatatagtc acctttgaga tccaggatgt agtccagtgc      900
ttggaatatg cttgtaggag gttattgtta ttatttttc aatgatagac tatactgcaa       960
atttgtttaa ttgatttaat tagtagctta aaactgttgt                           1000
```

<210> SEQ ID NO 20
<211> LENGTH: 999
<212> TYPE: DNA
<213> ORGANISM: Artificial
<220> FEATURE:
<223> OTHER INFORMATION: Fragment of ACTN2 regulatory element

<400> SEQUENCE: 20

```
agctgaagcc gtgggacgtc tgagcggcac atttttatgg tcatcacaga tggtgctggg       60
tttttccttt tttttttttt tttttttttg gtgagaagtc aattggccaa acttgaaatt      120
taccaataaa acccttaag tgttacaaaa tcactgggca aaggaataca tttgagatgt       180
ggtagcatct gtgaattcca tttacctaag agtatgaatt acaaaccaga tgaatgacag      240
attagttgtc atcaactaca cacagtttat ttttcatgt gagttgcact gtagactatt       300
tatgtttgca tattttcag gattgtgtac agtaaacctt aagtgaatac aaaggatcca      360
attgtcctgt aagactcact tcaattacag attgtgctca gtattaaact ttgctagtac      420
tttcaggatg cagtcaatca agaggcaggg aaaggtctgt cagcatccac agcctccttt      480
tcaaattgga cacttagtct ctggtccgaa taataggtgc ccccagtgtc acctcacaca      540
atggggtata cacagttttt aaaaatttat tttcagctgg gcacagtagc tcacacctaa      600
aatcccagca ctttgggagg ctgaggcagg tggatcacct gaggtcagga gttcaagacc      660
agcctggcca acgtggcaaa atcctgtctc tactaaaaat acaaaaatta accgggcatg      720
gtggtggcac ctgtagtccc agctactcgg gaggctgagg caggagaatc ttttgaaccc      780
gggaggcaga ggttgcagtg agccaagatc ccaccactgc actccagcct gggtgacaga     840
gtgagactgt gcctcaaaaa aaattaaaaa aagtattttc atttaaaaag gggcgagtca     900
ccaaccaccc tgaagtctag ttttagtgtc tttttatgtt ggagcttgtg gctgctcctg      960
cattgtcctt ttgaagtccc taagtgtcat cagaattta                            999
```

<210> SEQ ID NO 21
<211> LENGTH: 999
<212> TYPE: DNA

<213> ORGANISM: Artificial
<220> FEATURE:
<223> OTHER INFORMATION: Fragment of FLNC regulatory element

<400> SEQUENCE: 21

```
cacactgacc tccctggag cgagctcttg agtcagaggg aaagcaaggg aagctacgct    60
gggagttcct tctccctcc ctggcttcct ccggcctctc cacctgaaca gaggcgctca   120
gctggctggg ggacctcaga taatgcctgc aaaacaggac tgtggaccat tagggtctgt   180
aaagggctg tcagctccga gctacctcac cttaaccctt tctcctcccc agcagctcaa   240
agaggaatgc atcctttctc agatctgtgt ctcagtttac tcaccaggga ttcagaggca   300
gcactgctga accctgagcc cttggcacat caggttggct gtcagaagtc ggcctttgta   360
catacacagt tcccttgtga ggcccagctg cgtgtcctag gagcggggcc tctctccaca   420
gcagagctca gcctctcaag tgtatggaca gcacgggtgc ctgatgggtg gatttagcca   480
tgagttgaag gtggcttggg gagaatgaga gttctagaga tagggagaag gggttgccaa   540
taggagagtg gaattcctga gcacctcgtc acaggcagcc gacagaacat gagccgcagg   600
gcccaggcta tttatacctc gcctgtcact atcagggtcc ccacagctcc ccccacctcc   660
agccacacac agcaggtcct tttgctcttt ctggtcccctt ctctactcct ccccctccct   720
acctaaggac caggcaattt cattcataga cccctgtcat cataagcatt gcccccacag   780
aaccctgaca ctttttcctc agctccgtaa caggggggtgc cctcattggc ccttggggga   840
aagagccccc aaagatgctc actatcccctt cttttacacc aggtctaggg gtagaagagg   900
aattagatat aatgattcat ctaaaagggc ccagaacctt ccctggctta aagaaacttc   960
tcaggctcag atatggcctc ctagccagct cagctagac                          999
```

<210> SEQ ID NO 22
<211> LENGTH: 1000
<212> TYPE: DNA
<213> ORGANISM: Artificial
<220> FEATURE:
<223> OTHER INFORMATION: Fragment of FLNC regulatory element

<400> SEQUENCE: 22

```
aaaaaaaaaa gaaaaagaa aaagaaatac gttctctagc tctttctcct caccccaggc    60
cagagtctgt ttgggtgcct cggtttccct gctgttctat tccccaggcc tgcagccttt   120
ggcttgccct gagtgcagct ttgcctgggc atcccagctg gctcccttag gctctccctg   180
accactctgc ccctggtcct gcctacccac ctggtcacat ttccccctgg ctgctctggc   240
tggggctctc cctgtttctg cctggctgac ccacccttc cctggcagga tctgccctgt   300
ggcccaaatg ggcatgttgc ccaggggggct ccctggcact atgggggaag agtctctcct   360
tcccctctta tcatctcagt tgagtcagac ttgggggagg gggatacaca gtgtgagtca   420
ctgggtaccc ttttcctgag ctcagcttca taccgaggcg atgaggccaa acgggctggt   480
gacagggaca ctgagtcagg ggcagggggcc ccggtcttac tcctgggcct ctggatttgg   540
gccctacatg aggcttttct atctgtaaag tcaagcaatg gctgggaggc acacacaacc   600
cccgccccc ccgcaggctt ctccttcatt ggccgggca aggtcccctgc ttcctctcag   660
gccgtctctg cacaagcaca cacacttccc ttccctgtcc acaggtggac aatgccctgg   720
gctaggagcc agccctcgca ggccctgtca acagcctgcc accaactagt ctagaaaatt   780
ctgtgaacac cagatcagtg ggttttgccc taatcactgg cctcagtttc cccatttacc   840
tcttcagccc gtgcggggtg tggagggagc atatttcatt cctgacagtt tggtgtgttg   900
```

```
ggtgtggatg gagaactgtc ggccctcccc gccaccttcc agcgcggcgg caccggggc     960
ccaggggtg ggcgccctca accccgtccc gccgcccggg                           1000
```

<210> SEQ ID NO 23
<211> LENGTH: 1000
<212> TYPE: DNA
<213> ORGANISM: Artificial
<220> FEATURE:
<223> OTHER INFORMATION: Fragment of ATP2A1 regulatory element

<400> SEQUENCE: 23

```
ccctgtgggc atttgagttt ataacaccac cccattgtg gcacacccct ccaccccgta     60
aaacacaggc tctgctcttg gaatcagtct tcctgatctg tggctgtgcc ctccaacaga   120
gggcacccct gggcttccca gctctggggg tagtgggtgc caacaaggag gggcctgggg   180
ctgaagaatc ccaccgctg agctcggcct tctcccttcc ccactgtcca gctccgcctt    240
tcagcatcct gcctcactcc ccgcccaggc agcaaggagc ccacccctc atgcccctca    300
gcttcagccc ccacctccag gaggccctac ccacgctcat gaccttgcta ttctgggcct   360
tgtgtcctgt agggagatgg acaggagaca gctgggcttc caggccaccc aggcgggggg   420
ctagccgagg gaagcctgct ggctctcctg cttgctctaa tttctgggc tccccaaacc    480
ttggcctcag gagactgggg ataggaccgg ccttgaaagt gggggaagct ttggagagcc   540
gggtgctggg ttcttagtga gatggccagt gaaggctgtg gtgccccgag gtaagcaggg   600
cctgatcccc tcctaatctt ccagcagcaa ctggtgctct gaggctcccc ctcccccagc   660
cctgccagcc ttcagggacc tgccttccaa agatgggcag gggaggggga cgaggacacc   720
cacccactcc tcagaccagc atgtcttggc tgttggggcc tgagagactt ccctctaag    780
cctttcttta cagatggtta accgaagtt ctgcactcat cagggactgg ccagggtgtc    840
tctgtgtccc atgcttttag ctccagccct caggtgtgac aggaggatca ctttccatcc   900
ctgggcgtgg agaccctgt gggaagggat ccccgagggc gcctctggct cagcctccct    960
ccatggcagt tcacacccac agccttccct agagcagccc                          1000
```

<210> SEQ ID NO 24
<211> LENGTH: 999
<212> TYPE: DNA
<213> ORGANISM: Artificial
<220> FEATURE:
<223> OTHER INFORMATION: Fragment of TNNI1 regulatory element

<400> SEQUENCE: 24

```
gggccacagt gaaggcccag aggggcaagt agcagctggg ggaagaggac cattgggcta    60
accctgcatc tcttataagg caatatggaa atgaggcccc tgaacccatg ccccaaaagc   120
ccaagagggc taaagactca gctttcaggg atttttcagt ggctctggtg cacgtgggat   180
acgagggtgc ctggctgtgg ggagtgatgt gagcagtgtt gcaggctgac cccagtgagt   240
gtttccaggg ctgagcagaa tggcagtggc agcagggcac accttttatgc tcagggaggt   300
ctgagggtct gcagacactc tgcatccccc tccagatggg tttcctggaa tctagatttc   360
ccaggttcca aaggacaccc gagtctcatg cctggaactc agtgagacta attcacctct   420
cctctgccct aatcttcatc tccagccaga agccaacaga tcccagggga ctggagccac   480
aggggctgca cctgtttacc gggtattttt aggatggttg atgaacacat aatacccacc   540
ctatagtcag agaaagacaa tgcctgctat gttaatcctg tggctattat agtctgtcat   600
```

```
ctcatgggtt ggggcaggac actgacctc tcagaggcca gagagaggcc tcgcaagcag    660
gaggttaggg agccccagcc atgctcccca tttggagaag gagagagtaa tgggcagggg    720
tgtcctaagg agacacaccc cagtgcccac agaggtaaag gccctgccct ctctacaacg    780
acattctgct gcctaataga ggttgctcta attctgttct ggtcgggtca actttgagaa    840
gcctctatgt gagacggctg ccagggagaa atgacagggt ctggggaggc ataggggttg    900
gggacatagg attccaagtg gagaggctgt gatggataat gaaggcaggc tccagccaaa    960
aggagcagct agaggggaga aggaatttag gggcttttgc                          999
```

```
<210> SEQ ID NO 25
<211> LENGTH: 999
<212> TYPE: DNA
<213> ORGANISM: Artificial
<220> FEATURE:
<223> OTHER INFORMATION: Fragment of TNNI1 regulatory element

<400> SEQUENCE: 25
ttgtggggtc tgggaagtgg ggaattaaaa gacacttgta aagtgcctgc caataattgt     60
atcccagagc caccccttcc tctgccctaa ttctctcctt tcccttttgtg cccatgaagc   120 actatcccaa ccccaatgaa cacagctttg gccacctccc ctgaatctcc caacgggtca   180
gaaagccttc tgggcctccc tccacctctg cctccgccac caggggaggg taaggctggg   240
gtggaggagg tggaggtgta gtgtgacccc agagtctcag ctgtcatgct ggggcacaga   300
gggaggggta tggagacaat ccatgaattc ctgagatgct tggctggtat tagatttttat  360 gggcagctgc ttattcttag ggctctgctt ctccaaagac actgaggaag tccaaaggaa   420
acaccagctg gcgaagagcc acctccaggc ccatctgtcc atcatcagcc tccaggaatg   480
ccagtgtcca gagggcacca ggtctgcgtc tgtctccctg gatgtgcct tgtccttggt    540 gggcatttgg cagtgatcat gcctccctgt ctccctcaga gatccaactg tccccattgt   600
ggggccctac cttccaaggc cggtttacac ctcctgccaa gctccggggc ctgccccag    660 cctgcctcac tgacaaatgc cagaccaagg ggtcccacgt caggcaagag gcctcagcct  720
gtgctctgac acccctcaga cgggggccct tgccaggctc tgtggaagac aagcgaggac  780
tgataagtca ggatgaagat agcagccact ggaaggcttg gagagccagg attccatctc  840
ctctacaagt agcaagcaag gagataatga gaaaatcctc ccccgagggg ggggagcaaa  900
gagtctctgg tggttgcctc agagctgggc tttcccttcc ttgaggcttt gcagcgtgga  960
agggactatc cgctagacta tgagattgag tctgtgtgt                          999
```

```
<210> SEQ ID NO 26
<211> LENGTH: 1000
<212> TYPE: DNA
<213> ORGANISM: Artificial
<220> FEATURE:
<223> OTHER INFORMATION: Fragment of MYLPF1 regulatory element

<400> SEQUENCE: 26
tcttttgggg atccaaggcc ccagtcccgt caacccctct cccctcactg ccacatccct     60
ctgtgctcct catgttccac tgagaatccc gacctcaatc tcatgagcgc tccaggttgt   120
ccttagatca caagcataaa gacctgacgt tatgagctcc aaccttccaa cttctaaacg   180
ccctcttctt tctctgaccc ccatattctg atttccatat agcatccacc atcctggaat   240
tccagtgaga cctagctccc gacttctcag ctcctccttg gtttctgagt cctctaaggt   300
ccctcactcc caactcagcc ccatgtcctg tcaattccca ctcagtgtct gatctccttc   360
```

```
tcctcacctt tcccatctcc cgtttgaccc aagcttcctg agctctcctc ccattcccct    420 tttttggagtc ctcctcctct cccagaaccc agtaataagt gggctcctcc ctggcctgga    480 ccccgtggt aaccctataa ggcgaggcag ctgctgtctg aggcagggag gggctggtgt    540
gggaggctaa gggcagctgc taagtttagg gtggctcctt ctctcttctt agagacaaca    600
ggtggctggg gcctcagtgc ccagaaaaga aaatgtctta gaggtatcgg catgggcctg    660
gaggaggggg gacagggcag ggggaggcat cttcctcagg acatcgggtc ctagagggag    720
cgggaggaga aggagatggt tgtccttgcc aacttggggc ttcctcagcc actatttttc    780
cagacttctg ctgcatggag gggactgggt cactgaggcc cagagggaga agagagggta    840
catcaaagtc acacaatcag ccaagctggc tcttggccag aataaagtga gctgccactg    900
gctatcaagg cacctcacag aaagtgacca gctggctgtc cttttagggt cttttcctcc    960
cctcttgagt tccagcctcc acaccagtac ccagagaaaa                         1000

<210> SEQ ID NO 27
<211> LENGTH: 999
<212> TYPE: DNA
<213> ORGANISM: Artificial
<220> FEATURE:
<223> OTHER INFORMATION: Fragment of MYH1 regulatory element

<400> SEQUENCE: 27
gggatcatta gctaaatctc actggcctct tgagatttca actgaatgtt cctgtgaagt    60
accacatatt atgtctctac aaacactatt gcagttcctc ctgcctcctg ggaaaaaagt    120
gaaatatgct tggctcaaga tattcacttc tcatacagaa gatccttgac atttggaata    180
taattgagtc ctgagactcc ctctgcaggg tcctgtcgcc atataataga gggactacta    240
aaagcaacag tattaaagct cagactagga ataaatcaca tatcctcaat ccctggacaa    300
cttgtttact tctagtgtta gttttttctt aaaaaaaaaa ttgaaatcat tctgaggctg    360
gaatactttg gacatgccca gcagttcctg gcagttccca cagaagcatt acctcatgac    420
tggagtgggt aaagcatact gtgggctatg gataagactg acattaacca caagcatgtt    480
tggcagcaga ctggtgcttt acaagctcca tgttcagcag gagctgcaaa gtgttcctcc    540
aaaccaatat ttgtcattct tggattctat ttaggaggtc ctgttactca catgtttcaa    600
tatcagcaga agccagtttc cctgtggtac cgaagtggat cctgatgaat ttacccttgt    660
aagtaaaaaa aatgatgtta tacccaaagc ttgaagtacg tagtggggat gccactgaaa    720
taattcagac atgctttctc tggcatctaa aggcagagaa gacccttggg caaccaagag    780
acttacaaag cgagaggagt tgtcattcct cacggtcttg gcgttgccaa aggcctccag    840 taggggttg gcactgatga tttgatcttc cagagtcccc tgcaaaggca agagcagtcc    900
ttgcatctgg ggcttgggaa tttcctacct gagagtcccg acagagcctg gattctgact    960
aacaatcaga ctcacctgca ttttgccaga agtaacttc                          999

<210> SEQ ID NO 28
<211> LENGTH: 1000
<212> TYPE: DNA
<213> ORGANISM: Artificial
<220> FEATURE:
<223> OTHER INFORMATION: Fragment of TPM3 regulatory element

<400> SEQUENCE: 28
gtgcctacct gtttacttct ttcttctgcc tgcttctgct cagcttcagc ttgctctgcc    60
```

```
cgatccagag cattctcctt gtctaacttc agcatctgca tcttttctt gatggcctcc        120 atcatgagca gtggctgttg gtaggctcac ctgtgaacac tggagaactg gagactgggg        180
caagaaagaa ggggctgctg cctgagtgac caggaggtcc ccagacttga gtctttatct        240
gtgctcatag ctccacctt tgttcctaat atggtctttc cagctccctc caccccatca         300
ttgttctcct gggggaacac agggtgagac gctttgatga actgacatca ccagcaaaaa        360
aaatatctag caacagctga ggctgatttt agacaatgga aagtgggga gggaagaggt         420 tctccctgac cctgaaactt tccactcatt ctgggcagct ctatggatgt tttaaaagaa        480
gaggaagagg ggagggaaga acatttgaaat agagaagtgt actttggcaa ttctaggttg       540
gcagtttgca tccaggggt cctggttgcc tttcagcttc ccgtttcact ctccccaga          600 ctgtgttgaa tgctggtcaa actccgttag ttgagtttta gcttttgatt cctggtattc        660
aaggagcttg ggcacaggga agaggggagg tcactcatga tccttaacaa ttctcccaga        720
tccccagatc aaattgctgt gctattctgg gagtctccga ttggcaggga gacgtttttc        780
ctccccacca agagccacaa gagtagagta agaggtaggg ttggaatctc caaccctatc        840
cttgaaggct atcccagagc ttcaagtggg gtggggagag aaacagggga gggtcagaac        900
aatccagaca ggatcatacc ctttgttttc ccacagtaat cttaaaatag aactgttgta        960
cccacacaga ctttggtctg tgtggctctc tcctcttctt                             1000
```

<210> SEQ ID NO 29
<211> LENGTH: 999
<212> TYPE: DNA
<213> ORGANISM: Artificial
<220> FEATURE:
<223> OTHER INFORMATION: Fragment of ANKRD2 regulatory element

<400> SEQUENCE: 29

```
ggcatgcaat ctccagcaga gtgagcctgg aactgccagt cttctgggcc ctgatcccag         60 ctccctggt gtcctcatga gtcctcagga aaagccactc tttgctttc tttaaagcag         120 agccatgctg cctgccctgc ctcctccatc agttgctggg aggattaagc aggaagacag        180
atgtgaaagt gcttgcaagg cgaagacagc acctcaggaa ggtggtctgc tcctgcagca        240 agagggcta acttccggcc ctggagacgc tgtagccatc gtgatgttaa agcaaaatct        300
ctgacagatt tagatcgtgt gtcagaggtt tgtgtcagct tcccagcaag ggaaccagaa        360
aggaaaagga accggttcct catgcttcct aggggaatgc atgcatatct gaagagaagg       420
gaatcttata taaggctgtt tagctaaggg cagccaccag ccaggtgagc cttacagaag       480
cacagggctg ggtgtctgca gttccctagc agattaacct gggtcacagt gactcagagc      540
tccagcatgc gagttccagg tgtggaactg agcaagtaca gatctgcttt tgctccactt       600
gggagtattt ttccttctta gtgagcatgg gcagcctcct ggccagggaa gtctggcact       660
gtctgggcct gacagggaaa ccctgggagg gtagaaggat ccagagtagc tgctgttcct       720
cgctagctgg gcttagtgct ttccggagac cctttcttg aagcaagact ctgtaagccc       780
tgcagaggtc ccctgagcac ttaccaagag aggagacaga ttggataagg tttgttcatg       840
actaaaagtc acccagccaa atgcagtgat gcttaacggg gaagcatgtg ggaccccgga      900
gagccgaagg ccagcgtgag ctgtgatcag agagggagac agctgccctt cctgctacca      960
cggccctggc ctggacaagt agagtgtgac cctcctcac                             999
```

<210> SEQ ID NO 30
<211> LENGTH: 663

```
<212> TYPE: DNA
<213> ORGANISM: Artificial
<220> FEATURE:
<223> OTHER INFORMATION: CMV promoter

<400> SEQUENCE: 30
acgcgtggag ctagttatta atagtaatca attacggggt cattagttca tagcccatat    60
atggagttcc gcgttacata acttacggta aatggcccgc ctggctgacc gcccaacgac   120
ccccgcccat tgacgtcaat aatgacgtat gttcccatag taacgtcaat agggactttc   180
cattgacgtc aatgggtgga gtatttacgg taaactgccc acttggcagt acatcaagtg   240
tatcatatgc caagtacgcc ccctattgac gtcaatgacg gtaaatggcc cgcctggcat   300
tatgcccagt acatgacctt atgggacttt cctacttggc agtacatcta cgtattagtc   360
atcgctatta ccatggtgat gcggttttgg cagtacatca atgggcgtgg atagcggttt   420
gactcacggg gatttccaag tctccacccc attgacgtca atgggagttt gttttgcacc   480
aaaatcaacg ggactttcca aaatgtcgta caactccgcc ccattgacgc aaatgggcg    540
gtaggcgtgt acggtgggag gtctatataa gcagagctcg tttagtgaac cgtcagatcg   600
cctggagacg ccatccacgc tgttttgacc tccatagaag acaccgggac cgatccagcc   660
tcc                                                                 663

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
tgtgtccgtc gtggatctga                                                20

<210> SEQ ID NO 32
<211> LENGTH: 22
<212> TYPE: DNA
<213> ORGANISM: Artificial
<220> FEATURE:
<223> OTHER INFORMATION: primer

<400> SEQUENCE: 32
gcctgcttca ccaccttctt ga                                             22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gtccctcact cccaactcag                                                20

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
gaggagaagg agatcagaca ctg                                            23
```

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tagctgggcc tttccttctc                                        20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
cgtctcccta gcagcaacag                                        20

<210> SEQ ID NO 37
<211> LENGTH: 171
<212> TYPE: DNA
<213> ORGANISM: Artificial Sequence
<220> FEATURE:
<223> OTHER INFORMATION: Fragment a of skeletal muscle-specific
      regulatory element 4 (Sk-SH4a)

<400> SEQUENCE: 37
ctctaaggtc cctcactccc aactcagccc catgtcctgt caattcccac tcagtgtctg    60
atctccttct cctcacctttt cccatctccc gtttgaccca agcttcctga gctctcctcc  120
cattcccctt tttggagtcc tcctcctctc ccagaaccca gtaataagtg g            171

<210> SEQ ID NO 38
<211> LENGTH: 51
<212> TYPE: DNA
<213> ORGANISM: Artificial Sequence
<220> FEATURE:
<223> OTHER INFORMATION: Fragment b of skeletal muscle-specific
      regulatory element 4 (Sk-SH4b)

<400> SEQUENCE: 38
tggcctggac ccccgtggta accctataag gcgaggcagc tgctgtctga g            51

<210> SEQ ID NO 39
<211> LENGTH: 60
<212> TYPE: DNA
<213> ORGANISM: Artificial Sequence
<220> FEATURE:
<223> OTHER INFORMATION: Fragment c of skeletal muscle-specific
      regulatory element 4 (Sk-SH4c)

<400> SEQUENCE: 39
gcagggaggg gctggtgtgg gaggctaagg gcagctgcta agtttagggt ggctccttct    60

<210> SEQ ID NO 40
<211> LENGTH: 41
<212> TYPE: DNA
<213> ORGANISM: Artificial Sequence
<220> FEATURE:
<223> OTHER INFORMATION: Fragment d of skeletal muscle-specific
      regulatory element 4 (Sk-SH4d)

<400> SEQUENCE: 40
aggagggggg acagggcagg gggaggcatc ttcctcagga c                 41

<210> SEQ ID NO 41
<211> LENGTH: 120
<212> TYPE: DNA
<213> ORGANISM: Artificial Sequence
<220> FEATURE:
<223> OTHER INFORMATION: Fragment e of skeletal muscle-specific
      regulatory element 4 (Sk-SH4e)

<400> SEQUENCE: 41
gcagggaggg gctggtgtgg gaggctaagg gcagctgcta agtttagggt ggctccttct     60
ctcttcttag agacaacagg tggctggggc ctcagtgccc agaaaagaaa atgtcttaga    120

<210> SEQ ID NO 42
<211> LENGTH: 17
<212> TYPE: DNA
<213> ORGANISM: Artificial Sequence
<220> FEATURE:
<223> OTHER INFORMATION: primer

<400> SEQUENCE: 42
gtgccctact acatcaa                                                    17

<210> SEQ ID NO 43
<211> LENGTH: 16
<212> TYPE: DNA
<213> ORGANISM: Artificial Sequence
<220> FEATURE:
<223> OTHER INFORMATION: primer

<400> SEQUENCE: 43
aggttgtgct ggtcca                                                     16

<210> SEQ ID NO 44
<211> LENGTH: 8069
<212> TYPE: DNA
<213> ORGANISM: Artificial Sequence
<220> FEATURE:
<223> OTHER INFORMATION: AAVss-SkSH4-Des-MVM-MD1 plasmid construct

<400> SEQUENCE: 44
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tcgtacgttc tgagtcctct aaggtccctc actcccaact    180
cagccccatg tcctgtcaat tcccactcag tgtctgatct ccttctcctc accttttccca   240 tctcccgttt gacccaagct tcctgagctc tcctcccatt ccccttttg gagtcctcct    300 cctctcccag aacccagtaa taagtgggct cctccctggc ctggaccccc gtggtaaccc    360
tataaggcga ggcagctgct gtctgaggca ggaggggct ggtgtgggag gctaagggca    420
gctgctaagt ttagggtggc tccttctctc ttcttagaga caacaggtgg ctggggcctc    480
agtgcccaga aaagaaaatg tcttagaggt atcggcatgg gcctggagga gggggacag    540 ggcaggggga ggcatcttcc tcaggacatc gggtcctaga ggaccttgc ttcctagctg    600 ggcctttcct tctcctctat aaataccagc tctggtattt cgccttggca gctgttgctg    660
ctagggagac ggctggcttg acatgcatct cctgacaaaa cacaaacccg tggtgtgagt    720
gggtgtgggc ggtgtgagta gggggatgaa tcagagaggg ggcgagggag acagggcgc     780 aggagtcagg caaaggcgat gcggggtgc gactacacgc agttggaaac agtcgtcaga    840
agattctgga aactatcttg ctggctataa acttgaggga agcagaaggc caacattcct    900

```
cccaagggaa actgaggctc agagttaaaa cccaggtatc agtgatatgc atgtgccccg    960
gccagggtca ctctctgact aaccggtacc taccctacag gcctacctag agactctttt   1020
gaaaggatgg tagagacctg tccgggcttt gcccacagtc gttggaaacc tcagcatttt   1080
ctaggcaact tgtgcgaata aaacacttcg ggggtccttc ttgttcattc caataaccta   1140
aaacctctcc tcggagaaaa tagggggcct caaacaaacg aaattctcta gcccgctttc   1200
cccaggataa ggcaggcatc caaatggaaa aaaggggcc ggccgggggt ctcctgtcag    1260
ctccttgccc tgtgaaaccc agcaggcctg cctgtcttct gtcctcttgg ggctgtccag   1320
gggcgcaggc ctcttgcggg ggagctggcc tccccgcccc ctcgcctgtg gccgcccttt   1380
tcctggcagg acagagggat cctgcagctg tcagggagg ggcgccgggg ggtgatgtca    1440
ggagggctac aaatagtgca gacagctaag gggctccgtc acccatcttc acatccactc   1500
cagccggctg cccgcccgct gcctcctctg tgcgtccgcc cagccagcct cgtccacgcc   1560
gccacctcta gaaagaggta agggtttaag ggatggttgg ttggtggggt attaatgttt   1620
aattacctgg agcacctgcc tgaaatcact tttttttcagg ttggacgcgt gccaccatgc   1680
tgtggtggga ggaagtggag gactgctacg agagagagga cgtgcagaag aaaaccttca   1740
ccaagtgggt gaacgcccag ttcagcaagt tcggcaagca gcacatcgag aacctgttca   1800
gcgacctgca ggatggcagg agactgctgg atctgctgga gggactgacc ggccagaagc   1860
tgcccaagga gaagggcagc accagagtgc acgccctgaa caacgtgaac aaggccctga   1920
gagtgctgca gaacaacaac gtggacctgg tgaatatcgg cagcaccgac atcgtggacg   1980
gcaaccacaa gctgacccctg ggcctgatct ggaacatcat cctgcactgg caggtgaaga   2040
acgtgatgaa gaacatcatg gccggcctgc agcagaccaa cagcgagaag atcctgctga   2100
gctgggtgag gcagagcacc agaaactacc cccaggtgaa cgtgatcaac ttcaccacct   2160
cctggagcga cggcctggcc ctgaacgccc tgatccacag ccacagaccc gacctgttcg   2220
actggaacag cgtggtgtgt cagcagagcg ccacccagag actggagcac gccttcaaca   2280
tcgccagata ccagctgggc atcgagaagc tgctggaccc cgaggacgtg gacaccacct   2340
accccgacaa gaaaagcatc ctgatgtata ttacctctct gtttcaggtg ctgccccagc   2400
aggtgtccat cgaggccatc caggaagtgg aaatgctgcc caggcccccc accgtgtccc   2460
tggcccaggg ctatgagaga accagcagcc ccaagcccag attcaagagc accgtgtccc   2520
tggcccaggg ctatgagaga accagcagcc ccaagcccag attcaagagc tacgcctaca   2580
cccaggccgc ctacgtgacc acctccgacc ccaccagaag ccccttcccc agccagcacc   2640
tggaggcccc cgaggacaag agcttcggca gcagcctgat ggagagcgaa gtgaacctgg   2700
acagatacca gaccgccctg gaggaagtgc tgtcttggct gctgtccgcc gaggacaccc   2760
tgcaggccca gggcgagatc agcaacgacg tggaagtggt gaaggaccag ttccacaccc   2820
acgagggcta catgatggat ctgaccgccc ccaggcag agtgggcaat atcctgcagc     2880
tgggcagcaa gctgatcggc accggcaagc tgagcgagga cgaggagacc gaagtgcagg   2940
agcagatgaa cctgctgaac agcagatggg agtgcctgag agtggccagc atggagaagc   3000
agagcaacct gcaccgcgtg ctgatggacc tgcagaacca gaagctgaag gagctgaacg   3060
actggctgac caagaccgag gagcggacca gaaagatgga ggaggagccc ctgggccccg   3120
acctggagga cctgaagaga caggtgcagc agcacaaagt gctgcaggag gacctggaac   3180
aggagcaggt gcgcgtgaac agcctgaccc acatggtggt cgtggtggac gagagcagcg   3240
```

```
gcgaccacgc cacagccgcc ctggaagagc agctgaaagt gctgggcgac agatgggcca    3300
acatctgccg gtggaccgag gacagatggg tgctgctgca ggacatcctg ctgaagtggc    3360
agagactgac agaggagcag tgcctgttta gcgcctggct gagcgagaag gaggacgccg    3420
tgaacaagat ccacaccacc ggcttcaagg accagaacga gatgctgagc agcctgcaga    3480
agctggccgt gctgaaggcc gatctggaga agaaaaagca gagcatgggc aagctgtact    3540
ccctgaagca ggacctgctg tccaccctga gaacaagag cgtgacccag aaaaccgagg    3600
cctggctgga caatttcgcc cggtgctggg acaatctggt gcagaaactg gagaagagca    3660
ccgcccagat cagccaggcc gtgaccacca cccagcccag cctgacacag accaccgtga    3720
tggagaccgt gaccacagtg accaccaggg agcagatcct ggtgaagcac gcccaggagg    3780
agctgccccc tccccccct cagaagaagc ggcagatcac agtggacacc ctggagagac    3840
tgcaggagct gcaggaagcc accgacgagc tggacctgaa gctgagacag gccgaagtga    3900
tcaagggcag ctggcagcct gtgggcgatc tgctgatcga cagcctgcag gaccacctgg    3960
agaaagtgaa ggccctgcgg ggcgagatcg ccccctgaa ggagaatgtg agccacgtga    4020
acgacctggc cagacagctg accaccctgg gcatccagct gagcccctac aatctgagca    4080
ccctggaaga tctgaacacc cggtggaaac tgctgcaggt ggccgtggag gatagagtga    4140
ggcagctgca cgaggcccac agagacttcg gccctgcctc ccagcacttc ctgagcacca    4200
gcgtgcaggg cccctgggag agagccatct ccccaacaa agtgccctac tacatcaacc    4260
acgagaccca gaccctgc tgggaccacc ctaagatgac cgagctgtac cagagcctgg    4320
ccgacctgaa caatgtgcgg ttcagcgcct acagaaccgc catgaagctg cggagactgc    4380
agaaggccct gtgcctggac ctgctgagcc tgagcgccgc ctgcgacgcc ctggaccagc    4440
acaacctgaa gcagaacgac cagcccatgg acattctgca gatcatcaac tgcctgacca    4500
ccatctacga tcggctggag caggagcaca caacctggt gaacgtgccc ctgtgcgtgg    4560
acatgtgcct gaattggctg ctgaacgtgt acgacaccgg caggaccggc agaatcagag    4620
tgctgtcctt caagaccggc atcatcagcc tgtgcaaggc ccacctggag gataagtacc    4680
gctacctgtt caagcaggtg gccagcagca ccggcttctg cgatcagagg agactgggcc    4740
tgctgctgca cgatagcatc cagatcccta ggcagctggg cgaagtggcc agctttggcg    4800
gcagcaacat cgagccctct gtgaggagct gcttccagtt cgccaacaac aagcccgaga    4860
tcgaggccgc cctgttcctg gattggatga ggctggagcc ccagagcatg gtgtggctgc    4920
ctgtgctgca cagagtggcc gccgccgaga ccgccaagca ccaggccaag tgcaacatct    4980
gcaaggagtg ccccatcatc ggcttccggt acaggagcct gaagcacttc aactacgaca    5040
tctgccagag ctgcttttc agcggcagag tggccaaggg ccacaagatg cactacccca    5100
tggtggagta ctgcacccc accacctccg gcgaggatgt gagagacttc gccaaagtgc    5160
tgaagaataa gttccggacc aagcggtact tgccaagca ccccaggatg gctacctgc    5220 ccgtgcagac cgtgctggag ggcgacaaca tggagaccga caccatgtga tgatgactcg    5280
agaataaaag atctttattt tcattagatc tgtgtgttgg ttttttgtgt gaggaacccc    5340
tagtgatgga gttggccact ccctctctgc gcgctcgctc gctcactgag gccgggcgac    5400
caaaggtcgc ccgacgcccg ggctttgccc gggcggcctc agtgagcgag cgagcgcgca    5460
gctgcctgca ggggcgcctg atgcggtatt ttctccttac gcatctgtgc ggtatttcac    5520
accgcatacg tcaaagcaac catagtacgc gccctgtagc ggcgcattaa gcgcggcggg    5580
tgtggtggtt acgcgcagcg tgaccgctac acttgccagc gccctagcgc ccgctccttt    5640
```

```
cgctttcttc ccttcctttc tcgccacgtt cgccggcttt ccccgtcaag ctctaaatcg    5700
ggggctccct ttagggttcc gatttagtgc tttacggcac ctcgacccca aaaaacttga    5760
tttgggtgat ggttcacgta gtgggccatc gccctgatag acggtttttc gccctttgac    5820
gttggagtcc acgttcttta atagtggact cttgttccaa actggaacaa cactcaaccc    5880
tatctcgggc tattcttttg atttataagg gattttgccg atttcggcct attggttaaa    5940
aaatgagctg atttaacaaa aatttaacgc gaattttaac aaaatattaa cgtttacaat    6000
tttatggtgc actctcagta caatctgctc tgatgccgca tagttaagcc agccccgaca    6060
cccgccaaca cccgctgacg cgccctgacg ggcttgtctg ctcccggcat ccgcttacag    6120
acaagctgtg accgtctccg ggagctgcat gtgtcagagg ttttcaccgt catcaccgaa    6180
acgcgcgaga cgaaagggcc tcgtgatacg cctatttta taggttaatg tcatgataat    6240
aatggtttct tagacgtcag gtggcacttt tcggggaaat gtgcgcggaa cccctatttg    6300
tttatttttc taaatacatt caaatatgta tccgctcatg agacaataac cctgataaat    6360
gcttcaataa tattgaaaaa ggaagagtat gagtattcaa catttccgtg tcgcccttat    6420 tcccttttttt gcggcatttt gccttcctgt ttttgctcac ccagaaacgc tggtgaaagt    6480
aaaagatgct gaagatcagt tgggtgcacg agtgggttac atcgaactgg atctcaacag    6540
cggtaagatc cttgagagtt ttcgccccga agaacgtttt ccaatgatga gcacttttaa    6600
agttctgcta tgtggcgcgg tattatcccg tattgacgcc gggcaagagc aactcggtcg    6660
ccgcatacac tattctcaga atgacttggt tgagtactca ccagtcacag aaaagcatct    6720
tacggatggc atgacagtaa gagaattatg cagtgctgcc ataaccatga gtgataacac    6780
tgcggccaac ttacttctga caacgatcgg aggaccgaag gagctaaccg cttttttgca    6840
caacatgggg gatcatgtaa ctcgccttga tcgttgggaa ccggagctga atgaagccat    6900
accaaacgac gagcgtgaca ccacgatgcc tgtagcaatg gcaacaacgt tgcgcaaact    6960
attaactggc gaactactta ctctagcttc ccggcaacaa ttaatagact ggatggaggc    7020
ggataaagtt gcaggaccac ttctgcgctc ggcccttccg gctggctggt ttattgctga    7080
taaatctgga gccggtgagc gtgggtctcg cggtatcatt gcagcactgg ggccagatgg    7140
taagccctcc cgtatcgtag ttatctacac gacggggagt caggcaacta tggatgaacg    7200
aaatagacag atcgctgaga taggtgcctc actgattaag cattggtaac tgtcagacca    7260
agtttactca tatatacttt agattgattt aaaacttcat ttttaattta aaaggatcta    7320
ggtgaagatc ctttttgata atctcatgac caaaatccct taacgtgagt tttcgttcca    7380
ctgagcgtca gaccccgtag aaaagatcaa aggatcttct tgagatcctt ttttctgcg    7440 cgtaatctgc tgcttgcaaa caaaaaaacc accgctacca gcggtggttt gtttgccgga    7500
tcaagagcta ccaactcttt ttccgaaggt aactggcttc agcagagcgc agataccaaa    7560
tactgtcctt ctagtgtagc cgtagttagg ccaccacttc aagaactctg tagcaccgcc    7620
tacatacctc gctctgctaa tcctgttacc agtggctgct gccagtggcg ataagtcgtg    7680
tcttaccggg ttggactcaa gacgatagtt accggataag gcgcagcggt cgggctgaac    7740
ggggggttcg tgcacacagc ccagcttgga gcgaacgacc tacaccgaac tgagatacct    7800
acagcgtgag ctatgagaaa gcgccacgct tcccgaaggg agaaaggcgg acaggtatcc    7860
ggtaagcggc agggtcggaa caggagagcg cacgagggag cttccagggg gaaacgcctg    7920
gtatctttat agtcctgtcg ggtttcgcca cctctgactt gagcgtcgat ttttgtgatg    7980
```

<210> SEQ ID NO 45
<211> LENGTH: 7217
<212> TYPE: DNA
<213> ORGANISM: Artificial Sequence
<220> FEATURE:
<223> OTHER INFORMATION: AAVss-SkSH4-Des-MVM-FST-2A-Luc2 plasmid construct

<400> SEQUENCE: 45

```
ctcgtcaggg gggcggagcc tatggaaaaa cgccagcaac gcggcctttt tacggttcct    8040
ggccttttgc tggccttttg ctcacatgt                                      8069 cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tcgtacgttc tgagtcctct aaggtccctc actcccaact     180
cagccccatg tcctgtcaat tcccactcag tgtctgatct ccttctcctc accttttccca   240
tctcccgttt gacccaagct tcctgagctc tcctcccatt cccctttttg gagtcctcct    300
cctctcccag aacccagtaa taagtgggct cctcctggc ctgaccccc gtggtaaccc      360
tataaggcga gcagctgct gtctgaggca ggagggggc ggtgtgggag ctaagggca       420
gctgctaagt ttagggtggc tccttctctc ttcttagaga caacaggtgg ctggggcctc    480
agtgcccaga aagaaaatg tcttagaggt atcggcatgg gcctggagga ggggggacag    540
ggcagggga ggcatcttcc tcaggacatc gggtcctaga gggaccttgc ttcctagctg     600
ggcctttcct tctcctctat aaataccagc tctggtattt cgccttggca gctgttgctg    660
ctagggagac ggctggcttg acatgcatct cctgacaaaa cacaaacccg tggtgtgagt    720
gggtgtgggc ggtgtgagta gggggatgaa tcagagaggg ggcgagggag acaggggcgc    780
aggagtcagg caaaggcgat gcgggggtgc gactacacgc agttggaaac agtcgtcaga    840
agattctgga aactatcttg ctggctataa acttgaggga agcagaaggc caacattcct    900
cccaagggaa actgaggctc agagttaaaa cccaggtatc agtgatatgc atgtgccccg    960
gccagggtca ctctctgact aaccggtacc taccctacag gcctacctag agactcttt    1020
gaaaggatgg tagagacctg tccgggcttt gcccacagtc gttggaaacc tcagcatttt   1080
ctaggcaact tgtgcgaata aaacacttcg ggggtccttc ttgttcattc caataaccta   1140
aaacctctcc tcgagaaaaa tagggggcct caaacaaacg aaattctcta gcccgctttc   1200
cccaggataa ggcaggcatc caaatggaaa aaaggggcc ggccggggt ctcctgtcag    1260
ctccttgccc tgtgaaaccc agcaggcctg cctgtcttct gtcctcttgg ggctgtccag   1320
gggcgcaggc tcttgcgggg gagctggcc tccccgcccc ctcgcctgtg ccgcccttt    1380
tcctggcagg acagagggat cctgcagctg tcagggagg ggcgccgggg ggtgatgtca    1440
ggagggctac aaatagtgca gacagctaag gggctccgtc acccatcttc acatccactc   1500
cagccggctg cccgcccgct gcctcctctg tgcgtccgcc cagccagcct cgtccacgcc   1560
gccacctcta gaaagaggta agggtttaag ggatggttgg ttggtggggt attaatgttt   1620
aattacctgg agcacctgcc tgaaatcact tttttcagg ttggacgcgt atggtccgcg    1680
cgaggcacca gccgggtggg cttttgcctcc tgctgctgct gctctgccag ttcatggagg   1740
accgcagtgc ccaggctggg aactgctggc tccgtcaagc gaagaacggc cgctgccagg   1800
tcctgtacaa gaccgaactg agcaaggagg agtgctgcag caccgccgg ctgagcacct    1860
cgtggaccga ggaggacgtg aatgacaaca cactcttcaa gtggatgatt ttcaacgggg   1920
```

-continued

| | |
|---|---|
| gcgcccccaa ctgcatcccc tgtaaagaaa cgtgtgagaa cgtggactgt ggacctggga | 1980 |
| aaaaatgccg aatgaacaag aagaacaaac cccgctgcgt ctgcgcccg gattgttcca | 2040 |
| acatcacctg gaagggtcca gtctgcgggc tggatgggaa acctaccgc aatgaatgtg | 2100 |
| cactcctaaa ggcaagatgt aaagagcagc cagaactgga agtccagtac caaggcagat | 2160 |
| gtaaaaagac ttgtcgggat gttttctgtc caggcagctc cacatgtgtg gtggaccaga | 2220 |
| ccaataatgc ctactgtgtg acctgtaatc ggatttgccc agagcctgct tcctctgagc | 2280 |
| aatatctctg tgggaatgat ggagtcacct actccagtgc ctgccacctg agaaaggcta | 2340 |
| cctgcctgct gggcagatct attggattag cctatgaggg aaagtgtatc aaagcaaagt | 2400 |
| cctgtgaaga tatccagtgc actggtggga aaaaatgttt atgggatttc aaggttggga | 2460 |
| gaggccggtg ttccctctgt gatgagctgt gccctgacag taagtcggat gagcctgtct | 2520 |
| gtgccagtga caatgccact tatgccagcg agtgtgccat gaaggaagct gcctgctcct | 2580 |
| caggtgtgct actggaagta aagcactccg gatcttgcaa ctccatttcg gaagacaccg | 2640 |
| aggaagagga ggaagatgaa gaccaggact acagctttcc tatatcttct attctagagt | 2700 |
| gggtcgagag gtccggcggc ggagagggca gaggaagtct tctaacatgc ggtgacgtgg | 2760 |
| aggagaatcc cggcccaatg gaagatgcca aaaacattaa gaagggccca gcgccattct | 2820 |
| acccactcga agacgggacc gccggcgagc agctgcacaa agccatgaag cgctacgccc | 2880 |
| tggtgccccgg caccatcgcc tttaccgacg cacatatcga ggtggacatt acctacgccg | 2940 |
| agtacttcga gatgagcgtt cggctggcag aagctatgaa gcgctatggg ctgaatacaa | 3000 |
| accatcggat cgtggtgtgc agcgagaata gcttgcagtt cttcatgccc gtgttgggtg | 3060 |
| ccctgttcat cggtgtggct gtggccccag ctaacgacat ctacaacgag cgcgagctgc | 3120 |
| tgaacagcat gggcatcagc cagcccaccg tcgtattcgt gagcaagaaa gggctgcaaa | 3180 |
| agatcctcaa cgtgcaaaag aagctaccga tcatacaaaa gatcatcatc atggatagca | 3240 |
| agaccgacta ccagggcttc caaagcatgt acaccttcgt gacttcccat ttgccacccg | 3300 |
| gcttcaacga gtacgacttc gtgcccgaga gcttcgaccg ggacaaaacc atcgccctga | 3360 |
| tcatgaacag tagtggcagt accggattgc ccaaggcgt agccctaccg caccgcaccg | 3420 |
| cttgtgtccg attcagtcat gcccgcgacc ccatcttcgg caaccagatc atccccgaca | 3480 |
| ccgctatcct cagcgtggtg ccatttcacc acggcttcgg catgttcacc acgtgggct | 3540 |
| acttgatctg cggctttcgg gtcgtgctca tgtaccgctt cgaggaggag ctattcttgc | 3600 |
| gcagcttgca agactataag attcaatctg ccctgctggt gcccacacta tttagcttct | 3660 |
| tcgctaagag cactctcatc gacaagtacg acctaagcaa cttgcacgag atcgccagcg | 3720 |
| gcggggcgcc gctcagcaag gaggtaggtg aggccgtggc caaacgcttc cacctaccag | 3780 |
| gcatccgcca gggctacggc ctgacagaaa caaccagcgc cattctgatc accccgaag | 3840 |
| gggacgacaa gcctggcgca gtaggcaagg tggtgccctt cttcgaggct aaggtggtgg | 3900 |
| acttggacac cggtaagaca ctgggtgtga accagcgcgg cgagctgtgc gtccgtggcc | 3960 |
| ccatgatcat gagcggctac gttaacaacc ccgaggctac aaacgctctc atcgacaagg | 4020 |
| acggctggct gcacagcggc gacatcgcct actgggacga ggacgagcac ttcttcatcg | 4080 |
| tggaccggct gaagagcctg atcaaataca agggctacca ggtagcccca gccgaactgg | 4140 |
| agagcatcct gctgcaacac cccaacatct cgacgccgg ggtcgccggc ctgcccgacg | 4200 |
| acgatgccgc cgagctgccc gccgcagtcg tcgtgctgga acacggtaaa accatgaccg | 4260 |
| agaaggagat cgtggactat gtggccagcc aggttacaac cgccaagaag ctgcgcggtg | 4320 |

```
gtgttgtgtt cgtggacgag gtgcctaaag gactgaccgg caagttggac gcccgcaaga    4380
tccgcgagat tctcattaag gccaagaagg gcggcaagat cgccgtgtaa aataaaagat    4440 ctttatttc attagatctg tgtgttggtt ttttgtgtga ggaacccta gtgatggagt      4500 tggccactcc ctctctgcgc gctcgctcgc tcactgaggc cgggcgacca aaggtcgccc    4560
gacgcccggg ctttgcccgg gcggcctcag tgagcgagcg agcgcgcagc tgcctgcagg    4620
ggcgcctgat gcggtatttt ctccttacgc atctgtgcgg tatttcacac cgcatacgtc    4680
aaagcaacca tagtacgcgc cctgtagcgg cgcattaagc gcggcgggtg tggtggttac    4740
gcgcagcgtg accgctacac ttgccagcgc cctagcgccc gctcctttcg ctttcttccc    4800 ttccttttctc gccacgttcg ccggctttcc ccgtcaagct ctaaatcggg gctcccttt    4860 agggttccga tttagtgctt tacggcacct cgaccccaaa aaacttgatt tgggtgatgg    4920
ttcacgtagt gggccatcgc cctgatagac ggttttttcgc cctttgacgt tggagtccac   4980 gttcttaat agtggactct tgttccaaac tggaacaaca ctcaacccta tctcgggcta     5040
ttcttttgat ttataaggga ttttgccgat ttcggcctat tggttaaaaa atgagctgat    5100
ttaacaaaaa tttaacgcga attttaacaa aatattaacg tttacaattt tatggtgcac    5160
tctcagtaca atctgctctg atgccgcata gttaagccag ccccgacacc cgccaacacc    5220
cgctgacgcg ccctgacggg cttgtctgct cccggcatcc gcttacagac aagctgtgac    5280
cgtctccggg agctgcatgt gtcagaggtt ttcaccgtca tcaccgaaac gcgcgagacg    5340
aaagggcctc gtgatacgcc tatttttata ggttaatgtc atgataataa tggtttctta    5400
gacgtcaggt ggcactttc ggggaaatgt gcgcggaacc cctatttgtt tatttttcta    5460
aatacattca aatatgtatc cgctcatgag acaataaccc tgataaatgc ttcaataata    5520
ttgaaaaagg aagagtatga gtattcaaca tttccgtgtc gcccttattc ccttttttgc    5580
ggcattttgc cttcctgttt ttgctcaccc agaaacgctg gtgaaagtaa aagatgctga    5640
agatcagttg ggtgcacgag tgggttacat cgaactggat ctcaacagcg gtaagatcct    5700
tgagagtttt cgccccgaag aacgttttcc aatgatgagc acttttaaag ttctgctatg    5760
tggcgcggta ttatcccgta ttgacgccgg gcaagagcaa ctcggtcgcc gcatacacta    5820
ttctcagaat gacttggttg agtactcacc agtcacagaa aagcatctta cggatggcat    5880
gacagtaaga gaattatgca gtgctgccat aaccatgagt gataacactg cggccaactt    5940
acttctgaca acgatcggag gaccgaagga gctaaccgct ttttgcaca acatggggga    6000 tcatgtaact cgccttgatc gttgggaacc ggagctgaat gaagccatac caaacgacga    6060
gcgtgacacc acgatgcctg tagcaatggc aacaacgttg cgcaaactat taactggcga    6120
actacttact ctagcttccc ggcaacaatt aatagactgg atggaggcgg ataaagttgc    6180
aggaccactt ctgcgctcgg cccttccggc tggctggttt attgctgata atctggagc    6240 cggtgagcgt gggtctcgcg gtatcattgc agcactgggg ccagatggta agccctcccg    6300
tatcgtagtt atctacacga cggggagtca ggcaactatg gatgaacgaa atagacagat    6360
cgctgagata ggtgcctcac tgattaagca ttggtaactg tcagaccaag tttactcata    6420
tatactttag attgatttaa aacttcattt ttaatttaaa aggatctagg tgaagatcct    6480
ttttgataat ctcatgacca aaatccctta acgtgagttt tcgttccact gagcgtcaga    6540
ccccgtagaa aagatcaaag gatcttcttg agatcctttt tttctgcgcg taatctgctg    6600
cttgcaaaca aaaaaaccac cgctaccagc ggtggtttgt ttgccggatc aagagctacc    6660
```

```
aactcttttt ccgaaggtaa ctggcttcag cagagcgcag ataccaaata ctgtccttct   6720
agtgtagccg tagttaggcc accacttcaa gaactctgta gcaccgccta catacctcgc   6780
tctgctaatc ctgttaccag tggctgctgc cagtggcgat aagtcgtgtc ttaccgggtt   6840
ggactcaaga cgatagttac cggataaggc gcagcggtcg gcctgaacgg ggggttcgtg   6900
cacacagccc agcttggagc gaacgaccta caccgaactg agatacctac agcgtgagct   6960
atgagaaagc gccacgcttc ccgaagggag aaaggcggac aggtatccgg taagcggcag   7020
ggtcggaaca ggagagcgca cgagggagct tccaggggga aacgcctggt atctttatag   7080
tcctgtcggg tttcgccacc tctgacttga gcgtcgattt ttgtgatgct cgtcaggggg   7140
gcggagccta tggaaaaacg ccagcaacgc ggcctttta cggttcctgg ccttttgctg   7200 gcctttgct cacatgt                                                   7217

<210> SEQ ID NO 46
<211> LENGTH: 49
<212> TYPE: DNA
<213> ORGANISM: Artificial Sequence
<220> FEATURE:
<223> OTHER INFORMATION: Synthetic polyadenylation signal

<400> SEQUENCE: 46
aataaaagat ctttattttc attagatctg tgtgttggtt ttttgtgtg               49

<210> SEQ ID NO 47
<211> LENGTH: 1099
<212> TYPE: DNA
<213> ORGANISM: Artificial Sequence
<220> FEATURE:
<223> OTHER INFORMATION: human 1.0kb desmin promotor

<400> SEQUENCE: 47
tgtacaacgc gttacgcctc aggtaccccc tgcccccac agctcctctc ctgtgccttg    60
tttcccagcc atgcgttctc ctctataaat acccgctctg gtatttgggg ttggcagctg   120
ttgctgccag ggagatggtt gggttgacat gcggctcctg acaaaacaca aaccccctggt  180 gtgtgtgggc gtgggtggtg tgagtagggg gatgaatcag ggaggggggcg ggggacccag  240 ggggcaggag ccacacaaag tctgtgcggg ggtgggagcg cacatagcaa ttggaaactg   300
aaagcttatc agacccttc tggaaatcag cccactgttt ataaacttga ggccccaccc    360
tcgacagtac cggggaggaa gagggcctgc actagtccag agggaaactg aggctcaggg   420
ctagctcgcc catagacata catggcaggc aggctttggc caggatccct ccgcctgcca   480
ggcgtctccc tgccctccct tcctgcctag agaccccac cctcaagcct ggctggtctt    540
tgcctgagac ccaaacctct tcgacttcaa gagaatattt aggaacaagg tggtttaggg   600 ccttttcctgg gaacaggcct tgaccctta agaaatgacc caaagtctct ccttgaccaa   660 aaagggggacc ctcaaactaa agggaagcct ctcttctgct gtctcccctg accccactcc  720
cccccacccc aggacgagga gataaccagg gctgaaagag gcccgcctgg gggctgcaga   780
catgcttgct gcctgccctg gcgaaggatt ggcaggcttg cccgtcacag gaccccccgct 840 ggctgactca gggggcgcagg cctcttgcgg gggagctggc ctcccccgccc ccacggccac 900 gggccgccct ttcctggcag gacagcggga tcttgcagct gtcaggggag gggaggcggg   960
ggctgatgtc aggagggata caaatagtgc cgacggctgg gggccctgtc tcccctcgcc   1020
gcatccactc tccggccggc cgcctgcccg ccgcctcctc cgtgcgcccg ccagcctcgc   1080
ccgcgccgtc acctctaga                                                1099
```

<210> SEQ ID NO 48
<211> LENGTH: 1426
<212> TYPE: DNA
<213> ORGANISM: Artificial Sequence
<220> FEATURE:
<223> OTHER INFORMATION: human 1.4kb desmin promotor

<400> SEQUENCE: 48

| | | | | | |
|---|---|---|---|---|---|
| acacacctac | tagtaaccccc | tccagctggt | gatggcaggt | ctagggtagg | accagtgact | 60 |
| ggctcctaat | cgagcactct | attttcaggg | tttgcattcc | aaaagggtca | ggtccaagag | 120 |
| ggacctggag | tgccaagtgg | aggtgtagag | gcacggccag | tacccatgga | gaatggtgga | 180 |
| tgtccttagg | ggttagcaag | tgccgtgtgc | taaggagggg | gctttggagg | ttgggcaggc | 240 |
| cctctgtggg | gctccatttt | tgtggggtg | ggggctggag | cattataggg | ggtgggaagt | 300 |
| gattggggct | gtcaccctag | ccttccttat | ctgacgccca | cccatgcctc | ctcaggtacc | 360 |
| ccctgccccc | cacagctcct | ctcctgtgcc | ttgtttccca | gccatgcgtt | ctcctctata | 420 |
| aatacccgct | ctggtatttg | gggttggcag | ctgttgctgc | cagggagatg | gttgggttga | 480 |
| catgcggctc | ctgacaaaac | acaaacccct | ggtgtgtgtg | ggcgtgggtg | gtgtgagtag | 540 |
| ggggatgaat | cagggagggg | gcggggggacc | caggggggcag | gagccacaca | aagtctgtgc | 600 |
| ggggggtggga | gcgcacatag | caattggaaa | ctgaaagctt | atcagaccct | ttctggaaat | 660 |
| cagcccactg | tttataaact | tgaggcccca | ccctcgacag | taccggggag | gaagagggcc | 720 |
| tgcactagtc | cagagggaaa | ctgaggctca | gggctagctc | gcccatagac | atacatggca | 780 |
| ggcaggcttt | ggccaggatc | cctccgcctg | ccaggcgtct | cctgccctc | ccttcctgcc | 840 |
| tagagacccc | caccctcaag | cctggctggt | ctttgcctga | gacccaaacc | tcttcgactt | 900 |
| caagagaata | tttaggaaca | aggtggttta | gggccttttcc | tgggaacagg | ccttgaccct | 960 |
| ttaagaaatg | acccaaagtc | tctccttgac | caaaaagggg | accctcaaac | taaagggaag | 1020 |
| cctctcttct | gctgtctccc | ctgaccccac | tcccccccac | cccaggacga | ggagataacc | 1080 |
| agggctgaaa | gaggcccgcc | tggggggctgc | agacatgctt | gctgcctgcc | ctggcgaagg | 1140 |
| attggcaggc | ttgcccgtca | caggaccccc | gctggctgac | tcaggggcgc | aggcctcttg | 1200 |
| cgggggagct | ggcctccccg | cccccacggc | cacgggccgc | cctttcctgg | caggacagcg | 1260 |
| ggatcttgca | gctgtcaggg | gagggggaggc | ggggggctgat | gtcaggaggg | atacaaaatag | 1320 |
| tgccgacggc | tgggggccct | gtctcccctc | gccgcatcca | ctctccggcc | ggccgcctgc | 1380 |
| ccgccgcctc | ctccgtgcgc | ccgccagcct | cgcccgcgcc | gtcacc | | 1426 |

<210> SEQ ID NO 49
<211> LENGTH: 2859
<212> TYPE: DNA
<213> ORGANISM: Artificial Sequence
<220> FEATURE:
<223> OTHER INFORMATION: human GAA sequence

<400> SEQUENCE: 49

| | | | | | |
|---|---|---|---|---|---|
| atgggagtga | ggcacccgcc | ctgctcccac | cggctcctgg | ccgtctgcgc | cctcgtgtcc | 60 |
| ttggcaaccg | ctgcactcct | ggggcacatc | ctactccatg | atttcctgct | ggttccccga | 120 |
| gagctgagtg | gctcctcccc | agtcctggag | gagactcacc | cagctcacca | gcagggagcc | 180 |
| agcagaccag | ggccccggga | tgcccaggca | caccccggcc | gtcccagagc | agtgcccaca | 240 |
| cagtgcgacg | tccccccaa | cagccgcttc | gattgcgccc | ctgacaaggc | catcacccag | 300 |

```
gaacagtgcg aggcccgcgg ctgttgctac atccctgcaa agcagggct  gcagggagcc    360 cagatggggc agccctggtg cttcttccca cccagctacc ccagctacaa gctggagaac    420
ctgagctcct ctgaaatggg ctacacggcc accctgaccc gtaccacccc caccttcttc    480
cccaaggaca tcctgaccct gcggctggac gtgatgatgg agactgagaa ccgcctccac    540
ttcacgatca aagatccagc taacaggcgc tacgaggtgc ccttggagac cccgcatgtc    600
cacagccggg caccgtcccc actctacagc gtggagttct ccgaggagcc cttcggggtg    660
atcgtgcgcc ggcagctgga cggccgcgtg ctgctgaaca cgacggtggc gcccctgttc    720
tttgcggacc agttccttca gctgtccacc tcgctgccct cgcagtatat cacaggcctc    780
gccgagcacc tcagtcccct gatgctcagc accagctgga ccaggatcac cctgtggaac    840
cgggaccttg cgcccacgcc cggtgcgaac ctctacgggt ctcaccctt  ctacctggcg    900 ctggaggacg gcgggtcggc acacggggtg ttcctgctaa acagcaatgc catggatgtg    960
gtcctgcagc cgagccctgc ccttagctgg aggtcgacag gtgggatcct ggatgtctac   1020
atcttcctgg gcccagagcc caagagcgtg gtgcagcagt acctgacgt  tgtgggatac   1080 ccgttcatgc cgccatactg gggcctgggc ttccacctgt gccgctgggg ctactcctcc   1140
accgctatca cccgccaggt ggtggagaac atgaccaggg cccacttccc cctgacgtc    1200 cagtggaacg acctggacta catggactcc cggagggact tcacgttcaa caaggatggc   1260
ttccgggact tccggccat  ggtgcaggag ctgcaccagg cggccggcg  ctacatgatg   1320 atcgtggatc ctgccatcag cagctcgggc cctgccggga gctacaggcc ctacgacgag   1380
ggtctgcgga gggggtttt  catcaccaac gagaccggcc agccgctgat gggaaggta    1440 tggcccgggt ccactgcctt ccccgacttc accaacccca cagccctggc ctggtgggag   1500
gacatggtgg ctgagttcca tgaccaggtg cccttcgacg gcatgtggat tgacatgaac   1560
gagccttcca acttcatcag gggctctgag gacggctgcc caacaatga  gctggagaac   1620 ccaccctacg tgcctggggt ggttgggggg accctccagg cggccaccat ctgtgcctcc   1680
agccaccagt ttctctccac acactacaac ctgcacaacc tctacggcct gaccgaagcc   1740
atcgcctccc acagggcgct ggtgaaggct cggggacac  gcccatttgt gatctcccgc   1800
tcgacctttg ctggccacgg ccgatacgcc ggccactgga cggggacgt  gtggagctcc   1860 tgggagcagc tcgcctcctc cgtgccagaa atcctgcagt ttaacctgct gggggtgcct   1920
ctggtcgggg ccgacgtctg cggcttcctg ggcaacacct cagaggagct gtgtgtgcgc   1980
tggacccagc tggggggcctt ctacccctt  catgcggaacc acaacagcct gctcagtctg   2040
ccccaggagc cgtacagctt cagcgagccg gcccagcagg ccatgaggaa ggccctcacc   2100
ctgcgctacg cactcctccc ccacctctac acactgttcc accaggccca cgtcgcgggg   2160
gagaccgtgg cccggcccct cttcctggag ttccccaagg actctagcac ctggactgtg   2220
gaccaccagc tcctgtgggg ggaggccctg ctcatcaccc cagtgctcca ggccgggaag   2280
gccgaagtga ctggctactt cccccttggg c acatggtacg acctgcagac ggtgccagta   2340
gaggcccttg gcagcctccc acccccacct gcagctcccc gtgagccagc catccacagc   2400
gaggggcagt gggtgacgct gccggccccc ctggacacca tcaacgtcca cctccgggct   2460
gggtacatca tcccctgca  gggccctggc ctcacaacca cagagtcccg ccagcagccc   2520 atggcccctgg ctgtggccct gaccaagggt ggggaggccc gagggagct  gttctgggac   2580 gatggagaga gcctggaagt gctggagcga ggggcctaca cacaggtcat cttcctggcc   2640
aggaataaca cgatcgtgaa tgagctggta cgtgtgacca gtgagggagc tggcctgcag   2700
```

```
ctgcagaagg tgactgtcct gggcgtggcc acggcgcccc agcaggtcct ctccaacggt    2760
gtccctgtct ccaacttcac ctacagcccc gacaccaagg tcctggacat ctgtgtctcg    2820
ctgttgatgg gagagcagtt tctcgtcagc tggtgttag                           2859
```

<210> SEQ ID NO 50
<211> LENGTH: 2859
<212> TYPE: DNA
<213> ORGANISM: Artificial Sequence
<220> FEATURE:
<223> OTHER INFORMATION: human GAAco sequence

<400> SEQUENCE: 50

```
atgggcgtca gacatcctcc atgttctcac agactgctgg ccgtgtgtgc tctggtgtct      60
cttgctacag ctgccctgct gggacatatc ctgctgcacg attttctgct ggtgcccaga     120
gagctgtctg gcagctctcc tgtgctggaa gaaacacacc ctgcacatca gcagggcgcc     180
tctagacctg gacctagaga tgctcaagcc catcctggca gacctagagc cgtgcctaca     240
cagtgtgacg tgccacctaa cagcagattc gactgcgccc tgacaaggc catcacacaa     300 gagcagtgtg aagccagagg ctgctgctac attcctgcca acaaggact gcagggcgct     360 cagatgggac agccttggtg cttcttccca ccatcttacc ccagctacaa gctggaaaac     420
ctgagcagca gcgagatggg ctacaccgcc acactgacca aaccacacc tacattcttc     480 ccaaaggaca tcctgacact gcggctggac gtgatgatgg aaaccgagaa ccggctgcac     540
ttcaccatca aggaccccgc caatagaaga tacgaggtgc ccctggaaac ccctcacgtg     600
cactctagag ccccatctcc actgtacagc gtggaattca gcgaggaacc ctttggcgtg     660
atcgtgcgga cagctggga tgcagagtg ctgctgaata ccacagtggc ccctctgttc     720
ttcgccgacc agtttctgca gctgagcaca agcctgccta gcagtatat cacaggcctg     780 gccgaacacc tgtctccact gatgctgagc accagctgga ccagaatcac cctgtggaac     840
agagatctgg ccctacacc tggcgccaat ctgtacggct ctcacccttt ttatctggcc     900
ctggaagatg gcggaagcgc ccacggtgtc tttctgctga cagcaacgc catggacgtg     960 gtgctgcaac catctcctgc tctgtcttgg agaagcaccg gcggcatcct ggacgtgtac    1020
atctttctgg acccgagcc taagagcgtg gtgcagcagt atctggatgt cgtgggctac    1080
cccttcatgc ctccttattg gggcctgggc ttccacctgt gtagatgggg atacagctcc    1140
accgccatca ccagacaggt ggtggaaaac atgacccggg ctcacttccc actggatgtg    1200
cagtggaaca acctggacta catggactcc agacgggact tcacctttaa caaggacggc    1260
ttcagagact ccccgccat ggtgcaagaa ctgcatcaag cggcagacg gtacatgatg    1320 atcgtggatc ctgccatctc ttctagcggc cctgccggaa gctacagacc ttatgatgag    1380
ggcctgagaa gaggcgtgtt catcaccaat gagacaggcc agcctctgat cggcaaagtg    1440
tggcctggaa gcaccgcctt ccagacttc accaatccaa ccgctctggc ttggtgggaa    1500
gatatggtgg ccgagttcca cgatcaggtg cccttcgatg gcatgtggat cgacatgaac    1560
gagcccagca acttcatcag gggcagcgag gatggctgcc caacaacga actggaaaat    1620 cctccttacg tgccaggcgt tgtcggagga acactgcagg ccgccacaat ttgtgccagc    1680
agccatcagt ttctgagcac ccactacaac ctgcacaacc tgtacggcct gaccgaggcc    1740
attgcctctc atagagccct ggttaaggcc agaggcaccc ggccttttgt gatcagcaga    1800 agcacattg ccggccacgg cagatatgcc ggacattgga caggggacgt ttggtctagt    1860
```

| | |
|---|---:|
| tgggagcagc tggcctctag cgtgcccgag atcctgcagt ttaatctgct gggagtgccc | 1920 |
| ctcgtgggag ccgatgtttg tggatttctg ggcaacacct ccgaggaact gtgcgtcaga | 1980 |
| tggacacagc tgggcgcctt ctatcccttc atgagaaacc acaacagcct gctgagcctg | 2040 |
| cctcaagagc cttacagctt tagcgaaccc gcacagcagg ccatgagaaa ggccctgact | 2100 |
| ctgagatacg ctctgctgcc ccacctgtac accctgtttc atcaagctca tgtggccggc | 2160 |
| gagacagtgg ccagaccact gtttctggaa ttccccaagg acagcagcac ctggacagtg | 2220 |
| gatcatcagc tgctctgggg agaagccctg ctcattacac ctgtgctgca ggctggcaag | 2280 |
| gccgaagtga caggatactt tccccctcggc acttggtacg acctgcagac agttcctgtg | 2340 |
| gaagctctgg gatctctgcc tccacctcct gctgctccta gagagcctgc cattcactct | 2400 |
| gaaggccagt gggttacact gcccgctcca ctggacacca tcaatgtgca cctgagagcc | 2460 |
| ggctacatca tccctctgca aggccctgga ctgaccacaa ccgaaagcag acagcagcca | 2520 |
| atggctctgg ccgtggctct gacaaaaggc ggagaagcta gaggcgaact gttctgggat | 2580 |
| gacggcgaga gcctggaagt gctggaacgg ggagcctaca caagtgat ctttctcgcc | 2640 |
| cggaacaaca ccatcgtgaa cgaactcgtc agagtgacca gtgaaggtgc cggactgcag | 2700 |
| ctccagaaag tgacagtgct tggagtggcc acagcacccc agcaggtttt gtctaatggc | 2760 |
| gtgcccgtgt ccaacttcac atacagcccct gacaccaagg tgctggacat ctgtgtgtct | 2820 |
| ctgctgatgg gcgagcagtt cctggtgtcc tggtgttga | 2859 |

<210> SEQ ID NO 51
<211> LENGTH: 1812
<212> TYPE: DNA
<213> ORGANISM: Artificial Sequence
<220> FEATURE:
<223> OTHER INFORMATION: human MTM1 sequence

<400> SEQUENCE: 51

| | |
|---|---:|
| atggcttctg catcaacttc taaatataat tcacactcct tggagaatga gtctattaag | 60 |
| aggacgtctc gagatggagt caatcgagat ctcactgagg ctgttcctcg acttccagga | 120 |
| gaaacactaa tcactgacaa agaagttatt tacatatgtc ctttcaatgg ccccattaag | 180 |
| ggaagagttt acatcacaaa ttatcgtctt tatttaagaa gtttggaaac ggattcttct | 240 |
| ctaatacttg atgttcctct gggtgtgatc tcgagaattg aaaaaatggg aggcgcgaca | 300 |
| agtagaggag aaaattccta tggtctagat attacttgta agacatgag aaacctgagg | 360 |
| ttcgctttga acaggaagg ccacagcaga agagatatgt ttgagatcct cacgagatac | 420 |
| gcgtttcccc tggctcacag tctgccatta tttgcatttt taaatgaaga aaagtttaac | 480 |
| gtggatggat ggacagttta caatccagtg aagaatacaa ggaggcaggg cttgcccaat | 540 |
| caccattgga gaataacttt tattaataag tgctatgagc tctgtgacac ttaccctgct | 600 |
| cttttggtgg ttccgtatcg tgcctcagat gatgacctcc ggagagttgc aactttttagg | 660 |
| tcccgaaatc gaattccagt gctgtcatgg attcatccag aaaataagac ggtcattgtg | 720 |
| cgttgcagtc agcctcttgt cggtatgagt gggaaacgaa ataaagatga tgagaaatat | 780 |
| ctcgatgtta tcaggagac taataaacaa atttctaaac tcaccatttta tgatgcaaga | 840 |
| cccagcgtaa atgcagtggc caacaaggca acaggaggag gatatgaaag tgatgatgca | 900 |
| tatcataacg ccgaactttt cttcttagac attcataata ttcatgttat gcgggaatct | 960 |
| ttaaaaaaag tgaaggacat tgtttatcct aatgtagaag aatctcattg gttgtccagt | 1020 |
| ttggagtcta ctcattggtt agaacatatc aagctcgttt tgacaggagc cattcaagta | 1080 |

```
gcagacaaag tttcttcagg gaagagttca gtgcttgtgc attgcagtga cggatgggac   1140
aggactgctc agctgacatc cttggccatg ctgatgttgg atagcttcta taggagcatt   1200
gaagggttcg aaatactggt acaaaaaaaa tggataagtt ttggacataa atttgcatct   1260
cgaataggtc atggtgataa aaaccacacc gatgctgacc gttctcctat ttttctccag   1320
tttattgatt gtgtgtggca aatgtcaaaa cagttcccta cagcttttga attcaatgaa   1380
caatttttga ttataatttt ggatcatctg tatagttgcc gatttggtac tttcttattc   1440
aactgtgaat ctgctcgaga agacagaag gttacagaaa ggactgtttc tttatggtca    1500
ctgataaaca gtaataaaga aaaattcaaa aaccccttct atactaaaga aatcaatcga   1560
gttttatatc cagttgccag tatgcgtcac ttggaactct gggtgaatta ctacattaga   1620
tggaacccca ggatcaagca acaacagccg aatccagtgg agcagcgtta catggagctc   1680
ttagccttac gcgacgaata cataaagcgg cttgaggaac tgcagctcgc caactctgcc   1740
aagctttctg atcccccaac ttcaccttcc agtccttcgc aaatgatgcc ccatgtgcaa   1800
actcacttct ga                                                      1812

<210> SEQ ID NO 52
<211> LENGTH: 1812
<212> TYPE: DNA
<213> ORGANISM: Artificial Sequence
<220> FEATURE:
<223> OTHER INFORMATION: human MTM1co sequence

<400> SEQUENCE: 52
atggccagcg ccagcacaag caagtacaac agccacagcc tggaaaacga gagcatcaag     60
cggaccagca gagatggcgt gaacagagat ctgaccgagg ccgttcctag actgcctggc    120
gagacactga tcaccgacaa agaagtgatc tacatctgcc ccttcaacgg ccccatcaag    180
ggaagagtgt acatcaccaa ctaccggctg tacctgcggt ccctggaaac cgatagcagc    240
ctgattctgg atgtgcccct gggcgtgatc agccggattg aaaaaatggg cggagccacc    300
tccagaggcg agaatagcta tggcctggat atcacatgca aggacatgcg gaacctgaga    360
ttcgccctga gcaagagggg ccacagcaga cgggacatgt tcgagatcct gaccagatac    420
gcctttcctc tggctcactc tctgcccctg ttcgccttcc tgaacgaaga aagttcaac    480 gtggacgggct ggaccgtgta caaccccgtg aagagtata gacggcaggg actgcccaat    540
caccactggc ggatcacctt catcaacaag tgctacgagc tgtgcgacac atacccgca    600 ctgctggtgg tgccttacag agcctctgac gacgatctga aagagtggc cacctttcgg    660 agccggaaca gaatccctgt gctgagctgg attcacccg agaacaagac cgtgatcgtg    720
cggtgttctc agcctctcgt gggcatgagc ggcaagagaa acaaggacga cgagaagtac    780
ctggacgtga tccgcgagac aaacaagcag atcagcaagc tgaccatcta cgacgccaga    840
ccttctgtga acgccgtggc caacaaagcc acaggcggcg atatgagtc cgacgatgcc    900 tatcacaacg ccgagctgtt cttcctggac attcacaaca tccatgtgat gcgcgagagc    960
ctgaagaaag tgaaggacat cgtgtacccc aatgtggaag agagccactg gctgtctagc   1020
ctggaatcca cacactggct ggaacacatc aagctggtgc tgacaggcgc catccaggtg   1080
gcagacaaag tgtctagcgg caagtctagc gtgctggtgc actgtagcga cggatgggat   1140
agaacagccc agctgacatc cctggccatg ctgatgctgg acagcttcta cagatccatc   1200
gagggctttg agatcctggt gcagaagaag tggatcagct tcggccacaa gttcgcctct   1260
```

```
agaatcggac acggcgacaa gaaccacacc gacgccgata gaagcccat  cttcctgcag  1320 ttcatcgact gcgtgtggca gatgtccaag cagttcccta ccgccttcga gttcaacgag  1380
cagttcctga tcatcatcct ggaccacctg tactcttgca gattcggcac cttcctgttc  1440
aactgcgaga cgccagaga acggcagaaa gtgaccgaga aaccgtgtc  tctgtggtcc  1500 ctgatcaaca gcaacaaaga gaaattcaag aaccccttct acaccaaaga aatcaaccgg  1560
gtgctgtacc ccgtggccag catgagacat ctggaactgt gggtcaacta ctacatccgg  1620
tggaacccca gaatcaagca gcagcagccc aatcctgtgg aacagcggta tatggaactg  1680
ctggccctgc gggacgagta catcaagaga ctggaagaac tgcagctggc caacagcgcc  1740
aagctgagcg atcctcctac aagccctagc agccctctc  agatgatgcc ccatgtgcag  1800
acccactttt ga                                                     1812

<210> SEQ ID NO 53
<211> LENGTH: 334
<212> TYPE: DNA
<213> ORGANISM: Artificial Sequence
<220> FEATURE:
<223> OTHER INFORMATION: SPc-5-12 promotor

<400> SEQUENCE: 53
tggccaccgc cttcggcacc atcctcacga cacccaaata tggcgacggg tgaggaatgg   60
tggggagtta ttttagagc  ggtgaggaag gtgggcaggc agcaggtgtt ggcgctctaa  120
aaataactcc cgggagttat ttttagagcg gaggaatggt ggacacccaa atatggcgac  180
ggttcctcac ccgtcgccat atttgggtgt ccgccctcgg ccggggccgc attcctgggg  240
gccgggcggt gctcccgccc gcctcgataa aaggctccgg ggccggcggc ggcccacgag  300
ctacccggag gagcgggagg cgccaagctc taga                             334

<210> SEQ ID NO 54
<211> LENGTH: 92
<212> TYPE: DNA
<213> ORGANISM: Artificial Sequence
<220> FEATURE:
<223> OTHER INFORMATION: MVM intron

<400> SEQUENCE: 54
aagaggtaag ggtttaaggg atggttggtt ggtggggtat taatgtttaa ttacctggag   60
cacctgcctg aaatcacttt ttttcaggtt gg                                92

<210> SEQ ID NO 55
<211> LENGTH: 21
<212> TYPE: DNA
<213> ORGANISM: Artificial Sequence
<220> FEATURE:
<223> OTHER INFORMATION: forward primer GAA

<400> SEQUENCE: 55
tgccctcgca gtatatcaca g                                            21

<210> SEQ ID NO 56
<211> LENGTH: 19
<212> TYPE: DNA
<213> ORGANISM: Artificial Sequence
<220> FEATURE:
<223> OTHER INFORMATION: reverse primer GAA

<400> SEQUENCE: 56
gagacccgta gaggttcgc                                               19
```

<210> SEQ ID NO 57
<211> LENGTH: 20
<212> TYPE: DNA
<213> ORGANISM: Artificial Sequence
<220> FEATURE:
<223> OTHER INFORMATION: forward primer GAAco

<400> SEQUENCE: 57
accccttcat gcctccttat                                        20

<210> SEQ ID NO 58
<211> LENGTH: 20
<212> TYPE: DNA
<213> ORGANISM: Artificial Sequence
<220> FEATURE:
<223> OTHER INFORMATION: reverse primer GAAco

<400> SEQUENCE: 58
tccatgtagt ccaggtcgtt                                        20

<210> SEQ ID NO 59
<211> LENGTH: 23
<212> TYPE: DNA
<213> ORGANISM: Artificial Sequence
<220> FEATURE:
<223> OTHER INFORMATION: forward primer MTM1

<400> SEQUENCE: 59
gtttgagatc ctcacgagat acg                                    23

<210> SEQ ID NO 60
<211> LENGTH: 23
<212> TYPE: DNA
<213> ORGANISM: Artificial Sequence
<220> FEATURE:
<223> OTHER INFORMATION: reverse primer MTM1

<400> SEQUENCE: 60
gtccatccat ccacgttaaa ctt                                    23

<210> SEQ ID NO 61
<211> LENGTH: 20
<212> TYPE: DNA
<213> ORGANISM: Artificial Sequence
<220> FEATURE:
<223> OTHER INFORMATION: forward primer MTM1co

<400> SEQUENCE: 61
ggcaagagaa acaaggacga                                        20

<210> SEQ ID NO 62
<211> LENGTH: 20
<212> TYPE: DNA
<213> ORGANISM: Artificial Sequence
<220> FEATURE:
<223> OTHER INFORMATION: reverse primer MTM1co

<400> SEQUENCE: 62
ggcatcgtcg gactcatatc                                        20

<210> SEQ ID NO 63
<211> LENGTH: 6308
<212> TYPE: DNA
<213> ORGANISM: Artificial Sequence
<220> FEATURE:

<223> OTHER INFORMATION: plasmid pAAV-SPc5-12GTRM-MVM-hGAAopt-SynthpA

<400> SEQUENCE: 63

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggttcc tgcggccgca cgcgtaccgg ttggccaccg ccttcggcac    180
catcctcacg acacccaaat atggcgacgg gtgaggaatg gtggggagtt attttttagag  240
cggtgaggaa ggtgggcagg cagcaggtgt tggcgctcta aaaataactc ccgggagtta   300
tttttagagc ggaggaatgg tggacaccca aatatggcga cggttcctca cccgtcgcca   360
tatttgggtg tccgccctcg gccggggccg cattcctggg ggccgggcgg tgctcccgcc   420
cgcctcgata aaaggctccg gggcggcgg cggcccacga gctacccgga ggagcgggag    480
gcgccaagct ctagatctag aactagtaag aggtaagggt ttaagggatg gttggttggt   540
ggggtattaa tgtttaatta cctggagcac ctgcctgaaa tcacttttttt tcaggttggc   600
gtacggccac catgggcgtc agacatcctc catgttctca cagactgctg gccgtgtgtg   660
ctctggtgtc tcttgctaca gctgccctgc tgggacatat cctgctgcac gattttctgc   720
tggtgcccag agagctgtct ggcagctctc ctgtgctgga gaaacacac cctgcacatc    780
agcagggcgc ctctagacct ggacctagag atgctcaagc ccatcctggc agacctagag   840
ccgtgcctac acagtgtgac gtgccaccta acagcagatt cgactgcgcc cctgacaagg   900
ccatcacaca agagcagtgt gaagccagag gctgctgcta cattcctgcc aaacaaggac   960
tgcagggcgc tcagatggga cagccttggt gcttcttccc accatcttac cccagctaca  1020
agctggaaaa cctgagcagc agcgagatgg gctacaccgc cacactgacc agaaccacac  1080
ctacattctt cccaaaggac atcctgacac tgcggctgga cgtgatgatg gaaaccgaga  1140
accggctgca cttcaccatc aaggacccg ccaatagaag atacgaggtg cccctggaaa   1200
cccctcacgt gcactctaga gccccatctc cactgtacag cgtggaattc agcgaggaac  1260
cctttggcgt gatcgtgcgg agacagctgg atggcagagt gctgctgaat accacagtgg  1320
cccctctgtt cttcgccgac cagtttctgc agctgagcac aagcctgcct agccagtata  1380
tcacaggcct ggccgaacac ctgtctccac tgatgctgag caccagctgg accagaatca  1440
ccctgtggaa cagagatctg gcccctacac ctggcgccaa tctgtacggc tctcaccctt  1500
tttatctggc cctggaagat ggcggaagcg cccacggtgt ctttctgctg aacagcaacg  1560
ccatggacgt ggtgctgcaa ccatctcctg ctctgtcttg gagaagcacc ggcggcatcc  1620
tggacgtgta catctttctg ggacccgagc ctaagagcgt ggtgcagcag tatctggatg  1680
tcgtgggcta cccccttcatg cctccttatt ggggcctggg cttccacctg tgtagatggg  1740
gatacagctc caccgccatc accagacagg tggtggaaaa catgacccgg gctcacttcc  1800
cactggatgt gcagtggaac gacctggact acatggactc cagacgggac ttcacccttta  1860
acaaggacgg cttcagagac ttccccgcca tggtgcaaga actgcatcaa ggcggcagac  1920
ggtacatgat gatcgtggat cctgccatct cttctagcgg ccctgccgga agctacagac  1980
cttatgatga gggcctgaga agaggcgtgt tcatcaccaa tgagacaggc cagcctctga  2040
tcggcaaagt gtggcctgga agcaccgcct ttccagactt caccaatcca accgctctgg  2100
cttggtggga agatatggtg gccgagttcc acgatcaggt gcccttcgat ggcatgtgga  2160
tcgacatgaa cgagcccagc aacttcatca ggggcagcga ggatggctgc cccaacaacg  2220
aactggaaaa tcctccttac gtgccaggcg ttgtcggagg aacactgcag gccgccacaa  2280
```

```
tttgtgccag cagccatcag tttctgagca cccactacaa cctgcacaac ctgtacggcc    2340
tgaccgaggc cattgcctct catagagccc tggttaaggc cagaggcacc cggccttttg    2400
tgatcagcag aagcacattt gccggccacg gcagatatgc cggacattgg acagggacg     2460
tttggtctag ttgggagcag ctggcctcta gcgtgcccga gatcctgcag tttaatctgc    2520
tgggagtgcc cctcgtggga gccgatgttt gtggatttct gggcaacacc tccgaggaac    2580
tgtgcgtcag atggacacag ctgggcgcct tctatccctt catgagaaac cacaacagcc    2640
tgctgagcct gcctcaagag ccttacagct ttagcgaacc cgcacagcag gccatgagaa    2700
aggccctgac tctgagatac gctctgctgc cccacctgta caccctgttt catcaagctc    2760
atgtggccgg cgagacagtg gccagaccac tgtttctgga attccccaag gacagcagca    2820
cctggacagt ggatcatcag ctgctctggg gagaagccct gctcattaca cctgtgctgc    2880
aggctggcaa ggccgaagtg acaggatact tcccctcgg cacttggtac gacctgcaga    2940
cagttcctgt ggaagctctg ggatctctgc ctccacctcc tgctgctcct agagagcctg    3000
ccattcactc tgaaggccag tgggttacac tgcccgctcc actggacacc atcaatgtgc    3060
acctgagagc cggctacatc atccctctgc aaggccctgg actgaccaca accgaaagca    3120
gacagcagcc aatggctctg gccgtggctc tgacaaaagg cggagaagct agaggcgaac    3180
tgttctggga tgacgcgag agcctggaag tgctggaacg gggagcctac acacaagtga    3240
tctttctcgc ccggaacaac accatcgtga acgaactcgt cagagtgacc agtgaaggtg    3300
ccggactgca gctccagaaa gtgacagtgc ttggagtggc cacagcaccc cagcaggttt    3360
tgtctaatgg cgtgcccgtg tccaacttca catacagccc tgacaccaag gtgctggaca    3420
tctgtgtgtc tctgctgatg ggcgagcagt tcctggtgtc ctggtgttga cctaggaata    3480
aaagatcttt attttcatta gatctgtgtg ttggttttt gtgtgacccg tctgattttg     3540
taggtaacca cgtgcggacc gagcggccgc aggaacccct agtgatggag ttggccactc    3600
cctctctgcg cgctcgctcg ctcactgagg ccgggcgacc aaaggtcgcc cgacgcccgg    3660
gctttgcccg ggcggcctca gtgagcgagc gagcgcgcag ctgcctgcag gggcgcctga    3720
tgcggtattt tctccttacg catctgtgcg gtatttcaca ccgcatacgt caaagcaacc    3780
atagtacgcg ccctgtagcg cgcgcattaag cgcggcgggt gtggtggtta cgcgcagcgt    3840
gaccgctaca cttgccagcg ccctagcgcc cgctcctttc gctttcttcc cttcctttct    3900
cgccacgttc gccggctttc cccgtcaagc tctaaatcgg gggctccctt tagggttccg    3960
atttagtgct ttacggcacc tcgacccaa aaaacttgat tgggtgatg gttcacgtag      4020
tgggccatcg ccctgataga cggttttttcg ccctttgacg ttggagtcca cgttctttaa   4080
tagtggactc ttgttccaaa ctggacaaca actcaaccct atctcgggct attcttttga    4140
tttataaggg attttgccga tttcggccta ttggttaaaa aatgagctga tttaacaaaa    4200
atttaacgcg aattttaaca aaatattaac gtttacaatt ttatggtgca ctctcagtac    4260
aatctgctct gatgccgcat agttaagcca gccccgacac ccgccaacac ccgctgacgc    4320
gccctgacgg gcttgtctgc tcccggcatc cgcttacaga caagctgtga ccgtctccgg    4380
gagctgcatg tgtcagaggt tttcaccgtc atcaccgaaa cgcgcgagac gaaagggcct    4440
cgtgatacgc ctattttat aggttaatgt catgataata atggtttctt agacgtcagg     4500
tggcactttt cggggaaatg tgcgcggaac ccctatttgt ttattttct aaatacattc     4560
aaatatgtat ccgctcatga gacaataacc ctgataaatg cttcaataat attgaaaaag    4620
```

```
gaagagtatg agtattcaac atttccgtgt cgcccttatt cccttttttg cggcattttg    4680
ccttcctgtt tttgctcacc cagaaacgct ggtgaaagta aaagatgctg aagatcagtt    4740
gggtgcacga gtgggttaca tcgaactgga tctcaacagc ggtaagatcc ttgagagttt    4800
tcgccccgaa gaacgttttc caatgatgag cacttttaaa gttctgctat gtggcgcggt    4860
attatcccgt attgacgccg ggcaagagca actcggtcgc cgcatacact attctcagaa    4920
tgacttggtt gagtactcac cagtcacaga aaagcatctt acggatggca tgacagtaag    4980
agaattatgc agtgctgcca taaccatgag tgataacact gcggccaact tacttctgac    5040
aacgatcgga ggaccgaagg agctaaccgc ttttttgcac aacatggggg atcatgtaac    5100
tcgccttgat cgttgggaac cggagctgaa tgaagccata ccaaacgacg agcgtgacac    5160
cacgatgcct gtagcaatgg caacaacgtt gcgcaaacta ttaactggcg aactacttac    5220
tctagcttcc cggcaacaat taatagactg gatggaggcg gataaagttg caggaccact    5280
tctgcgctcg gcccttccgg ctggctggtt tattgctgat aaatctggag ccggtgagcg    5340
tgggtctcgc ggtatcattg cagcactggg gccagatggt aagccctccc gtatcgtagt    5400
tatctacacg acggggagtc aggcaactat ggatgaacga aatagacaga tcgctgagat    5460
aggtgcctca ctgattaagc attggtaact gtcagaccaa gtttactcat atatacttta    5520
gattgattta aaacttcatt tttaatttaa aaggatctag gtgaagatcc tttttgataa    5580
tctcatgacc aaaatccctt aacgtgagtt ttcgttccac tgagcgtcag accccgtaga    5640
aaagatcaaa ggatcttctt gagatccttt ttttctgcgc gtaatctgct gcttgcaaac    5700
aaaaaaacca ccgctaccag cggtggtttg tttgccggat caagagctac caactctttt    5760
tccgaaggta actggcttca gcagagcgca gataccaaat actgtccttc tagtgtagcc    5820
gtagttaggc caccacttca agaactctgt agcaccgcct acatacctcg ctctgctaat    5880
cctgttacca gtggctgctg ccagtggcga taagtcgtgt cttaccgggt tggactcaag    5940
acgatagtta ccggataagg cgcagcggtc gggctgaacg ggggttcgt gcacacagcc    6000 cagcttggag cgaacgacct acaccgaact gagatacccta cagcgtgagc tatgagaaag    6060
cgccacgctt cccgaaggga gaaaggcgga caggtatccg gtaagcggca gggtcggaac    6120
aggagagcgc acgagggagc ttccaggggg aaacgcctgg tatctttata gtcctgtcgg    6180
gtttcgccac ctctgacttg agcgtcgatt tttgtgatgc tcgtcagggg gcggagcct    6240 atggaaaaac gccagcaacg cggccttttt acggttcctg gccttttgct ggccttttgc    6300
tcacatgt                                                              6308
```

<210> SEQ ID NO 64
<211> LENGTH: 6355
<212> TYPE: DNA
<213> ORGANISM: Artificial Sequence
<220> FEATURE:
<223> OTHER INFORMATION: plasmid pAAV-hDES1.4kb-MVM-hMTM1opt-SynthpA

<400> SEQUENCE: 64

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgcg cgcgccacc ggtacacacc tactagtaac      180
ccctccagct ggtgatggca ggtctagggt aggaccagtg actggctcct aatcgagcac     240
tctattttca gggtttgcat tccaaaaggg tcaggtccaa gagggacctg gagtgccaag     300
tggaggtgta gaggcacggc cagtacccat ggagaatggt ggatgtcctt aggggttagc     360
```

```
aagtgccgtg tgctaaggag ggggctttgg aggttgggca ggccctctgt ggggctccat    420 tttttgtgggg gtgggggctg gagcattata gggggtggga agtgattggg gctgtcaccc    480
tagccttcct tatctgacgc ccacccatgc ctcctcaggt acccccctgcc ccccacagct    540 cctctcctgt gccttgtttc ccagccatgc gttctcctct ataaataccc gctctggtat    600
ttggggttgg cagctgttgc tgccagggag atggttgggt tgacatgcgg ctcctgacaa    660
aacacaaacc cctggtgtgt gtgggcgtgg gtggtgtgag taggggatg aatcagggag    720 ggggcgggggg acccagggggg caggagccac acaaagtctg tgcgggggtg ggagcgcaca    780
tagcaattgg aaactgaaag cttatcagac cctttctgga aatcagccca ctgtttataa    840
acttgaggcc ccaccctcga cagtaccggg gaggaagagg gcctgcacta gtccagaggg    900
aaactgaggc tcagggctag ctcgcccata gacatacatg gcaggcaggc tttggccagg    960
atccctccgc ctgccaggcg tctccctgcc ctcccttcct gcctagagac ccccacccctc   1020 aagcctggct ggtctttgcc tgagacccaa acctcttcga cttcaagaga atattaggga    1080
acaaggtggt ttagggcctt tcctgggaac aggccttgac cctttaagaa atgacccaaa   1140
gtctctcctt gaccaaaaag gggacccctca aactaaaggg aagcctctct tctgctgtct    1200
cccctgaccc cactccccccc cacccccagga cgaggagata accagggctg aaagaggccc   1260 gcctggggggc tgcagacatg cttgctgcct gccctggcga aggattggca ggcttgcccg   1320
tcacaggacc cccgctggct gactcagggg cgcaggcctc ttgcggggga gctggcctcc    1380
ccgcccccac ggccacgggc cgcccttttcc tggcaggaca gcgggatctt gcagctgtca   1440
ggggagggga ggcgggggct gatgtcagga gggatacaaa tagtgccgac ggctgggggc   1500
cctgtctccc ctcgccgcat ccactctccg gccggccgcc tgcccgccgc ctcctccgtg   1560
cgcccgccag cctcgcccgc gccgtcacct ctagaactag taagaggtaa gggtttaagg   1620
gatggttggt tggtggggta ttaatgttta attacctgga gcacctgcct gaaatcactt   1680
tttttcaggt tggcgtacgg ccaccatggc cagcgccagc acaagcaagt acaacagcca   1740
cagcctggaa aacgagagca tcaagcggac cagcagagat ggcgtgaaca gagatctgac   1800
cgaggccgtt cctagactgc ctggcgagac actgatcacc gacaaagaag tgatctacat   1860 ctgcccctttc aacggcccca tcaagggaag agtgtacatc accaactacc ggctgtacct   1920
gcggtccctg gaaaccgata gcagcctgat tctggatgtg ccctgggcg tgatcagccg   1980 gattgaaaaa atgggcggag ccacctccag aggcgagaat agctatggcc tggatatcac   2040
atgcaaggac atgcggaacc tgagattcgc cctgaagcaa gagggccaca gcagacggga   2100
catgttcgag atcctgacca gatacgcctt tcctctggct cactctctgc cctgttcgc    2160 cttcctgaac gaagagaagt tcaacgtgga cggctgacc gtgtacaacc ccgtggaaga   2220
gtatagacgg caggactgc ccaatcacca ctggcggatc accttcatca acaagtgcta   2280
cgagctgtgc gacacatacc ccgcactgct ggtggtgcct tacagagcct ctgacgacga   2340
tctgagaaga gtggccacct ttcggagccg gaacagaatc cctgtgctga gctggattca   2400
ccccgagaac aagaccgtga tcgtgcggtg ttctcagcct ctcgtgggca tgagcggcaa   2460
gagaaacaag gacgacgaga agtacctgga cgtgatccgc gagacaaaca gcagatcag   2520 caagctgacc atctacgacg ccagaccttc tgtgaacgcc gtggccaaca aagccacagg   2580
cggcggatat gagtccgacg atgcctatca aacgccgag ctgttcttcc tggacattca   2640
caacatccat gtgatgcgcg agagcctgaa gaaagtgaag gacatcgtgt accccaatgt   2700
```

```
ggaagagagc cactggctgt ctagcctgga atccacacac tggctggaac acatcaagct    2760
ggtgctgaca ggcgccatcc aggtggcaga caaagtgtct agcggcaagt ctagcgtgct    2820
ggtgcactgt agcgacggat gggatagaac agcccagctg acatccctgg ccatgctgat    2880
gctggacagc ttctacagat ccatcgaggg ctttgagatc ctggtgcaga gaagtggat     2940 cagcttcggc cacaagttcg cctctagaat cggacacggc gacaagaacc acaccgacgc    3000
cgatagaagc cccatcttcc tgcagttcat cgactgcgtg tggcagatgt ccaagcagtt    3060
ccctaccgcc ttcgagttca acgagcagtt cctgatcatc atcctggacc acctgtactc    3120
ttgcagattc ggcaccttcc tgttcaactg cgagagcgcc agagaacggc agaaagtgac    3180
cgagagaacc gtgtctctgt ggtccctgat caacagcaac aaagagaaat tcaagaaccc    3240
cttctcacac aaagaaatca accgggtgct gtaccccgtg gccagcatga gacatctgga    3300
actgtgggtc aactactaca tccggtggaa ccccagaatc aagcagcagc agcccaatcc    3360
tgtggaacag cggtatatgg aactgctggc cctgcgggac gagtacatca agagactgga    3420
agaactgcag ctggccaaca gcgccaagct gagcgatcct cctacaagcc ctagcagccc    3480
ctctcagatg atgccccatg tgcagaccca cttttgacct aggaataaaa gatctttatt    3540
ttcattagat ctgtgtgttg gttttttgtg tgacccgtct gattttgtag gtaaccacgt    3600
gcggaccgag cggccgcagg aaccctagt gatggagttg ccactccct ctctgcgcgc     3660 tcgctcgctc actgaggccg gcgaccaaa ggtcgcccga cgcccgggct ttgcccgggc    3720
ggcctcagtg agcgagcgag cgcgcagctg cctgcagggg cgcctgatgc ggtatttct     3780 ccttacgcat ctgtgcggta tttcacaccg catacgtcaa agcaaccata gtacgcgccc    3840
tgtagcggcg cattaagcgc ggcgggtgtg gtggttacgc gcagcgtgac cgctacactt    3900
gccagcgccc tagcgcccgc tcctttcgct ttcttccctt cctttctcgc cacgttcgcc    3960
ggctttcccc gtcaagctct aaatcggggg ctccctttag ggttccgatt tagtgcttta    4020
cggcacctcg accccaaaaa acttgatttg ggtgatggtt cacgtagtgg gccatcgccc    4080
tgatagacgg ttttcgccc tttgacgttg gagtccacgt tctttaatag tggactcttg     4140
ttccaaactg gaacaacact caaccctatc tcgggctatt cttttgattt ataagggatt    4200
ttgccgattt cggcctattg gttaaaaaat gagctgattt aacaaaaatt taacgcgaat    4260
tttaacaaaa tattaacgtt tacaatttta tggtgcactc tcagtacaat ctgctctgat    4320
gccgcatagt taagccagcc ccgacacccg ccaacacccg ctgacgcgcc ctgacgggct    4380
tgtctgctcc cggcatccgc ttacagacaa gctgtgaccg tctccgggag ctgcatgtgt    4440
cagaggtttt caccgtcatc accgaaacgc gcgagacgaa agggcctcgt gatacgccta    4500
tttttatagg ttaatgtcat gataataatg gtttcttaga cgtcaggtgg cacttttcgg    4560
ggaaatgtgc gcggaacccc tatttgttta ttttctaaa tacattcaaa tatgtatccg     4620
ctcatgagac aataaccctg ataaatgctt caataatatt gaaaaaggaa gagtatgagt    4680
attcaacatt tccgtgtcgc ccttattccc ttttttgcgg catttgcct tcctgttttt     4740 gctcacccag aaacgctggt gaaagtaaaa gatgctgaag atcagttggg tgcacgagtg    4800
ggttacatcg aactggatct caacagcggt aagatccttg agagttttcg ccccgaagaa    4860
cgttttccaa tgatgagcac ttttaaagtt ctgctatgtg gcgcggtatt atcccgtatt    4920
gacgccgggc aagagcaact cggtcgccgc atacactatt ctcagaatga cttggttgag    4980
tactcaccag tcacagaaaa gcatcttacg gatggcatga cagtaagaga attatgcagt    5040
gctgccataa ccatgagtga taacactgcg gccaacttac ttctgacaac gatcggagga    5100
```

```
ccgaaggagc taaccgcttt tttgcacaac atggggatc  atgtaactcg ccttgatcgt   5160
tgggaaccgg agctgaatga agccatacca aacgacgagc gtgacaccac gatgcctgta   5220
gcaatggcaa caacgttgcg caaactatta actggcgaac tacttactct agcttcccgg   5280
caacaattaa tagactggat ggaggcggat aaagttgcag gaccacttct cgctcggcc    5340 cttccggctg gctggtttat tgctgataaa tctggagccg gtgagcgtgg gtctcgcggt   5400
atcattgcag cactggggcc agatggtaag ccctcccgta tcgtagttat ctacacgacg   5460
gggagtcagg caactatgga tgaacgaaat agacagatcg ctgagatagg tgcctcactg   5520
attaagcatt ggtaactgtc agaccaagtt tactcatata tactttagat tgatttaaaa   5580
cttcattttt aatttaaaag gatctaggtg aagatccttt ttgataatct catgaccaaa   5640
atcccttaac gtgagttttc gttccactga gcgtcagacc ccgtagaaaa gatcaaagga   5700
tcttcttgag atcctttttt tctgcgcgta atctgctgct tgcaaacaaa aaaaccaccg   5760
ctaccagcgg tggtttgttt gccggatcaa gagctaccaa ctcttttcc  gaaggtaact   5820 ggcttcagca gagcgcagat accaaatact gtccttctag tgtagccgta gttaggccac   5880
cacttcaaga actctgtagc accgcctaca tacctcgctc tgctaatcct gttaccagtg   5940
gctgctgcca gtggcgataa gtcgtgtctt accgggttgg actcaagacg atagttaccg   6000
gataaggcgc agcggtcggg ctgaacgggg ggttcgtgca cacagcccag cttggagcga   6060
acgacctaca ccgaactgag atacctacag cgtgagctat gagaaagcgc cacgcttccc   6120
gaagggagaa aggcggacag gtatccggta agcggcaggg tcggaacagg agagcgcacg   6180
agggagcttc cagggggaaa cgcctggtat ctttatagtc ctgtcgggtt cgccacctc   6240 tgacttgagc gtcgattttt gtgatgctcg tcagggggc  ggagcctatg gaaaaacgcc   6300
agcaacgcgg cctttttacg gttcctggcc ttttgctggc cttttgctca catgt         6355
```

<210> SEQ ID NO 65
<211> LENGTH: 6780
<212> TYPE: DNA
<213> ORGANISM: Artificial Sequence
<220> FEATURE:
<223> OTHER INFORMATION: plasmid pAAV-CSkSH5-SPc5-12GTRM-MVM-hGAA-SynthpA

<400> SEQUENCE: 65

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtaccgg tcagtttact caccagggat    180
tcagaggcag cactgctgaa ccctgagccc ttggcacatc aggttggctg tcagaagtcg    240 gccttttgtac atacacagtt cccttgtgag gcccagctgc gtgtcctagg agcggggcct    300
ctctccacag cagagctcag cctctcaagt gtatggacag cacgggtgcc tgatgggtgg    360
atttagccat gagttgaagg tggcttgggg agaatgagag ttctagagat agggagaagg    420
ggttgccaat aggagagtgg aattcctgag cacctcgtca caggcagccg acagaacatg    480
agccgcaggg cccaggctat ttatacctcg cctgtcacta tcagggtccc cacagctccc    540
cccacctcca gccacacaca gcaggtcctt ttgctctttc tggtcccttc tctactcctc    600
cccctcccta cctaaggtac ccaacccgtt acgtggccac cgccttcggc accatcctca    660 cgacaccccaa atatggcgac gggtgaggaa tggtggggag ttattttag  agcggtgagg    720 aaggtgggca ggcagcaggt gttggcgctc taaaaataac tcccgggagt tattttaga    780
```

| | |
|---|---|
| gcggaggaat ggtggacacc caaatatggc gacggttcct cacccgtcgc catatttggg | 840 |
| tgtccgccct cggccggggc cgcattcctg ggggccgggc ggtgctcccg cccgcctcga | 900 |
| taaaaggctc cggggccggc ggcggccac gagctacccg gaggagcggg aggcgccaag | 960 |
| ctctagatct agaactagta agaggtaagg gtttaaggga tggttggttg gtggggtatt | 1020 |
| aatgttttaat tacctggagc acctgcctga aatcactttt tttcaggttg gcgtacggcc | 1080 |
| accatgggag tgaggcaccc gccctgctcc caccggctcc tggccgtctg cgccctcgtg | 1140 |
| tccttggcaa ccgctgcact cctggggcac atcctactcc atgatttcct gctggttccc | 1200 |
| cgagagctga gtggctcctc cccagtcctg gaggagactc acccagctca ccagcaggga | 1260 |
| gccagcagac cagggccccg ggatgccag gcacaccccg ccgtcccag agcagtgccc | 1320 |
| acacagtgcg acgtcccccc caacagccgc ttcgattgcg ccctgacaa ggccatcacc | 1380 |
| caggaacagt gcgaggcccg cggctgttgc tacatccctg caaagcaggg gctgcaggga | 1440 |
| gcccagatgg ggcagccctg gtgcttcttc ccacccagct accccagcta caagctggag | 1500 |
| aacctgagct cctctgaaat gggctacacg gccaccctga cccgtaccac ccccaccttc | 1560 |
| ttccccaagg acatcctgac cctgcggctg gacgtgatga tggagactga gaaccgcctc | 1620 |
| cacttcacga tcaaagatcc agctaacagg cgctacgagg tgcccttgga gaccccgcat | 1680 |
| gtccacagcc gggcaccgtc cccactctac agcgtggagt tctccgagga gcccttcggg | 1740 |
| gtgatcgtgc gccggcagct ggacggccgc gtgctgctga acacgacggt ggcgcccctg | 1800 |
| ttctttgcgg accagttcct tcagctgtcc acctcgctgc cctcgcagta tatcacaggc | 1860 |
| ctcgccgagc acctcagtcc cctgatgctc agcaccagct ggaccaggat cacccgtgtgg | 1920 |
| aaccgggacc ttgcgcccac gcccggtgcg aacctctacg ggtctcaccc tttctacctg | 1980 |
| gcgctggagg acggcgggtc ggcacacggg gtgttcctgc taaacagcaa tgccatggat | 2040 |
| gtggtcctgc agccgagccc tgcccttagc tggaggtcga caggtgggat cctggatgtc | 2100 |
| tacatcttcc tgggcccaga gcccaagagc gtggtgcagc agtacctgga cgttgtggga | 2160 |
| tacccgttca tgccgccata ctggggcctg gcttccacc tgtgccgctg gggctactcc | 2220 |
| tccaccgcta tcacccgcca ggtggtggag aacatgacca gggcccactt cccccctggac | 2280 |
| gtccagtgga acgacctgga ctacatggac tcccggaggg acttcacgtt caacaaggat | 2340 |
| ggcttccggg acttccccggc catggtgcag gagctgcacc agggcggccg gcgctacatg | 2400 |
| atgatcgtgg atcctgccat cagcagctcg ggccctgccg ggagctacag gccctacgac | 2460 |
| gagggtctgc ggaggggggt tttcatcacc aacgagaccg ccagccgct gattgggaag | 2520 |
| gtatggcccg ggtccactgc cttccccgac ttcaccaacc ccacagccct ggcctggtgg | 2580 |
| gaggacatgt ggctgagtt ccatgaccag gtgcccttcg acggcatgtg gattgacatg | 2640 |
| aacgagcctt ccaacttcat caggggctct gaggacggct gccccaacaa tgagctggag | 2700 |
| aacccacccct acgtgcctgg ggtggttggg gggaccctcc aggcggccac catctgtgcc | 2760 |
| tccagccacc agtttctctc cacacactac aacctgcaca acctctacgg cctgaccgaa | 2820 |
| gccatcgcct cccacagggc gctggtgaag gctcggggga cacgcccatt tgtgatctcc | 2880 |
| cgctcgacct ttgctggcca cggccgatac gccggccact ggacggggga cgtgtggagc | 2940 |
| tcctgggagc agctcgcctc ctccgtgcca gaaatcctgc agtttaacct gctggggtg | 3000 |
| cctctggtcg gggccgacgt ctgcggcttc ctgggcaaca cctcagagga gctgtgtgtg | 3060 |
| cgctggaccc agctgggggc cttctacccc ttcatgcgga accacaacag cctgctcagt | 3120 |

```
ctgccccagg agccgtacag cttcagcgag ccggcccagc aggccatgag gaaggccctc    3180
accctgcgct acgcactcct ccccaccctc tacacactgt tccaccaggc ccacgtcgcg    3240
ggggagaccg tggcccggcc cctcttcctg gagttcccca aggactctag cacctggact    3300
gtggaccacc agctcctgtg gggggaggcc ctgctcatca ccccagtgct ccaggccggg    3360
aaggccgaag tgactggcta cttccccttg ggcacatggt acgacctgca gacggtgcca    3420
gtagaggccc ttggcagcct cccaccccca cctgcagctc cccgtgagcc agccatccac    3480
agcgaggggc agtgggtgac gctgccggcc ccctggaca ccatcaacgt ccacctccgg     3540
gctgggtaca tcatcccct gcagggcccct ggcctcacaa ccacagagtc ccgccagcag    3600
cccatggccc tggctgtggc cctgaccaag ggtggggagg cccgagggga gctgttctgg    3660
gacgatggag agagcctgga agtgctggag cgaggggcct acacacaggt catcttcctg    3720
gccaggaata acacgatcgt gaatgagctg gtacgtgtga ccagtgaggg agctggcctg    3780
cagctgcaga aggtgactgt cctgggcgtg gccacggcgc cccagcaggt cctctccaac    3840
ggtgtccctg tctccaactt cacctacagc cccgacacca aggtcctgga catctgtgtc    3900
tcgctgttga tgggagagca gtttctcgtc agctggtgtt agcctaggaa taaaagatct    3960
ttatttcat tagatctgtg tgttggtttt ttgtgtgacc cgtctgattt tgtaggtaac     4020
cacgtgcgga ccgagcggcc gcaggaaccc ctagtgatgg agttggccac tccctctctg    4080
cgcgctcgct cgctcactga ggccgggcga ccaaaggtcg cccgacgccc gggctttgcc    4140
cgggcggcct cagtgagcga gcgagcgcgc agctgcctgc aggggcgcct gatgcggtat    4200
tttctcctta cgcatctgtg cggtatttca caccgcatac gtcaaagcaa ccatagtacg    4260
cgccctgtag cggcgcatta agcgcggcgg gtgtggtggt tacgcgcagc gtgaccgcta    4320
cacttgccag cgccctagcg cccgctcctt tcgctttctt cccttccttt ctcgccacgt    4380
tcgccggctt tccccgtcaa gctctaaatc gggggctccc tttagggttc cgatttagtg    4440
ctttacggca cctcgacccc aaaaaacttg atttgggtga tggttcacgt agtgggccat    4500
cgccctgata cacggttttt cgcccttga cgttggagtc cacgttcttt aatagtggac    4560
tcttgttcca aactgaaaca acactcaacc ctatctcggg ctattctttt gatttataag    4620
ggattttgcc gatttcggcc tattggttaa aaaatgagct gatttaacaa aaatttaacg    4680
cgaattttaa caaaatatta acgtttacaa ttttatggtg cactctcagt acaatctgct    4740
ctgatgccgc atagttaagc cagccccgac acccgccaac acccgctgac gcgccctgac    4800
gggcttgtct gctcccggca tccgcttaca gacaagctgt gaccgtctcc gggagctgca    4860
tgtgtcagag gttttcaccg tcatcaccga aacgcgcgag acgaaagggc ctcgtgatac    4920
gcctattttt ataggttaat gtcatgataa taatggtttc ttagacgtca ggtggcactt    4980
ttcggggaaa tgtgcgcgga accctatttt gtttatttt ctaaatacat tcaaatatgt      5040
atccgctcat gagacaataa ccctgataaa tgcttcaata atattgaaaa aggaagagta    5100
tgagtattca acatttccgt gtcgccctta ttcccttttt tgcggcattt tgccttcctg    5160
ttttgctca cccagaaacg ctggtgaaag taaaagatgc tgaagatcag ttgggtgcac    5220
gagtgggtta catcgaactg gatctcaaca gcggtaagat ccttgagagt tttcgccccg    5280
aagaacgttt tccaatgatg agcacttta aagttctgct atgtggcgcg gtattatccc     5340
gtattgacgc cgggcaagag caactcggtc gccgcataca ctattctcag aatgacttgg    5400
ttgagtactc accagtcaca gaaaagcatc ttacggatgg catgacagta agagaattat    5460
gcagtgctgc cataaccatg agtgataaca ctgcggccaa cttacttctg acaacgatcg    5520
```

```
gaggaccgaa ggagctaacc gcttttttgc acaacatggg ggatcatgta actcgccttg    5580
atcgttggga accggagctg aatgaagcca taccaaacga cgagcgtgac accacgatgc    5640
ctgtagcaat ggcaacaacg ttgcgcaaac tattaactgg cgaactactt actctagctt    5700
cccggcaaca attaatagac tggatggagg cggataaagt tgcaggacca cttctgcgct    5760
cggcccttcc ggctggctgg tttattgctg ataaatctgg agccggtgag cgtgggtctc    5820
gcggtatcat tgcagcactg gggccagatg gtaagccctc ccgtatcgta gttatctaca    5880
cgacggggag tcaggcaact atggatgaac gaaatagaca gatcgctgag ataggtgcct    5940
cactgattaa gcattggtaa ctgtcagacc aagtttactc atatatactt tagattgatt    6000
taaaacttca ttttttaattt aaaaggatct aggtgaagat cctttttgat aatctcatga    6060
ccaaaatccc ttaacgtgag ttttcgttcc actgagcgtc agaccccgta gaaaagatca    6120
aaggatcttc ttgagatcct ttttttctgc gcgtaatctg ctgcttgcaa acaaaaaaac    6180
caccgctacc agcggtggtt tgtttgccgg atcaagagct accaactctt tttccgaagg    6240
taactggctt cagcagagcg cagataccaa atactgtcct tctagtgtag ccgtagttag    6300
gccaccactt caagaactct gtagcaccgc ctacatacct cgctctgcta atcctgttac    6360
cagtggctgc tgccagtggc gataagtcgt gtcttaccgg gttggactca agacgatagt    6420
taccggataa ggcgcagcgg tcgggctgaa cggggggttc gtgcacacag cccagcttgg    6480
agcgaacgac ctacaccgaa ctgagatacc tacagcgtga gctatgagaa agcgccacgc    6540
ttcccgaagg gagaaaggcg gacaggtatc cggtaagcgg cagggtcgga acaggagagc    6600
gcacgaggga gcttccaggg ggaaacgcct ggtatcttta tagtcctgtc gggtttcgcc    6660
acctctgact tgagcgtcga tttttgtgat gctcgtcagg gggcggagc ctatggaaaa    6720 acgccagcaa cgcggccttt ttacggttcc tggccttttg ctggcctttt gctcacatgt    6780
```

<210> SEQ ID NO 66
<211> LENGTH: 6780
<212> TYPE: DNA
<213> ORGANISM: Artificial Sequence
<220> FEATURE:
<223> OTHER INFORMATION: plasmid pAAV-CSkSH5-SPc5-12GTRM-MVM-hGAAopt-
    SynthpA

<400> SEQUENCE: 66

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggtcc tgcggccgca cgcgtaccgg tcagtttact caccagggat      180
tcagaggcag cactgctgaa ccctgagccc ttggcacatc aggttggctg tcagaagtcg     240
gcctttgtac atacacagtt cccttgtgag gcccagctgc gtgtcctagg agcggggcct     300
ctctccacag cagagctcag cctctcaagt gtatggacag cacgggtgcc tgatgggtgg     360
atttagccat gagttgaagg tggcttgggg agaatgagag ttctagagat agggagaagg     420
ggttgccaat aggagagtgg aattcctgag cacctcgtca caggcagccg acagaacatg     480
agccgcaggg cccaggctat ttatacctcg cctgtcacta tcagggtccc cacagctccc     540
cccacctcca gccacacaca gcaggtcctt ttgctctttc tggtcccttc tctactcctc     600
cccctcccta cctaaggtac ccaacccgtt acgtggccac cgccttcggc accatcctca     660
cgacacccca atatggcgac gggtgaggaa tggtggggag ttattttag agcggtgagg     720 aaggtgggca ggcagcaggt gttggcgctc taaaaataac tcccgggagt tatttttaga     780
```

-continued

```
gcggaggaat ggtggacacc caaatatggc gacggttcct cacccgtcgc catatttggg      840
tgtccgccct cggccggggc cgcattcctg ggggccgggc ggtgctcccg cccgcctcga      900
taaaaggctc cggggccggc ggcggcccac gagctacccg gaggagcggg aggcgccaag      960
ctctagatct agaactagta agaggtaagg gtttaaggga tggttggttg gtggggtatt     1020 aatgttttaat tacctggagc acctgcctga aatcactttt tttcaggttg gcgtacggcc    1080
accatgggcg tcagacatcc tccatgttct cacagactgc tggccgtgtg tgctctggtg     1140
tctcttgcta cagctgccct gctgggacat atcctgctgc acgattttct gctggtgccc     1200
agagagctgt ctggcagctc tcctgtgctg aagaaacac accctgcaca tcagcagggc      1260
gcctctagac ctggacctag agatgctcaa gcccatcctg gcagacctag agccgtgcct     1320
acacagtgtg acgtgccacc taacagcaga ttcgactgcg ccctgacaa ggccatcaca      1380 caagagcagt gtgaagccag aggctgctgc tacattcctg ccaaacaagg actgcagggc     1440
gctcagatgg gacagccttg gtgcttcttc ccaccatctt accccagcta caagctggaa     1500
aacctgagca gcagcgagat gggctacacc gccacactga ccagaaccac acctacattc     1560
ttcccaaagg acatcctgac actgcggctg gacgtgatga tggaaaccga gaaccggctg     1620
cacttcacca tcaaggaccc cgccaataga agatacgagg tgccctgga aaccctcac      1680 gtgcactcta gagccccatc tccactgtac agcgtggaat tcagcgagga acctttggc     1740 gtgatcgtgc ggagacagct ggatggcaga gtgctgctga ataccacagt ggcccctctg     1800
ttcttcgccg accagtttct gcagctgagc acaagcctgc ctagccagta tatcacaggc    1860
ctggccgaac acctgtctcc actgatgctg agcaccagct ggaccagaat caccctgtgg    1920
aacagagatc tggcccctac acctggcgcc aatctgtacg gctctcaccc ttttatctg     1980 gccctggaag atggcggaag cgcccacggt gtctttctgc tgaacagcaa cgccatggac    2040
gtggtgctgc aaccatctcc tgctctgtct tggagaagca ccggcggcat cctggacgtg    2100 tacatcttc tgggacccga gcctaagagc gtggtgcagc agtatctgga tgtcgtgggc     2160 tacccctca tgcctcctta ttggggcctg ggcttccacc tgtgtagatg gggatacagc     2220
tccaccgcca tcaccagaca ggtggtggaa aacatgaccc gggctcactt cccactggat     2280
gtgcagtgga acgacctgga ctacatggac tccagacggg acttcacctt taacaaggac     2340
ggcttcagag acttccccgc catggtgcaa gaactgcatc aaggcggcag acggtacatg     2400
atgatcgtgg atcctgccat ctcttctagc ggccctgccg gaagctacag accttatgat     2460
gagggcctga agaggcgt gttcatcacc aatgagacag gccagcctct gatcggcaaa     2520
gtgtggcctg gaagcaccgc ctttccagac ttcaccaatc caaccgctct ggcttggtgg    2580
gaagatatgg tggccgagtt ccacgatcag gtgcccttcg atggcatgtg gatcgacatg    2640
aacgagccca gcaacttcat caggggcagc gaggatggct gccccaacaa cgaactggaa    2700
aatcctcctt acgtgccagg cgttgtcgga ggaacactgc aggccgccac aatttgtgcc    2760
agcagccatc agtttctgag caccactac aacctgcaca acctgtacgg cctgaccgag    2820
gccattgcct ctcatagagc cctggttaag gccagaggca cccggccttt tgtgatcagc    2880
agaagcacat ttgccggcca cggcagatat gccggacatt ggacagggga cgtttggtct    2940
agttgggagc agctggcctc tagcgtgccc gagatcctgc agtttaatct gctgggagtg     3000
cccctcgtgg gagccgatgt tgtggattt ctgggcaaca cctccgagga actgtgcgtc     3060
agatggacac agctgggcgc cttctatccc ttcatgagaa accacaacag cctgctgagc    3120
```

```
ctgcctcaag agccttacag ctttagcgaa cccgcacagc aggccatgag aaaggccctg    3180
actctgagat acgctctgct gccccacctg tacaccctgt tcatcaagc tcatgtggcc    3240 ggcgagacag tggccagacc actgtttctg gaattcccca aggacagcag cacctggaca    3300
gtggatcatc agctgctctg gggagaagcc ctgctcatta cacctgtgct gcaggctggc    3360
aaggccgaag tgacaggata ctttcccctc ggcacttggt acgacctgca gacagttcct    3420
gtggaagctc tgggatctct gcctccacct cctgctgctc ctagagagcc tgccattcac    3480
tctgaaggcc agtgggttac actgcccgct ccactggaca ccatcaatgt gcacctgaga    3540
gccggctaca tcatccctct gcaaggccct ggactgacca caaccgaaag cagacagcag    3600
ccaatggctc tggccgtggc tctgacaaaa ggcggagaag ctagaggcga actgttctgg    3660
gatgacggcg agagcctgga agtgctggaa cggggagcct acacacaagt gatctttctc    3720
gcccggaaca acaccatcgt gaacgaactc gtcagagtga ccagtgaagg tgccggactg    3780
cagctccaga aagtgacagt gcttggagtg ccacagcac cccagcaggt tttgtctaat    3840
ggcgtgcccg tgtccaactt cacatacagc cctgacacca aggtgctgga catctgtgtg    3900
tctctgctga tgggcgagca gttcctggtg tcctggtgtt gacctaggaa taaaagatct    3960
ttattttcat tagatctgtg tgttggtttt ttgtgtgacc cgtctgattt tgtaggtaac    4020
cacgtgcgga ccgagcggcc gcaggaaccc ctagtgatgg agttggccac tccctctctg    4080
cgcgctcgct cgctcactga ggccgggcga ccaaaggtcg cccgacgccc gggctttgcc    4140
cgggcggcct cagtgagcga gcagcgcgc agctgcctgc aggggcgcct gatgcggtat    4200
tttctcctta cgcatctgtg cggtatttca caccgcatac gtcaaagcaa ccatagtacg    4260
cgccctgtag cggcgcatta agcgcggcgg gtgtggtggt tacgcgcagc gtgaccgcta    4320
cacttgccag cgccctagcg cccgctcctt tcgctttctt cccttccttt ctcgccacgt    4380
tcgccggctt tccccgtcaa gctctaaatc gggggctccc tttagggttc cgatttagtg    4440
ctttacggca cctcgacccc aaaaaacttg atttgggtga tggttcacgt agtgggccat    4500
cgccctgata cggttttt cgcccttga cgttggagtc cacgttcttt aatagtggac    4560
tcttgttcca aactgaaaca acactcaacc ctatctcggg ctattctttt gatttataag    4620
ggattttgcc gatttcggcc tattggttaa aaaatgagct gatttaacaa aaatttaacg    4680
cgaattttaa caaaatatta cgtttacaa ttttatggtg cactctcagt acaatctgct    4740
ctgatgccgc atagttaagc cagccccgac acccgccaac acccgctgac gcgccctgac    4800
gggcttgtct gctcccggca tccgcttaca gacaagctgt gaccgtctcc gggagctgca    4860
tgtgtcagag gttttcaccg tcatcaccga aacgcgcgag acgaaagggc ctcgtgatac    4920
gcctattttt ataggttaat gtcatgataa taatggtttc ttagacgtca ggtggcactt    4980
ttcggggaaa tgtgcgcgga acccctattt gtttattttt ctaaatacat tcaaatatgt    5040
atccgctcat gagacaataa ccctgataaa tgcttcaata atattgaaaa aggaagagta    5100
tgagtattca acatttccgt gtcgccctta ttcccttttt tgcggcattt tgccttcctg    5160
tttttgctca cccagaaacg ctggtgaaag taaaagatgc tgaagatcag ttgggtgcac    5220
gagtgggtta catcgaactg gatctcaaca gcggtaagat ccttgagagt tttcgccccg    5280
aagaacgttt tccaatgatg agcactttta agttctgct atgtggcgcg gtattatccc    5340
gtattgacgc cgggcaagag caactcggtc gccgcataca ctattctcag aatgacttgg    5400
ttgagtactc accagtcaca gaaaagcatc ttacggatgg catgacagta agagaattat    5460
gcagtgctgc cataaccatg agtgataaca ctgcggccaa cttacttctg acaacgatcg    5520
```

```
gaggaccgaa ggagctaacc gcttttttgc acaacatggg ggatcatgta actcgccttg    5580
atcgttggga accggagctg aatgaagcca taccaaacga cgagcgtgac accacgatgc    5640
ctgtagcaat ggcaacaacg ttgcgcaaac tattaactgg cgaactactt actctagctt    5700
cccggcaaca attaatagac tggatggagg cggataaagt tgcaggacca cttctgcgct    5760
cggcccttcc ggctggctgg tttattgctg ataaatctgg agccggtgag cgtgggtctc    5820
gcggtatcat tgcagcactg gggccagatg gtaagccctc ccgtatcgta gttatctaca    5880
cgacggggag tcaggcaact atggatgaac gaaatagaca gatcgctgag ataggtgcct    5940
cactgattaa gcattggtaa ctgtcagacc aagtttactc atatatactt tagattgatt    6000
taaaacttca tttttaattt aaaaggatct aggtgaagat cctttttgat aatctcatga    6060
ccaaaatccc ttaacgtgag ttttcgttcc actgagcgtc agaccccgta gaaaagatca    6120
aaggatcttc ttgagatcct ttttttctgc gcgtaatctg ctgcttgcaa acaaaaaaac    6180
caccgctacc agcggtggtt tgtttgccgg atcaagagct accaactctt tttccgaagg    6240
taactggctt cagcagagcg cagataccaa atactgtcct tctagtgtag ccgtagttag    6300
gccaccactt caagaactct gtagcaccgc ctacatacct cgctctgcta atcctgttac    6360
cagtggctgc tgccagtggc gataagtcgt gtcttaccgg gttggactca agacgatagt    6420
taccggataa ggcgcagcgg tcgggctgaa cggggggttc gtgcacacag cccagcttgg    6480
agcgaacgac ctacaccgaa ctgagatacc tacagcgtga gctatgagaa agcgccacgc    6540
ttcccgaagg gagaaaggcg gacaggtatc cggtaagcgg cagggtcgga acaggagagc    6600
gcacgaggga gcttccaggg ggaaacgcct ggtatcttta tagtcctgtc gggtttcgcc    6660
acctctgact tgagcgtcga tttttgtgat gctcgtcagg ggggcggagc ctatggaaaa    6720
acgccagcaa cgcggccttt ttacggttcc tggccttttg ctggccttttt gctcacatgt    6780
```

<210> SEQ ID NO 67
<211> LENGTH: 6808
<212> TYPE: DNA
<213> ORGANISM: Artificial Sequence
<220> FEATURE:
<223> OTHER INFORMATION: plasmid pAAV-SKCRM4 -hDES1.4kb-MVM-hMTM1-
      SynthpA

<400> SEQUENCE: 67

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgcg gcgcgccacc ggtttctgag tcctctaagg    180
tccctcactc ccaactcagc cccatgtcct gtcaattccc actcagtgtc tgatctcctt     240
ctcctcacct ttcccatctc ccgtttgacc caagcttcct gagctctcct cccattcccc     300
tttttggagt cctcctcctc tcccagaacc cagtaataag tgggctcctc cctggcctgg    360
acccccgtgg taaccctata aggcgaggca gctgctgtct gaggcaggga ggggctggtg    420
tgggaggcta agggcagctg ctaagtttag ggtggctcct tctctcttct tagagacaac    480
aggtggctgg ggcctcagtg cccagaaaag aaaatgtctt agaggtatcg gcatgggcct    540
ggaggagggg ggacagggca gggggaggca tcttcctcag gacatcgggt cctagagggg    600
tacccaacgg gttacgacac acctactagt aaccccctcca gctggtgatg gcaggtctag    660
ggtaggacca gtgactggct cctaatcgag cactctattt tcagggtttg cattccaaaa    720
gggtcaggtc caagagggac ctggagtgcc aagtggaggt gtagaggcac ggccagtacc    780
```

-continued

```
catggagaat ggtggatgtc cttaggggtt agcaagtgcc gtgtgctaag gagggggctt      840
tggaggttgg gcaggccctc tgtgggctc cattttttgtg ggggtgggg ctggagcatt       900 ataggggtg ggaagtgatt ggggctgtca ccctagcctt ccttatctga cgcccaccca       960
tgcctcctca ggtacccct gcccccaca gctcctctcc tgtgccttgt ttcccagcca       1020
tgcgttctcc tctataaata cccgctctgg tatttggggt tggcagctgt tgctgccagg     1080
gagatggttg ggttgacatg cggctcctga caaaacacaa accctggtg tgtgtgggcg      1140 tgggtggtgt gagtaggggg atgaatcagg gaggggcgg gggacccagg gggcaggagc     1200
cacacaaagt ctgtgcgggg gtgggagcgc acatagcaat tggaaactga aagcttatca    1260 gacccttct ggaaatcagc ccactgttta taaacttgag gccccaccct cgacagtacc      1320
ggggaggaag agggcctgca ctagtccaga gggaaactga ggctcagggc tagctcgccc    1380
atagacatac atggcaggca ggctttggcc aggatccctc cgcctgccag gcgtctccct    1440
gccctccctt cctgcctaga gacccccacc ctcaagcctg gctggtcttt gcctgagacc    1500
caaacctctt cgacttcaag agaatattta ggaacaaggt ggtttagggc ctttcctggg    1560
aacaggcctt gacctttaa gaaatgaccc aaagtctctc cttgaccaaa aaggggaccc    1620
tcaaactaaa gggaagcctc tcttctgctg tctccctga ccccactccc ccccacccca     1680
ggacgaggag ataaccaggg ctgaaagagg cccgcctggg ggctgcagac atgcttgctg    1740
cctgccctgg cgaaggattg gcaggcttgc ccgtcacagg acccccgctg gctgactcag    1800
gggcgcaggc ctcttgcggg ggagctggcc tccccgcccc cacggccacg ggccgccctt    1860
tcctggcagg acagcgggat cttgcagctg tcaggggagg ggaggcgggg gctgatgtca   1920
ggagggatac aaatagtgcc gacggctggg ggccctgtct cccctcgccg catccactct    1980
ccggccggcc gcctgcccgc cgcctcctcc gtgcgcccgc cagcctcgcc cgcgccgtca    2040
cctctagaac tagtaagagg taagggttta agggatggtt ggttggtggg gtattaatgt    2100
ttaattacct ggagcacctg cctgaaatca cttttttca ggttggcgta cggccaccat     2160
ggcttctgca tcaacttcta aatataattc acactccttg gagaatgagt ctattaagag    2220
gacgtctcga gatggagtca atcgagatct cactgaggct gttcctcgac ttccaggaga    2280
aacactaatc actgacaaag aagttattta catatgtcct ttcaatggcc ccattaaggg    2340
aagagtttac atcacaaatt atcgtctttta tttaagaagt ttggaaacgg attcttctct    2400
aatacttgat gttcctctgg gtgtgatctc gagaattgaa aaaatgggag gcgcgacaag    2460
tagaggagaa aattcctatg gtctagatat tacttgtaaa gacatgagaa acctgaggtt    2520
cgctttgaaa caggaaggcc acagcagaag agatatgttt gagatcctca cgagatacgc    2580
gtttcccctg gctcacagtc tgccattatt tgcatttttta aatgaagaaa agtttaacgt    2640
ggatggatgg acagtttaca atccagtgga agaatacagg aggcagggct tgcccaatca    2700
ccattggaga ataactttta ttaataagtg ctatgagctc tgtgacactt accctgctct    2760
tttggtggtt ccgtatcgtg cctcagatga tgacctccgg agagttgcaa cttttaggtc    2820
ccgaaatcga attccagtgc tgtcatggat tcatccagaa aataagacgg tcattgtgcg    2880
ttgcagtcag cctcttgtcg gtatgagtgg gaaacgaaat aaagatgatg agaaatatct    2940
cgatgttatc agggagacta ataaacaaat ttctaaactc accatttatg atgcaagacc    3000
cagcgtaaat gcagtggcca acaaggcaac aggaggagga tatgaaagtg atgatgcata    3060
tcataacgcc gaacttttct tcttagacat tcataatatt catgttatgc gggaatcttt    3120
```

```
aaaaaaagtg aaggacattg tttatcctaa tgtagaagaa tctcattggt tgtccagttt    3180
ggagtctact cattggttag aacatatcaa gctcgttttg acaggagcca ttcaagtagc    3240
agacaaagtt tcttcaggga agagttcagt gcttgtgcat tgcagtgacg gatgggacag    3300
gactgctcag ctgacatcct tggccatgct gatgttggat agcttctata ggagcattga    3360
agggttcgaa atactggtac aaaaaaaatg gataagtttt ggacataaat ttgcatctcg    3420
aataggtcat ggtgataaaa accacaccga tgctgaccgt tctcctattt ttctccagtt    3480
tattgattgt gtgtggcaaa tgtcaaaaca gttccctaca gcttttgaat tcaatgaaca    3540 attttttgatt ataattttgg atcatctgta tagttgccga tttggtactt tcttattcaa    3600
ctgtgaatct gctcgagaaa gacagaaggt tacagaaagg actgtttctt tatggtcact    3660
gataaacagt aataaagaaa aattcaaaaa ccccttctat actaaagaaa tcaatcgagt    3720
tttatatcca gttgccagta tgcgtcactt ggaactctgg gtgaattact acattagatg    3780 gaacccagg atcaagcaac aacagccgaa tccagtggag cagcgttaca tggagctctt    3840
agccttacgc gacgaataca taaagcggct tgaggaactg cagctcgcca actctgccaa    3900
gctttctgat cccccaactt caccttccag tccttcgcaa atgatgcccc atgtgcaaac    3960
tcacttctga cctaggaata aaagatcttt attttcatta gatctgtgtg ttggtttttt    4020
gtgtgacccg tctgattttg taggtaacca cgtgcggacc gagcggccgc aggaacccct    4080
agtgatggag ttggccactc cctctctgcg cgctcgctcg ctcactgagg ccgggcgacc    4140
aaaggtcgcc cgacgcccgg gctttgcccg ggcggcctca gtgagcgagc gagcgcgcag    4200
ctgcctgcag gggcgcctga tgcggtattt tctccttacg catctgtgcg gtatttcaca    4260
ccgcatacgt caaagcaacc atagtacgcg ccctgtagcg gcgcattaag cgcggcgggt    4320
gtggtggtta cgcgcagcgt gaccgctaca cttgccagcg ccctagcgcc cgctcctttc    4380
gctttcttcc cttcctttct cgccacgttc gccggctttc cccgtcaagc tctaaatcgg    4440
gggctccctt tagggttccg atttagtgct ttacggcacc tcgaccccaa aaaacttgat    4500
ttgggtgatg gttcacgtag tgggccatcg ccctgataga cggttttttcg ccctttgacg    4560 ttggagtcca cgttctttaa tagtggactc ttgttccaaa ctggaacaac actcaaccct    4620
atctcgggct attcttttga tttataaggg attttgccga tttcggccta ttggttaaaa    4680
aatgagctga tttaacaaaa atttaacgcg aattttaaca aaatattaac gtttacaatt    4740
ttatggtgca ctctcagtac aatctgctct gatgccgcat agttaagcca gccccgacac    4800
ccgccaacac ccgctgacgc gccctgacgg gcttgtctgc tcccggcatc cgcttacaga    4860
caagctgtga ccgtctccgg gagctgcatg tgtcagaggt tttcaccgtc atcaccgaaa    4920
cgcgcgagac gaaagggcct cgtgatacgc ctatttttat aggttaatgt catgataata    4980
atggtttctt agacgtcagg tggcactttt cggggaaatg tgcgcggaac ccctatttgt    5040
ttatttttct aaatacattc aaatatgtat ccgctcatga caataaccct gataaatg    5100 cttcaataat attgaaaaag gaagagtatg agtattcaac atttccgtgt cgcccttatt    5160
cccttttttg cggcattttg ccttcctgtt tttgctcacc cagaaacgct ggtgaaagta    5220
aaagatgctg aagatcagtt gggtgcacga gtgggttaca tcgaactgga tctcaacagc    5280
ggtaagatcc ttgagagttt tcgccccgaa gaacgttttc caatgatgag cacttttaaa    5340
gttctgctat gtggcgcggt attatcccgt attgacgccg ggcaagagca actcggtcgc    5400
cgcatacact attctcagaa tgacttggtt gagtactcac cagtcacaga aaagcatctt    5460
acggatggca tgacagtaag agaattatgc agtgctgcca taaccatgag tgataacact    5520
```

```
gcggccaact tacttctgac aacgatcgga ggaccgaagg agctaaccgc ttttttgcac    5580
aacatggggg atcatgtaac tcgccttgat cgttgggaac cggagctgaa tgaagccata    5640
ccaaacgacg agcgtgacac cacgatgcct gtagcaatgg caacaacgtt gcgcaaacta    5700
ttaactggcg aactacttac tctagcttcc cggcaacaat taatagactg gatggaggcg    5760
gataaagttg caggaccact tctgcgctcg gcccttccgg ctggctggtt tattgctgat    5820
aaatctggag ccgtgagcg tgggtctcgc ggtatcattg cagcactggg gccagatggt    5880
aagccctccc gtatcgtagt tatctacacg acggggagtc aggcaactat ggatgaacga    5940
aatagacaga tcgctgagat aggtgcctca ctgattaagc attggtaact gtcagaccaa    6000
gtttactcat atatacttta gattgattta aaacttcatt tttaatttaa aaggatctag    6060
gtgaagatcc ttttgataa tctcatgacc aaaatccctt aacgtgagtt tcgttccac     6120 tgagcgtcag accccgtaga aagatcaaa ggatcttctt gagatccttt ttttctgcgc     6180
gtaatctgct gcttgcaaac aaaaaaacca ccgctaccag cggtggtttg tttgccggat    6240
caagagctac caactctttt tccgaaggta actggcttca gcagagcgca gataccaaat    6300
actgtccttc tagtgtagcc gtagttaggc caccacttca agaactctgt agcaccgcct    6360
acatacctcg ctctgctaat cctgttacca gtggctgctg ccagtggcga taagtcgtgt    6420
cttaccgggt tggactcaag acgatagtta ccggataagg cgcagcggtc gggctgaacg    6480
gggggttcgt gcacacagcc cagcttggag cgaacgacct acaccgaact gagatacta    6540 cagcgtgagc tatgagaaag cgccacgctt cccgaaggga gaaaggcgga caggtatccg    6600
gtaagcggca gggtcggaac aggagagcgc acgagggagc ttccagggg aaacgcctgg     6660 tatctttata gtcctgtcgg gtttcgccac ctctgacttg agcgtcgatt tttgtgatgc    6720
tcgtcagggg ggcggagcct atggaaaaac gccagcaacg cggccttttt acggttcctg    6780
gccttttgct ggccttttgc tcacatgt                                       6808

<210> SEQ ID NO 68
<211> LENGTH: 6808
<212> TYPE: DNA
<213> ORGANISM: Artificial Sequence
<220> FEATURE:
<223> OTHER INFORMATION: plasmid pAAV-SKCRM4-hDES1.4kb-MVM-hMTM1opt-
      SynthpA

<400> SEQUENCE: 68
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgcg gcgcgccacc ggtttctgag tcctctaagg     180
tccctcactc ccaactcagc cccatgtcct gtcaattccc actcagtgtc tgatctcctt     240
ctcctcacct ttcccatctc ccgtttgacc caagcttcct gagctctcct cccattcccc     300
tttttggagt cctcctcctc tcccagaacc cagtaataag tgggctcctc cctgcctgg     360 accccgtgg taaccctata aggcgaggca gctgctgtct gaggcaggga ggggctggtg     420
tgggaggcta aggcagctg ctaagtttag ggtggctcct tctctcttct tagagacaac     480
aggtggctgg ggcctcagtg cccagaaaag aaaatgtctt agaggtatcg gcatgggcct    540
ggaggagggg ggacagggca gggggaggca tcttcctcag acatcgggt cctagagggg     600 tacccaacgg gttacgacac acctactagt aacccctcca gctggtgatg gcaggtctag    660
ggtaggacca gtgactggct cctaatcgag cactctattt tcagggtttg cattccaaaa    720
```

```
gggtcaggtc caagagggac ctggagtgcc aagtggaggt gtagaggcac ggccagtacc    780 catgagaat  ggtggatgtc cttaggggtt agcaagtgcc gtgtgctaag gagggggctt    840
tggaggttgg gcaggccctc tgtggggctc cattttttgtg ggggtggggg ctggagcatt   900 ataggggtg  ggaagtgatt ggggctgtca ccctagcctt ccttatctga cgcccaccca   960
tgcctcctca ggtaccccct gcccccaca  gctcctctcc tgtgccttgt ttcccagcca  1020
tgcgttctcc tctataaata cccgctctgg tatttggggt tggcagctgt tgctgccagg  1080
gagatggttg ggttgacatg cggctcctga caaaacacaa accctggtg  tgtgtgggcg  1140 tgggtggtgt gagtagggg  atgaatcagg gaggggggcgg gggacccagg gggcaggagc  1200
cacacaaagt ctgtgcgggg gtgggagcgc acatagcaat tggaaactga aagcttatca   1260 gacccttct  ggaaatcagc ccactgttta taaacttgag gccccaccct cgacagtacc   1320
ggggaggaag agggcctgca ctagtccaga gggaaactga ggctcagggc tagctcgccc  1380
atagacatac atggcaggca ggctttggcc aggatccctc cgcctgccag gcgtctccct   1440
gccctccctt cctgcctaga gacccccacc ctcaagcctg gctggtcttt gcctgagacc   1500
caaacctctt cgacttcaag agaatattta ggaacaaggt ggtttagggc ctttcctggg   1560
aacaggcctt gacccttta  gaaatgaccc aaagtctctc cttgaccaaa aaggggaccc   1620
tcaaactaaa gggaagcctc tcttctgctg tctccctga  ccccactccc cccaccccca   1680
ggacgaggag ataaccaggg ctgaagaggg cccgcctggg ggctgcagac atgcttgctg   1740
cctgccctgg cgaaggattg gcaggcttgc ccgtcacagg accccgctg  gctgactcag   1800 gggcgcaggc ctcttgcggg ggagctggcc tccccgcccc cacggccacg ggccgccctt   1860
tcctggcagg acagcgggat cttgcagctg tcagggggagg ggaggcgggg gctgatgtca  1920
ggagggatac aaatagtgcc gacggctggg ggccctgtct cccctcgccg catccactct   1980
ccggccggcc gcctgcccgc cgcctcctcc gtgcgcccgc cagcctcgcc cgcgccgtca   2040
cctctagaac tagtaagagg taagggttta agggatggtt ggttggtggg gtattaatgt   2100
ttaattacct ggagcacctg cctgaaatca cttttttttca ggttggcgta cggccaccat  2160
ggccagcgcc agcacaagca agtacaacag ccacagcctg gaaaacgaga gcatcaagcg   2220
gaccagcaga gatggcgtga acagagatct gaccgaggcc gttcctagac tgcctggcga   2280
gacactgatc accgacaaag aagtgatcta catctgcccc ttcaacgcc  ccatcaaggg   2340 aagagtgtac atcaccaact accggctgta cctgcggtcc ctggaaaccg atagcagcct   2400
gattctggat gtgcccctgg gcgtgatcag ccggattgaa aaaatgggcg agccacctc   2460 cagaggcgag aatagctatg cctggatat  cacatgcaag gacatgcgga acctgagatt   2520
cgccctgaag caagagggcc acagcagacg ggacatgttc gagatcctga ccagatacgc   2580 cttcctctg  gctcactctc tgccctgtt  cgccttcctg aacgaagaga agttcaacgt   2640
ggacggctga accgtgtaca accccgtgga agagtatga  cggcagggac tgcccaatca   2700
ccactggcgg atcaccttca tcaacaagtg ctacgagctg tgcgacacat accccgcact   2760
gctggtggtg ccttacagag cctctgacga cgatctgaga agagtggcca cctttcggag   2820
ccggaacaga atccctgtgc tgagctggat tcaccccgag aacaagaccg tgatcgtgcg   2880
gtgttctcag cctctcgtgg gcatgagcgg caagagaaac aaggacgacg agaagtacct   2940
ggacgtgatc cgcgagacaa acaagcagat cagcaagctg accatctacg acgccagacc   3000
ttctgtgaac gccgtggcca acaaagccac aggcggcgga tatgagtccg acgatgccta   3060
```

```
tcacaacgcc gagctgttct tcctggacat tcacaacatc catgtgatgc gcgagagcct    3120
gaagaaagtg aaggacatcg tgtaccccaa tgtggaagag agccactggc tgtctagcct    3180
ggaatccaca cactggctgg aacacatcaa gctggtgctg acaggcgcca tccaggtggc    3240
agacaaagtg tctagcggca gtctagcgt gctggtgcac tgtagcgacg gatgggatag    3300
aacagcccag ctgacatccc tggccatgct gatgctggac agcttctaca gatccatcga    3360
gggctttgag atcctggtgc agaagaagtg gatcagcttc ggccacaagt tcgcctctag    3420
aatcggacac ggcgacaaga accacaccga cgccgataga agccccatct tcctgcagtt    3480
catcgactgc gtgtggcaga tgtccaagca gttccctacc gccttcgagt tcaacgagca    3540
gttcctgatc atcatcctgg accacctgta ctcttgcaga ttcggcacct tcctgttcaa    3600
ctgcgagagc gccagagaac ggcagaaagt gaccgagaga accgtgtctc tgtggtccct    3660
gatcaacagc aacaaagaga aattcaagaa cccttctac accaaagaaa tcaaccgggt    3720
gctgtacccc gtggccagca tgagacatct ggaactgtgg gtcaactact acatccggtg    3780
gaacccccaga atcaagcagc agcagcccaa tcctgtggaa cagcggtata tggaactgct    3840
ggccctgcgg gacgagtaca tcaagagact ggaagaactg cagctggcca acagcgccaa    3900
gctgagcgat cctcctacaa gccctagcag ccccctcag atgatgcccc atgtgcagac    3960
ccacttttga cctaggaata aaagatcttt attttcatta gatctgtgtg ttggtttttt    4020
gtgtgacccg tctgattttg taggtaacca cgtgcgacc gagcggccgc aggaacccct    4080
agtgatggag ttggccactc cctctctgcg cgctcgctcg ctcactgagg ccgggcgacc    4140
aaaggtcgcc cgacgcccgg gctttgcccg ggcggcctca gtgagcgagc gagcgcgcag    4200
ctgcctgcag gggcgcctga tgcggtattt tctccttacg catctgtgcg gtatttcaca    4260
ccgcatacgt caaagcaacc atagtacgcg ccctgtagcg gcgcattaag cgcggcgggt    4320
gtggtggtta cgcgcagcgt gaccgctaca cttgccagcg ccctagcgcc cgctcctttc    4380
gctttcttcc cttcctttct cgccacgttc gccggctttc cccgtcaagc tctaaatcgg    4440
gggctccctt tagggttccg atttagtgct ttacggcacc tcgaccccaa aaaacttgat    4500
ttgggtgatg gttcacgtag tgggccatcg ccctgataga cggttttccg ccctttgacg    4560
ttggagtcca cgttctttaa tagtggactc ttgttccaaa ctggaacaac actcaaccct    4620
atctcgggct attcttttga tttataaggg attttgccga tttcggccta ttggttaaaa    4680
aatgagctga tttaacaaaa attttaacgcg aattttaaca aaatattaac gtttacaatt    4740
ttatggtgca ctctcagtac aatctgctct gatgccgcat agttaagcca gccccgacac    4800
ccgccaacac ccgctgacgc gccctgacgg gcttgtctgc tcccggcatc cgcttacaga    4860
caagctgtga ccgtctccgg gagctgcatg tgtcagaggt tttcaccgtc atcaccgaaa    4920
cgcgcgagac gaaagggcct cgtgatacgc ctatttttat aggttaatgt catgataata    4980
atggtttctt agacgtcagg tggcactttt cggggaaatg tgcgcggaac ccctatttgt    5040
ttatttttct aaatacattc aaatatgtat ccgctcatga caataaacc ctgataaatg    5100
cttcaataat attgaaaaag gaagagtatg agtattcaac atttccgtgt cgcccttatt    5160
ccctttttg cggcattttg ccttcctgtt tttgctcacc cagaaacgct ggtgaaagta    5220
aaagatgctg aagatcagtt gggtgcacga gtgggttaca tcgaactgga tctcaacagc    5280
ggtaagatcc ttgagagttt tcgccccgaa aacgttttc caatgatgag cacttttaaa    5340
gttctgctat gtggcgcggt attatcccgt attgacgccg gcaagagca actcggtcgc    5400
cgcatacact attctcagaa tgacttggtt gagtactcac cagtcacaga aaagcatctt    5460
```

```
acggatggca tgacagtaag agaattatgc agtgctgcca taaccatgag tgataacact    5520
gcggccaact tacttctgac aacgatcgga ggaccgaagg agctaaccgc ttttttgcac    5580
aacatggggg atcatgtaac tcgccttgat cgttgggaac cggagctgaa tgaagccata    5640
ccaaacgacg agcgtgacac cacgatgcct gtagcaatgg caacaacgtt gcgcaaacta    5700
ttaactggcg aactacttac tctagcttcc cggcaacaat taatagactg gatggaggcg    5760
gataaagttg caggaccact tctgcgctcg gcccttccgg ctggctggtt tattgctgat    5820
aaatctggag ccggtgagcg tgggtctcgc ggtatcattg cagcactggg gccagatggt    5880
aagccctccc gtatcgtagt tatctacacg acggggagtc aggcaactat ggatgaacga    5940
aatagacaga tcgctgagat aggtgcctca ctgattaagc attggtaact gtcagaccaa    6000
gtttactcat atatacttta gattgattta aaacttcatt tttaatttaa aaggatctag    6060
gtgaagatcc ttttttgataa tctcatgacc aaaatccctt aacgtgagtt ttcgttccac    6120
tgagcgtcag accccgtaga aaagatcaaa ggatcttctt gagatccttt ttttctgcgc    6180
gtaatctgct gcttgcaaac aaaaaaacca ccgctaccag cggtggtttg tttgccggat    6240
caagagctac caactctttt tccgaaggta actggcttca gcagagcgca gataccaaat    6300
actgtccttc tagtgtagcc gtagttaggc caccacttca agaactctgt agcaccgcct    6360
acatacctcg ctctgctaat cctgttacca gtggctgctg ccagtggcga taagtcgtgt    6420
cttaccgggt tggactcaag acgatagtta ccggataagg cgcagcggtc gggctgaacg    6480
gggggttcgt gcacacagcc cagcttggag cgaacgacct acaccgaact gagatacccta   6540 cagcgtgagc tatgagaaag cgccacgctt cccgaaggga gaaaggcgga caggtatccg    6600
gtaagcggca gggtcggaac aggagagcgc acgagggagc ttccaggggg aaacgcctgg    6660
tatctttata gtcctgtcgg gtttcgccac ctctgacttg agcgtcgatt tttgtgatgc    6720
tcgtcagggg gcggagccta tggaaaaacg ccagcaacg cggccttttt acggttcctg    6780
gccttttgct ggccttttgc tcacatgt                                        6808
```

<210> SEQ ID NO 69
<211> LENGTH: 6645
<212> TYPE: DNA
<213> ORGANISM: Artificial Sequence
<220> FEATURE:
<223> OTHER INFORMATION: plasmid pAAVss-SkSH4-hDES1.4kb-Luc2

<400> SEQUENCE: 69

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gccggcgcgc cacgcgtttc tgagtcctct     180
aaggtccctc actcccaact cagccccatg tcctgtcaat tcccactcag tgtctgatct     240
ccttctcctc acctttccca tctcccgttt gacccaagct tcctgagctc tcctcccatt     300 ccccttttg gagtcctcct cctctcccag aacccagtaa taagtgggct cctccctggc     360
ctggaccccc gtggtaaccc tataaggcga ggcagctgct gtctgaggca gggagggggct   420 ggtgtgggag gctaagggca gctgctaagt ttagggtggc tccttctctc ttcttagaga    480
caacaggtgg ctgggccctc agtgcccaga aaagaaaatg tcttagaggt atcggcatgg    540
gcctggagga gggggacag ggcagggga ggcatcttcc tcaggacatc gggtcctaga       600 ggggtacccca acgggttacg acacacctac tagtaaccccc tccagctggt gatggcaggt    660
```

```
ctagggtagg accagtgact ggctcctaat cgagcactct attttcaggg tttgcattcc      720
aaaagggtca ggtccaagag ggacctggag tgccaagtgg aggtgtagag gcacggccag      780
tacccatgga gaatggtgga tgtccttagg ggttagcaag tgccgtgtgc taaggagggg      840
gctttggagg ttgggcaggc cctctgtggg gctccatttt tgtggggtg ggggctggag       900
cattataggg ggtgggaagt gattggggct gtcaccctag ccttccttat ctgacgccca      960
cccatgcctc ctcaggtacc ccctgccccc cacagctcct ctcctgtgcc ttgtttccca     1020
gccatgcgtt ctcctctata aatacccgct ctggtatttg gggttggcag ctgttgctgc     1080
cagggagatg gttgggttga catgcggctc ctgacaaaac acaaacccct ggtgtgtgtg     1140
ggcgtgggtg gtgtgagtag ggggatgaat cagggagggg gcggggggacc caggggggcag   1200
gagccacaca aagtctgtgc gggggtggga gcgcacatag caattggaaa ctgaaagctt     1260
atcagaccct ttctggaaat cagcccactg tttataaact tgaggcccca ccctcgacag     1320
taccggggag gaagagggcc tgcactagtc cagagggaaa ctgaggctca gggctagctc     1380
gcccatagac atacatggca ggcaggcttt ggccaggatc cctccgcctg ccaggcgtct     1440
ccctgccctc ccttcctgcc tagagacccc caccctcaag cctggctggt ctttgcctga    1500
gacccaaacc tcttcgactt caagagaata tttaggaaca aggtggttta gggccttcc    1560
tgggaacagg ccttgaccct ttaagaaatg acccaaagtc tctccttgac caaaaagggg    1620
accctcaaac taaagggaag cctctcttct gctgtctccc ctgaccccac tcccccccac    1680
cccaggacga ggagataacc agggctgaaa gaggcccgcc tgggggctgc agacatgctt    1740
gctgcctgcc ctggcgaagg attggcaggc ttgcccgtca caggaccccc gctggctgac    1800
tcaggggcgc aggcctcttg cgggggagct ggcctccccg ccccacggc cacgggccgc     1860
cctttcctgg caggacagcg ggatcttgca gctgtcaggg gaggggaggc ggggggctgat   1920
gtcaggaggg atacaaatag tgccgacggc tgggggccct gtctcccctc gccgcatcca    1980
ctctccggcc ggccgcctgc ccgccgcctc tccgtgcgc ccgccagcct cgcccgcgcc    2040
gtcacctcta gaaagaggta agggtttaag ggatggttgg ttggtggggt attaatgttt    2100
aattacctgg agcacctgcc tgaaatcact tttttcagg ttggaagctt atggaagatg     2160
ccaaaaacat taagaagggc ccagcgccat tctacccact cgaggacggg accgccggcg    2220
agcagctgca caaagccatg aagcgctacg ccctggtgcc cggcaccatc gcctttaccg    2280
acgcacatat cgaggtggac attacctacg ccgagtactt cgagatgagc gttcggctgg    2340
cagaagctat gaagcgctat gggctgaata caaaccatcg gatcgtggtg tgcagcgaga    2400
atagcttgca gttcttcatg cccgtgttgg gtgccctgtt catcggtgtg gctgtggccc    2460
cagctaacga catctacaac gagcgcgagc tgctgaacag catgggcatc agccagccca    2520
ccgtcgtatt cgtgagcaag aaagggctgc aaaagatcct caacgtgcaa agaagctac   2580
cgatcataca aaagatcatc atcatggata gcaagaccga ctaccagggc ttccaaagca    2640
tgtacacctt cgtgacttcc catttgccac ccggcttcaa cgagtacgac ttcgtgcccg    2700
agagcttcga ccgggacaaa accatcgccc tgatcatgaa cagtagtggc agtaccggat    2760
tgcccaaggg cgtagcccta ccgcaccgca ccgcttgtgt ccgattcagt catgcccgcg    2820
accccatctt cggcaaccag atcatccccg acaccgctat cctcagcgtg gtgccatttc    2880
accacggctt cggcatgttc accacgctgg gctacttgat ctgcggcttt cgggtcgtgc    2940
tcatgtaccg cttcgaggag gagctattct tgcgcagctt gcaagactat aagattcaat    3000
ctgccctgct ggtgcccaca ctatttagct tcttcgctaa gagcactctc atcgacaagt    3060
```

```
acgacctaag caacttgcac gagatcgcca gcggcggggc gccgctcagc aaggaggtag    3120
gtgaggccgt ggccaaacgc ttccacctac caggcatccg ccagggctac ggcctgacag    3180
aaacaaccag cgccattctg atcacccccg aaggggacga caagcctggc gcagtaggca    3240
aggtggtgcc cttcttcgag gctaaggtgg tggacttgga caccggtaag acactgggtg    3300
tgaaccagcg cggcgagctg tgcgtccgtg gccccatgat catgagcggc tacgttaaca    3360
accccgaggc tacaaacgct ctcatcgaca aggacggctg gctgcacagc ggcgacatcg    3420
cctactggga cgaggacgag cacttcttca tcgtggaccg gctgaagagc ctgatcaaat    3480
acaagggcta ccaggtagcc ccagccgaac tggagagcat cctgctgcaa caccccaaca    3540
tcttcgacgc cggggtcgcc ggcctgcccg acgacgatgc cggcgagctg cccgccgcag    3600
tcgtcgtgct ggaacacggt aaaaccatga ccgagaagga gatcgtggac tatgtggcca    3660
gccaggttac aaccgccaag aagctgcgcg gtggtgttgt gttcgtggac gaggtgccta    3720
aaggactgac cggcaagttg gacgcccgca agatccgcga gattctcatt aaggccaaga    3780
agggcggcaa gatcgccgtg taattcgaaa cgttccgtcc atcttgagca tctgacttct    3840
ggctaaataa aagatcttta ttttcattag atctgtgtgt tggttttttg tgtgcgtcga    3900
gatccacggc cgcaggaacc cctagtgatg gagttggcca ctccctctct gcgcgctcgc    3960
tcgctcactg aggccgggcg accaaaggtc gcccgacgcc cgggctttgc ccgggcggcc    4020
tcagtgagcg agcgagcgcg cagctgcctg caggggcgcc tgatgcggta ttttctcctt    4080
acgcatctgt gcggtatttc acaccgcata cgtcaaagca accatagtac gcgccctgta    4140
gcggcgcatt aagcgcggcg ggtgtggtgg ttacgcgcag cgtgaccgct acacttgcca    4200
gcgccctagc gcccgctcct ttcgctttct tcccttcctt tctcgccacg ttcgccggct    4260
ttccccgtca gctctaaatc ggggggctcc ctttagggtt ccgatttagt gctttacggc    4320
acctcgaccc caaaaaactt gatttgggtg atggttcacg tagtgggcca tcgccctgat    4380
agacggtttt tcgccctttg acgttggagt ccacgttctt taatagtgga ctcttgttcc    4440
aaactggaac aacactcaac cctatctcgg gctattcttt tgatttataa gggattttgc    4500
cgatttcggc ctattggtta aaaaatgagc tgatttaaca aaaatttaac gcgaatttta    4560
acaaaatatt aacgtttaca attttatggt gcactctcag tacaatctgc tctgatgccg    4620
catagttaag ccagccccga cacccgccaa cacccgctga cgcgccctga cgggcttgtc    4680
tgctcccggc atccgcttac agacaagctg tgaccgtctc cgggagctgc atgtgtcaga    4740
ggttttcacc gtcatcaccg aaacgcgcga gacgaaaggg cctcgtgata cgcctatttt    4800
tataggttaa tgtcatgata ataatggttt cttagacgtc aggtggcact tttcggggaa    4860
atgtgcgcgg aacccctatt tgtttatttt tctaaataca ttcaaatatg tatccgctca    4920
tgagacaata accctgataa atgcttcaat aatattgaaa aaggaagagt atgagtattc    4980
aacatttccg tgtcgccctt attcccttt ttgcggcatt ttgccttcct gttttgctc     5040 acccagaaac gctggtgaaa gtaaaagatg ctgaagatca gttgggtgca cgagtgggtt    5100
acatcgaact ggatctcaac agcggtaaga tccttgagag ttttcgcccc gaagaacgtt    5160
ttccaatgat gagcactttt aaagttctgc tatgtggcgc ggtattatcc cgtattgacg    5220
ccgggcaaga gcaactcggt cgccgcatac actattctca gaatgacttg gttgagtact    5280
caccagtcac agaaaagcat cttacggatg gcatgacagt aagagaatta tgcagtgctg    5340
ccataaccat gagtgataac actgcggcca acttacttct gacaacgatc ggaggaccga    5400
```

```
aggagctaac cgcttttttg cacaacatgg gggatcatgt aactcgcctt gatcgttggg    5460
aaccggagct gaatgaagcc ataccaaacg acgagcgtga caccacgatg cctgtagcaa    5520
tggcaacaac gttgcgcaaa ctattaactg gcgaactact tactctagct tcccggcaac    5580
aattaataga ctggatggag gcggataaag ttgcaggacc acttctgcgc tcggcccttc    5640
cggctggctg gtttattgct gataaatctg gagccggtga gcgtgggtct cgcggtatca    5700
ttgcagcact ggggccagat ggtaagccct cccgtatcgt agttatctac acgacgggga    5760
gtcaggcaac tatggatgaa cgaaatagac agatcgctga gataggtgcc tcactgatta    5820
agcattggta actgtcagac caagtttact catatatact ttagattgat ttaaaacttc    5880
atttttaatt taaaaggatc taggtgaaga tcctttttga taatctcatg accaaaatcc    5940
cttaacgtga gttttcgttc cactgagcgt cagaccccgt agaaaagatc aaaggatctt    6000
cttgagatcc ttttttctg cgcgtaatct gctgcttgca acaaaaaaa ccaccgctac    6060 cagcggtggt ttgtttgccg gatcaagagc taccaactct ttttccgaag gtaactggct    6120
tcagcagagc gcagatacca aatactgtcc ttctagtgta gccgtagtta ggccaccact    6180
tcaagaactc tgtagcaccg cctacatacc tcgctctgct aatcctgtta ccagtggctg    6240
ctgccagtgg cgataagtcg tgtcttaccg ggttggactc aagacgatag ttaccggata    6300
aggcgcagcg gtcgggctga acggggggtt cgtgcacaca gcccagcttg gagcgaacga    6360
cctacaccga actgagatac ctacagcgtg agctatgaga aagcgccacg cttcccgaag    6420
ggagaaaggc ggacaggtat ccggtaagcg gcagggtcgg aacaggagag cgcacgaggg    6480
agcttccagg gggaaacgcc tggtatcttt atagtcctgt cgggtttcgc cacctctgac    6540
ttgagcgtcg atttttgtga tgctcgtcag ggggggcggag cctatggaaa aacgccagca    6600
acgcggcctt tttacggttc ctggcctttt gctggccttt tgctc                    6645
```

<210> SEQ ID NO 70
<211> LENGTH: 5572
<212> TYPE: DNA
<213> ORGANISM: Artificial Sequence
<220> FEATURE:
<223> OTHER INFORMATION: plasmid pAAVss-CSkSH5-SPc5-12_GTRM-Luc2

<400> SEQUENCE: 70

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag    120
tggccaactc catcactagg ggttcctgcg gccggcgcgc cacgcgtcag tttactcacc    180
agggattcag aggcagcact gctgaaccct gagcccttgg cacatcaggt tggctgtcag    240
aagtcggcct ttgtacatac acagttccct tgtgaggccc agctgcgtgt cctaggagcg    300
gggcctctct ccacagcaga gctcagcctc tcaagtgtat ggacagcacg ggtgcctgat    360
gggtggattt agccatgagt tgaaggtggc ttggggagaa tgagagttct agagataggg    420
agaaggggtt gccaatagga gagtggaatt cctgagcacc tcgtcacagg cagccgacag    480
aacatgagcc gcagggccca ggctatttat acctcgcctg tcactatcag ggtccccaca    540
gctcccccca cctccagcca cacacagcag gtccttttgc tctttctggt cccttctcta    600
ctcctccccc tccctaccta aggtacccaa cgcgttacgt ggccaccgcc ttcggcacca    660
tcctcacgac acccaaatat ggcgacgggt gaggaatggt ggggagttat ttttagagcg    720
gtgaggaagg tgggcaggca gcaggtgttg gcgctctaaa aataactccc gggagttatt    780
tttagagcgg aggaatggtg gacacccaaa tatggcgacg gttcctcacc cgtcgccata    840
```

```
tttgggtgtc cgccctcggc cggggccgca ttcctggggg ccgggcggtg ctcccgcccg    900
cctcgataaa aggctccggg gccggcggcg gcccacgagc tacccggagg agcgggaggc    960
gccaagctct agatctagaa agaggtaagg gtttaaggga tggttggttg gtggggtatt   1020
aatgtttaat tacctggagc acctgcctga aatcactttt tttcaggttg gaagcttatg   1080
gaagatgcca aaacattaa gaagggccca gcgccattct acccactcga ggacgggacc    1140
gccggcgagc agctgcacaa agccatgaag cgctacgccc tggtgcccgg caccatcgcc   1200
tttaccgacg cacatatcga ggtggacatt acctacgccg agtacttcga tgagcgtt     1260 cggctggcag aagctatgaa cgctatggg ctgaatacaa accatcggat cgtggtgtgc    1320
agcgagaata gcttgcagtt cttcatgccc gtgttgggtg ccctgttcat cggtgtggct   1380
gtggccccag ctaacgacat ctacaacgag cgcgagctgc tgaacagcat gggcatcagc   1440
cagcccaccg tcgtattcgt gagcaagaaa gggctgcaaa agatcctcaa cgtgcaaaag   1500
aagctaccga tcatacaaaa gatcatcatc atggatagca agaccgacta ccagggcttc   1560
caaagcatgt acaccttcgt gacttcccat ttgccacccg gcttcaacga gtacgacttc   1620
gtgcccgaga gcttcgaccg ggacaaaacc atcgccctga tcatgaacag tagtggcagt   1680
accggattgc ccaagggcgt agccctaccg caccgcaccg cttgtgtccg attcagtcat   1740
gcccgcgacc ccatcttcgg caaccagatc atccccgaca ccgctatcct cagcgtggtg   1800
ccatttcacc acggcttcgg catgttcacc acgctgggct acttgatctg cggctttcgg   1860
gtcgtgctca tgtaccgctt cgaggaggag ctattcttgc gcagcttgca agactataag   1920
attcaatctg ccctgctggt gcccacacta tttagcttct tcgctaagag cactctcatc   1980
gacaagtacg acctaagcaa cttgcacgag atcgccagcg gcgggcgcc gctcagcaag    2040 gaggtaggtg aggccgtggc caaacgcttc cacctaccag gcatccgcca gggctacggc   2100
ctgacagaaa caaccagcgc cattctgatc accccgaag gggacgacaa gcctggcgca    2160
gtaggcaagg tggtgcccct cttcgaggct aaggtggtgg acttggacac cggtaagaca   2220
ctgggtgtga accagcgcgg cgagctgtgc gtccgtggcc ccatgatcat gagcggctac   2280
gttaacaacc ccgaggctac aaacgctctc atcgacaagg acggctggct gcacagcggc   2340
gacatcgcct actgggacga ggacgagcac ttcttcatcg tggaccggct gaagagcctg   2400
atcaaataca agggctacca ggtagccca gccgaactgg agagcatcct gctgcaacac    2460
cccaacatct tcgacgccgg ggtcgccggc ctgcccgacg acgatgccgg cgagctgccc   2520
gccgcagtcg tcgtgctgga acacggtaaa accatgaccg agaaggagat cgtggactat   2580
gtggccagcc aggttacaac cgccaagaag ctgcgcggtg gtgttgtgtt cgtggacgag   2640
gtgcctaaag gactgaccgg caagttggac gcccgcaaga tccgcgagat ctctcattaag   2700 gccaagaagg gcggcaagat cgccgtgtaa ttcgaaacgt tcggtccatc ttgagcatct   2760
gacttctggc taaataaaag atctttattt tcattagatc tgtgtgttgg ttttttgtgt   2820
gcgtcgagat ccacggccgc aggaaccct agtgatggag ttggccactc cctctctgcg    2880
cgctcgctcg ctcactgagg ccgggcgacc aaaggtcgcc cgacgcccgg gctttgcccg   2940
ggcggcctca gtgagcgagc gagcgcgcag ctgcctgcag gggcgcctga tgcggtattt   3000
tctccttacg catctgtgcg gtatttcaca ccgcatacgt caaagcaacc atagtacgcg   3060
ccctgtagcg gcgcattaag cgcggcgggt gtggtggtta cgcgcagcgt gaccgctaca   3120
cttgccagcg ccctagcgcc cgctcctttc gctttcttcc cttcctttct cgccacgttc   3180
```

```
gccggctttc cccgtcaagc tctaaatcgg gggctcccctt tagggttccg atttagtgct    3240
ttacggcacc tcgaccccaa aaaacttgat ttgggtgatg gttcacgtag tgggccatcg    3300
ccctgataga cggttttccg cccttgacg ttggagtcca cgttctttaa tagtggactc     3360
ttgttccaaa ctggaacaac actcaaccct atctcgggct attcttttga tttataaggg    3420
attttgccga tttcggccta ttggttaaaa aatgagctga tttaacaaaa atttaacgcg    3480
aattttaaca aaatattaac gtttacaatt ttatggtgca ctctcagtac aatctgctct    3540
gatgccgcat agttaagcca gccccgacac ccgccaacac ccgctgacgc gccctgacgg    3600
gcttgtctgc tcccggcatc cgcttacaga caagctgtga ccgtctccgg gagctgcatg    3660
tgtcagaggt tttcaccgtc atcaccgaaa cgcgcgagac gaaagggcct cgtgatacgc    3720
ctatttttat aggttaatgt catgataata atggtttctt agacgtcagg tggcactttt    3780
cggggaaatg tgcgcggaac ccctatttgt ttatttttct aaatacattc aaatatgtat    3840
ccgctcatga acaataacc ctgataaatg cttcaataat attgaaaaag gaagagtatg     3900
agtattcaac atttccgtgt cgcccttatt cccttttttg cggcattttg ccttcctgtt    3960
tttgctcacc cagaaacgct ggtgaaagta aaagatgctg aagatcagtt gggtgcacga    4020
gtgggttaca tcgaactgga tctcaacagc ggtaagatcc ttgagagttt tcgccccgaa    4080
gaacgttttc caatgatgag cacttttaaa gttctgctat gtggcgcggt attatcccgt    4140
attgacgccg ggcaagagca actcggtcgc cgcatacact attctcagaa tgacttggtt    4200
gagtactcac cagtcacaga aaagcatctt acggatggca tgacagtaag agaattatgc    4260
agtgctgcca taaccatgag tgataacact gcggccaact tacttctgac aacgatcgga    4320
ggaccgaagg agctaaccgc ttttttgcac aacatggggg atcatgtaac tcgccttgat    4380
cgttgggaac cggagctgaa tgaagccata ccaaacgacg agcgtgacac cacgatgcct    4440
gtagcaatgg caacaacgtt gcgcaaacta ttaactggcg aactacttac tctagcttcc    4500
cggcaacaat taatagactg gatggaggcg gataaagttg caggaccact tctgcgctcg    4560
gcccttccgg ctggctggtt tattgctgat aaatctggag ccggtgagcg tgggtctcgc    4620
ggtatcattg cagcactggg gccagatggt aagccctccc gtatcgtagt tatctacacg    4680
acggggagtc aggcaactat ggatgaacga atagacaga tcgctgagat aggtgcctca    4740
ctgattaagc attggtaact gtcagaccaa gtttactcat atatacttta gattgattta    4800
aaacttcatt tttaatttaa aaggatctag gtgaagatcc ttttgataa tctcatgacc    4860
aaaatccctt aacgtgagtt ttcgttccac tgagcgtcag accccgtaga aaagatcaaa   4920
ggatcttctt gagatccttt ttttctgcgc gtaatctgct gcttgcaaac aaaaaaacca    4980
ccgctaccag cggtggtttg tttgccggat caagagctac caactctttt tccgaaggta    5040
actggcttca gcagagcgca gataccaaat actgtccttc tagtgtagcc gtagttaggc    5100
caccacttca agaactctgt agcaccgcct acatacctcg ctctgctaat cctgttacca    5160
gtggctgctg ccagtggcga taagtcgtgt cttaccgggt tggactcaag acgatagtta    5220
ccggataagg cgcagcggtc gggctgaacg gggggttcgt gcacacagcc cagcttggag    5280
cgaacgacct acaccgaact gagataccta cagcgtgagc tatgagaaag cgccacgctt    5340
cccgaaggga gaaaggcgga caggtatccg gtaagcggca gggtcggaac aggagagcgc    5400
```

-continued

```
acgagggagc ttccaggggg aaacgcctgg tatctttata gtcctgtcgg gtttcgccac    5460
ctctgacttg agcgtcgatt tttgtgatgc tcgtcagggg ggcggagcct atggaaaaac    5520
gccagcaacg cggccttttt acggttcctg gccttttgct ggccttttgc tc            5572
```

MUSCLE-SPECIFIC NUCLEIC ACID REGULATORY ELEMENTS AND METHODS AND USE THEREOF

CROSS-REFERENCE TO RELATED APPLICATIONS

This application is a division of U.S. patent application Ser. No. 15/470,367, which is a continuation-in-part of U.S. patent application Ser. No. 15/112,795, which is the National Stage of International Application No. PCT/EP2015/051081, filed Jan. 21, 2015, which claims priority to European Patent Application No. 14151960.3 filed Jan. 21, 2014, the disclosure of each of which is hereby incorporated by cross-reference in its entirety.

FIELD

The present invention relates to nucleic acid regulatory elements that are able to enhance muscle-specific expression of genes, methods employing these regulatory elements and use thereof. The invention further encompasses expression cassettes, vectors and pharmaceutical compositions comprising these regulatory elements. The present invention is particularly useful for applications using gene therapy, more particularly muscle-directed gene therapy, and for vaccination purposes.

BACKGROUND

Muscle is an attractive target for gene therapy. Gene delivery to muscle can be used to augment expression of muscle structural proteins, such as dystrophin and sarcoglycans, e.g. to treat muscular dystrophy. In addition, muscle can be used as a therapeutic platform to express non-muscle secretory/regulatory pathway proteins for diabetes, atherosclerosis, hemophilia, cancer, etc.

Efforts to deliver transgenes to muscle have focused on vectors derived from adenoviruses, retroviruses, lentiviruses, and adeno-associated viruses (AAV), and plasmids. Adenoviral vectors have a relatively large cloning capacity can be produced at high titers and display relatively efficient transduction of muscle. Unfortunately, these vectors can elicit a robust cellular immune response against viral and some transgene proteins. Moreover, they can evoke a rapid activation of the innate immune system that can contribute to a dose-limiting and potentially dangerous inflammatory immune response. Adenoviral vectors do not integrate into the host genome, so their ability to persist for long periods of time is unclear. Retroviral and lentiviral vectors integrate stably into the target cell genome, potentially allowing persistent gene transfer. Whereas lentiviral vectors can transduce both dividing and non-dividing cells, conventional retroviral vectors derived from Moloney murine leukemia virus (MoMLV) can only transduce dividing cells. Consequently, lentiviral vectors can be used to transduce non-dividing skeletal muscle cells, whereas these are refractory to transduction by direct injection with retroviral vectors. Nevertheless, even lentiviral transduction of skeletal muscle is not very efficient. Naked plasmid DNA displays a remarkable ability to transfer genes to muscle. Plasmids display minimal immunogenicity and toxicity, and have an extremely large cloning capacity. The primary disadvantage of plasmids is their relatively poor transfection efficiency under typical delivery protocols. Retention of plasmids is another important consideration.

Adeno-associated viral vector (AAV) is by far the most promising gene delivery vehicle for muscle-directed gene therapy. AAV's natural tropism to muscle cells, their long-term persistent transgene expression, their multiple serotypes, as well as their minimal immune response have made AAV vectors well suited for muscle-directed gene therapy. AAV vector can be delivered into both skeletal muscle and cardiac muscle by means of local, regional, and systemic administrations.

There however remain concerns regarding the efficacy and safety of some gene delivery approaches. The major limiting factors are: insufficient and/or transient transgene expression levels, and inappropriate expression of the transgene in unwanted cell types. In particular, it has been shown that inadvertent transgene expression in antigen-presenting cells (APCs), increases the risk of untoward immune responses against the gene-modified cells and/or the therapeutic transgene product that consequently curtails long-term gene expression.

Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take into account the importance of including evolutionary conserved regulatory motifs into the expression modules, which is particularly relevant for clinical translation.

A computational approach depending upon a modified distance difference matrix (DDM)-multidimensional scaling (MDS) strategy (De Bleser et al. 2007. Genome Biol 8, R83) has proven to be useful for the in silico identification of clusters of evolutionary conserved transcription factor binding site (TFBS) motifs associated with robust tissue-specific expression in liver (WO 2009/130208) and heart (WO2011/051450).

There remains a need in the art for safe and efficient gene delivery to muscle.

SUMMARY

The present inventors have relied on a modified DDM-MDS strategy (De Bleser et al., 2007) combined with an enhanced screening strategy to identify evolutionarily conserved transcription factor binding site (TFBS) motifs associated with highly expressed muscle-specific genes defined herein as nucleic acid regulatory elements. As shown in the experimental section, the inventors could identify nucleic acid regulatory elements that specifically enhanced gene expression in both heart and skeletal muscle, and skeletal muscle-specific nucleic acid regulatory elements. These regulatory elements were subsequently validated in vivo yielding efficient and tissue-specific gene expression. This approach hence, allows for the use of lower and thus safer vector doses, while maximizing therapeutic efficacy.

The invention therefore provides the following aspects:

Aspect 1: a nucleic acid regulatory element for enhancing muscle-specific gene expression comprising, consisting essentially of, or consisting of a functional fragment of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

Aspect 2: the nucleic acid regulatory element according to aspect 1 for enhancing cardiac and skeletal muscle-specific gene expression, comprising a functional fragment of a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

Aspect 3: the nucleic acid regulatory element according to aspect 1 for enhancing skeletal muscle-specific gene expression comprising a functional fragment of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

Aspect 4: the nucleic acid regulatory element according to aspect 1, 2, or 3, comprising, consisting essentially of, or consisting of a sequence selected from the group consisting of: the nucleotide sequence from position 33 to 58 in SEQ ID NO:1; the nucleotide sequence from position 90 to 142 in SEQ ID NO:1; the nucleotide sequence from position 143 to 233 in SEQ ID NO:1; the nucleotide sequence from position 240 to 310 in SEQ ID NO:1; the nucleotide sequence from position 90 to 233 in SEQ ID NO:1; the nucleotide sequence from position 47 to 130 in SEQ ID NO:5; the nucleotide sequence from position 252 to 293 in SEQ ID NO:5; the nucleotide sequence from position 330 to 450 in SEQ ID NO:5; the nucleotide sequence from position 10 to 180 in SEQ ID NO:10 (i.e. SEQ ID NO:37); the nucleotide sequence from position 190 to 240 in SEQ ID NO:10 (i.e. SEQ ID NO:38); the nucleotide sequence from position 241 to 300 in SEQ ID NO:10 (i.e. SEQ ID NO:39); the nucleotide sequence from position 241 to 360 in SEQ ID NO:10 (i.e. SEQ ID NO:41); the nucleotide sequence from position 380 to 420 in SEQ ID NO:10 (i.e. SEQ ID NO:40); or a sequence having at least 95% identity to any of said sequences.

Aspect 5: the nucleic acid regulatory element according to any one of aspects 1 to 4 comprising, consisting essentially of or consisting of a sequence selected from the group consisting of: the nucleotide sequence from position 33 to 310 in SEQ ID NO:1; the nucleotide sequence from position 47 to 450 in SEQ ID NO:5; the nucleotide sequence from position 10 to 420 in SEQ ID NO:10, or a sequence having at least 95% identity to any of said sequences.

Aspect 6: the nucleic acid regulatory element according to any one of aspects 1 to 5, comprising, consisting essentially of, or consisting of a sequence selected from the group consisting of: SEQ ID NO:1, SEQ ID NO:2, SEQ ID NO:3, SEQ ID NO:4, SEQ ID NO:5 SEQ ID NO:6, SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 7: the nucleic acid regulatory element according to any one of aspects 1, 2, or 4 to 6 for enhancing cardiac and skeletal muscle-specific gene expression comprising, consisting essentially of, or consisting of a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences.

Aspect 8: the nucleic acid regulatory element according to any one of aspects 1, 3 to 6 for enhancing skeletal muscle-specific gene expression comprising, consisting essentially of, or consisting of a sequence selected from the group consisting of: SEQ ID NO:7, SEQ ID NO:8 SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 9: the nucleic acid regulatory element according to any one of aspects 1 to 8, comprising, consisting essentially of, or consisting of a sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 10: the nucleic acid regulatory element according to any one of aspects 1, 2, 4 to 7, 9, comprising, consisting essentially of, or consisting of a sequence selected from the group consisting of: SEQ ID NO:17, SEQ ID NO:18, SEQ ID NO:19, SEQ ID NO:20, SEQ ID NO:21, SEQ ID NO:22, a functional fragment thereof comprising SEQ ID NO:1, SEQ ID NO:2, SEQ ID NO:3, SEQ ID NO:4, SEQ ID NO:5, or SEQ ID NO:6, or a sequence having at least 80%, preferably at least 85%, more preferably at least 90%, even more preferably at least 95%, such as 95%, 96%, 97%, 98%, or 99%, identity to any of these sequences.

Aspect 11: the nucleic acid regulatory element according to any one of aspects 1, 3 to 6, 8, or 9, comprising, consisting essentially of, or consisting of a sequence selected from the group consisting of: SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 12: a nucleic acid regulatory element for enhancing muscle-specific gene expression comprising, consisting essentially of, or consisting of the complement of a sequence as defined in any one of aspects 1 to 11.

Aspect 13: a nucleic acid regulatory element for enhancing muscle-specific gene expression hybridizing under stringent conditions to the nucleic acid regulatory element according to any one of aspects 1 to 12.

Aspect 14: the nucleic acid regulatory element according to any one of aspects 1 to 13, having a maximal length of 1000 nucleotides, preferably 800 nucleotides, more preferably 600 nucleotides, such as 550 nucleotides, 500 nucleotides, 450 nucleotides, 400 nucleotides, 350 nucleotides, or 300 nucleotides, still comprising the regulatory element defined by any one of SEQ ID Nos: 1-13, or any one of the functional fragments thereof defined in any one of aspects 3 to 5.

Aspect 15: use of the nucleic acid regulatory element according to any one aspects 1 to 14 in a nucleic acid expression cassette, or a vector, more particularly for enhancing muscle-specific expression of said nucleic acid expression cassette or vector.

Aspect 16: a nucleic acid expression cassette comprising at least one, such as one, two, three, four, five or more, nucleic acid regulatory element according to any one of aspects 1 to 14, operably linked to a promoter.

Aspect 17: the nucleic acid expression cassette according to aspect 16, wherein the nucleic acid regulatory element is operably linked to a promoter and a transgene.

Aspect 18: the nucleic acid expression cassette according any one of aspects 16 or 17, wherein the promoter is a muscle-specific promoter, preferably the promoter from the desmin (DES) gene such as the murine DES promoter having SEQ ID NO:16, the human 1.0 kb DES promoter having SEQ ID NO:4 or the human 1.4 kb DES promoter having SEQ ID NO:48, or the SPc5-12 promoter such as the synthetic SPc5-12 promoter having SEQ ID NO: 53.

Aspect 19: the nucleic acid expression cassette according to any one of aspects 17 or 18, wherein the transgene encodes a therapeutic protein or an immunogenic protein, preferably the transgene encodes alpha-glucosidase (GAA) or myotubularin 1 (MTM1) more preferably the transgene encodes a codon-optimized version of GAA or MTM1, even more preferably the transgene comprises a codon-optimized version of the human GAA gene having SEQ ID NO:50 or a codon-optimized version of the human MTM1 gene having SEQ ID NO:52.

Aspect 20: the nucleic acid expression cassette according to any one of aspects 17 to 19, wherein the transgene encodes a secretable protein or a structural protein, such as dystrophin or sarcoglycan.

Aspect 21: the nucleic acid expression cassette according to any one of aspects 16 to 20, further comprising an intron, preferably the Minute Virus of Mouse (MVM) intron, more preferably the MVM intron having SEQ ID NO:54.

Aspect 22: the nucleic acid expression cassette according to any one of aspects 16 to 21, further comprising a polyadenylation signal, preferably the Simian Virus 40 (SV40) polyadenylation signal, more preferably the polyadenylation signal having SEQ ID NO:46.

Aspect 23: a vector comprising the nucleic acid regulatory element according to any one of aspects 1 to 14, or the nucleic acid expression cassette according to any one of aspects 16 to 22.

Aspect 24: the vector according to aspect 23, which is a viral vector, preferably an adeno-associated viral (AAV) vector, more preferably an AAV9 vector.

Aspect 25: the vector according to aspect 23, which is a non-viral vector, preferably a plasmid, a minicircle or a transposon-based vector, such as a PiggyBac-based vector or a Sleeping Beauty-based vector.

Aspect 26: a pharmaceutical composition comprising the nucleic acid expression cassette according to any one of aspects 16 to 22, or the vector according to any one of aspects 23 to 25, and a pharmaceutically acceptable carrier.

Aspect 27: the nucleic acid regulatory element according to any one of aspects 1 to 14, the nucleic acid expression cassette according to any one of aspects 16 to 22, the vector according to any one of aspects 23 to 25, or the pharmaceutical composition according to aspect 26 for use in medicine.

Aspect 28: the nucleic acid regulatory element according to any one of aspects 1 to 14, the nucleic acid expression cassette according to any one of aspects 16 to 22, the vector according to any one of aspects 23 to 25, or the pharmaceutical composition according to aspect 26 for use in gene therapy, preferably muscle-directed gene therapy.

Aspect 29: the nucleic acid regulatory element, the nucleic acid expression cassette, the vector, or the pharmaceutical composition according for use according to aspect 28, wherein the gene therapy is neuromuscular disorders and heart diseases, such as Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystrophic Myotonia (Schwartz-Jampel Syndrome), Chudley Sydrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy), Welander's Distal Myopathy, Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barré Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type 1), Zebra Body Myopathy, Nuclear Envelop Disease, muscular dystrophy (e.g. Duchenne muscular dystrophy (DMD)/Becker muscular dystrophy (BMD)), motor neuron diseases (MND), such as e.g. Charcot-Marie-Tooth Diseases (CMT) such as CMT Type I, CMT Type II, CMT Type III (Dejerine-Sottas Disease), CMT Type IV (Refsum's Disease), CMT Type V, spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes.

Aspect 30: a method for gene therapy comprising administering to a subject an effective amount of
a) the nucleic acid regulatory element according to aspect 1;
b) a nucleic acid expression cassette comprising at least one nucleic acid regulatory element according to aspect 1, operably linked to a promoter and a transgene;
c) a vector comprising the nucleic acid regulatory element according to aspect 1 or the nucleic acid expression cassette; or
d) a pharmaceutical composition comprising the nucleic acid expression cassette or vector and a pharmaceutically acceptable carrier.

Aspect 31: a method of treating a subject requiring restoration of GAA expression or increase of GAA expression comprising administering to said subject an effective amount of a) a nucleic acid expression cassette comprising at least one nucleic acid regulatory element according to aspect 1, operably linked to a promoter and a GAA transgene;
b) a vector comprising the nucleic acid expression cassette according to a); or
c) a pharmaceutical composition comprising the nucleic acid expression cassette of a) or vector of b) and a pharmaceutically acceptable carrier.

Aspect 32: the method according to aspect 31, wherein said subject is suffering from Pompe disease or Duchenne muscular dystrophy.

Aspect 33: the method according to aspect 32, wherein said GAA transgene is the codon-optimised GAA gene defined by SEQ ID NO:50.

Aspect 34: a method of treating a subject requiring restoration of MTM1 expression or increase of GAA expression comprising administering to a subject an effective amount of
a) a nucleic acid expression cassette comprising at least one nucleic acid regulatory element according to aspect 1, operably linked to a promoter and the MTM1 transgene;
b) a vector comprising the nucleic acid expression cassette of a); or
c) a pharmaceutical composition comprising the nucleic acid expression cassette of a) or vector of b) and a pharmaceutically acceptable carrier.

Aspect 35: the method according to aspect 34, wherein said subject is suffering from myotubular myopathy or Duchenne muscular dystrophy.

Aspect 36: the method according to aspect 35, wherein said MTM1 transgene is the codon-optimised MTM1 gene defined by SEQ ID NO:52.

Aspect 37: the nucleic acid regulatory element according to any one of aspects 1 to 14, the nucleic acid expression cassette according to any one of aspects 16 to 22, the vector according to any one of aspects 23 to 25, or the pharmaceutical composition according to aspect 26 for use as a vaccine, preferably a prophylactic vaccine, or for use in vaccination therapy, preferably prophylactic vaccination.

Aspect 38. a method of vaccination comprising administering to a subject an effective amount of a) the nucleic acid regulatory element according to aspect 1;
b) a nucleic acid expression cassette comprising at least one nucleic acid regulatory element according to aspect 1, operably linked to a promoter and a transgene;
c) a vector comprising the nucleic acid regulatory element according to aspect 1 or the nucleic acid expression cassette; or
d) a pharmaceutical composition comprising the nucleic acid expression cassette or vector and a pharmaceutically acceptable carrier.

Aspect 39: a method, preferably an in vitro or ex vivo method, for expressing a transgene product in muscle cells, preferably heart muscle cells and/or skeletal muscle cells, comprising:
introducing the nucleic acid expression cassette according to any one of aspects 16 to 22, or the vector according to any one of aspects 23 to 25 into the muscle cells;
expressing the transgene product in the muscle cells.

Aspect 40: a codon-optimised human GAA gene as defined in SEQ ID NO: 50

Aspect 41: the codon-optimised human GAA gene for use in gene therapy, more particularly for use in treatment of diseases requiring restoration of GAA expression or increase of GAA expression. More preferably, said disease is Pompe disease or Duchenne muscular dystrophy.

Aspect 42: a codon-optimised human MTM1 gene as defined in SEQ ID NO: 52

Aspect 43: the codon-optimised human MTM1 gene for use in gene therapy, more particularly for use in treatment of diseases requiring restoration of MTM1 expression or increase of MTM expression. More preferably, said disease is MTM disease or Duchenne muscular dystrophy.

Aspect 44: a vector comprising the codon-optimised human GAA gene of aspect 40.

Aspect 45: a vector comprising the codon-optimised human MTM1 gene of aspect 42.

Aspect 46: a pharmaceutical composition comprising the vector according to aspect 44 or 45.

Aspect 47: a vector according to any one of aspect 23, comprising the codon-optimised human GAA gene of aspect 40.

Aspect 48: a vector according to any one of aspect 23, comprising the codon-optimised human MTM1 gene of aspect 42.

BRIEF DESCRIPTION OF DRAWINGS

FIG. 2: Nucleotide sequences of the cardiac and skeletal muscle-specific regulatory elements CSk-SH1 (A, SEQ ID NO: 1), CSk-SH2 (B, SEQ ID NO: 2), CSk-SH3 (C, SEQ ID NO: 3), CSk-SH4 (D, SEQ ID NO: 4), CSk-SH5 (E, SEQ ID NO: 5), and CSk-SH6 (F, SEQ ID NO: 6).

FIG. 6: Transduction efficiency in different organs of mice injected with AAV9sc-CSk-SH1-Des-Luc2 (CSk-SH1) (A) or AAV9sc-Sk-SH5-Des-Luc2 (CSk-SH5) (B). AAV copy number relative to 100 ng of genomic DNA was determined for both constructs at a dose of 5×10$^9$ vg/mouse.

FIG. 7: Nucleotide sequences of the muscle-specific regulatory elements Sk-SH1 (A, SEQ ID NO: 7), Sk-SH2 (B, SEQ ID NO: 8), Sk-SH3 (C, SEQ ID NO:9), Sk-SH4 (D, SEQ ID NO: 10), Sk-SH5 (E, SEQ ID NO: 11), Sk-SH6 (F, SEQ ID NO: 12), Sk-SH7 (G, SEQ ID NO: 13).

FIG. 13: Transduction efficiency in different organs of mice injected with AAV9sc-Sk-SH4-Des-MVM-Luc-pA vector (A) or AAV9sc-Sk-SH1-Des-MVM-Luc-pA vector (B). AAV copy number relative to 100 ng of genomic DNA was determined for both vectors (n=3).

FIG. 15: Chromatin immunoprecipitation (CHIP) assay for heart (A, C) and muscle (B, D) tissue of mice injected with AAV9sc-Sk-SH4-Des-Luc (A, B) or AAV9sc-CSk-SH5-Des-Luc (C,D) (5×10 vg/mouse). Antibodies specific for the transcription factors CEBP, SRF and MEF2 were used. PCR primers were designed to amplify a region of Sk-SH4 that binds CEBP and SRF, or a region of CSk-SH5 that bind CEBP and MEF2, and as negative control (−) an un-transcribed region on chromosome 17 was used. Binding events for 10$^3$ cells were determined for each of the corresponding primer pairs. Results are presented as mean±standard error of the mean. Significant difference compared to the negative control is indicated (t-test, *P≤0.05).

FIG. 18: (A) Hematoxylin/eosin staining of gastrocnemius muscle tissues of MDX/SCID mice injected with PBS (a, control), AAVss-Sk-SH4-Des-MVM-FST-2A-Luc (b), AAVss-Sk-SH4-Des-MVM-MD1 (c) or the combination of AAVss-Sk-SH4-Des-MVM-MD1 and AAVss-Sk-SH4-Des-MVM-FST-2A-Luc (d). (B) Quantification of centrally nucleated cells in wild-type C57Bl/6 mice, untreated MDX/SCID mice (control), and MDX/SCID mice injected with AAVss-Sk-SH4-Des-MVM-MD1 (MD1), AAVss-Sk-SH4-Des-MVM-FST-2A-Luc (FST) or both (FST+MD1) therapeutic vectors. Statistical analysis was performed on H&E-stained transversally transected myofibers of gastronemius muscle embedded in paraffin. ***≤0.0001 *≤0.001 *≤0.05

FIG. 20 shows schematic representations of self-complementary (sc) AAV constructs disclosed herein, which comprise the luciferase (Luc) transgene regulated by (a) the cardiac and skeletal muscle-specific desmin (Desmin) promoter, (b) the SPc5-12 promoter, (c) the cytomegalovirus (CMV) promoter, (d) the Desmin promoter operably linked to a muscle-specific (Sk-SH) nucleic acid regulatory element cloned upstream of the Desmin promoter, or (e) the SPc5-12 promoter operably linked to a muscle-specific (Sk-SH) nucleic acid regulatory element cloned upstream of the SPc5-12 promoter. Expression cassettes (a), (b), (d) and (e) further comprise the Minute Virus of Mouse (MVM) intron and a polyadenylation signal (pA). The expression cassettes are flanked by inverted terminal repeats (ITR).

FIG. 22: Nucleotide sequence of (a) mouse desmin promotor (SEQ ID NO: 16), (b) human desmin promotor 1.0 kb (SEQ ID NO: 47), (c) human desmin promotor 1.4 kb (SEQ ID NO: 48) and (d) Spc5-12 promoter (SEQ ID NO:53).

FIG. 23: In vivo comparison of desmin promoters. Comparison of the luciferase expression induced by AAV9-luciferase vectors containing Sk-SH4 in combination with different desmin promoters: Sk-SH4-hDES1.4 kb, Sk-SH4-hDES1.0 kb or Sk-SH4-mDES quantified as Photons signal, in murine Biceps (A), diaphragm (B), gastrocnemius (C), heart (D), quadriceps (E), tibialis (F) and triceps (G).

FIG. 24: Nucleotide sequence of (a) human Glucosidase alpha, acid (hGAA) coding sequence (SEQ ID NO: 49) or (b) its codon-optimised variant (hGAAco) according to the present invention (SEQ ID NO: 50) and of (c) human myotubularin 1 (hMTM1) coding sequence (SEQ ID NO: 51) or (d) its codon-optimised variant (hMTM1co) according to the present invention (SEQ ID NO: 52).

DESCRIPTION

Figure 1:
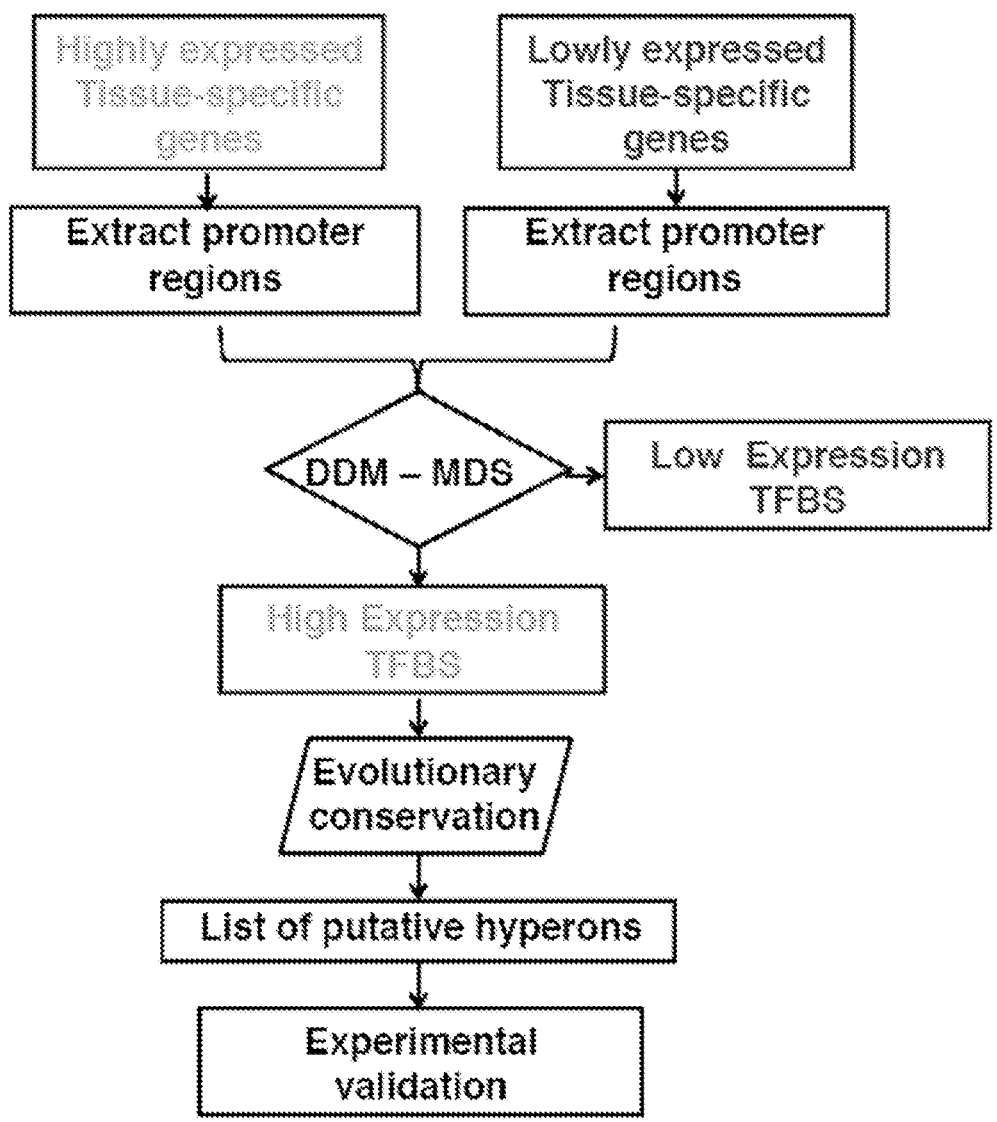
FIG. 1: Flow diagram of the identification and validation of nucleic acid regulatory elements. A computational approach was used to identify the nucleic acid regulatory elements involving the following steps: (1) identification of tissue-specific genes that are highly expressed e.g. based on statistical analysis of micro-array expression data of normal human tissues; (2) extraction of the corresponding promoter sequences from publicly available databases; (3) identification of the regulatory modules and the transcription factor binding sites (TFBS) they contain (4) Next, the genomic context of the highly expressed genes was searched for evolutionary conserved dusters of TFBS (i.e. nucleic acid regulatory elements). The identified nucleic acid regulatory elements were de novo designed and validated in vivo by testing whether inclusion in a construct increases expression of a reporter gene.

As used herein, the singular forms "a", "an", and "the" include both singular and plural referents unless the context dearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter ala to well-known textbooks, including, e.g., "Molecular Cloning: A Laboratory Manual, 2nd Ed." (Sambrook et al., 1989), "Current Protocols in Molecular Biology" (Ausubel et al., 1987).

In an aspect, the invention relates to a nucleic acid regulatory element for enhancing muscle-specific gene expression comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of a sequence selected from the group consisting of: SEQ ID NO:1. SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof (i.e. a functional fragment of a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, or of a sequence having high percentage sequence identity to any of said sequences).

A 'regulatory element' as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a muscle-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory element hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter all pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or party or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for transcription factor 3, also known as TCF3 or E2A; binding sites for nuclear factor I, also known as NF1; binding sites for CCAAT-enhancer-binding protein, also known as C/EBP; binding sites for myogenic differentiation, also known as MyoD; binding sites for sterol regulatory element-binding protein, also known as SREBP; binding sites for leukemia/lymphoma-related factor, also known as LRF; binding sites for protein 53, also known as p53; binding sites for hepatocyte nuclear factor 3-alpha, also known as HNF3a; binding sites for hepatocyte nuclear factor 3-beta, also known as HNF3b; binding sites for hepatocyte nuclear factor 4, also known as HNF4; binding sites for myocyte-specific enhancer factor 2A, also known as MEF2A or RSRFC4; binding sites for peroxisome proliferator-activated receptor, also known as PPAR; binding sites for serum response factor, also known as SRF: binding sites for transcription activator-like protein 1b, also known as Tal1_b. Transcription factor binding sites may be found in databases such as Transfac®.

Sequences disclosed herein may be part of sequences of regulatory elements capable of controlling transcription of muscle-specific genes in vivo, in particular controlling the following genes: desmin also known as DES, CSM1 or CSM2; actinin, alpha 2 also known as ACTN2 or CMD1AA; filamin-C (FLNC) also known as actin-binding-like protein (ABLP), filamin-2 (FLN2), ABP-280, ABP280A, ABPA, ABPL, MFM5, or MPD4; sarcoplasmic/endoplasmic reticulum calcium ATPase 1 also known as ATP2A1, ATP2A, or SERCA1; troponin I type 1 (slow skeletal muscle) also known as TNNI1, SSTNI, or TNN1; myosin light chain phosphorylatable fast skeletal muscle (MYLPF); myosin-1 also known as MYH1, MYHSA1, MYHa; MyHC-2X/D, or MyHC-2x; tropomyosin alpha-3 chain also known as TPM3, CFTD, NEM1, OK/SW-cl.5, TM-5, TM3, TM30, TM30 nm, TM5, TPMsk3, TRK, hTM5, or hscp30; and ankyrin repeat domain-containing protein 2 also known as ANKRD2, or ARPP. Accordingly, in embodiments, the nucleic acid regulatory elements disclosed herein comprise a sequence from Des regulatory elements, i.e. regulatory elements that control expression of the Des gene in vivo, e.g. regulatory elements comprising SEQ ID NO:1, SEQ ID NO: 17, SEQ ID NO:2, SEQ ID NO:18, or functional fragments thereof. In embodiments, the nucleic acid regulatory elements disclosed herein comprise a sequence from ACTN2 regulatory elements, i.e. regulatory elements that control expression of the ACTN2 gene in vivo, e.g. regulatory elements comprising SEQ ID NO:3, SEQ ID NO:19, SEQ ID NO:4 SEQ ID NO:20, or functional fragments thereof. In embodiments, the nucleic acid regulatory elements disclosed herein comprise a sequence from FLNC regulatory elements, i.e. regulatory elements that control expression of the FLNC gene in vivo, e.g. regulatory elements comprising SEQ ID NO:5, SEQ ID NO:21, SEQ ID NO:6, SEQ ID NO:22, or functional fragments thereof. In embodiments, the nucleic acid regulatory elements disclosed herein comprise a sequence from ATP2A1 regulatory elements, i.e. regulatory elements that control expression of the ATP2A1 gene in vivo, e.g. regulatory elements comprising SEQ ID NO:7, SEQ ID NO:23, or functional fragments thereof. In embodiments, the nucleic acid regulatory elements disclosed herein comprise a sequence from TNNI1 regulatory elements, i.e. regulatory elements that control expression of the TNNI1 gene in vivo, e.g. regulatory elements comprising SEQ ID NO:8, SEQ ID NO:24, SEQ ID NO:9, SEQ ID NO:25, or functional fragments thereof. In embodiments, the nucleic acid regulatory elements disclosed herein comprise a sequence from MYLPF regulatory elements, i.e. regulatory elements that control expression of the MYLPF gene in vivo, e.g. regulatory elements comprising SEQ ID NO:10, SEQ ID NO:26, or functional fragments thereof, such as regulatory elements comprising or consisting of SEQ ID NO:37, SEQ ID NO:38, SEQ ID NO:39, SEQ ID NO:40 or SEQ ID NO:41. In embodiments, the nucleic acid regulatory elements disclosed herein comprise a sequence from MYH1 regulatory elements, i.e. regulatory elements that control expression of the MYH1 gene in vivo, e.g. regulatory elements comprising SEQ ID NO:11, SEQ ID NO:27, or functional fragments thereof. In embodiments, the nucleic acid regulatory elements disclosed herein comprise a sequence from TPM3 regulatory elements, i.e. regulatory elements that control expression of the TPM3 gene in vim, e.g. regulatory elements comprising SEQ ID NO:12, SEQ ID NO:28, or functional fragments thereof. In embodiments, the nucleic acid regulatory elements disclosed herein comprise a sequence from ANKRD2 regulatory elements, i.e. regulatory elements that control expression of the ANKRD2 gene in vivo, e.g. regulatory elements comprising SEQ ID NO:13, SEQ ID NO:29, or functional fragments thereof.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term 'functional fragment' as used in the application refers to fragments of the regulatory element sequences disclosed herein that retain the capability of regulating muscle-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

"Muscle-specific expression" as used in the application, refers to the preferential or predominant expression of a (trans)gene (as RNA and/or polypeptide) in muscles or muscle tissue, as compared to other (i.e. non-muscle) tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within muscle. According to a particular embodiment, muscle-specific expression entails that there is no 'leakage' of expressed gene product to other organs or tissue than muscle, such as lung, liver, brain, kidney and/or spleen.

As used herein "cardiac and skeletal muscle-specific expression" refers to the preferential or predominant expression of a (trans)gene in heart, in particular heart muscle, and skeletal muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within heart and skeletal muscle. Thus, according to particular embodiments, less than 10%, less than 5%, less than 2% or even less than 1% of the (trans) gene expression occurs in an organ or tissue other than heart and skeletal muscle.

As used herein "skeletal muscle-specific expression" refers to the preferential or predominant expression of a (trans)gene in skeletal muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within skeletal muscle. Thus, according to particular embodiments, less than 10%, less than 5%, less than 2% or even less than 1% of the (trans) gene expression occurs in an organ or tissue other than skeletal muscle.

The same applies mutatis mutandis for myocyte-specific and myoblast-specific expression, which may be considered as a particular form of muscle-specific expression. Throughout the application, where muscle-specific is mentioned in the context of expression, myocyte-specific and myoblast-specific expression are also explicitly envisaged. Similarly, where cardiac and skeletal muscle-specific expression is used in the application, cardiomyocyte and skeletal myocyte-specific expression and cardiac myoblast and skeletal myoblast-specific expression is also explicitly envisaged. Similarly, where skeletal muscle-specific expression is used in the application, skeletal myocyte-specific and skeletal myoblast-specific expression is also explicitly envisaged.

As used herein, the terms "heart muscle" or "cardiac muscle" refer to the autonomically regulated, striated muscle type found in the heart.

As used herein, the term "skeletal muscle" refers to the voluntarily controlled, striated muscle type that is attached to the skeleton. Non-limiting examples of skeletal muscle include the biceps, the triceps, the quadriceps, the tibialis interior, and the gastrocnemius muscle.

The term "myocyte," as used herein, refers to a cell that has been differentiated from a progenitor myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The term "myoblast" as used herein, refers to an embryonic cell in the mesoderm that differentiates to give rise to a muscle cell or myocyte. The term includes cells in vivo and cells cultured ex vivo regardless of whether such cells are primary or passaged.

In embodiments, the invention relates to a nucleic acid regulatory element for enhancing muscle-specific gene expression comprising, consisting essentially of, or consisting of a functional fragment of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8 SEQ ID NO:9, SEQ ID NO:10, SEQ ID NO:11, SEQ ID NO:12 SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In further embodiments, the invention relates to a nucleic acid regulatory element for enhancing cardiac and skeletal muscle-specific gene expression comprising a functional fragment of a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In yet further embodiments, the invention relates to a nucleic acid regulatory element for enhancing cardiac and skeletal muscle-specific gene expression comprising a functional fragment of a sequence selected from the group consisting of: SEQ ID NO:1 and SEQ ID NO:5, or a sequence having at least 80%, preferably at least 85%, more preferably at least 90%, even more preferably at least 95%, such as 95%, 96%, 97%, 98%, or 99%, identity to any of these sequences, wherein said functional fragment consists of the nucleotide sequence from position 33 to 58 in SEQ ID NO:1; the nucleotide sequence from position 90 to 142 in SEQ ID NO:1; the nucleotide sequence from position 143 to 233 in SEQ ID NO:1; the nucleotide sequence from position 240 to 310 in SEQ ID NO:1; the nucleotide sequence from position 90 to 233 in SEQ ID NO:1; the nucleotide sequence from position 47 to 130 in SEQ ID NO:5; the nucleotide sequence from position 252 to 293 in SEQ ID NO:5; or the nucleotide sequence from position 330 to 450 in SEQ ID NO:5.

In further embodiments, the invention relates to a nucleic acid regulatory element for enhancing skeletal muscle-specific gene expression comprising a functional fragment of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In yet further embodiments, the invention relates to a nucleic acid regulatory element for enhancing skeletal muscle-specific gene expression comprising a functional fragment of SEQ ID NO:10 or a sequence having at least 80%, preferably at least 85%, more preferably at least 90%, even more preferably at least 95%, such as 95%, 96%, 97%, 98%, or 99%, identity to SEQ ID NO:10, wherein said functional fragment consists of the nucleotide sequence from position 10 to 180 in SEQ ID NO:10; the nucleotide sequence from position 190 to 240 in SEQ ID NO:10; the nucleotide sequence from position 241 to 300 in SEQ ID NO:10; the nucleotide sequence from position 241 to 360 in SEQ ID NO:10; or the nucleotide sequence from position 380 to 420 in SEQ ID NO:10.

In certain embodiments, the nucleic acid regulatory elements of the invention comprise or consist of a sequence selected from the group consisting of: the nucleotide sequence from position 33 to 58 in SEQ ID NO:1; the nucleotide sequence from position 90 to 142 in SEQ ID NO:1; the nucleotide sequence from position 143 to 233 in SEQ ID NO:1; the nucleotide sequence from position 240 to 310 in SEQ ID NO:1; the nucleotide sequence from position 90 to 233 in SEQ ID NO:1; the nucleotide sequence from position 47 to 130 in SEQ ID NO:5; the nucleotide sequence from position 252 to 293 in SEQ ID NO:5; the nucleotide sequence from position 330 to 450 in SEQ ID NO:5; the nucleotide sequence from position 10 to 180 in SEQ ID NO:10; the nucleotide sequence from position 190 to 240 in SEQ ID NO:10; the nucleotide sequence from position 241 to 300 in SEQ ID NO:10; the nucleotide sequence from position 241 to 360 in SEQ ID NO:10; the nucleotide sequence from position 380 to 420 in SEQ ID NO:10; or a sequence having at least 95% identity to any of said sequences.

In certain embodiments, the nucleic acid regulatory elements of the invention comprise or consist of a sequence selected from the group consisting of the nucleotide sequence from position 33 to 310 in SEQ ID NO:1; the nucleotide sequence from position 47 to 450 in SEQ ID NO:5; the nucleotide sequence from position 10 to 420 in SEQ ID NO:10, or a sequence having at least 95% identity to any of said sequences.

In further embodiments, the invention provides a nucleic acid regulatory element for enhancing muscle-specific gene expression comprising, consisting essentially of, or consisting of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

In yet further embodiments, the invention provides for a nucleic acid regulatory element for enhancing cardiac and skeletal muscle-specific gene expression comprising a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences.

In yet further embodiments, the invention provides for a nucleic acid regulatory element for enhancing skeletal muscle-specific gene expression comprising, consisting essentially of, or consisting of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

In further embodiments, the nucleic acid regulatory elements for enhancing muscle-specific gene expression, comprise, consist essentially of, or consist of a sequence selected from the group consisting of: SEQ ID NO:17, SEQ ID NO:18, SEQ ID NO:19, SEQ ID NO:20 SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

In further embodiments, the nucleic acid regulatory elements for enhancing cardiac and skeletal muscle-specific gene expression comprise, consist essentially of, or consist of a sequence selected from the group consisting of: SEQ ID NO:17, SEQ ID NO:18, SEQ ID NO:19, SEQ ID NO:20, SEQ ID NO:21, SEQ ID NO:22, a functional fragment thereof comprising SEQ ID NO:1, SEQ ID NO:2, SEQ ID NO:3, SEQ ID NO:4, SEQ ID NO:5, or SEQ ID NO:6, or a sequence having at least 80%, preferably at least 85%, more preferably at least 90%, even more preferably at least 95%, such as 95%, 96%, 97%, 98%, or 99%, identity to any of these sequences.

In further embodiments, the nucleic acid regulatory elements for enhancing skeletal muscle-specific gene expression comprise, consist essentially of, or consist of a sequence selected from the group consisting of: SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

It is also possible to make nucleic acid regulatory elements that comprise an artificial sequence by combining two or more identical or different sequences disclosed herein or functional fragments thereof. Accordingly, in certain embodiments a nucleic acid regulatory element for enhancing muscle-specific gene expression is provided comprising at least two sequences selected from the group consisting of: SEQ ID NO:1, SEQ ID NO:2, SEQ ID NO:3, SEQ ID NO:4, SEQ ID NO:5, SEQ ID NO:6, , SEQ ID NO:7, SEQ ID NO:8, SEQ ID NO:9, SEQ ID NO:10, SEQ ID NO:11, SEQ ID NO:12, SEQ ID NO:13, a sequence having at least 90%, preferably at least 95%, such as 95%, 96%, 97%, 98%, or 99%, identity to any of these sequences, or a functional fragment thereof.

Also disclosed herein is a nucleic acid regulatory element for enhancing muscle-specific gene expression, in particular cardiac and skeletal muscle-specific gene expression, comprising at least two sequences selected from the group consisting of: SEQ ID NO:1. SEQ ID NO:2, SEQ ID NO:3, SEQ ID NO:4, SEQ ID NO:5, SEQ ID NO:6, a sequence having at least 90%, preferably at least 95%, such as 95%, 96%, 97%, 98%, or 99%, identity to any of these sequences, or a fragment thereof.

Also disclosed herein is a nucleic acid regulatory element for enhancing muscle-specific gene expression, in particular skeletal muscle-specific gene expression, comprising at least two sequences selected from the group consisting of: SEQ ID NO:7, SEQ ID NO:8, SEQ ID NO:9, SEQ ID NO:10, SEQ ID NO:11, SEQ ID NO:12, SEQ ID NO:13, a sequence having at least 90%, preferably at least 95%, such as 95%, 96%, 97%, 98%, or 99%, identity to any of these sequences, or a fragment thereof.

For example, disclosed herein is a nucleic acid regulatory element comprising, consisting essentially of, or consisting of SEQ ID NO:1 and SEQ ID NO:5; a nucleic acid regulatory element comprising, consisting essentially of, or consisting of SEQ ID NO:1 and SEQ ID NO:10; a nucleic acid regulatory element comprising, consisting essentially of, or consisting of SEQ ID NO:1, SEQ ID NO:5, and SEQ ID NO:10; a nucleic acid regulatory element comprising, consisting essentially of, or consisting of 2, 3, 4, or 5 repeats, e.g. tandem repeats, of SEQ ID NO:1; a nucleic acid regulatory element comprising, consisting essentially of, or consisting of 2, 3, 4, or 5 repeats, e.g. tandem repeats, of SEQ ID NO:5; or a nucleic acid regulatory element comprising, consisting essentially of, or consisting of 2, 3, 4, or 5 repeats, e.g. tandem repeats, of SEQ ID NO:10.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing muscle-specific gene expression, in particular cardiac and skeletal muscle-specific gene expression, comprising binding sites for E2A, HNH1, NF1, C/EBP, LRF, MyoD, and SREBP; or for E2A, NF1, p53, C/EBP, LRF, and SREBP; or for E2A, HNH1, HNF3a, HNF3b, NF1, C/EBP, LRF, MyoD, and SREBP; or E2A, HNF3a, NF1, C/EBP, LRF, MyoD, and SREBP; or for E2A, HNF3a, NF1, CEBP, LRF, MyoD, and SREBP; or for HNF4, NF1, RSRFC4, C/EBP, LRF, and MyoD, or NF1, PPAR, p53, C/EBP, LRF, and MyoD. For example, also disclosed herein is a nucleic acid regulatory element for enhancing muscle-specific gene expression, in particular skeletal muscle-specific gene expression, comprising binding sites for E2A, NF1, SRFC, p53, C/EBP, LRF, and MyoD; or for E2A, NF1, C/EBP, LRF, MyoD, and SREBP; or for E2A, HNF3a, CEBP, LRF, MyoD, SEREBP, and Tal1_b; or for E2A, SRF, p53, C/EBP, LRF, MyoD, and SREBP; or for HNF4, NF1, RSRFC4, C/EBP, LRF, and SREBP; or for E2A, HNF3a, HNF3b, NF1, SRF, C/EBP, LRF, MyoD, and SREBP; or for E2A, CEBP, and MyoD. In further examples, these nucleic acid regulatory elements comprise at least two, such as 2, 3, 4, or more copies of one or more of the recited TFBSs.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing muscle-specific gene expression comprising, consisting essentially of, or consisting of the complement of a sequence described herein, in particular a sequence selected from the group consisting of: SEQ ID NO:1, SEQ ID NO:2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof.

Also disclosed herein is a nucleic acid regulatory element for enhancing muscle-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 90%, preferably at least 95%, such as 95%, 96%, 97%, 98%, or 99%, identity to any of these sequences, a functional fragment thereof, or to its complement. Said nucleic acid regulatory elements do not need to be of equal length as the sequence they hybridize to. In preferred embodiments, the size of said hybridizing nucleic acid regulatory element does not differ more than 25% in length, in particular 20% in length, more in particular 15% in length, most in particular 10% in length from the sequence it hybridizes to.

The expression 'hybridize under stringent conditions', refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 1500 nucleotides or less, 1000 nucleotides or less, 900 nucleotides or less, 800 nucleotides or less, 700 nucleotides or less, more preferably 600 nucleotides or less, such as 550 nucleotides or less, 500 nucleotides or less, 450 nucleotides or less, 400 nucleotides or less, 350 nucleotides or less, or 300 nucleotides or less (i.e. the nucleic acid regulatory element has a maximal length of 1500 nucleotides, 1000 nucleotides, 900 nucleotides, 800 nucleotides, 700 nucleotides, preferably 600 nucleotides, such as 550 nucleotides, 500 nucleotides, 450 nucleotides, 400 nucleotides, 350 nucleotides, or 300 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 200 nucleotides, 250 nucleotides, 300 nucleotides, 350 nucleotides or 400 nucleotides.

In certain embodiments, the invention provides for a nucleic acid regulatory element of 1000 nucleotides or less, preferably 600 nucleotides or less, such as 550 nucleotides or less, 500 nucleotides or less, 450 nucleotides or less, 400 nucleotides or less, 350 nucleotides or less, or 300 nucleotides or less, for enhancing muscle-specific gene expression comprising a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof.

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when property oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein. In alternative embodiments, the nucleic acid expression cassette comprises two or more, such as, e.g., 2, 3, 4, 5, 6, 7, 8, 9, or 10, nucleic acid regulatory elements as described herein, i.e. they are combined modularly to enhance their regulatory (and/or enhancing) effect.

In further embodiments, at least two of the two or more nucleic acid regulatory elements are identical or substantially identical. In yet further embodiments, all of the two or more regulatory elements are identical or substantially identical. The copies of the identical or substantially identical nucleic acid regulatory elements may be provided as tandem repeats in the nucleic acid expression cassette. In alternative further embodiments, at least two of the two or more nucleic acid regulatory elements are different from each other. The nucleic acid expression cassette may also comprise a combination of identical and substantially identical nucleic acid regulatory elements and non-identical nucleic acid regulatory elements.

For example, the nucleic acid expression cassette may comprise a nucleic acid regulatory element comprising SEQ ID NO:1, and a nucleic acid regulatory element comprising SEQ ID NO:5; or the nucleic acid expression cassette may comprise a nucleic acid regulatory element comprising SEQ ID NO:1 and a nucleic acid regulatory element comprising SEQ ID NO:10; or the nucleic acid expression cassette may comprise a nucleic acid regulatory element comprising SEQ ID NO:1, a nucleic acid regulatory element comprising SEQ ID NO:5, and a nucleic acid regulatory element comprising SEQ ID NO:1; or the nucleic acid regulatory element may comprise 2, 3, 4, or 5 nucleic acid regulatory elements comprising SEQ ID NO:1; or the nucleic acid regulatory element may comprise 2, 3, 4, or 5 nucleic acid regulatory elements comprising SEQ ID NO:5; or the nucleic acid regulatory element may comprise 2, 3, 4, or 5 nucleic acid regulatory elements comprising SEQ ID NO:10.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of muscle-specific, in particular cardiac and skeletal muscle-specific or skeletal muscle-specific, expression in vivo (and/or in myoblasts, myocytes, or muscle-derived cell lines, in particular cardiac and skeletal or skeletal myoblasts, cardiac and skeletal or skeletal myocytes, or cardiac and skeletal muscle or skeletal muscle-derived cell lines in vitro) of the transgene, and/or (2) can increase the level of expression of the transgene in muscle, in particular cardiac and skeletal muscle or skeletal muscle (and/or in myoblasts, myocytes, or muscle-derived cell lines, in particular cardiac and skeletal or skeletal myoblasts, cardiac and skeletal or skeletal myocytes, or cardiac and skeletal muscle or skeletal muscle-derived cell lines in vitro).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

The enrichment in muscle-specific TFBS in the nucleic acid regulatory elements disclosed herein in principle allows the regulatory elements to direct muscle-specific expression even from a promoter that itself is not muscle-specific. Hence, the regulatory elements disclosed herein can be used in nucleic acid expression cassettes in conjunction with their natural promoter, as well as with another promoter. Preferably, the nucleic acid expression cassettes disclosed herein comprise a muscle-specific promoter. This to increase muscle-specificity and/or avoid leakage of expression in other tissues. Non-limiting examples of muscle-specific promoters, include the desmin (DES, also known as CSM1 or CSM2) promoter, the alpha 2 actinin (ACTN2, also known as CMD1AA) promoter, the filamin-C (FLNC, also known as actin-binding-like protein (ABLP), filamin-2 (FLN2), ABP-280, ABP280A, ABPA, ABPL, MFM5 or MPD4) promoter, the sarcoplasmic/endoplasmic reticulum calcium ATPase 1 (ATP2A1, also known as ATP2A or SERCA1) promoter, the troponin I type 1 (TNNI1, also known as SSTNI or 25TTNI) promoter, the myosin-1 (MYH1) promoter, the phosphorylatable, fast skeletal muscle myosin light chain (MYLPF) promoter, myosin 1 (MYH1, also known as MYHSA1, MYHa, MyC-2X/D or MyHC-2x) promoter, the alpha-3 chain tropomyosin (TPM3, also known as CFTD, NEM1, OK/Scl.5, TM-5, TM3, TM30, TM30 nm, TM5, TPMsk3, TRK, h TM5 or hscp30) promoter, the ankyrin repeat domain-containing protein 2 (ANKRD2, also known as ARPP) promoter, the myosin heavy-chain (MHC) promoter, the myosin light-chain (MLC) promoter, the muscle creatine kinase (MCK) promoter, synthetic muscle promoters as described in U et al. (1999. Nat Biotechnol. 17:241-245), such as the SPc5-12 promoter, the muscle creatine kinase (MCK) promoter, the dMCK promoter, the tMCK promoter consisting of respectively, a double or triple tandem of the MCK enhancer to the MCK basal promoter as described in Wang et al. (2008. Gene Ther. 15:1489-1499) and hybrid promoters such as the hybrid alpha-myosin heavy chain enhancer/MCK enhancer (MHCK7; 770 bp); the MCK-C5-12 promoter as described in Wang et al. (2008. Gene Ther. 15:1489-1499) and the cardiac and skeletal muscle-specific myosin chaperone Unc45b (195 bp) promoter as described in Rudeck S et al. (2016, Genesis. 54(8): 431-8). Non-limiting examples of heart-specific promoters include the calsequestrin 2 (also known as PDIB2, FLJ26321, FLJ93514 or CASQ2 (GeneID 845 for the human gene)) promoter, the ankyrin repeat domain 1 (also known as cardiac ankyrin repeat protein) promoter, the cytokine inducible nuclear protein promoter; the liver ankyrin repeat domain 1 (ANKRD1; GeneID 27063 for the human gene) promoter; the myosin, light chain 2, regulatory, cardiac, slow (MYL2; GeneID 4633 for the human gene) promoter; the myosin, light chain 3, alkali; ventricular, skeletal, 10 slow (MYL3; GeneID 4634 for the human gene) promoter; the bromodomain containing 7 (also known as BP75, CELTIX1, NAG4(BRD7; GeneID 29117 for the human gene)) promoter; the alpha myosin heavy chain (aMHC) promoter; the cardiac troponin C promoter and the promoter of the cardiac sodium-calcium exchanger (NCX1) which confers cardiac specificity.

In particularly preferred embodiments, the promoter is a mammalian muscle-specific promoter, in particular a murine or human muscle-specific promoter.

In preferred embodiments, the promoter is from the desmin gene, in particular the murine or human desmin gene, such as the promoter as defined in SEQ ID NO: 16 (murine desmin promoter), SEQ ID NO:47 (1 kb human desmin promoter) or SEQ ID NO:48 (1.4 kb human desmin promoter). For example, the murine desmin promoter is commercially available as pDRIVE-mDesmin (Invivogen). The desmin promoter is expressed in both cardiac muscle and skeletal muscle.

In embodiments, the promoter is a skeletal muscle-specific promoter, in particular a muscle creatine kinase (MCK) promoter, more particularly the double MCK promoter or triple MCK promoter consisting of a double or triple tandem of MCK enhancer and MCK basal promoter as described in Wang et al. (2008. Gene Ther. 15:1489-1499).

In embodiments, the promoter is the SPc5-12 promoter as described in U et al. (1999. Nat Biotechnol. 17:241-245) (SEQ ID NO:53).

Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted-that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less.

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, antisense RNA. RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. A non-exhaustive and non-limiting list of transgenes envisaged in the application includes angiogenic factors for therapeutic angiogenesis such as VEGF, PlGF, or guidance molecules such as ephrins, semaphorins, Slits and netrins or their cognate receptors; cytokines and/or growth factors such as erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), proteins involved in calcium handling such as SERCA (Sarco/Endoplasmic Reticulum Ca2+-ATPase), calcineurin, microdystrophin 1 (MD1), follistatin (FST), alpha-glucosidase (GAA), myotubularin 1 (MTM1), transgenes encoding antibodies, nanobodies, anti-viral dominant-negative proteins, and fragments, subunits or mutants thereof.

The transgene may be homologous or heterologous to the promoter (and/or to the animal, in particular mammal, in which it is introduced, e.g. in cases where the nucleic acid expression cassette is used for gene therapy).

The transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein. The therapeutic protein may be a secretable protein. The secretable protein may be a circulating protein in skeletal muscle or heart. Non-limiting examples of secretable proteins, in particular secretable therapeutic proteins, include clotting factors, such as factor VII or factor IX, insulin, erythropoietin, lipoprotein lipase, antibodies or nanobodies, growth factors, cytokines, chemokines, plasma factors, etc. The therapeutic protein may also be a structural protein. Non-limiting examples of structural proteins, in particular structural therapeutic proteins, include dystrophin and sarcoglycans. In embodiments, the transgene comprises microdystrophin 1 (MD1) gene or follistatin (FST) gene.

In embodiments, the transgene encodes a therapeutic protein for Pompe disease or Duchenne muscular dystrophy (DMD). Non-limiting examples of therapeutic proteins for Pompe disease include alpha-glucosidase (GAA). In embodiments, the transgene comprises alpha-glucosidase (GAA) gene.

In embodiments, the transgene encodes a therapeutic protein for myotubular myopathy, such as myotubular myopathy (MTM) or Duchenne muscular dystrophy (DMD). Non-limiting examples of therapeutic proteins for myotubular myopathy include myotubularin 1 (MTM1). In embodiments, the transgene comprises myotubularin 1 (MTM1) gene.

In embodiments, the transgene comprises the human GAA gene (SEQ ID NO: 49) or human MTM1 (SEQ ID NO: 51) gene.

In embodiments, the transgene is a codon-optimized variant of the original transgene.

In embodiments, the transgene comprises a codon-optimized variant of the GAA or MTM1 gene, preferably a codon-optimized variant of human GAA gene encoded by the nucleic acid sequence as provided in SEQ ID NO:50 or a codon-optimized variant of human MTM1 gene encoded by the nucleic acid sequence as provided in SEQ ID NO:52.

In embodiments, the transgene encodes an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-1), factor IX (FIX) intron A, Simian virus 40 (SV40) small-t intron, and beta-actin intron.

Preferably, the intron is MVM intron, more preferably the MVM intron having SEQ ID NO: 54.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit □-globin (mRBG) gene, and the synthetic polyA s(SPA) site as described in Levitt et al. (1989, Genes Dev 3:1019-1025) (SEQ ID NO:46).

Preferably, the polyadenylation signal is derived from SV40 (i.e. SV40 pA), more preferably the polyadenylation signal having SEQ ID NO:46.

In particular embodiments, the invention provides a nucleic acid expression cassette comprising a nucleic acid regulatory element consisting of SEQ ID NO:10 or a sequence having 95% identity to said sequence or SEQ ID NO:5 or a sequence having 95% identity to said sequence, operably linked to a promoter, preferably a promoter selected from the group consisting of the promoter from the desmin gene or the SPc5-12 promoter, more preferably the desmin promoter having SEQ ID NO: 16, 47 or 48 or the SPc5-12 promoter having SEQ ID NO:53, and a transgene, preferably a transgene encoding a luciferase. In further embodiments, the nucleic acid expression cassette further comprises an MVM intron, preferably an MVM intron SEQ ID NO: 54. In yet further embodiments the nucleic acid expression cassette further comprises a polyadenylation signal, preferably a polyadenylation signal derived from SV40, preferably a polyadenylation signal consisting of SEQ ID NO:46.

In particular embodiments, the invention provides a nucleic acid expression cassette comprising a nucleic acid regulatory element consisting of: SEQ ID NO:10 or a sequence having 95% identity to said sequence, operably linked to a promoter, preferably the promoter from the desmin gene, more preferably the desmin promoter consisting of: SEQ ID NO: 16, 47 or 48 and a transgene, preferably a transgene encoding microdystrophin 1, follistatin, GAA or MTM1, more preferably human GAA, even more preferably a codon-optimized variant of human GAA. In further embodiments, the nucleic acid expression cassette further comprises an MVM intron, preferably an MVM intron consisting of: SEQ ID NO: 54. In yet further embodiments, the nucleic acid expression cassette further comprises a polyadenylation signal, preferably wherein the polyadenylation signal has SEQ ID NO:46.

In particular embodiments, the invention provides a nucleic acid expression cassette comprising a nucleic acid regulatory element consisting of SEQ ID NO:5 or a sequence having 95% identity to said sequence, operably linked to a promoter, preferably the SPc5-12 promoter, more preferably the SPc5-12 promoter consisting of SEQ ID NO:53, and a transgene, preferably a transgene encoding microdystrophin 1, follistatin, GAA or MTM1, more preferably human MTM1, even more preferably a codon-optimized variant of human MTM1. In further embodiments, the nucleic acid expression cassette further comprises an MVM intron, preferably an MVM intron consisting of SEQ ID NO: 54. In yet further embodiments, the nucleic acid expression cassette further comprises a polyadenylation signal, preferably wherein the polyadenylation signal has SEQ ID NO:46.

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu at al., 2008), although the use of single-stranded AAV vectors (ssAAV) are also encompassed herein.

AAV serotype 9 (AAV9) is ideally suited to achieve efficient transduction in heart and skeletal muscle. Accordingly, in particularly preferred embodiments, the vector is an AAV9 vector, more particularly a self-complementary AAV9 vector (scAAV9).

In other embodiments, the vector is a non-viral vector, preferably a plasmid, a minicircle, or a transposon-based vector, such as a Sleeping Beauty(SB)-based vector or piggyBac(PB)-based vector.

In yet other embodiments, the vector comprises viral and non-viral elements.

In particular embodiments, the invention provides a vector comprising a nucleic acid expression cassette comprising a nucleic acid regulatory element element consisting of SEQ ID NO:10, a promoter, preferably the promoter from the desmin gene, an MVM intron, a transgene, preferably a transgene encoding microdystrophin 1, and a polyadenylation signal, preferably the polyadenylation signal having SEQ ID NO:46. In particular embodiments, said vector has SEQ ID NO: 44.

In particular embodiments, the invention provides a vector comprising a nucleic acid expression cassette comprising a nucleic acid regulatory element consisting of SEQ ID NO:10, a promoter, preferably the promoter from the desmin gene, an MVM intron, a transgene, preferably a transgene encoding follistatin, and a polyadenylation signal, preferably the polyadenylation signal having SEQ ID NO:46. In particular embodiments, said vector has SEQ ID NO: 45.

In particular embodiments, the invention provides a vector comprising a nucleic acid expression cassette comprising a nucleic acid regulatory element consisting of SEQ ID NO:10; a promoter, preferably the promoter from the desmin gene, more preferably the promotor from the human desmin gene, even more preferably the human DES1.4 kb promotor having SEQ ID NO:48; an MVM intron, preferably a MVM intron having SEQ ID NO:54; a transgene, preferably a transgene encoding human MTM1, even more preferably a transgene encoding codon-optimised human MTM1, even more preferably a transgene encoding codon-optimised human MTM1 having SEQ ID NO:52; and a polyadenylation signal, preferably the polyadenylation signal having SEQ ID NO:46. In particular embodiments, said vector has SEQ ID NO: 67 or 68, preferably SEQ ID NO: 68.

In particular embodiments, the invention provides a vector comprising a nucleic acid expression cassette comprising a nucleic acid regulatory element consisting of SEQ ID NO:5, a promoter, preferably a SPc5-12 promoter, even more preferably the synthetic SPc5-12 promoter having SEQ ID NO: 53; an MVM intron, preferably a MVM intron having SEQ ID NO:54; a transgene, preferably a transgene encoding human GAA, more preferably a transgene encoding codon-optimised human GAA, even more preferably a transgene encoding codon-optimised human GAA having SEQ ID NO:50; and a polyadenylation signal, preferably the polyadenylation signal having SEQ ID NO:46. In particular embodiments, said vector has SEQ ID NO: 65 or 66, preferably SEQ ID NO: 66. The nucleic acid expression cassettes and vectors disclosed herein may be used, for example, to express proteins that are normally expressed and utilized in muscle (i.e. structural proteins), or to express proteins that are expressed in muscle and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement. In embodiments, the nucleic acid regulatory elements, the nucleic acid expression cassettes, the vectors, or the pharmaceutical compositions described herein may be for use in gene therapy, in particular muscle-directed gene therapy, more particularly heart and skeletal muscle-directed gene therapy or skeletal muscle-directed gene therapy.

Also disclosed herein is the use of the nucleic acid regulatory elements, the nucleic acid expression cassettes, the vectors, or the pharmaceutical compositions described herein for the manufacture of a medicament for gene therapy, in particular muscle-directed gene therapy, more particularly heart and skeletal muscle-directed gene therapy or skeletal muscle-directed gene therapy.

Also disclosed herein is a method for gene therapy, in particular muscle-directed gene therapy, more particularly heart and skeletal muscle-directed gene therapy or skeletal muscle-directed gene therapy, in a subject in need of said gene therapy comprising:

introducing in the subject, in particular in muscle of the subject, more particularly in heart muscle or skeletal muscle of the subject, a nucleic acid expression cassette, a vector or a pharmaceutical composition described herein, wherein the nucleic acid expression cassette, the vector or the pharmaceutical composition comprises a nucleic acid regulatory element described herein operably linked to a promoter and a transgene; and expressing a therapeutically effective amount of the transgene product in the subject, in particular in muscle of the subject, more particularly in heart and skeletal muscle or in skeletal muscle of the subject.

The transgene product may be a polypeptide, in particular a structural protein such as, e.g., dystrophin or a sarcoglycan, or a secretable protein such as, e.g., a clotting factor, e.g., factor IX or factor VIII, a cytokine, a growth factor, an antibody or nanobody, a chemokine, a plasma factor, insulin, erythropoietin, lipoprotein lipase. In particular embodiments, the transgene product is follistatin or microdystrophin, in particular microdystrophin 1. In particular embodiments, the transgene product is GAA or MTM1, preferably human GAA or human MTM1, more preferably codon optimized human GAA (hGAAco) or codon-optimized human MTM1 (hMTMco) as defined herein elsewhere. Alternatively, the transgene product may be RNA, such as siRNA.

Exemplary diseases and disorders that may benefit from gene therapy using the nucleic acid regulatory elements, the nucleic acid expression cassettes, the vectors, or the pharmaceutical compositions described herein include both neuromuscular disorders affecting the skeletal muscles and heart diseases, such as Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystrophic Myotonia (Schwartz-Jampel Syndrome), Chudley Sydrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy), Welander's Distal Myopathy, Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type II (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barré Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type II), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy, Nuclear Envelop Disease, muscular dystrophy (e.g. Duchenne muscular dystrophy (DMD)/Becker muscular dystrophy (BMD)), motor neuron diseases (MND), such as e.g. Charcot-Marie-Tooth Diseases (CMT) such as CMT Type I, CMT Type I, CMT Type III (Dejerine-Sottas Disease), CMT Type IV (Refsum's Disease), CMT Type V., spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes.

In embodiments, the diseases and disorders that may benefit from gene therapy using the Sk-SH4 (SEQ ID NO:10) nucleic acid regulatory element, a DES promoter such as the murine DES promoter (SEQ ID NO:16), the human DES 1.0 kb promoter (SEQ ID NO:47), or the human DES 1.4 kb promoter (SEQ ID NO:48), a combination of Sk-SH4 and a DES promoter or the nucleic acid expression cassettes, the vectors, or the pharmaceutical compositions comprising said nucleic acid regulatory element and/or promoter as described herein are diseases that affect the skeletal muscle, and include Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystropic Myotonia (Schwartz-Jampel Syndrome), Chudley Sydrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy) and Welander's Distal Myopathy.

In embodiments, the disease and disorder that may benefit from gene therapy using the Sk-SH4 (SEQ ID NO:10) nucleic acid regulatory element, a DES promoter such as the murine DES promoter SEQ ID NO:16), the human DES 1.0 kb promoter (SEQ ID NO:47), or the human DES1.4 kb promoter (SEQ ID NO:48), a combination of Sk-SH4 and a DES promoter or the nucleic acid expression cassettes, the vectors, or the pharmaceutical compositions comprising said nucleic acid regulatory element and/or promoter as described herein is myotubular myopathy (MTM) or Duchenne muscular dystrophy. The skilled person will understand that for some diseases, such as myotubular myopathy which affects the skeletal muscle and not heart function, expression in the heart may be preferably avoided due to potential cardiotoxic effects.

In embodiments, the diseases and disorders that may benefit from gene therapy using the CSk-SH5 (SEQ ID NO:5) nucleic acid regulatory element, a SPc5-12 promoter such as the synthetic SPc5-12 promoter (SEQ ID NO:53), a combination of CSk-SH5 and the SPc5-12 promoter or the nucleic acid expression cassettes, the vectors, or the pharmaceutical compositions comprising said nucleic acid regulatory element and/or promoter as described herein are diseases that affect both the skeletal muscle and heart, and include Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barré Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy and Nuclear Envelop Disease.

In embodiments, the diseases and disorders that may benefit from gene therapy using the CSk-SH5 (SEQ ID NO:5) nucleic acid regulatory element, a SPc5-12 promoter such as the synthetic SPc5-12 promoter (SEQ ID NO:53), a combination of CSk-SH5 and the SPc5-12 promoter or the nucleic acid expression cassettes, the vectors, or the pharmaceutical compositions comprising said nucleic acid regulatory element and/or promoter as described herein is Pompe disease.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993). In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of a vaccine, in particular for the manufacture of a prophylactic vaccine.

Also disclosed herein is a method of vaccination, in particular prophylactic vaccination, of a subject in need of said vaccination comprising:
  introducing in the subject, in particular in muscle of the subject, more particularly in heart muscle or skeletal muscle of the subject a nucleic acid expression cassette, a vector or a pharmaceutical composition described herein, wherein the nucleic acid expression cassette, the vector or the pharmaceutical composition comprises a nucleic acid regulatory element described herein operably linked to a promoter and a transgene; and expressing an immunologically effective amount of the transgene product in the subject, in particular in muscle of the subject, more particularly in heart and skeletal muscle or in skeletal muscle of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one muscle-specific nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Moreover, the higher expression remains specific to muscle, in particular both heart and skeletal muscle or skeletal muscle alone. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product. Also disclosed herein is the use of the nucleic acid regulatory elements, the nucleic acid expression cassettes, or the vectors disclosed herein for transfecting or transducing muscle cells, preferably heart muscle cells and/or skeletal muscle cells.

Further disclosed herein is the use of the nucleic acid expression cassettes or the vectors disclosed herein for expressing a transgene product in muscle cells, preferably heart muscle cells and/or skeletal muscle cells, wherein the nucleic acid expression cassette or the vector comprises a nucleic acid regulatory element disclosed herein operably linked to a promoter and a transgene.

Further disclosed herein is a method for expressing a transgene product in muscle cells, preferably heart muscle cells and/or skeletal muscle cells, comprising:

transfecting or transducing the muscle cells with a nucleic acid expression cassette or a vector disclosed herein, wherein the nucleic acid expression cassette or the vector comprises a nucleic acid regulatory element disclosed herein operably linked to a promoter and a transgene; and expressing the transgene product in the muscle cells.

Non-viral transfection or viral vector-mediated transduction of muscle cells may be performed by in vitro, ex vivo or in vivo procedures. The in vitro approach requires the in vitro transfection or transduction of muscle cells, e.g. muscle cells previously harvested from a subject, muscle cell lines or muscle cells differentiated from e.g. induced pluripotent stem cells or embryonic cells. The ex vivo approach requires harvesting of the muscle cells from a subject, in vitro transfection or transduction, and optionally re-introduction of the transfected muscle cells into the subject. The in vivo approach requires the administration of the nucleic acid expression cassette or the vector disclosed herein into a subject. In preferred embodiments, the transfection of the muscle cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into myogenic cells, transgenic models for over-expression of proteins in muscle, enhancement of expression of recombinant protein in vitro in genetically engineered cell lines for the production of recombinant proteins, etc.

The invention is further explained by the following non-limiting examples

EXAMPLES

Example 1: Identification of Cardiac and Skeletal Muscle-Specific Regulatory Elements Experimental Procedures Genes highly expressed both in heart and muscle, but showing only minimal expression in other tissues, were identified using the Specificity Measure (SPM) method described in Xiao et al. (2010. Bioinfomatics 26:1273-

1275). As data set we used the U133A/GNF1H Gene Alas (GSE1133) of the human protein-encoding transcriptomes (Su et al. 2004. Proc. Natl. Acad. Sci. USA 101:6062-6067). This resulted in a short list of 5 genes: filamin-c gene (FLNC), actinin, alpha 2 gene (ACTN2), myosin regulatory light chain 2, ventricular/cardiac muscle isoform gene (MYL2), desmin gene (DES) and telethonin gene (TCAP). Next, the genomic context of these genes was searched for cross-species conserved regions enriched for transcription factor binding sites (TFBS) associated with high expression in muscle and heart. Additional filtering was done by selecting the putative nucleic acid regulatory elements that either overlapped or contained regions bearing reproducible biochemical features associated with transcription regulation and/or a open chromatin structure as defined in the ENCODE project (The ENCODE Project Consortium. 2012. Nature 489:57-74).

For the heart-specific regulatory elements we used a high-density gene expression database of 18,927 unique genes based on microarrays that were derived from 158 normal human samples from 19 different organs of 30 different individuals (Son, S. et al. 2005. Database of mRNA gene expression profiles of multiple human organs. Genome Res. 15:443-450). This was used to identify a set of most highly expressed (i.e. 'over-expressed') genes in the heart compared to any of the other tissues. A two-tailed t-test was used for each pairwise comparison. Conversely, a set of 'under-expressed' genes was identified, corresponding to those genes that exhibited the lowest expression in these respective organs compared to any of the other tissues. This analysis resulted in a set of 43 over-expressed genes and a collection of 37 under-expressed heart-specific genes. Next, the Reference Sequence (RefSeq) identifiers (IDs) lists of these 'over-expressed' and 'under-expressed' heart-specific genes were used to extract the corresponding promoter sequences upstream the reported transcription start sites (TSSs) by 1000 bases (NCBI36/hg18 genome assembly), using the transcription start location data stored in the refGene table of the UCSC Genome Browser (http://genome.ucsc.edu) database.

This resulted in two sets of heart-specific promoter sequences corresponding to promoters of 'over-expressed' or 'under-expressed' genes. In order to make a non-redundant set of representative promoter sequences, the promoter sequences were filtered using 'uclust' (http://www.drive5.com/usearch/).

The two sets of non-redundant tissue-specific promoter sequences corresponding to promoters of 'over-expressed' or 'under-expressed' genes were used as input for the DDM/MDS method, described in detail in De Bleser et al. (2007. Genome Biol 8:R83), which is specifically incorporated by reference herein. The observed differential behaviour might be explained by the presence of one or more TFBS elements characteristic of the promoters of the up-regulated or down-regulated group of genes. These 'differential' TFBS elements could be found using following procedure. First, a library of TFBS positional weight matrices (PWMs) (TRANSFAC® 2010.3) was used to predict TFBS on every promoter sequence. For the muscle-specific promoters we used the Find Individual Motif Occurrences (fimo) application with a P-value cut-off of $10^{-3}$. The number of predicted TFBS elements per PWM per promoter was collected in the form of a matrix in which each row corresponds to a promoter sequence, while the columns corresponded to the used PWM. Two TFBS were considered correlated if their corresponding columns in the matrix were similar what could be measured using a distance function. With this approach, distance matrices summarizing all TFBS associations were constructed for the TFBS in both sets of promoters. Finally, by calculating the distance difference matrix (DDM) and performing multidimensional scaling on this DDM to visualize its content in two dimensions, TFBS could be distinguished that did not contribute to the observed differential gene expression as they were mapped near the origin of the DDM-MDS plot from 'deviating' TFBS that are likely responsible for the observed differential gene expression. As the MDS procedure plots TFBS that are strongly associated closer together than less associated ones, it was able to highlight interactions between TFBS in the promoter datasets. This procedure resulted in a list of TFBS associated with high tissue-specific expression for heart-specific promoters.

For the muscle-specific regulatory elements, a list of muscle-specific genes was extracted from the Tissue-specific Gene Expression and Regulation (TiGER) database. This was used to identify a set of the most highly expressed (i.e. 'over-expressed') genes in muscle tissue. Conversely, a set of 'under-expressed' genes was identified, corresponding to those genes that exhibited the lowest expression in muscle. Next, the Reference Sequence (RefSeq) identifiers (IDs) lists of these 'over-expressed' and 'under-expressed' muscle-specific genes were used to extract the corresponding promoter sequences upstream the reported transcription start sites (TSSs) by 1000 bases (NCBI36/hg18 genome assembly), using the transcription start location data stored in the refGene table of the UCSC Genome Browser (http://genome.ucsc.edu) database. This resulted in two sets of muscle-specific promoter sequences corresponding to promoters of 'over-expressed' or 'under-expressed' genes. In order to make a non-redundant set of representative promoter sequences, the promoter sequences were filtered using 'uclust' (http://www.drive5.com/usearch/).

The two sets of non-redundant tissue-specific promoter sequences corresponding to promoters of 'over-expressed' or 'under-expressed' genes were used as input for the DDM/MDS method, described in detail in De Bleser et al. (2007. Genome Biol 8:R83), which is specifically incorporated by reference herein. The observed differential behaviour might be explained by the presence of one or more TFBS elements characteristic of the promoters of the up-regulated or down-regulated group of genes. These 'differential' TFBS elements could be found using following procedure. First, a library of TFBS positional weight matrices (PWMs) (TRANSFAC® 2010.3) was used to predict TFBS on every promoter sequence. For the muscle-specific promoters we used the Find Individual Motif Occurrences (fimo) application with a P-value cut-off of $10_{-3}$. The number of predicted TFBS elements per PWM per promoter was collected in the form of a matrix in which each row corresponds to a promoter sequence, while the columns corresponded to the used PWM. Two TFBS were considered correlated if their corresponding columns in the matrix were similar what could be measured using a distance function. With this approach, distance matrices summarizing all TFBS associations were constructed for the TFBS in both sets of promoters. Finally, by calculating the distance difference matrix (DDM) and performing multidimensional scaling on this DDM to visualize its content in two dimensions, TFBS could be distinguished that did not contribute to the observed differential gene expression as they were mapped near the origin of the DDM-MDS plot from 'deviating' TFBS that are likely responsible for the observed differential gene expression. As the MDS procedure plots TFBS that are strongly associated closer together than less associated ones, it was able to highlight interactions between TFBS in the promoter datasets. This procedure resulted in a list of TFBS associated with high tissue-specific expression for muscle-specific promoters.

Results

This computational approach led to the identification of 6 cardiac and skeletal muscle-specific regulatory sequences, summarized in Table 1.

TABLE 1

Cardiac and skeletal muscle-specific regulatory elements.

| Sequence | Name | Gene regulated by sequence | Size (bp) | Conserved TFBS present |
|---|---|---|---|---|
| SEQ ID NO: 1 | CSk-SH1 | Des | 381 | E2A, HNH1, NF1, CEBP, LRF, MyoD, SREBP |
| SEQ ID NO: 2 | CSk-SH2 | Des | 435 | E2A, NF1, p53, CEBP, LRF, SREBP |
| SEQ ID NO: 3 | CSk-SH3 | ACTN2 | 551 | E2A, HNH1, HNF3a, HNF3b, NF1, CEBP, LRF, MyoD, SREBP |
| SEQ ID NO: 4 | CSk-SH4 | ACTN2 | 430 | E2A, HNF3a, NF1, CEBP, LRF, MyoD, SREBP |
| SEQ ID NO: 5 | CSk-SH5 | FLNC | 454 | HNF4, NF1, RSRFC4, CEBP, LRF, MyoD |
| SEQ ID NO: 6 | CSk-SH6 | FLNC | 453 | NF1, PPAR, p53, CEBP, LRF, MyoD |

Bp: base pairs.

Example 2: In Vivo Validation of Cardiac and Skeletal Muscle-Specific Regulatory Elements Via AAV Vectors Experimental Procedures
Generation of the AAV Plasmid Constructs (pAAV-CSk-SH-Des-Luc2)

Figure 3:
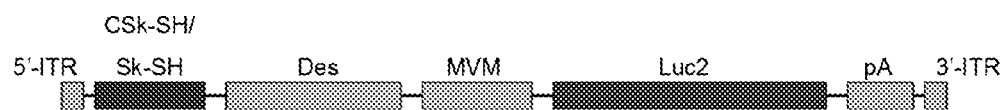
FIG. 3 shows a schematic representation of the AAV9sc-CSk-SH/Sk-SH-Des-Luc2 vectors disclosed herein. The expression cassette was packaged in a self-complementary (sc) adeno-associated virus, serotype 9 (AAV9). The cardiac and skeletal muscle-specific desmin (Des) promoter regulates transcription of the luciferase (Luc2) transgene. The identified cardiac and skeletal muscle-specific (CSk-SH) or muscle-specific (Sk-SH) nucleic acid regulatory elements were cloned upstream of the Des promoter. The expression cassette further comprises the Minute Virus of Mouse (MVM) intron and a Simian virus 40 (SV40) polyadenylation signal (pA). The expression cassette is flanked by inverted terminal repeats (ITR) from adeno-associated virus, serotype 2 (AAV2).

The cardiac and skeletal muscle-specific regulatory elements (CSk-SH1 to CSk-SH6) were synthesized by conventional oligonucleotide synthesis and flanked with Acc65I and MluI restriction sites. The different CSk-SHs were cloned upstream of the Desmin (Des) promoter that drives expression of a Firefly Luciferase (Luc2) reporter gene in the context of an adeno-associated viral vector (AAV) backbone (designated as pAAV-Des-Luc2), schematically represented in FIG. 3. The corresponding AAV plasmid constructs were designated as pAAV-CSk-SH-Des-Luc2. The plasmids also contained a Minute Virus of Mouse (MVM) intron and a Simian Virus 40 (SV40) polyadenylation site (pA).

AAV Vector Production (AAV9sc.CSk-SH1-6.Des.Luc2) and Purification

AAV9 vectors were produced by calcium phosphate (Invitrogen Corp, Carlsbad, CA) co-transfection of 293T human embryonic kidney cells with the pAAV plasmid of interest, an adenoviral helper plasmid and a chimeric packaging construct that delivers the AAV2 rep gene together with the AAV9 cap gene, as described in Vandendriessche et al. (2007. J Thromb Haemost 5:16-24), which is specifically incorporated by reference herein.

Briefly, two days post transfection, cells were harvested and vector particles were purified using isopycnic centrifugation methods. Harvested cells were lysed by successive freeze/thaw cycles and sonication, treated with benzonase (Novagen, Madison, WI) and deoxycholic acid (Sigma-Aldrich, St. Louis, MO) and subsequently subjected to 3 successive rounds of cesium chloride (Invitrogen Corp, Carlsbad, CA) density gradient ultracentrifugation. Fractions containing the AAV vector were collected, concentrated in 1 mM $MgCl_2$ in Dulbecco's phosphate buffered saline (PBS) (Gibco, BRL) and stored at $-80°$ C.

Vector titers (in viral genomes (vg)/ml) were determined by quantitative real-time PCR using SYBR Green mix (which included SYBR Green dye, Taqman polymerase, ROX and dNTP's all in one) and luciferase specific primers on an ABI 7500 Real-Time PCR System (Applied Biosystem, Foster city, CA, USA). The forward and reverse primers used were 5'-CCCACCGTCGTATTCGTGAG-3' (SEQ ID NO: 14) and 5'-TCAGGGCGATGGTTTTGTCCC-3' (SEQ ID NO: 15), respectively.

Typically, for all vectors titers in the range of $1.5-6.1\times10^{11}$ vg/ml were achieved from a small production batch of 20 petri dishes of producer cells. If higher number of petri dishes such as 60 dishes of producer cells were used, a higher titer typically in the range of $10^{12}-10^{13}$ gc/ml of AAV particles were achieved. Known copy numbers ($10^2-10^7$) of the respective vector plasmids used to generate the corresponding AAV vectors, carrying the appropriate cDNAs were used to generate the standard curves.

Animal Studies

All animal procedures were approved by the institutional animal ethics committee of the Free University of Brussels (VUB) (Brussels, Belgium). All mice were housed under specific pathogen-free conditions; food and water were provided ad libitum.

Two-days old CB.17/IcrTac/Prkdcscid mice were intravenously injected into the periorbital vein with 50 µl of concentrated vectors ($5\times10^9$ vg/mouse) containing the different CSk-SH (i.e. CSk-SH1 to CSk-SH6) regulatory elements or AAV9-Des-Luc2 control vector ($5\times10^9$ vg/mouse) as summarized in Table 2.

TABLE 2

Experimental design for the injection of cardiac and skeletal muscle-specific regulatory elements.

| Vector | Mouse number (n) | Dose | Titre (gc/ml) | Volume vector (µl) | Volume PBS (µl) | Total volume (µl) |
|---|---|---|---|---|---|---|
| AAV9sc.Des.Luc2 | 3 | $5 \times 10^9$ | $5.7 \times 10^{11}$ | 8.7 | 41.3 | 50 |
| AAV9sc.CSk-SH1.Des.Luc2 | 4 | $5 \times 10^9$ | $6.1 \times 10^{11}$ | 8.2 | 41.8 | 50 |
| AAV9sc.CSk-SH2.Des.Luc2 | 2 | $5 \times 10^9$ | $6.0 \times 10^{11}$ | 8.3 | 41.7 | 50 |
| AAV9sc.CSk-SH3.Des.Luc2 | 5 | $5 \times 10^9$ | $1.5 \times 10^{11}$ | 33.3 | 16.7 | 50 |
| AAV9sc.CSk-SH4.Des.Luc2 | 3 | $5 \times 10^9$ | $5.2 \times 10^{11}$ | 9.6 | 40.4 | 50 |
| AAV9sc.CSk-SH5.Des.Luc2 | 4 | $5 \times 10^9$ | $1.7 \times 10^{11}$ | 39.4 | 20.6 | 50 |
| AAV9sc.CSk-SH6.Des.Luc2 | 4 | $5 \times 10^9$ | $3.1 \times 10^{11}$ | 16.1 | 33.9 | 50 |

Mice were imaged between 5 and 8 weeks post-injection once per week using a biospace In Vivo photo Imaging System (VS). The CCD was cooled to $-120°$ C. and the field of view (FOV) set at 25 cm height of the sample shelf. The charged coupled device (CCD) camera operates by converting photons that strike the CCD pixel into electrons at wavelengths between 400-100 nm, allowing detection of visible imaged infrared light through by anesthetizing with 2% isofluorane and oxygen. D-luciferin substrate was injected intravenously, at a dose of 150 µg/g of body weight.

Mice were euthanized 9 weeks post injection and intact organs were harvested and imaged using a biospace In Vivo photo Imaging System (IVIS).

mRNA Analysis

Total RNA was extracted from different organs of the mice by a silica-membrane based purification kit according to the manufacturer's instructions (Invitrogen Corp, Carlsbad, CA, USA). Subsequently, 50 ng of total RNA from each sample was subjected to reverse transcription (RT) using a cDNA synthesis kit (Invitrogen Corp, Carlsbad, CA, USA). Next, a cDNA amount corresponding to 10 ng of total RNA was amplified by quantitative (q) PCR on an ABI 7700 (Applied Biosystems, Foster City, CA, USA), using 5'-CCCACCGTCGTATTCGTGAG-3' (SEQ ID NO: 14) as a forward primer and 5'-TCAGGGCGATGGTTTTGTCCC-3' (SEQ ID NO: 15) as reverse primer (amplicon 217 bp). The qPCR standards consisted of serially diluted AAV9-CSk-SH-Des-Luc2 plasmids of known quantity. The Luc2 mRNA levels were normalized to mRNA levels of the endogenous murine glyceraldehyde-3-phosphate dehydrogenase (mGAPDH) gene, using 5'-TGTGTCCGTCGTGGATCTGA-3' (SEQ ID NO:31) as forward primer and 5'-GCCTGCTTCACCACCTTCTTGA-3' (SEQ ID NO:32) as the reverse primer (amplicon 82 bp). RNA samples were amplified with and without reverse transcriptase to exclude DNA amplification. The size of the amplified PCR fragments was verified on a 1.8% agarose gel.

Transduction Efficiency and Vector Biodistribution

Transduction efficiency of the viral vectors and biodistribution were evaluated by quantifying Luc2 transgene copy numbers in the different organs and tissues as described previously (Pacak, C. A., et al. 2008. Genet Vaccines Ther 6:13). Briefly, genomic DNA was extracted from 30 mg of each tissue according to DNeasy Blood & Tissue Kit protocol (Qiagen, Chatsworth, CA, USA) and 100 ng of genomic DNA from each sample was subjected to qPCR, using the Luc2-specific forward primer 5'-CCCACCGTCGTATTCGTGAG-3' (SEQ ID NO: 14) and reverse primer 5'-TCAGGGCGATGGTTTTGTCCC-3' (SEQ ID NO: 15) (amplicon 217 bp). Known copy numbers ($10^2$-$10^7$) of the corresponding plasmid pAAV-CSk-SH-Des-Luc2 were used to generate the standard curve. The results were expressed as mean AAV copy number/100 ng of genomic DNA.

Results

To assess the effect of the in silico identified cardiac and skeletal muscle-specific regulatory elements (CSk-SH) in vivo, adeno-associated vectors were generated that expressed the luciferase gene luc2 from a chimeric promoter. This promoter was composed of the muscle-specific desmin (Des) promoter linked to the cardiac and skeletal muscle-specific regulatory elements CSk-SH1-6. The vectors were intravenously injected in mice and whole body images were taken from the mice at 5 and 6 weeks post-injection to examine luciferase expression level.

All mice injected with a vector comprising a cardiac and skeletal muscle-specific regulatory element (CSk-SH1-6) showed increased luciferase activity compared to control mice that were injected with a corresponding AAV9 vector without a regulatory element, indicating that all of the regulatory elements tested increased luciferase expression (data not shown). We observed very robust and enhanced luciferase activity in mice that were injected with AAV9 vector comprising the regulatory element CSk-SH1, CSk-SH3 or CSk-SH5 at 5 and 6 weeks post-injection as compared to luciferase activity of the control mice.

Figures 4, 4A:
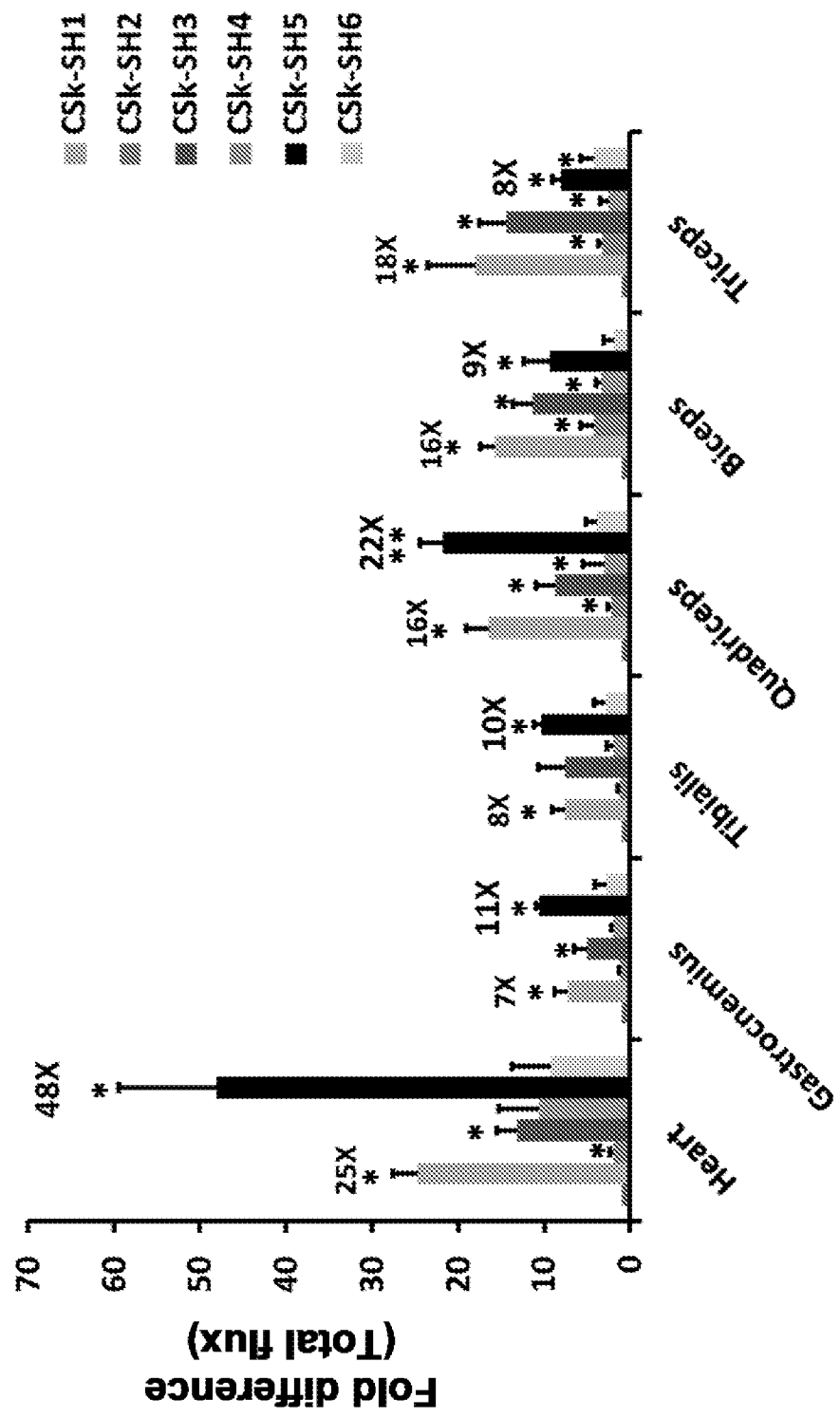
FIG. 4: Difference in luciferase expression (A) and Luc mRNA level (B) in heart and muscle tissue of mice that were intravenously injected with, from left to right, AAV9sc-CSk-SH1-Des-Luc2 (CSk-SH1), AAV9sc-CSk-SH2-Des-Luc2 (CSk-SH2), AAV9sc-CSk-SH3-Des-Luc2 (CSk-SH3), AAV9sc-CSk-SH4-Des-Luc2 (CSk-SH4), AAV9sc-CSk-SH5-Des-Luc2 (CSk-SH5), or AAV9sc-CSk-SH6-Des-Luc2 (CSk-SH6) vector compared to mice that were injected with the control vector AAV9sc-Des-Luc2 without nucleic acid regulatory element (control, no Csk-SH). Luciferase expression was measured as total flux, expressed in photons per second per centimetre squared per steradian (photons/sec/cm$^2$/sr), released by luciferase activity in the selected tissues at 9 weeks post-injection. Results were presented as mean±standard error of the mean, *p<0.05; *p<0.001. Luc mRNA levels were measured by a quantitative RT-PCR method (qRT-PCR) at the end of the experiment from total RNA extracted from biopsies from the indicated tissues. Results were presented as mean±standard error of the mean, *p<0.05; *p<0.001.
Figure 4:
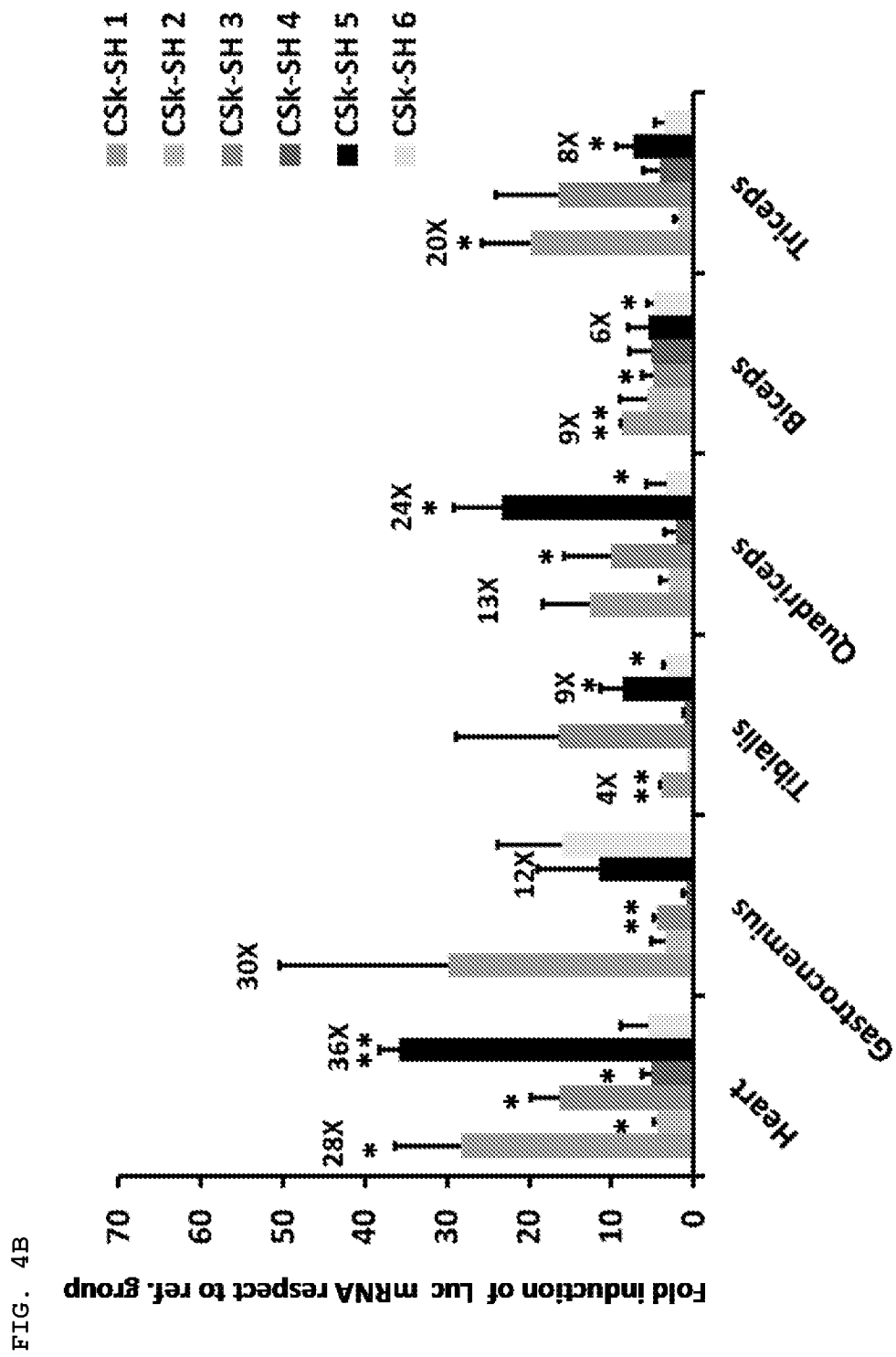
Figures 5, 5A:
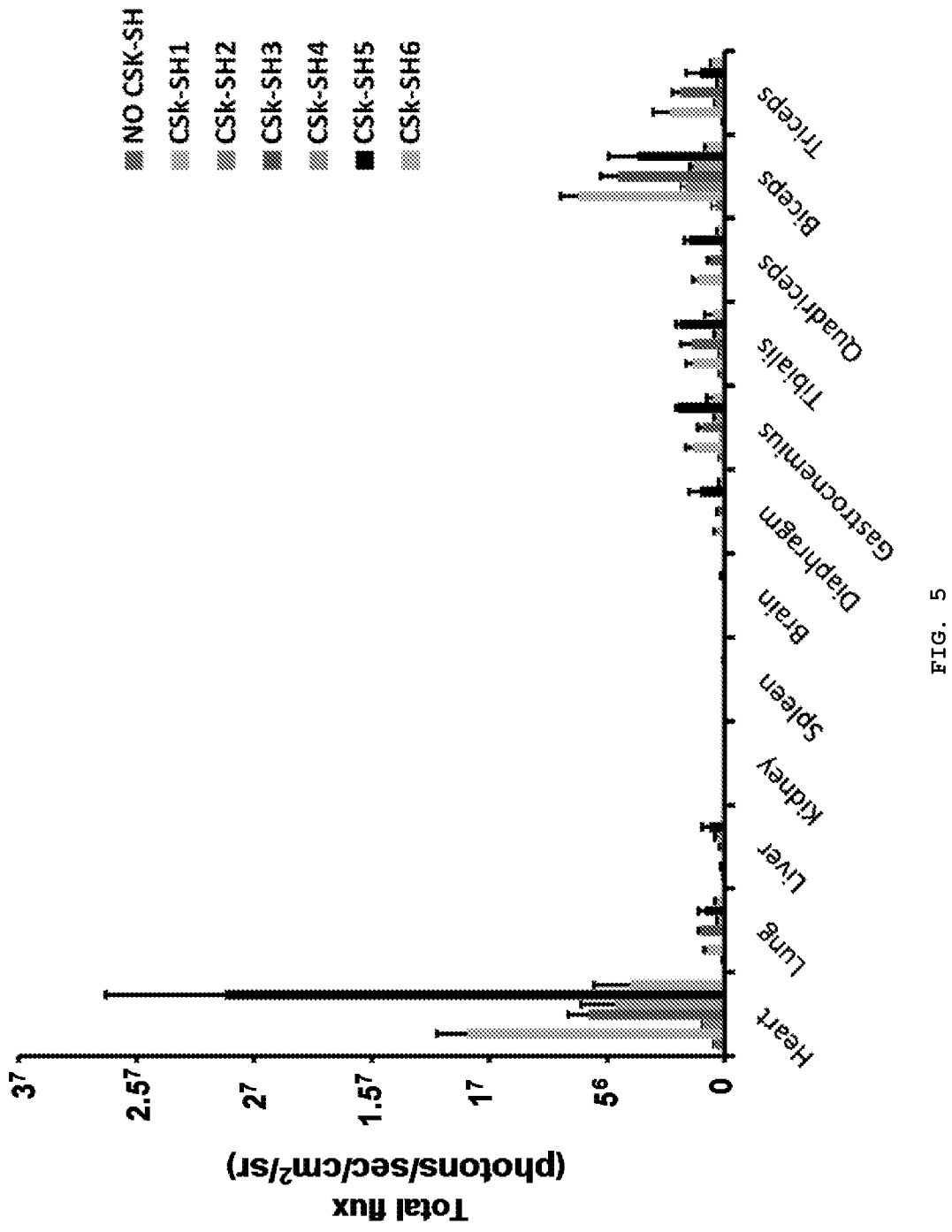
FIG. 5: (A) Luciferase expression in selected tissues of mice that were intravenously injected with, from left to right, AAV9sc-Des-Luc2 (control, no CSk-SH), AAV9sc-CSk-SH1-Des-Luc2 (CSk-SH1), AAV9sc-CSk-SH2-Des-Luc2 (CSk-SH2), AAV9sc-CSk-SH3-Des-Luc2 (CSk-SH3), AAV9sc-CSk-SH4-Des-Luc2 (CSk-SH4), AAV9sc-CSk-SH5-Des-Luc2 (CSk-SH5), or AAV9sc-Sk-SH6-Des-Luc2 (CSk-SH6) vector. Luciferase expression was measured as total flux, expressed in photons per second per centimetre squared per steradian (photons/sec/cm$^2$/sr), released by luciferase activity in the selected tissue at 9 weeks post-injection. Results were presented as mean t standard error of the mean. (B) Luc mRNA level in selected tissues of mice that were intravenously injected with, from left to right, AAV9sc-CSk-SH1-Des-Luc2 (CSk-SH1), AAV9sc-Sk-SH2-Des-Luc2 (CSk-SH2), AAV9sc-CSk-SH3-Des-Luc2 (CSk-SH3), AAV9sc-CSk-SH4-Des-Luc2 (CSk-SH4), AAV9sc-CSk-SH5-Des-Luc2 (CSk-SH5), or AAV9sc-CSk-SH6-Des-Luc2 (CSk-SH6) vector compared to mice that were injected with the control vector AAV9sc-Des-Luc2 (control, no Csk-SH). Luc mRNA levels were measured by a quantitative RT-PCR method (qRT-PCR) at the end of the experiment from total RNA extracted from biopsies from the indicated tissues. Results were presented as mean±standard error of the mean.
Figure 5:
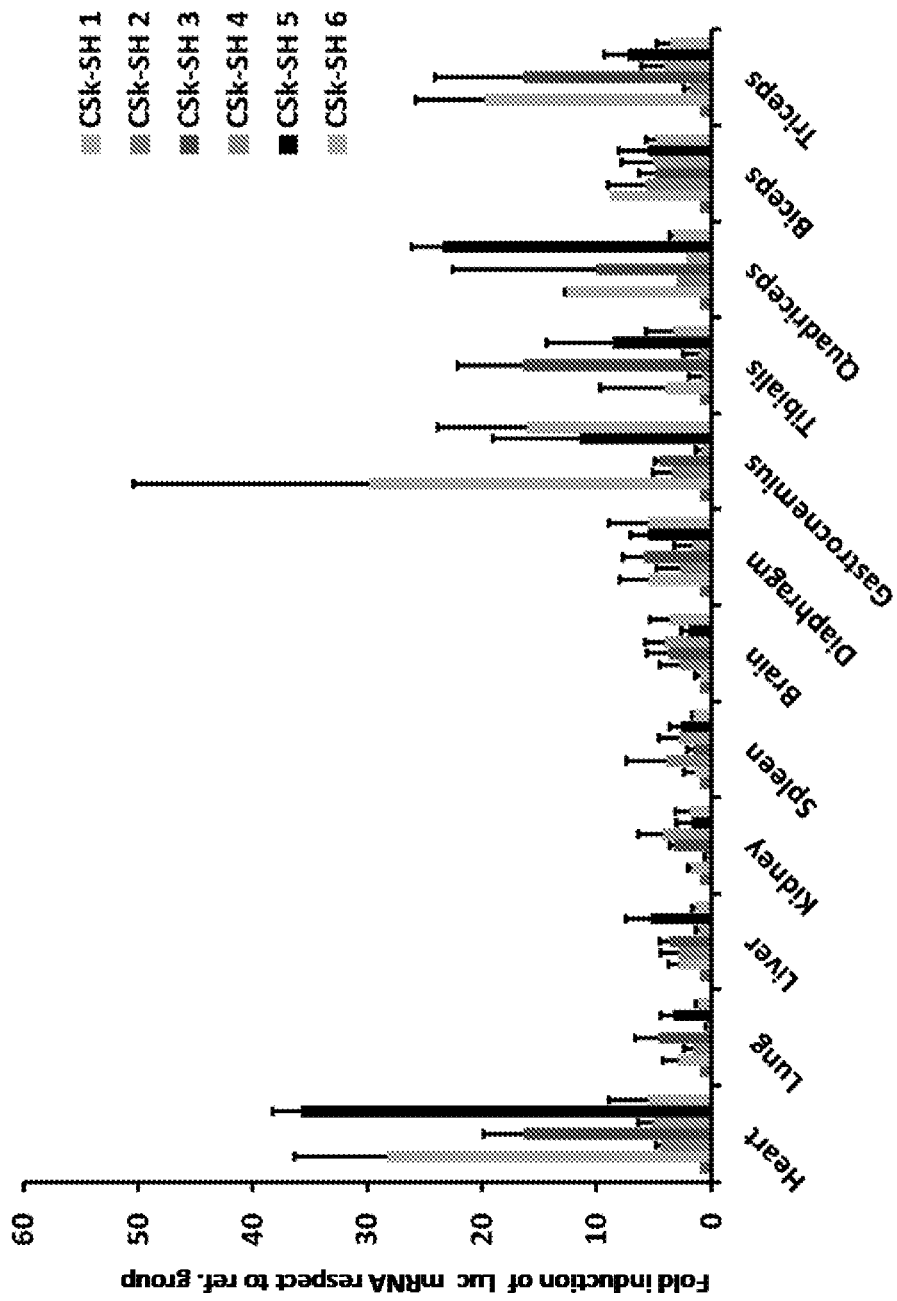

We also determined luciferase activity in the individual organs. Nine weeks post injection, the mice were euthanized and individual organs were analyzed to evaluate luciferase expression and the biodistribution pattern. We observed significantly increased levels of luciferase activity in the heart, the biceps, the triceps, the quadriceps, the tibialis interior, and the gastrocnemius muscle of mice injected with AAV vector comprising a regulatory element CSk-SH1-6 as compared to control mice. Up to 48-fold augmentation of luciferase activity was measured in the heart of mice injected with AAV vector comprising the CSk-SH5 regulatory element as compared to control mice (FIG. 4A). This regulatory element was also the most robust in muscle, in particular gastrocnemius muscle, tibialis interior, quadriceps, biceps and triceps. Hence, the most potent regulatory element was CSk-SH5. The second most robust regulatory element was CSk-SH1. A 25-fold augmentation of luciferase activity was measured in the heart of mice injected with AAV vector comprising CSK-SH1 when compared to control mice. Robust luciferase activity was also measured in other muscle of mice injected with CSk-SH1. The third robust regulatory element was CSk-SH3, followed by CSk-SH6, CSk-SH4 and CSk-SH2. Furthermore the expression was specific for cardiac and skeletal muscle as luciferase expression was absent or limited in all other organs (FIG. 5A), despite transduction of the vector into the other organs (FIG. 6A-B). The level of luciferase activity measured in the organs was consistent with the luciferase mRNA levels measured in the respective organs (FIGS. 4B, 5B). These in vivo data show that the nucleic acid regulatory elements CSk-SH, in particular CSk-SH1, CSk-SH3 and CSk-SH5, more particularly CSk-SH1 and Csk-SH5, can enhance heart and skeletal muscle-specific luciferase expression.

Example 3: Identification of Skeletal Muscle-Specific Regulatory Elements

Experimental Procedures

First, a list of muscle-specific genes was extracted from the Tissue-specific Gene Expression and Regulation (TiGER) database. This was used to identify a set of the most highly expressed (i.e. 'over-expressed') genes in muscle tissue. Conversely, a set of 'under-expressed' genes was identified, corresponding to those genes that exhibited the lowest expression in muscle. Next, the Reference Sequence (RefSeq) identifiers (IDs) lists of these 'over-expressed' and 'under-expressed' muscle-specific genes were used to extract the corresponding promoter sequences upstream the reported transcription start sites (TSSs) by 1000 bases (NCBI36/hg18 genome assembly), using the transcription start location data stored in the refGene table of the UCSC Genome Browser (http://genome.ucsc.edu) database. This resulted in two sets of muscle-specific promoter sequences corresponding to promoters of 'over-expressed' or 'under-expressed' genes. In order to make a non-redundant set of representative promoter sequences, the promoter sequences were filtered using 'uclust' (http://www.drive5.com/usearch/).

The two sets of non-redundant tissue-specific promoter sequences corresponding to promoters of 'over-expressed' or 'under-expressed' genes were used as input for the DDM/MDS method, described in detail in De Bleser et al. (2007. Genome Bio 8:R83), which is specifically incorporated by reference herein. The observed differential behaviour might be explained by the presence of one or more TFBS elements characteristic of the promoters of the up-regulated or down-regulated group of genes. These 'differential' TFBS elements could be found using following procedure. First, a library of TFBS positional weight matrices (PWMs) (TRANSFAC® 2010.3) was used to predict TFBS on every promoter sequence. For the muscle-specific promoters we used the Find Individual Motif Occurrences (fimo) application with a P-value cut-off of $10^{-3}$. The number of predicted TFBS elements per PWM per promoter was collected in the form of a matrix in which each row corresponds to a promoter sequence, while the columns corresponded to the used PWM. Two TFBS were considered correlated if their corresponding columns in the matrix were similar what could be measured using a distance function. With this approach, distance matrices summarizing all TFBS associations were constructed for the TFBS in both sets of promoters. Finally, by calculating the distance difference matrix (DDM) and performing multidimensional scaling on this DDM to visualize its content in two dimensions, TFBS could be distinguished that did not contribute to the observed differential gene expression as they were mapped near the origin of the DDM-MDS plot from 'deviating' TFBS that are likely responsible for the observed differential gene expression. As the MDS procedure plots TFBS that are strongly associated closer together than less associated ones, it was able to highlight interactions between TFBS in the promoter datasets. This procedure resulted in a list of TFBS associated with high tissue-specific expression for muscle-specific promoters.

Next, the genomic context of the tissue-specific over-expressed genes was searched for cross-species conserved regions for the TFBS associated with high tissue-specific gene expression. For that purpose, the sequences of all conserved sequence elements in the NCBI36/hg18 genome assembly were downloaded based on the information stored in the phastConsElements44 way table of the UCSC Genome Browser (http://genome.ucsc.edu) database. The predicted conserved sequence elements are assigned a log-odds score equal to its log probability under the conserved model minus its log probability under the non-conserved model. This allows to restrict the search for putative regulatory elements that coincide with the most conserved sequence elements. The conserved sequence elements were scanned for TFBS associated with high tissue-specific expression using the fimo application, as described above. Using internally developed Per scripts, this led to the identification of highly conserved sequence elements containing clusters of TFBS associated with high tissue-specific expression (i.e. nucleic acid regulatory elements). Additional filtering was done by selecting the putative nucleic acid regulatory elements that either overlapped or contained regions bearing reproducible biochemical features associated with transcription regulation and/or a open chromatin structure as defined in the ENCODE project (The ENCODE Project Consortium. 2012. Nature 489:57-74).

Results

This computational approach led to the identification of 6 muscle-specific regulatory sequences, summarized in Table 3.

TABLE 3

Muscle-specific regulatory elements.

| Sequence | Name | Gene regulated by sequence | Size (bp) | Conserved TFBS present |
|---|---|---|---|---|
| SEQ ID NO: 7 | Sk-SH1 | ATP2A1 | 495 | E2A, NF1, SRFC, p53, CEBP, LRF, MyoD |
| SEQ ID NO: 8 | Sk-SH2 | TNNI1 | 344 | E2A, NF1, CEBP, LRF, MyoD, SREBR |
| SEQ ID NO: 9 | Sk-SH3 | TNNI1 | 430 | E2A, HNF3a, CEBP, LRF, MyoD, SREBP, Tal1_b |
| SEQ ID NO: 10 | Sk-SH4 | MYLPF | 435 | E2A, SRF, p53, CEBP, LRF, MyoD, SREBP |
| SEQ ID NO: 11 | Sk-SH5 | MYFI1 | 474 | HNF4, NF1, RSRFC4, CEBP, LRF, SREBP |
| SEQ ID NO: 12 | Sk-SH6 | TPM3 | 519 | E2A, HNF3a, HNF3b, NF1, SRF, CEBP, LRF, MyoD, SREBP |
| SEQ ID NO: 13 | Sk-SH7 | ANKRD2 | 372 | E2A, CEBP, MyoD |

Bp: base pairs.

Example 4: In Vivo Validation of Skeletal Muscle-Specific Regulatory Elements Via AAV Vectors Comprising D Desmin Promoter Experimental Procedures AAV plasmid constructs comprising a skeletal muscle-specific regulatory element (pAAV-Sk-SH4Des-Luc2) were generated according to the protocol described in Example 2. Briefly, the skeletal muscle-specific regulatory elements were synthesized by conventional oligonucleotide synthesis and flanked with Acc65I and MluI restriction sites (Sk-SH1, 2, 3, 4, 5 and 7) or BsiWI and MluI restriction sites (Sk-SH6). The different Sk-SHs were cloned upstream of the Desmin (Des) promoter that drives expression of a Firefly Luciferase (Luc2) reporter gene in the context of the AAV vector backbone pAAV-Des-Luc2. The plasmids also contained a Minute Virus of Mouse (MVM) intron and a Simian Virus 40 (SV4) polyadenylation site (pA).

AAV vector production and purification and animal studies were carried out as described in Example 2. The experimental design is summarized in Table 4.

TABLE 4

Experimental desgn for the injection of skeletal muscle-specific regulatory elements.

| Vector | Mouse number (n) | Dose | Titre (gc/ml) | Volume vector (μl) | Volume PBS (μl) | Total volume (μl) |
|---|---|---|---|---|---|---|
| AAV9sc. Des.Luc2 | 5 | $5 \times 10^9$ | $5.7 \times 10^{11}$ | 8.7 | 41.3 | 50 |
| AAV9sc. Sk-SH1.Des.Luc2 | 4 | $5 \times 10^9$ | $1.7 \times 10^{11}$ | 29.4 | 20.6 | 50 |
| AAV9sc. Sk-SH2.Des.Luc2 | 4 | $5 \times 10^9$ | $1.8 \times 10^{11}$ | 27.7 | 22.3 | 50 |
| AAV9sc. Sk-SH3.Des.Luc2 | 4 | $5 \times 10^9$ | $1.9 \times 10^{11}$ | 26.3 | 23.7 | 50 |
| AAV9sc. Sk-SH4.Des.Luc2 | 4 | $5 \times 10^9$ | $1.6 \times 10^{11}$ | 31.3 | 18.7 | 50 |
| AAV9sc. Sk-SH5.Des.Luc2 | 1 | $5 \times 10^9$ | $8.1 \times 10^{11}$ | 62 | 3 | 65 |
| AAV9sc. Sk-SH6.Des.Luc2 | 3 | $5 \times 10^9$ | $1.4 \times 10^{11}$ | 35.7 | 14.3 | 50 |
| AAV9sc. Sk-SH7.Des.Luc2 | 4 | $5 \times 10^9$ | $1.8 \times 10^{11}$ | 27.7 | 22.3 | 50 | mRNA analysis and transduction efficiency and vector biodistribution were assessed as described in Example 2.

Results

Adeno-associated vectors were generated that expressed the luciferase gene luc2 from a chimeric promoter composed of the desmin (Des) promoter linked to the skeletal muscle-specific regulatory elements Sk-SH1-7. The vectors were intravenously injected in mice and whole body images were taken from the mice at 5 and 6 weeks post-injection to examine luciferase expression level.

All mice injected with a vector comprising a skeletal muscle-specific regulatory element (Sk-SH1-7) showed increased luciferase activity compared to control mice that were injected with a corresponding AAV9 vector without a regulatory element, indicating that all of the regulatory elements tested increased luciferase expression from the desmin promoter (data not shown). We observed very robust and enhanced luciferase activity in mice that were injected with AAV9 vector comprising the regulatory element Sk-SH1 or Sk-SH4 at 5 and 6 weeks post-injection as compared to luciferase activity of the control mice.

Figure 8:
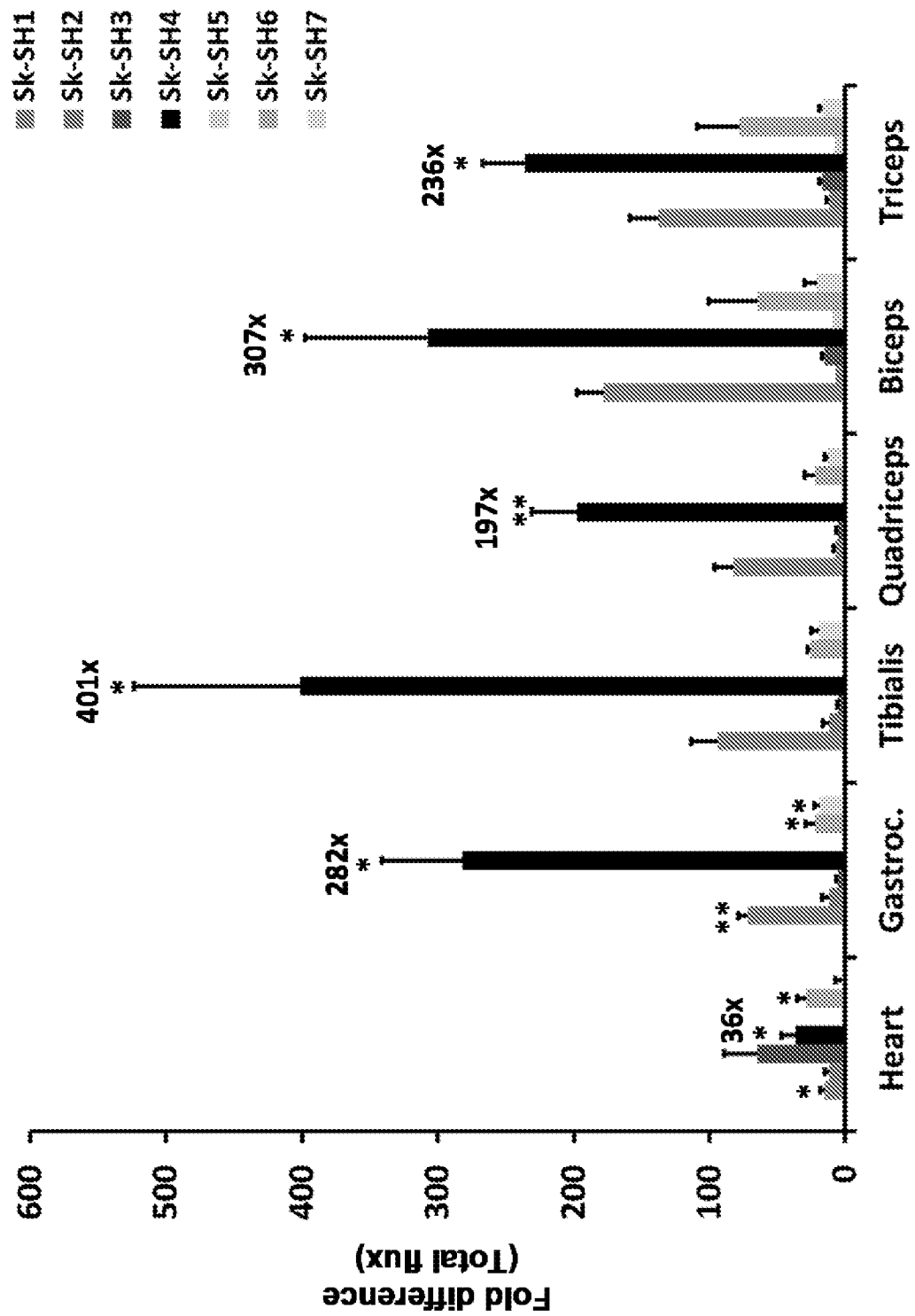
FIG. 8 shows difference in luciferase expression in heart and muscle tissue of mice that were intravenously injected with, from left to right, AAV9sc-Sk-SH1-Des-Luc2 (Sk-SH1, n=4), AAV9sc-Sk-SH2-Des-Luc2 (Sk-SH2, n=4), AAV9sc-SkSH3-Des-Luc2 (Sk-SH3, n=4), AAV9sc-SkSH4-Des-Luc2 (Sk-SH4, n=4), AAV9sc-Sk-SH5-Des-Luc2 (Sk-SH5, n=1), AAV9sc-Sk-SH6-Des-Luc2 (Sk-SH5, n=3) or AAV9sc-Sk-SH7-Des-Luc2 (Sk-SH6, n=4) vector compared to mice that were injected with the control vector AAV9sc-Des-Luc2 without nucleic acid regulatory element (control, no Sk-SH, n=5). Luciferase expression was measured as total flux, expressed in photons per second per centimetre squared per steradian (photons/sec/cm$^2$/sr), released by luciferase activity in the selected tissues at 7 weeks post-injection. Results were presented as mean±standard error of the mean, *p<0.05; **p<0.001.
Figure 9:
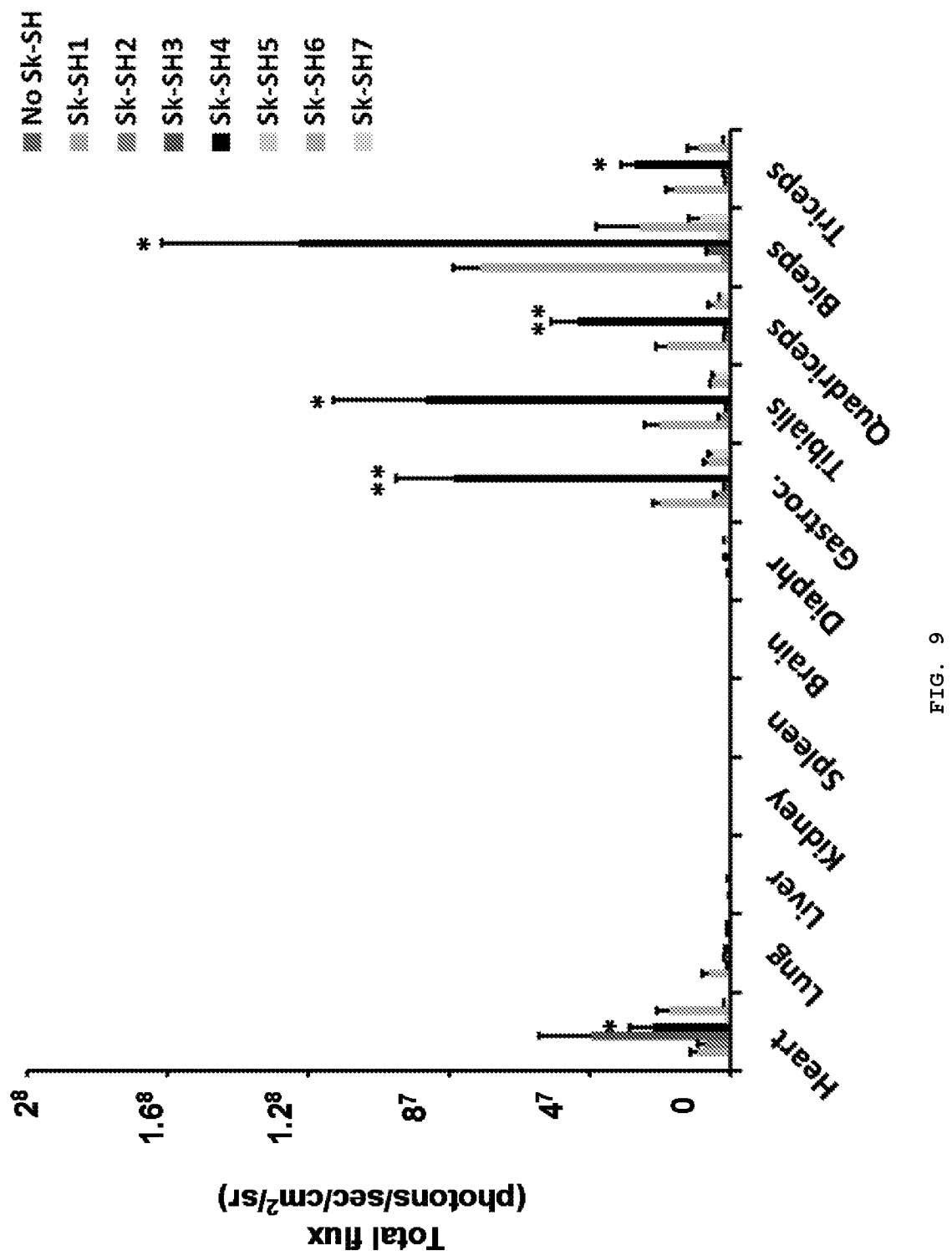
FIG. 9 shows luciferase expression in selected tissues of mice that were intravenously injected with, from left to right, AAV9sc-Des-Luc2 (control, no Sk-SH, n=5), AAV9sc-Sk-SH1-Des-Luc2 (Sk-SH1, n=4), AAV9sc-Sk-SH2-Des-Luc2 (Sk-SH2, n=4), AAV9sc-Sk-SH3-Des-Luc2 (Sk-SH3, n=4), AAV9sc-Sk-SH4-Des-Luc2 (Sk-SH4, n=4), AAV9sc-Sk-SH5-Des-Luc2 (Sk-SH5, n=1), AAV9sc-Sk-SH6-Des-Luc2 (Sk-SH5, n=3), or AAV9sc-Sk-SH7-Des-Luc2 (Sk-SH6, n=4) vector. Luciferase expression was measured as total flux, expressed in photons per second per centimetre squared per steradian (photons/sec/cm$^2$/sr), released by luciferase activity in the selected tissue at 7 weeks post-injection. Results were presented as mean±standard error of the mean, *p<0.05; **p<0.001.

7 weeks post injection, the mice were euthanized and individual organs were analyzed to evaluate luciferase expression and the biodistribution pattern (FIGS. 8 and 9). Up to 200 to 400-fold augmentation of luciferase activity was measured in skeletal muscle, in particular gastrocnemius muscle, tibialis interior, quadriceps, biceps and triceps, of mice injected with AAV vector comprising the Sk-SH4 regulatory element as compared to control mice (FIG. 8). There was still a 36-fold augmentation of luciferase activity measured in the heart of said mice (FIG. 8), due to the use of the desmin promoter, which is specific for both, heart and skeletal muscle. Luciferase expression was absent or limited in all other organs than cardiac and skeletal muscle tissue (FIG. 9). The second most robust regulatory element was Sk-SH1, which also specifically increased luciferase expression from the desmin promoter in skeletal muscle, and to a lesser extent in heart muscle.

Figure 12:
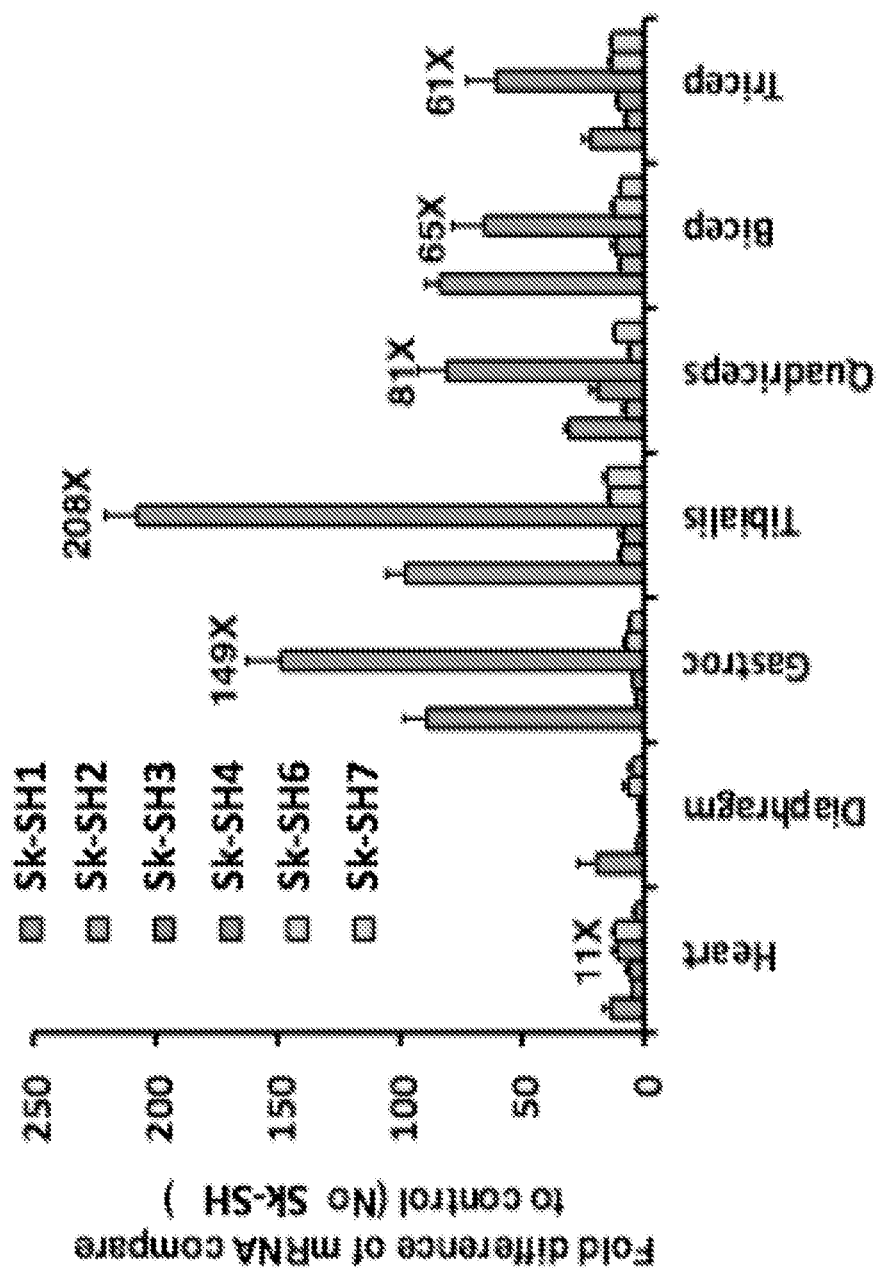
FIG. 12: Difference in Luc mRNA level in heart and muscle tissue of mice that were intravenously injected with, from left to right, AAV9sc-Sk-SH1-Des-Luc2 (Sk-SH1), AAV9sc-Sk-SH2-Des-Luc2 (Sk-SH2), AAV9sc-Sk-SH3-Des-Luc2 (Sk-SH3), AAV9sc-Sk-SH4-Des-Luc2 (Sk-SH4), AAV9sc-Sk-SH6-Des-Luc2 (Sk-SH6), or AAV9sc-Sk-SH7-Des-Luc2 (Sk-SH7) vector compared to mice that were injected with the control vector AAV9sc-Des-Luc2 without nucleic acid regulatory element (control, no Sk-SH). Luc mRNA levels were measured by a quantitative RT-PCR method (qRT-PCR) from total RNA extracted from biopsies from the indicated tissues. Results were presented as mean±standard error of the mean, *p<0.05; **p<0.001.

The level of luciferase activity measured in the heart and different skeletal muscles was consistent with the luciferase mRNA levels measured in the respective organs (FIG. 12). Notwithstanding the transduction of the vector into different organs as shown in FIG. 13, luciferase expression was absent or limited in all other organs than cardiac and skeletal muscle tissue (FIG. 9).

These in vivo data show that the nucleic acid regulatory elements Sk-SH, in particular Sk-SH1 and Sk-SH4, can enhance heart and skeletal muscle-specific luciferase expression. The nucleic acid regulatory element Sk-SH4 is by far the most robust element that led to the highest level of luciferase expression in the heart and skeletal muscle as compared to the other 5 regulatory elements that were identified. The highest activity that we measured was a 400-fold upregulation of luciferase activity in the tibialis.

Example 5: In Vivo Comparison of Muscle-Specific Regulatory Elements and CMV Promoter Experimental Procedures AAV plasmid constructs comprising a muscle-specific regulatory element (pAAV-Sk-SH4-Des-Luc2, pAAV-CSk-SH1-Des-Luc2, pAAV-CSk-SH5-Des-Luc2) were generated according to the protocol described in Example 2. Briefly, the muscle-specific regulatory elements were synthesized by conventional oligonucleotide synthesis and cloned upstream of the Desmin (Des) promoter that drives expression of a Firefly Luciferase (Luc2) reporter gene in the context of the AAV vector backbone pAAV-Des-Luc2. The plasmids also contained a Minute Virus of Mouse (MVM) intron and a Simian Virus 40 (SV40) polyadenylation site (pA).

Figures 10, 10A:
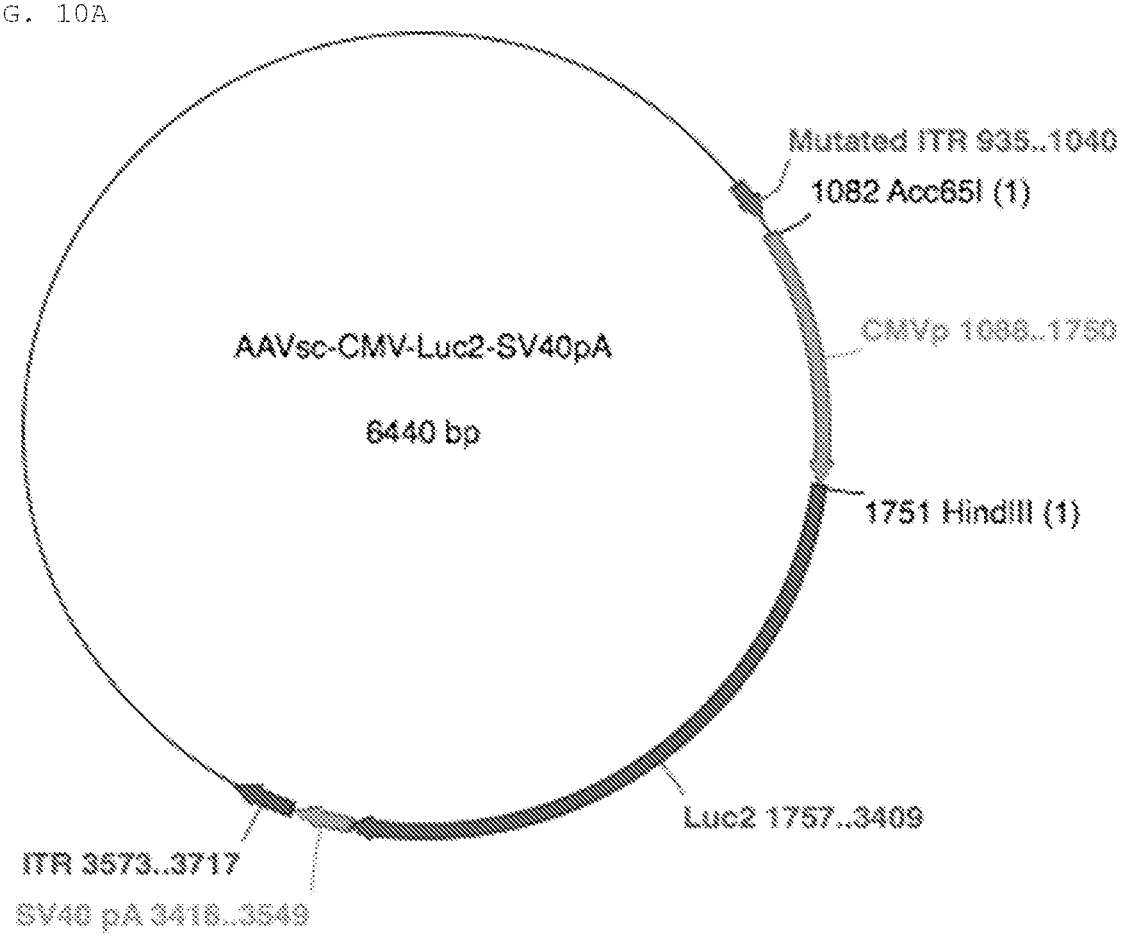
FIG. 10: (A) Schematic diagram of the AAV-sc-CMV-Luc2-SV40pA plasmid construct with indication where the Cytomegalovirus promoter (CMVp) is cloned upstream of the Firefly Luciferase gene (Luc2). Abbreviations used are: ITR: viral inverted terminal repeat; SV40pA: Simian Virus 40 polyadenylation site. (B) Luciferase expression in selected tissues of mice that were intravenously injected with, from left to right, AAV9sc-CMV-Luc2 (CMV, n=4), AAV9sc-Sk-SH4-Des-Luc2 (Sk-SH4, n=2), AAV9sc-CSk-SH1-Des-Luc2 (CSk-SH1, n=4), or AAV9sc-CSk-SH5-Des-Luc2 (CSk-SH5, n=4) vector. Luciferase expression was measured as total flux, expressed in photons per second per centimetre squared per steradian (photons/sec/cm$^2$/sr), released by luciferase activity in the selected tissue. Results were presented as mean±standard error of the mean. (C) Difference in luciferase expression in heart and muscle tissue of mice that were intravenously injected with, from left to right, AAV9sc-Sk-SH4-Des-Luc2 (Sk-SH4, n=2), AAV9sc-CSk-SH1-Des-Luc2 (CSk-SH1, n=4), or AAV9sc-CSk-SH5-Des-Luc2 (CSk-SH5, n=4) vector compared to mice that were injected with vector AAV9sc-CMV-Luc2 (CMV, n=4). Luciferase expression was measured as total flux, expressed in photons per second per centimetre squared per steradian (photons/sec/cm$^2$/sr), released by luciferase activity in the selected tissues at 7 weeks post-injection. Results were presented as mean±standard error of the mean.
Figure 10:
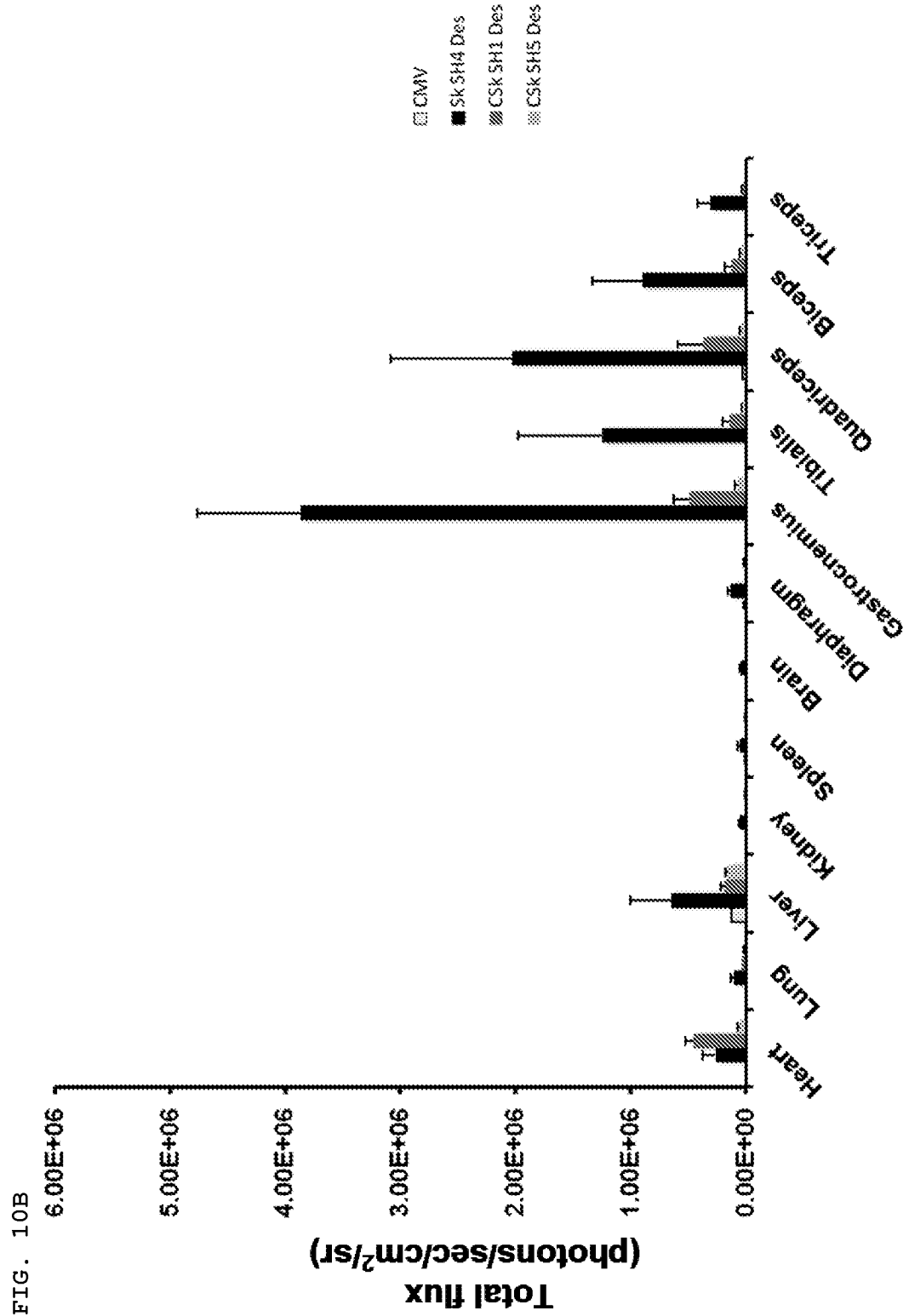
Figure 10:
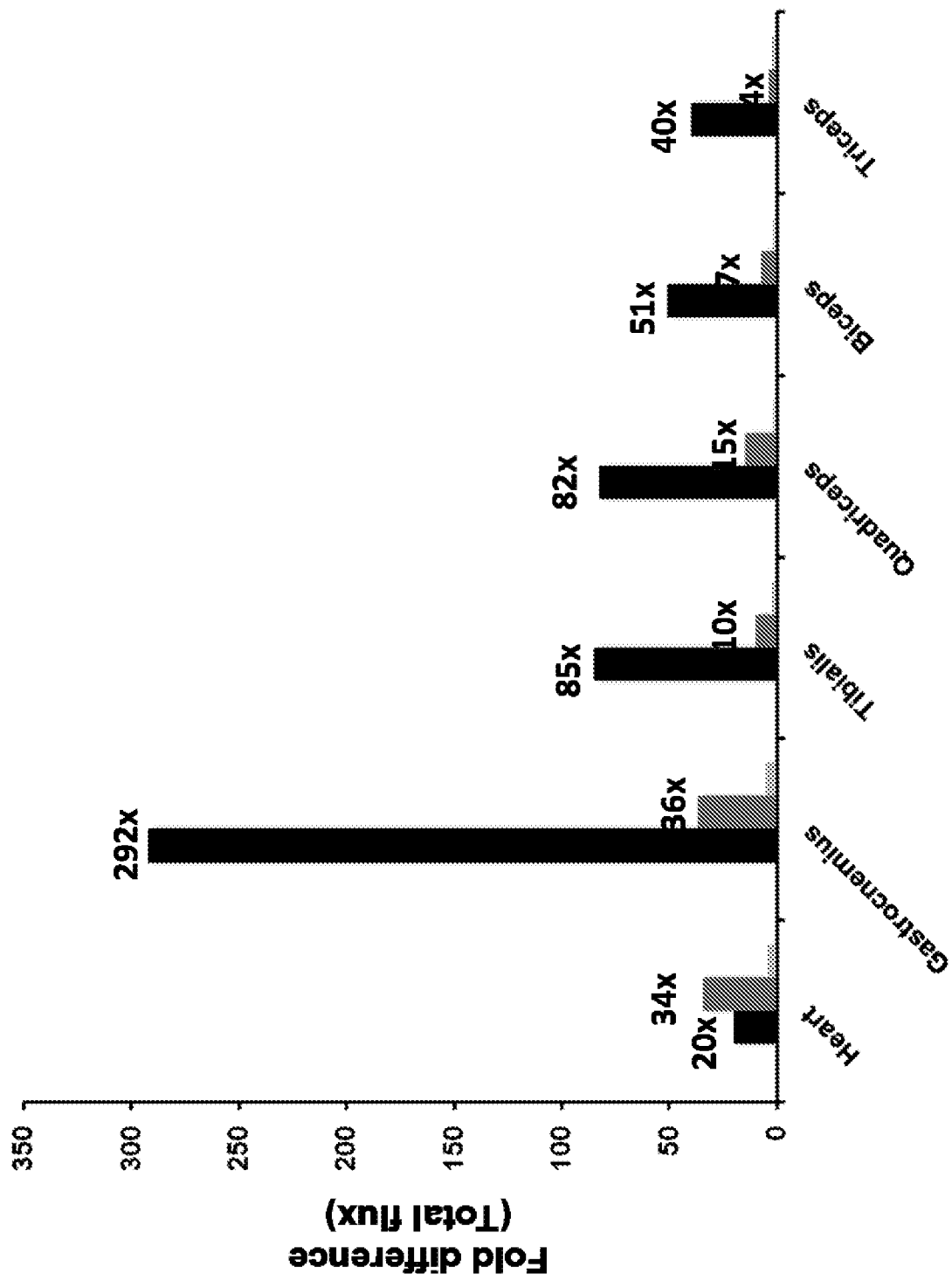

A pAAVsc-CMV-Luc2-SV40pA plasmid construct was generated, wherein the Cytomegalovirus (CMV) promoter (SEQ ID NO: 30) is cloned upstream the Firefly Luciferase (Luc2) reporter gene instead of the desmin promoter in the context of the AAV vector backbone pAAV-Des-Luc2. The plasmid also contained a Simian Virus 40 (SV40) polyadenylation site (pA). A schematic representation of pAAVsc-CMV-Luc2-SV40pA is shown in FIG. 10A. For the cloning of the AAVsc-CMV-Luc2-SV40pA, the fragment 5'-Acc65I-CMV-HindIII-3' was synthesised and cloned into an AAVsc-Luc2-SV40pA vector which was restricted with the same pair of enzymes (i.e. Acc65I and HindIII).

AAV vector production and purification were carried out as described in Example 2.

6 weeks old male CB17 SC SCID mice having an average weight of 17.4±1.6 g were intravenously injected into the periorbital vein with $1×10^{10}$ vg/mouse of concentrated vectors. Mice were imaged 4 weeks post-injection as described in Example 2. Mice were euthanized 5 weeks post-injection and intact organs were harvested and imaged as described in Example 2.

Results

Luciferase activity was compared in mice that were injected with a vector that expressed the luciferase gene luc2 from the desmin (Des) promoter operably linked to a muscle-specific regulatory element SK-SH4, CSk-SH1 or CSk-SH5, versus mice that were injected with a vector that expressed the luciferase gene luc2 from the Cytomegalovirus (CMV) promoter. The CMV promoter is considered one of the most powerful promoters known to allow robust gene expression in the heart. No muscle-specific regulatory element was present in the latter vectors.

FIGS. 10A and 10B show that the vectors comprising a muscle-specific regulatory element of the invention operably linked to the desmin promoter allow for much better expression than the vector comprising the CMV promoter.

Example 6: In Vivo Validation of Skeletal Muscle-Specific Regulatory Elements Via AAV Vectors Comprising a Skeletal Muscle-Specific Promoter Experimental Procedures AAV plasmids are constructed as described in Example 4, wherein the desmin promoter is replaced by the muscle-specific promoter described in Wang et al. (2008. Gene Ther. 15:1489-1499).

AAV vector production and purification and animal studies are carried out as described in Example 2.

Results

When using a skeletal muscle-specific promoter instead of the desmin promoter, the increase in luciferase expression is confined to skeletal muscle only, showing that the nucleic acid regulatory elements Sk-SH1-7, in particular Sk-SH4 and Sk-SH1 enhance skeletal muscle-specific luciferase expression.

Figures 11, 11A:
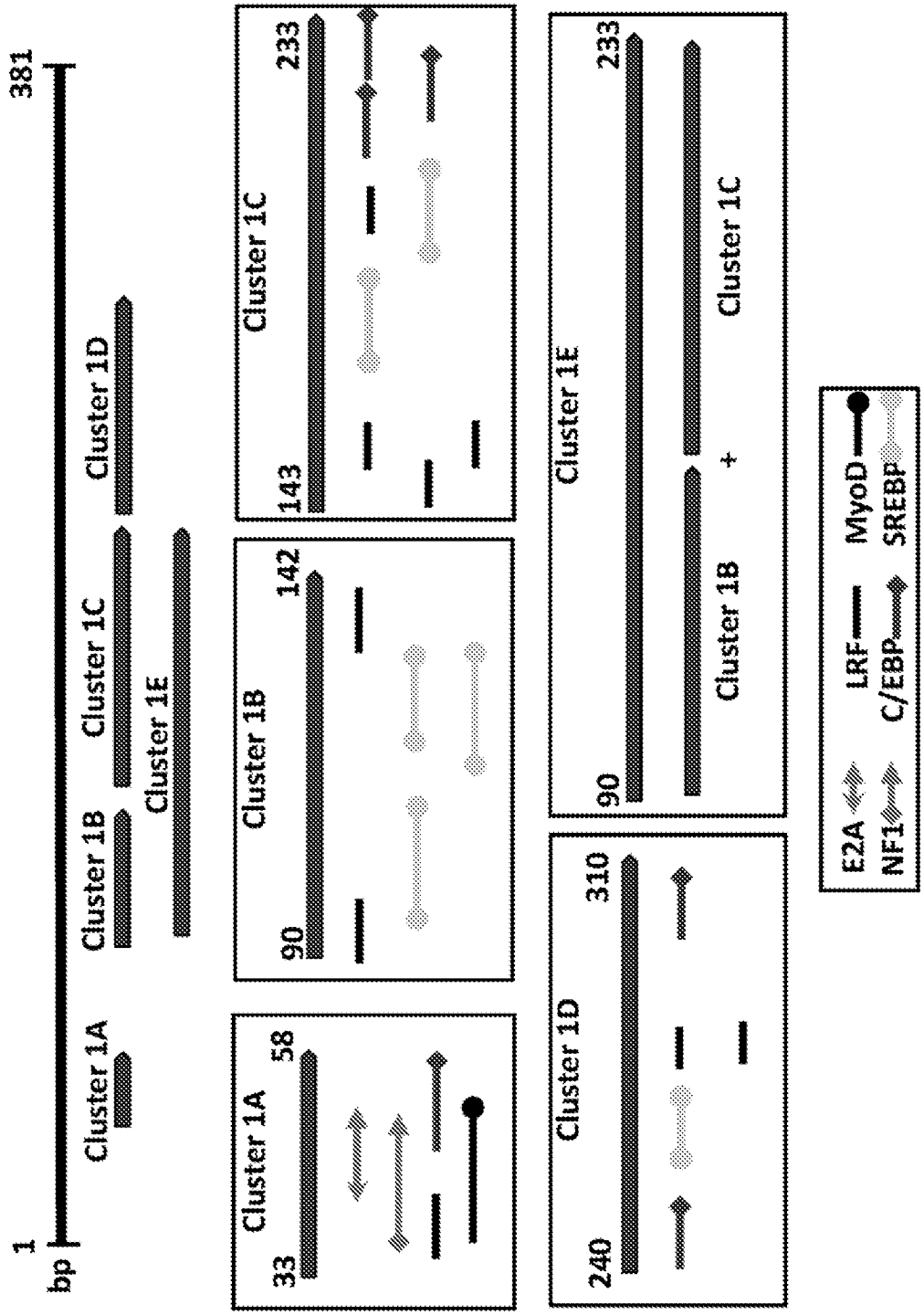
FIG. 11 shows functional fragments and the indicated transcription binding sites (TFBS) of CSk-SH1 (A), CSk-SH-5 (B), and Sk-SH4 (C) mapped on a schematic representation of respectively. SEQ ID NO:1 (A), SEQ ID NO:5 (B), and SEQ ID NO:10 (C).
Figure 11:
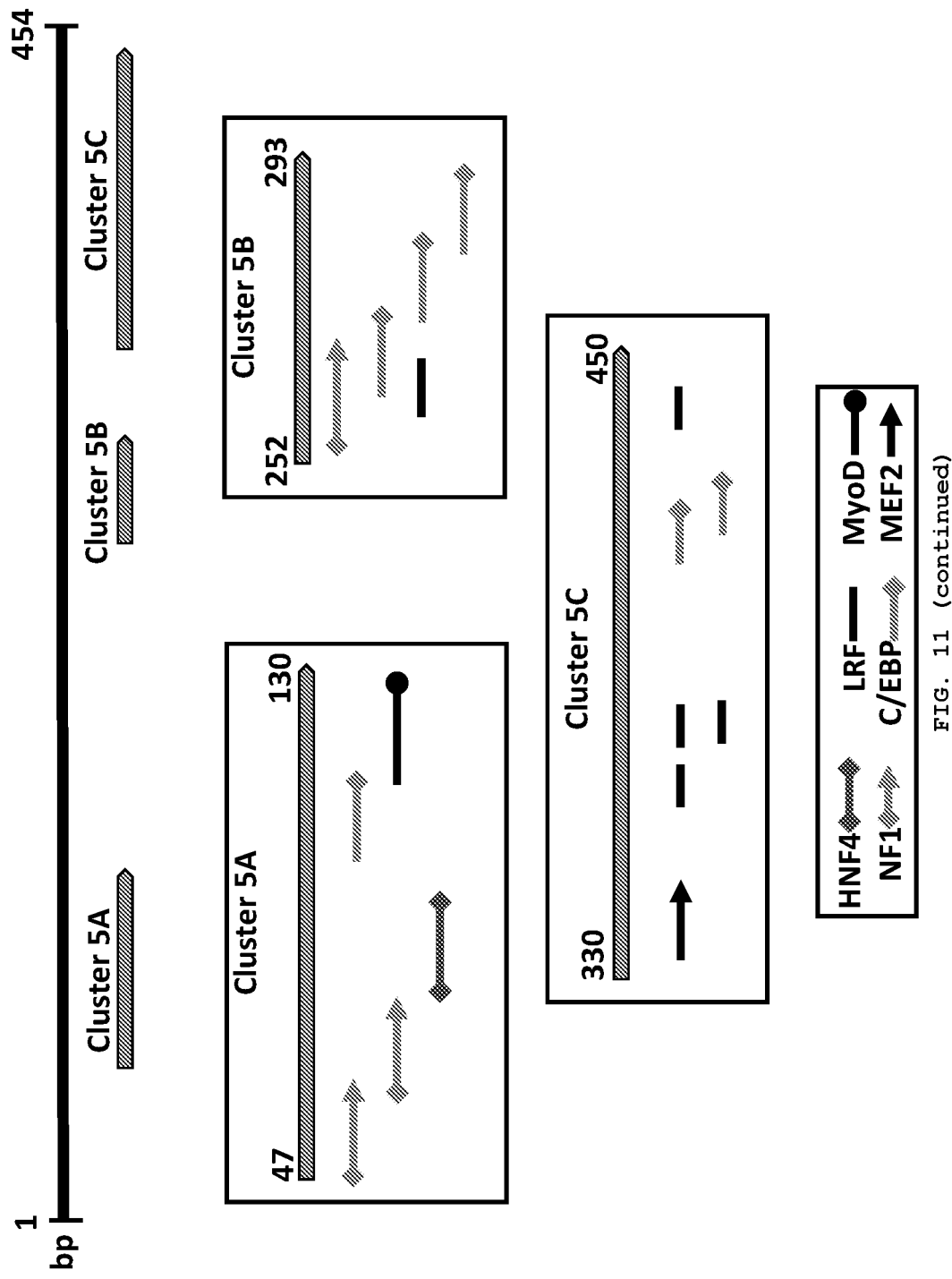
Figures 11, 11C:
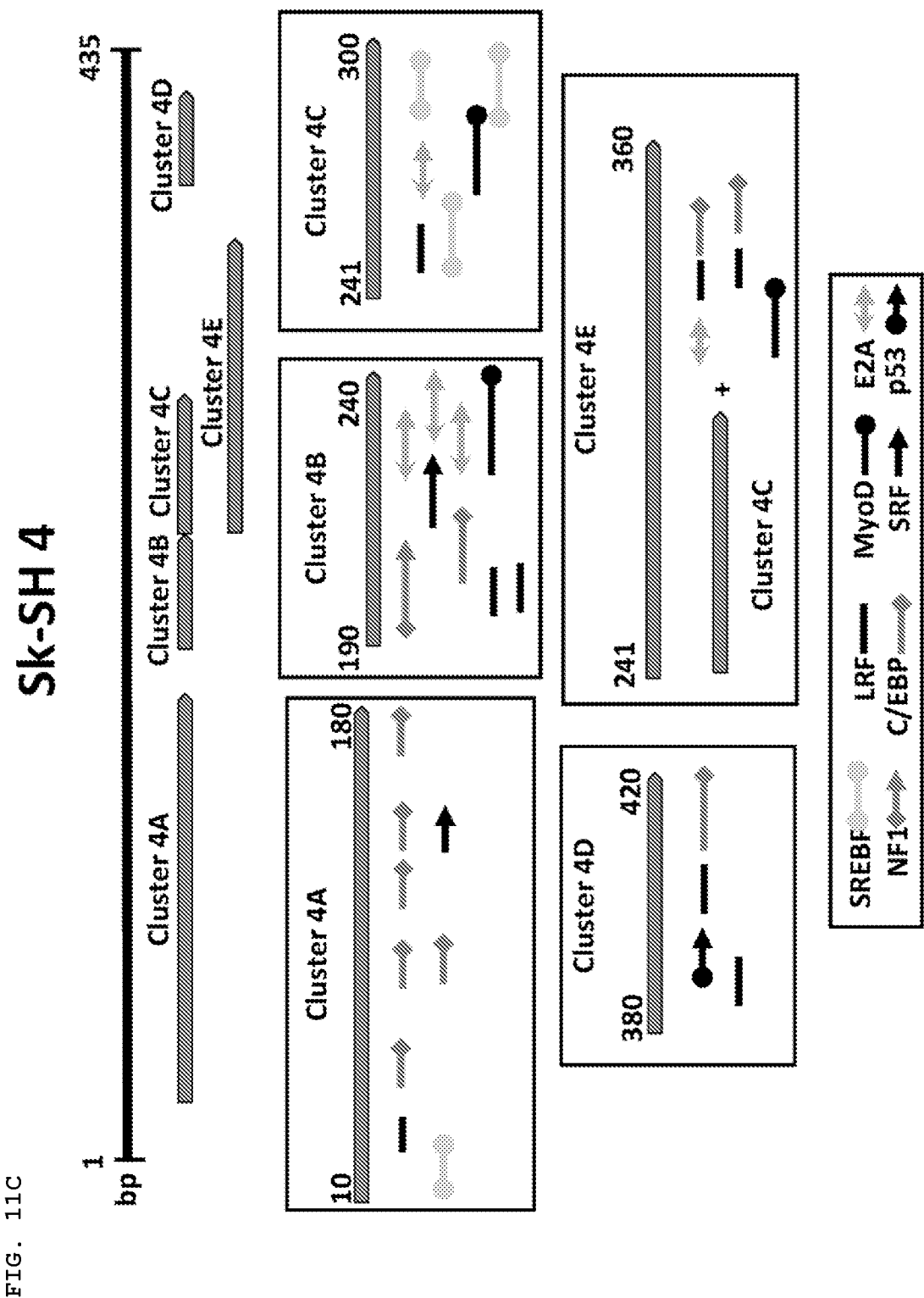

Example 7: In Vivo Validation of Functional Fragments of the Identified Muscle-Specific Regulatory Elements Experimental Procedures The identified nucleic acid regulatory elements CSk-SH1 (SEQ ID NO: 1; 381 bp), CSk-SH5 (SEQ ID NO:5; 454 bp) and Sk-SH4 (SEQ ID NO:10; 435 bp) were split into smaller functional fragments. The transcription factor binding sites (TFBS) of the regulatory elements were mapped on the respective sequence (FIG. 11A-C), and functional fragments were generated by randomly clustering regions with TFBS. The following functional fragments were generated:
Functional Fragments of SEQ ID NO:1:
  Cluster 1A: the nucleotide sequence from position 33 to 58 in SEQ ID NO:1
  Cluster 1B: the nucleotide sequence from position 90 to 142 in SEQ ID NO:1
  Cluster 1C: the nucleotide sequence from position 143 to 233 in SEQ ID NO:1
  Cluster 1D: the nucleotide sequence from position 240 to 310 in SEQ ID NO:1
  Cluster 1E: the nucleotide sequence from position 90 to 233 in SEQ ID NO:1
Functional Fragments of SEQ ID NO:5:
  Cluster 5A: the nucleotide sequence from position 47 to 130 in SEQ ID NO:5
  Cluster 5B: the nucleotide sequence from position 252 to 293 in SEQ ID NO:5
  Cluster 5C: the nucleotide sequence from position 330 to 450 in SEQ ID NO:5
Functional Fragments of SEQ ID NO:10:
  Cluster 4A: the nucleotide sequence from position 10 to 180 in SEQ ID NO:10 (SEQ ID NO: 37);
  Cluster 4B: the nucleotide sequence from position 190 to 240 in SEQ ID NO:10 (SEQ ID NO: 38);
  Cluster 4C: the nucleotide sequence from position 241 to 300 in SEQ ID NO:10 (SEQ ID NO: 39);
  Cluster 4E: the nucleotide sequence from position 241 to 360 in SEQ ID NO:10 (SEQ ID NO:41)
  Cluster 4D: the nucleotide sequence from position 380 to 420 in SEQ ID NO:10 (SEQ ID NO: 40)

The functional fragments of Sk-SH4 are summarized in Table 5.

TABLE 5

Functional fragments of the muscle-specific regulatory element Sk-SH4.

| Sequence | Name | Gene regulated by sequence | Size (bp) | Conserved TFBS present |
|---|---|---|---|---|
| SEQ ID NO: 37 | Sk-SH4$^a$ | MYLPF | 171 | CEBP, E2A, LRF, SRFb, SRFc |
| SEQ ID NO: 38 | Sk-SH4$^b$ | MYLPF | 51 | CEBP, E2A, LRF, SRFb |
| SEQ ID NO: 39 | Sk-SH4$^c$ | MYLPF | 60 | E2A, LRF, SRFb, MyoD |
| SEQ ID NO: 40 | Sk-SH4$^d$ | MYLPF | 41 | LRF, SRFb, p53, MyoD |
| SEQ ID NO: 41 | Sk-SH4$^e$ | MYLPF | 120 | CEBP, E2A, LRF, SRFb |

Bp: base pairs.

The functional fragments of Sk-SH4 were synthesized by conventional oligonucleotide synthesis and cloned into the pAAV9sc-Des-Luc2 vector as described in Example 2. AAV vector production and purification were carried out as described in Example 2. 6 weeks old CB17/IcrTac/Prkdc scid adult mice with an average weight of about 17-18 g per mouse were intravenously injected with the AAV vectors at a dose of $1 \times 10^{10}$ vg per mouse. After 2 and 4 weeks post injection, the mice were subjected to imaging using the same biospace In Vivo photo Imaging System as described in Example 2.

Results

Figure 14:
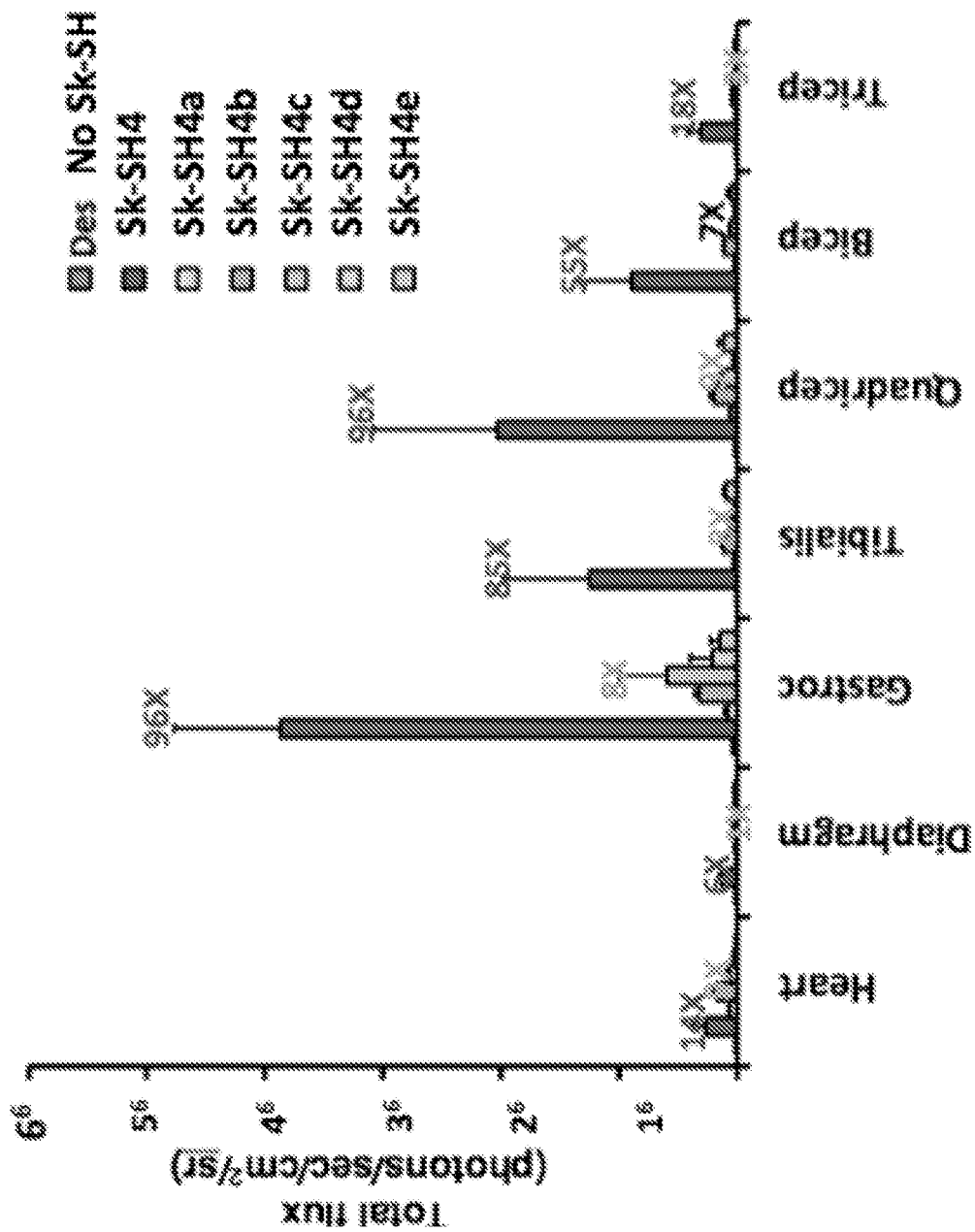
FIG. 14 shows luciferase expression in heart and muscle tissue of mice that were intravenously injected with, from left to right, AAV9sc-Des-Luc (control, no Sk-SH), AAV9sc-Sk-SH4-Des-Luc (Sk-SH4), AAV9sc-Sk-SH4$^a$-Des-Luc (Sk-SH4*), AAV9sc-Sk-SH4$^b$-Des-Luc (Sk-SH4$^b$), AAV9sc-Sk-SH4$^c$-Des-Luc (Sk-SH4$^d$), AAV9sc-Sk-SH4$^d$-Des-Luc (Sk-SH4$^e$), or AAV9sc-Sk-SH4$^e$-Des-Luc (Sk-SH4$^e$) vector. Luciferase expression was measured as total flux, expressed in photons per second per centimetre squared per steradian (photons/sec/cm$^2$/sr), released by luciferase activity in the selected tissue 5 weeks post-injection. Results were presented as mean±standard error of the mean. The fold difference in luciferase expression in mice injected with Sk-SH4 and Sk-SH4$^b$ compared to mice that were injected with the control vector AAV9sc-Des-Luc2 without nucleic acid regulatory element is indicated.

The results shown in FIG. 14 show that all 5 fragments of the Sk-SH4 regulatory element were capable of augmenting the expression of the luciferase gene driven from the desmin promoter when compared to the reference construct without any regulatory element. The fragment Sk-SH4$^b$ showed the highest luciferase expression compared to the other fragments. However, none of the fragments could achieve higher or equal luciferase expression when compared to the expression induced by the full length Sk-SH4 fragment.

Example 8: In Vivo Validation of Modules of Muscle-Specific Regulatory Elements

The muscle-specific regulatory elements are further validated by making different combinations of the regulatory elements and/or by using several copies of the same regulatory element (e.g. CSk-SH1 combined with CSk-SH5; CSk-SH1 combined with Sk-SH4; CSk-SH1 combined with CSk-SH5 and SkSH4; CSk-SH1 repeated 3× or 4×; CSk-SH5 repeated 3× or 4×; Sk-SH4 repeated 3× or 4×). These constructs are incorporated upstream of the Des promoter in accordance with the protocol described in Example 2. AAV vector production and purification and animal studies are carried out as described in Example 2.

Further combinations are made with functional fragments of the identified muscle-specific regulatory elements as generated in Example 7.

Example 9: Binding of Transcription Factors to Muscle-Specific Regulatory Elements Experimental Procedures 4 weeks old mice were intravenously injected in the periorbital vein with AVV vectors containing a Sk-SH4 and CSk-SH5 regulatory element, i.e. AAV9sc-Sk-SH4-Des-Luc and AAV9sc-CSk-SH5-Des-Luc, at a dose of $5 \times 10^9$ vg/per mouse.

Heart and muscle tissues harvested from the mice, were submersed in phosphate buffered saline (PBS) containing 1% formaldehyde, cut into small pieces and incubated at room temperature for 15 minutes. Fixation was stopped by the addition of 0.125 M glycine (final concentration). The tissue pieces were then treated with a Tissue-Tearer and finally spun down and washed twice in PBS. Chromatin was isolated by the addition of lysis buffer, followed by disruption with a Dounce homogenizer. Lysates were sonicated and the DNA sheared to an average length of 300-500 bp. Genomic DNA (input) was prepared by treating aliquots of chromatin with RNase, proteinase K and heat for de-cross-linking, followed by ethanol precipitation. Pellets were re-suspended and the resulting DNA was quantified on a NanoDrop spectrophotometer. Extrapolation to the original chromatin volume allowed quantitation of the total chromatin yield. An aliquot of chromatin (30 µg) was pre-cleared with protein A agarose beads (Invitrogen, catalogue number 15918-014). Genomic DNA regions of interest were isolated using 4 µg of antibody against MEF2 (Santa Cruz, sc-313), SRF (Santa Cruz, sc-335) and CEBP (Santa Cruz, sc-150). Complexes were washed, eluted from the beads with SDS buffer, and subjected to RNase and proteinase K treatment. Crosslinks were reversed by incubation overnight at 65° C., and ChIP DNA was purified by phenol-chloroform extraction and ethanol precipitation. Quantitative PCR (QPCR) reactions were carried out in triplicate on specific genomic regions using SYBR Green Supermix (Bio-Rad). The resulting signals were normalized for primer efficiency by carrying out QPCR for each primer pair using Input DNA. Primer sequences for Sk-SH4 were: 5'-GTCCCTCACTCC-CAACTCAG-3' (SEQ ID NO: 33; forward) and 5'-GAG-GAGAAGGAGATCAGACACTG-3' (SEQ ID NO: 34; reverse); for CSk-SH5: 5'-TAGCTGGGCCTTTCCTTCTC-3' (SEQ ID NO: 35; forward) and 5'-CGTCTCCCTAGCAGCAACAG-3' (SEQ ID NO: 36;

reverse). Negative control primers were purchased from Active Motif (Carlsbad, CA, USA) (#71012) and are specific for non-transcribed gene sequences on chromosome 17.
Results The muscle-specific regulatory element Sk-SH4 contains several putative transcription factor binding binding sites (TFBS), including E2A, SRF, p53, CEBP, LRF, MyoD and SREBP. Using a chromatin immuno-precipitation (CHIP) assay, binding of CEBP and SRF on the Sk-SH4 element was confirmed in the heart and skeletal muscle from mice that were injected with AAV9sc-Sk-SH4-Des-Luc vector (FIG. 15 A,B). Similarly, binding of CEBP and MEF2 element on the CSk-SH5 regulatory element was shown in the heart and skeletal muscle from mice injected with AAV9sc-CSk-SH5-Des-Luc (FIG. 15 C,D).

Figures 16, 16A:
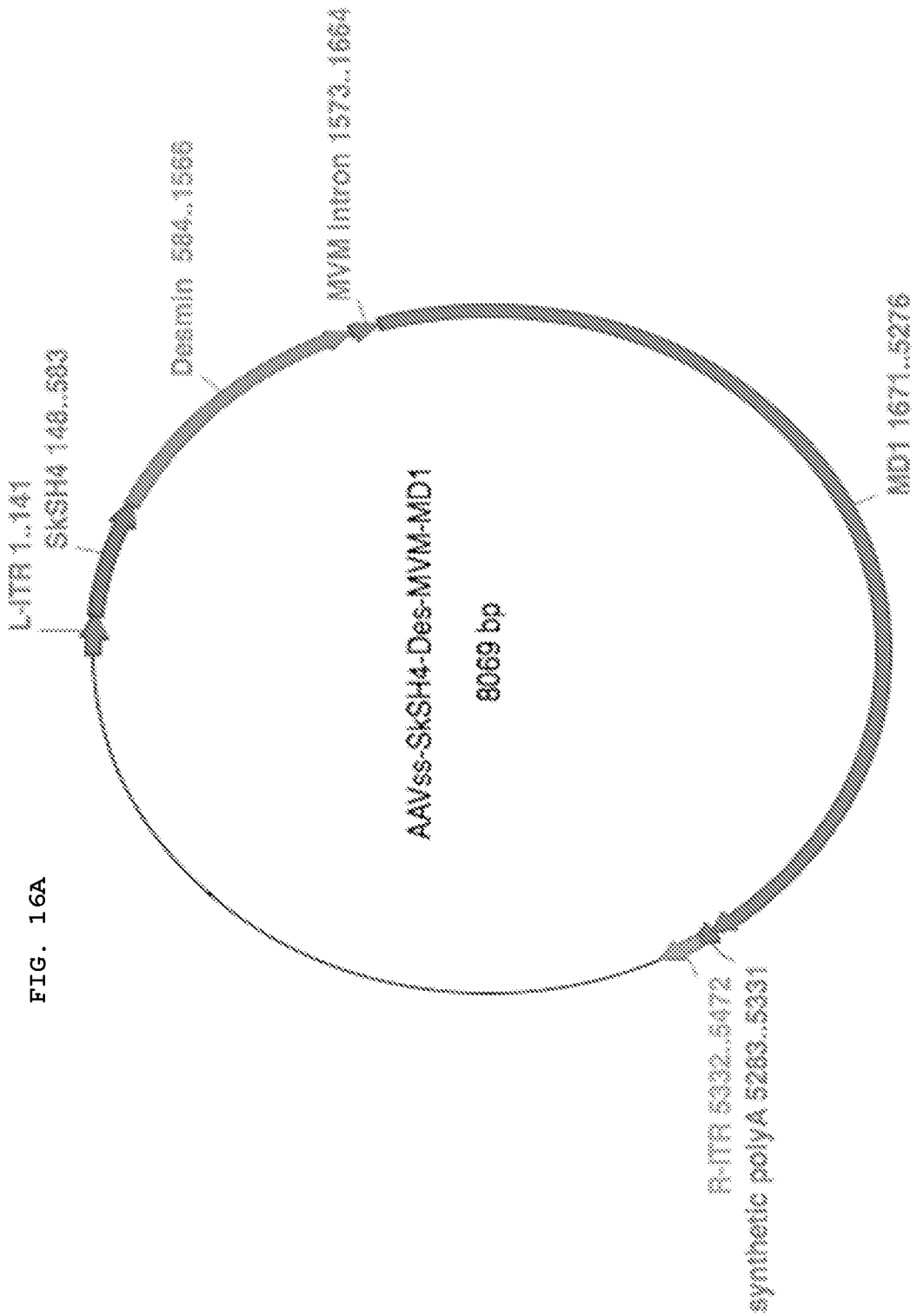
FIG. 16 shows schematic representations of single-stranded (ss) AAV plasmid constructs disclosed herein, which comprise the microdystrophin1 (MD1) (A, AAVss-SkSH4-Des-MVM-MD1) or follistatin (FST) (C, AAVssSkSH4-Des-MVM-FST-2A-Luc2) transgene regulated by the Desmin promoter operably linked to the muscle-specific nucleic acid regulatory element SkSH4 cloned upstream of the Desmin promoter. The follistatin gene was linked to the Luc2 reporter gene via a 2A peptide. The expression cassettes further comprise the Minute Virus of Mouse (MVM) intron and the 49 bp synthetic Proudfoot polyadenylation site (pA). The expression cassettes are flanked by inverted terminal repeats (ITR). (B) Nucleotide sequence of the AAVss-SkSH4-Des-MVM-MD1 plasmid construct (SEQ ID NO:44). (D) Nucleotide sequence of the AAVss-SkSH4-Des-MVM-FST-2A-Luc2 plasmid construct (SEQ ID NO:45).
Figure 16:
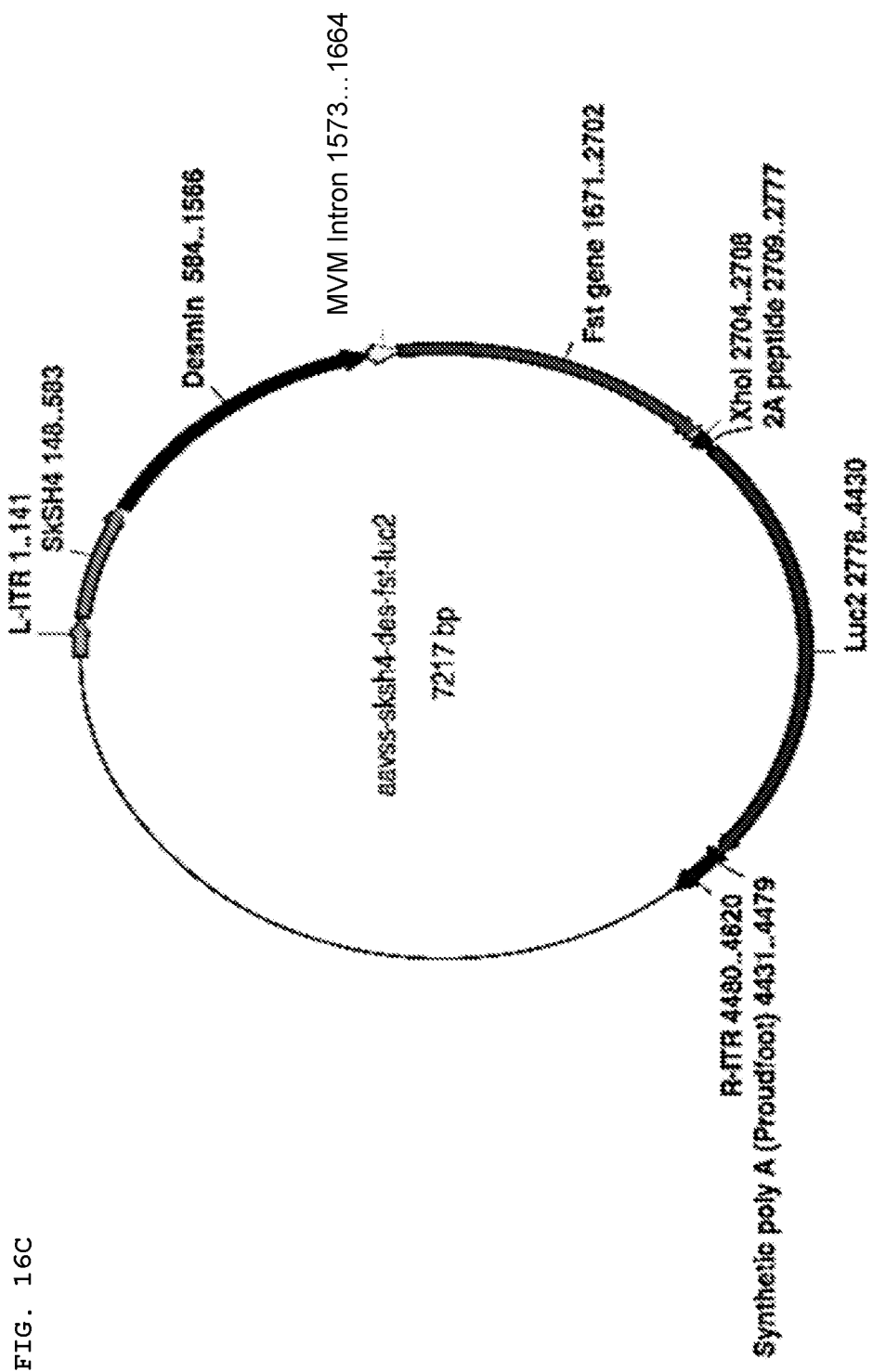

Example 10: Therapeutic Evaluation of Muscle-Specific Regulatory Elements Via AAV Vectors Comprising a Desmin Promoter The effect of the muscle-specific regulatory element Sk-SH4 on the expression and therapeutic efficacy of two therapeutic genes, in particular micro-dystrophin and follistatin, which have therapeutic potential for the treatment of muscle disease such as Duchenne muscular dystrophy (DMD) by gene therapy, was evaluated. MDX-SCID mice replicate the disease manifestations of Duchenne muscular dystrophy in patients and are therefore well suited to assess therapeutic efficacy of the AAVss-Sk-H4-Des-MVM-MD1 and AAVss-Sk-SH4-Des-MVM-FST-2A-Luc vectors.
Experimental Procedures
Cloning Follistatin and MD1 Genes into AAV The microdystrophin 1 (MD1) (Koo et al., 2011) and follistatin (FST) (Kota et al., 2009) genes were cloned and driven from desmin promoter, which was operably linked to the muscle-specific regulatory element Sk-SH4. The MD1 gene was flanked by MluI and XhoI restriction sites at the 5' and 3' ends, while the FST gene was flanked by MluI and SalI restriction sites at the 5' and 3' ends, respectively and were synthesized by conventional oligonucleotide synthesis. The Sk-SH4 regulatory element, operably linked to the desmin promoter, was cloned upstream of the MVM intron in the context of a single stranded adeno-associated viral vector (AAVss) backbone. The vector also contained a 49 bp synthetic proudfoot polyadenylation site (Levitt N et al, 1989). The follistatin gene was linked to a luciferase reporter gene via a 2A polypeptide. The generated constructs were designated as pAAVss-Sk-SH4-Des-MVM-MD1 and pAAVss-Sk-CRM4-Des-MVM-FST-2A-Luc, respectively, and are schematically shown in FIG. 16.

Figure 17:
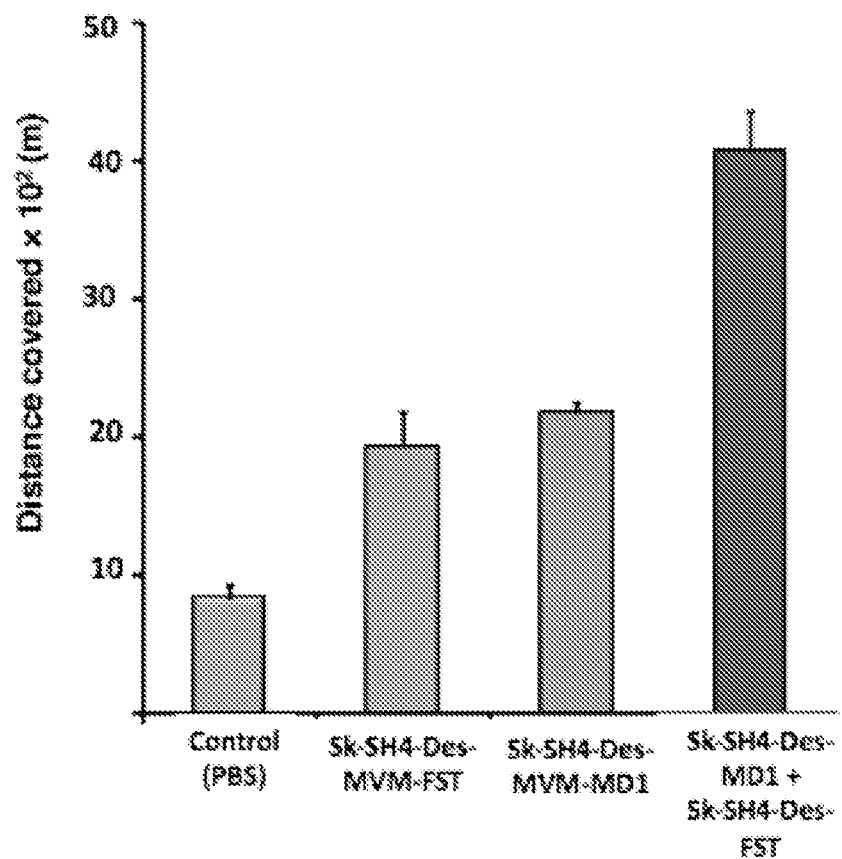
FIG. 17: Treadmill test for MDX-SCID mice injected with, from left to right, PBS (control), AAVss-Sk-SH4-Des-MVM-FST-2A-Luc, AAVss-Sk-SH4-Des-MVM-MD1, or the combination of AAVss-Sk-SH4-Des-MVM-FST-2A-Luc and AAVss-Sk-SH4-Des-MVM-MD1. Results are expressed as the calculated distance covered by each group of mice when run on a treadmill machine.

AAV vector production and purification were carried out as described in Example 2.
Treadmill Test for Phenotypic Connection of MDX-SCID Mice 4 weeks old MDX-SCID mice (bred in house) were injected intravenously in a total volume of 100 µl with a dose of $2 \times 10^{10}$ vg per mouse of the AAVss-Sk-SH4-Des-MVM-MD1 and AAVss-Sk-SH4-Des-MVM-FST-2A-Luc vectors, individually or in combination. 8 weeks post-injection, the treated and control (injected with PBS) MDX-SCID mice were subjected to the treadmill test. The treadmill tests were performed using the Exer-3/6 open treadmill (Columbus instruments, USA). The inclination of the belt was adjusted to 10° uphill before performing the test. The initial speed was set at 10 m/min and thereafter the speed was increased by 1 m every minute. The test was terminated at a point when the mice sat for ≥5 seconds on the pulse grill. At that point the distance covered by the mice was recorded and the total distance covered by the mice during the course of the test was calculated by using the formula, distance=((N+n)/2)(N−n+1) where N is the time (in min) at the point of termination of the test and n is the time (in minutes) at the start of the test.
mRNA Analysis mRNA analysis was performed as described in Example 2. To quantify the mRNA of the microdystrophin and follistatin genes, a qPCR-based method was used using the primers 5'-GTGCCCTACTACATCAA-3' (SEQ ID NO:42) as forward primer and 5'-AGGTTGTGCTGGTCCA-3' (SEQ ID NO:43) as reverse primer (amplicon 206 bp) for the microdystrophin, and the Luc2-specific forward primer 5'-CCCACCGTCGTATTCGTGAG-3' (SEQ ID NO: 14) and reverse primer 5'-TCAGGGCGATGGTTTTGTCCC-3' (SEQ ID NO: 15) (amplicon 217 bp) for the follistatin gene.
Results The results of the treadmill test clearly showed that the mice treated by gene therapy with either MD1 or FST or the combination of both, outperformed the untreated control MDX-SCID mice (FIG. 17). The MDX-SCID mice injected with either the AAVss-Sk-SH4-Des-MVM-MD1 or the AAVss-Sk-SH4-Des-MVM-FST-2A-Luc vector covered twice the distance covered by the control mice. When both vectors were co-injected into the MDX-SCID mice, a distance of 4 km was covered, which is 4 times more than the distance covered by the control MDX-SCID mice injected with PBS. These results clearly demonstrate that therapeutic efficacy can be achieved using these vectors.

The significant physiologic effect of the gene therapy using the AAVss-Sk-SH4-Des-MVM-MD1 or the AAVss-Sk-SH4-Des-MVM-FST-2A-Luc vector or their combined use was confirmed by histologic examination. Hematoxylin/eosin-stained muscle sections were scored for % centrally nucleated cells for the different experimental groups (FIG. 18). The muscle sections of C5716 wild-type mice showed predominantly peripheral localization of the nucleus in the myofibers (data not shown) and a minimal percentage (<2%) of the nuclei was centrally located (FIG. 18B). In untreated, control, MDX/SCID mice, the nuclei were predominantly (about 50% of the nuclei) centrally located in the transversally transected myofibers (FIG. 18Aa, FIG. 18). MDX/SCID mice injected with AAVss-Sk-SH4-Des-MVM-MD1 (AAV9-MD1) (FIG. 18Ac, FIG. 18B) or AAVss-Sk-SH4-Des-MVM-FST-2A-Luc (AAV9-FST) (FIG. 18Ab, FIG. 18B), all showed a decreased number of myofibers that are centrally nucleated. Co-administration of both, AAVss-Sk-SH4-Des-MVM-MD1 and AAVss-Sk-SH4-Des-MVM-FST-2A-Luc vectors, resulted in an even more profound shift in nuclear localization towards the periphery of the myofibers, and a further reduction in the percentage of centrally located nuclei (FIG. 18Ad, FIG. 18B). These results are indicative of a reduced regenerative stimulus and phenotypic correction after the gene therapy. Consequently, the shift of nuclear localization from a central to a more peripheral location in the myofibers is consistent with the phenotypic correction as shown by the improved muscle strength and mobility in the treadmill assay.

Figures 19, 19C:
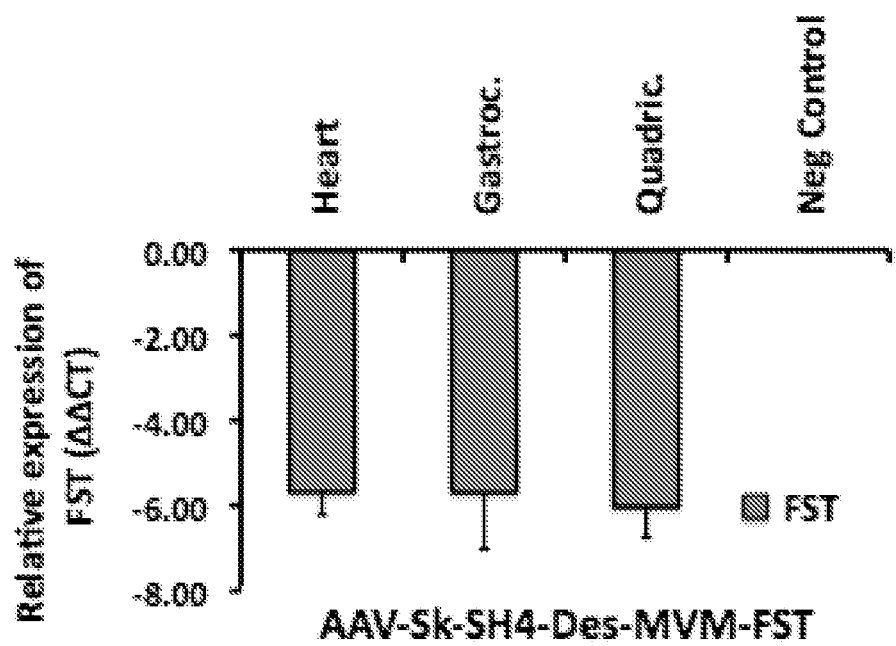
FIG. 19: Microdystrophin1 (MD1) (A,B) and follistatin (FST) (C) mRNA levels in heart and muscle (gastrocnemius and quadriceps) tissues from mice that were intravenously injected with the AAVss-Sk-SH4-Des-MVM-MD1 vector (A), the combination of AAVss-Sk-SH4-Des-MVM-MD1 and AAVss-Sk-SH4-Des-MVM-FST-2A-Luc (B), or AAVss-Sk-SH4-Des-MVM-FST (C) relative to expression of endogenous housekeeping gene (GAPDH: Glyceraldehyde-3-phosphate dehydrogenase). Results are presented as relative expression of MD1 or FST (□□CT).

Using quantitative RT-PCR, the expression of the microdystrophin (MD1) and the follistatin (FST) genes in biopsies from heart and muscle tissues, in particular gastrocnemius and quadriceps, of the mice injected with the pAAVss-Sk-SH4-Des-MVM-MD1 construct, the pAAVss-Sk-SH4-Des- MVM-FST-2A-Luc construct or the combination of both constructs was assessed (FIG. 19).

Example 11: In Vivo Comparison of Muscle-Specific Regulatory Elements with CMV and SPc5-12 Promoters Experimental Procedures AAV vector production and purification were carried out as described in Example 2.

The AAVsc-Des-MVM-Luc vector is a self-complementary AAV vector containing a luciferase (Luc) transgene driven from the desmin promoter. The scAAV vector backbone also contained a Minute Virus of Mouse (MVM) intron and a Simian Virus 40 (SV40) polyadenylation site (pA).

The AAVsc-SPc5-12-MVM-Luc vector had the same configuration as the AAVsc-Des-MVM-Luc vector, but the desmin promoter was replaced by the SPc5-12 promoter.

AAV vectors comprising the muscle-specific regulatory element Sk-SH4 were generated according to the protocol described in Example 2. Briefly, the muscle-specific regulatory element Sk-SH4 was synthesized by conventional oligonucleotide synthesis and cloned upstream of the desmin or the SPc5-12 promoter in the context of the AAV vector backbone of AAVsc-Des-MVM-Luc or AAVsc-SPc5-12-MVM-Luc, respectively.

The AAVsc-CMV-Luc vector was generated by cloning the Cytomegalovirus (CMV) promoter (SEQ ID NO: 30) upstream the luciferase reporter gene instead of the desmin promoter in the context of the AAV vector backbone of AAVsc-Des-Luc, which also contained a polyadenylation site (pA).

A schematic representation of the different vectors is shown in FIG. 20.

Adult CB17/IcrTac/Prkdcscid mice were intravenously injected with the different vectors (n=3) at a dose of 1×10$^{10}$ vg/mouse.

mRNA analysis was performed as described in Example 3.

Results

Figure 21:
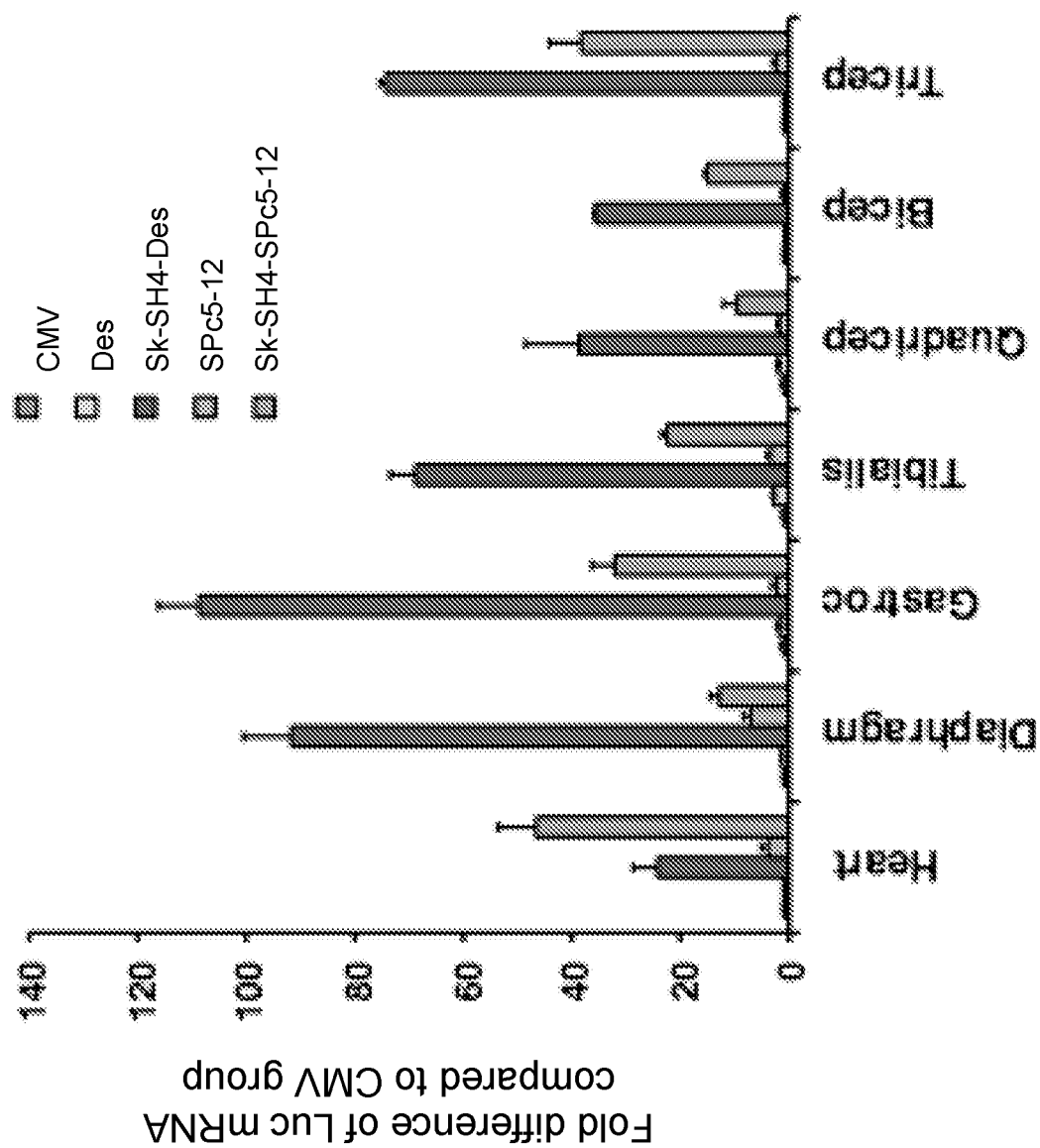
FIG. 21: Difference in Luc mRNA levels in selected tissues of CB17/IcrTac/Prkdcscid mice that were intravenously injected with, from left to right, AAVsc-CMV-Luc, AAVsc-Des-MVM-Luc, AAVsc-Sk-SH4-Des-MVM-Luc, AAVsc-SPc5-12-MVM-Luc or AAVscSk-SH4-SPc5-12-MVM-Luc vector as schematically shown in FIG. 20, compared to mice that were injected with AAVsc-CMV-Luc vector. Luc mRNA levels were measured by qRT-PCR from total RNA extracted from biopsies of the indicated tissues. Results were presented as mean±standard error of the mean, *p<0.05; **p<0.001.

Luciferase mRNA levels in mice injected with a vector that expressed the luciferase gene from the desmin promoter operably linked to the muscle-specific regulatory element Sk-SH4 were compared versus mice that were injected with a vector that expressed the luciferase gene from the Cytomegalovirus (CMV) or the SPc5-12 promoters, which were not operably linked to a muscle-specific regulatory element. The CMV and SPc5-12 promoters are considered the most powerful promoters known to allow robust gene expression in the heart and skeletal muscles. FIG. 21 shows that the vector comprising the Sk-SH4 muscle-specific regulatory element of the invention operably linked to the desmin promoter allows for much better expression than the vectors comprising the CMV or the SPc5-12 promoter without muscle-specific regulatory element.

Similarly, when the Sk-SH4 muscle-specific regulatory element was operably linked to the SPc5-12 promoter, increased luciferase mRNA levels were observed in the heart and all skeletal muscle types tested (FIG. 21). However, the mRNA level induced from this construct was lower than when the Sk-SH4 muscle-specific regulatory element of the invention is operably linked to the desmin promoter.

Example 12: In Vivo Comparison of Desmin Promoters

Experimental Procedures

AAV vectors comprising the muscle-specific regulatory element Sk-SH4 were generated according to the protocol described in Example 2. Briefly, the muscle-specific regulatory element Sk-SH4 was synthesized by conventional oligonucleotide synthesis and cloned upstream of the human desmin 1.4 kb promoter (SEQ ID NO:48) in the context of the AAV vector backbone of AAVsc-hDes1.4 kb-MVM-Luc, upstream of the human desmin 1.0 kb promoter (SEQ ID NO:47) in the context of the AAV vector backbone of AAVsc-hDes1.0 kb-MVM-Luc or upstream of the murine desmin promoter (SEQ ID NO:16) in the context of the AAV vector backbone of AAVsc-mDes-MVM-Luc.

Adult CB17/IcrTac/Prkdcscid mice were intravenously injected with the different vectors (n=5) at a dose of 1×10$^{10}$ vg/mouse.

Mice were sacrificed at two weeks and four weeks after injection of the vectors and the different muscle types (biceps, diaphragm, gastrocnemius, heart, quadriceps, tibialis and triceps) were isolated and quantified using bioluminescence imaging as described in Keyaerts M1, Caveliers V, Lahoutte T. Trends Mol Med. 2012 March; 18(3):164-72. doi: 10.1016/j.molmed.2012.01.005. Epub 2012 Feb. 8. Bioluminescence imaging: looking beyond the light.

Results

Comparison of the luciferase expression induced by the different AAV vectors quantified as Photons signal shows that the expression cassette comprising Sk-SH4-hDES1.0 kb or Sk-SH4-hDES1.4 kb, and especially Sk-SH4-hDES1.4 kb, leads to a higher luciferase expression in the different muscle types of mice (Biceps, diaphragm, gastrocnemius, heart, quadriceps, tibialis and triceps) compared to the expression cassette comprising Sk-SH4-mDES (FIG. 22).

Example 13: Muscle Specific Regulatory Element-Mediated Upregulation of GAA and MTM1 Expression Experimental Procedures
Generation of the AAV Plasmid Constructs The human alpha-glucosidase (hGAA) gene and the human myotubularin 1 (hMTM1) gene were codon-optimized using the Gene optimizer (GeneArt, Life technologies, Germany).

The hGAA gene (SEQ ID NO:49) and its codon-optimized variant hGAAco (SEQ ID NO:50) were cloned and driven from the SPc5-12 promoter (SEQ ID NO:53), which was operably linked to the regulatory element CSk-SH5 (SEQ ID NO:5).

On the other hand, the hMTM1 gene (SEQ ID NO:51) and its codon-optimized variant hMTM1co (SEQ ID NO:52) were cloned and driven from the hDES1.4 kb promoter (SEQ ID NO:48), which was operably linked to the regulatory element Sk-SH4 (SEQ ID NO:10).

The hGAA and hGAAco genes and hMTM1 and hMTM1co genes were flanked by BsiWI and XmaJI restriction sites at the 5' and 3' ends respectively and were synthesized by conventional oligonucleotide synthesis.

The Sk-SH4 (SEQ ID NO:10) regulatory element, operably linked to the SPc5-12 promoter (SEQ ID NO:53) and the CSk-SH5 (SEQ ID NO:5) regulatory element, operably linked to the hDES1.4 kb promoter (SEQ ID NO:48), were cloned upstream of the MVM intron (SEQ ID NO:54) in the context of a single stranded adeno-associated viral vector (AAVss) backbone. The vector also contained a 49 bp synthetic proudfoot polyadenylation site (Levitt N et al, 1989) (SEQ ID NO:46). The generated constructs were designated as pAAVss-SkSH4-hDES1.4 kb-MVMhMTM1-SynthpA (SEQ ID NO: 67), pAAVss-SkSH4-hDES1.4 kb-MVM-hMTM1co-SynthpA (SEQ ID NO: 68), pAAVss-CSkSH5-SPc5-12-MVM-hGAA-SynthpA (SEQ ID NO: 65) and pAAVss-CSkSH5-SPc5-12-MVM-hGAAco-SynthpA (SEQ ID NO: 66).

AAV Vector Production and Purification

AAV vector production and purification were carried out as described in Example 2.

Animal Studies

All animal procedures were approved by the institutional animal ethics committee of the Free University of Brussels (VUB) (Brussels, Belgium). All mice were housed under specific pathogen-free conditions; food and water were provided ad libitum.

The concentrated vectors ($5\times10^{11}$ vg/mouse) were injected into the tail-vein of 4 week old CB.17-SCID mice (Janvier, France). Four to five weeks post injection, the mice were euthanized and individual organs were analyzed to evaluate mRNA and protein expression.

hGAA(co) and hMTM1(co) ELISA

The ELISA for hGAA(co) and hMTM1(co) was performed as indicated by manufacturer's instruction (MyBiosources). The total proteins from different organs of the mice (liver (positive control), diaphragm, gastrocnemius, heart) were extracted regarding to the manufacturer's protocol (Thermofisher Scientific, USA). For each ELISA, 50 mg of the organ tissue was taken from frozen storage. Then 500 μL of cold PBS with protease inhibitor was added to the tissue and then homogenized with Matrix D (MPBio) for 3 cycles of 20 s. The protease inhibitor cocktail (Invitrogen, USA) was added to inhibit the protease activity and maximize the quality of the samples. Afterward, the lysates were centrifuged at 13,000 rpm for 5 minutes at 4° C. The supernatants were collected and processed as mentioned in each ELISA kits or stored at −20 C until analysis.

The total proteins were diluted with the samples buffer, which consisted of cold PBS with protease inhibitors, to about 50 mg of total protein and loaded into the hGAA ELISA plate. The background was subtracted with non-injected mice. The detection range for hGAA(co) was 1.600-25 pg/mL and the detection range for hMTM1(co) was 3.125-100 ng/mL.

mRNA Analysis

Total RNA was extracted from 30-50 mg homogenised organ tissue (diaphragm, gastrocnemius, or heart) of the CB.17-SCID mice by RNA Nucleospin purification kit according to the manufacturer's instructions (Macherey-Nagel). Homogenization of the samples was performed using Matrix D (MPBio) for 2 cycles of 20 s. Subsequently, the cDNAs were synthesised using SuperScript III cDNA synthesis kit (Invitrogen, USA) according to the manufacture's protocol. Next, a cDNA amount corresponding to 10 ng of total RNA was amplified by quantitative (q) PCR on an ABI 7700 (Applied Biosystems, Foster City, CA, USA), using 5'-TGCCCTCGCAGTATATCACAG-3'(SEQ ID NO: 55) as a forward primer and 5'-GAGACCCGTAG-AGGTTCGC-3' (SEQ ID NO: 56) as reverse primer (amplicon 129 bp) for the hGAA gene, using 5-ACCCCTT-CATGCCTCCTTAT-3' (SEQ ID NO: 57) as a forward primer and 5'-TCCATGTAGTCCAGGTCGTT-3' (SEQ ID NO: 58) as reverse primer (amplicon 148 bp) for the hGAAco gene, using 5'-GTTTGAGATCCTCACGAGA-TACG-3' (SEQ ID NO: x59) as a forward primer and 5'-GTCCATCCATCCACGTTAAACTT-3'(SEQ ID NO: 60) as reverse primer (amplicon 96 bp) for the hMTM1 gene and using 5'-GGCAAGAGAAACAAGGACGA-3' (SEQ ID NO: 61) as a forward primer and 5'-GGCATCGTCGGACT-CATATC-3' (SEQ ID NO: 62) as reverse primer (amplicon 150 bp) for the hMTM1co gene. The qPCR standards consisted of serially diluted plasmids of known quantity. The hGAA(co) and hMTM1(co) mRNA levels were normalized to mRNA levels of the endogenous murine glyceraldehyde-3-phosphate dehydrogenase (mGAPDH) gene, using 5'-TGTGTCCGTCGTGGATCTGA-3' (SEQ ID NO: 31) as forward primer and 5'-GCCTGCTTCACCACCTTCTTGA-3' (SEQ ID NO: 32) as the reverse primer (amplicon 82 bp). RNA samples were amplified with and without reverse transciptase to exclude DNA amplification. The size of the amplified PCR fragments was verified on a 1.8% agarose gel.

Results hGAA(Co) Expression

Figures 25, 25A:
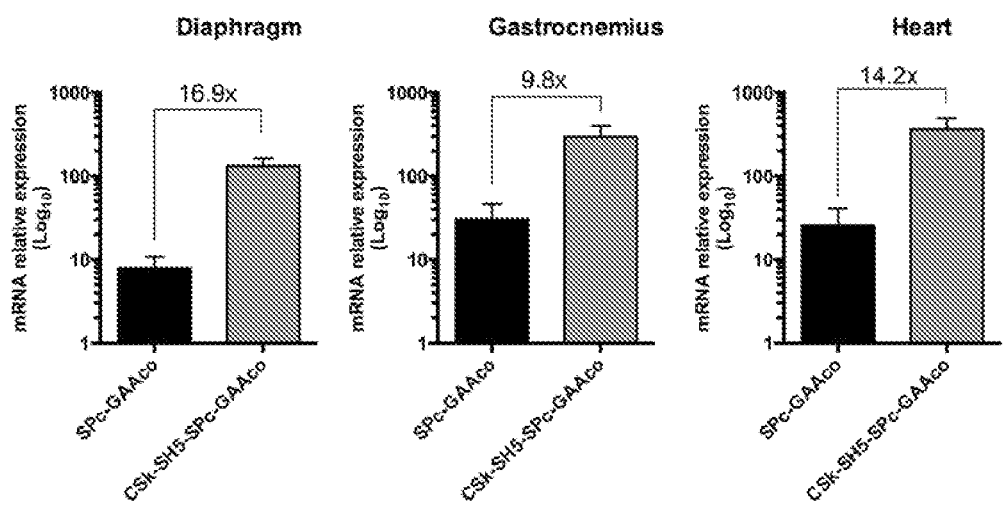
FIG. 25: A) Effect of the cis regulatory element (CSK-SH5) on the mRNA expression of human codon optimized GAA gene. B) The increasing of GAA protein expression. The total proteins from the mice organs were extracted according to the manufacturer's protocol. The total proteins were diluted with the samples buffer and loaded into the hGAA ELISA plate. The background were subtracted with non-injected mice. The results show that codon-optimized hGAA sequence can improve the translation efficiency resulting in 2-3 folds higher expression.
Figures 25, 25B:
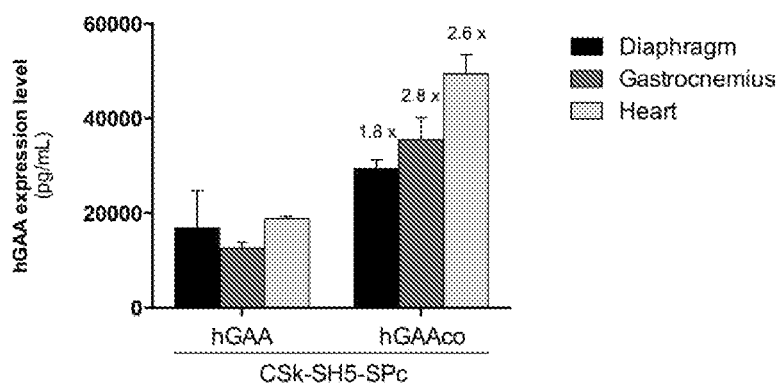

Using quantitative RT-PCR and ELISA, the expression of the hGAA and hGAAco genes in diaphragm, gastrocnemius, and heart of CB.17-SCID mice injected with the pAAVss-SPc5-12-MVM-hGAAco-SynthpA (referred to as "Spc-(h)GAAco" in FIG. 25), pAAVss-CSkSH5-SPc5-12-MVM-hGAA-SynthpA (referred to as "CSk-SHSSPc-hGAA" in FIG. 25) (SEQ ID NO: 65) and pAAVss-CSkSH5-SPc5-12-MVM-hGAAco-SynthpA (referred to as "CSk-SH5-SPc-(h)GAAco" in FIG. 25) (SEQ ID NO: 66) constructs was assessed. The results show that CSk-SH5 can increase the hGAAco mRNA expression up to 16.9 times (FIG. 25a). Furthermore, FIG. 25b shows that codon-optimized hGAA sequence can improve the translation efficiency resulting in >2 folds higher hGAA protein expression in diaphragm, gastrocnemius, and heart of CB.17-SCID mice, compared to non-optimized.

hMTM1(Co) Expression

Figures 26, 26A:
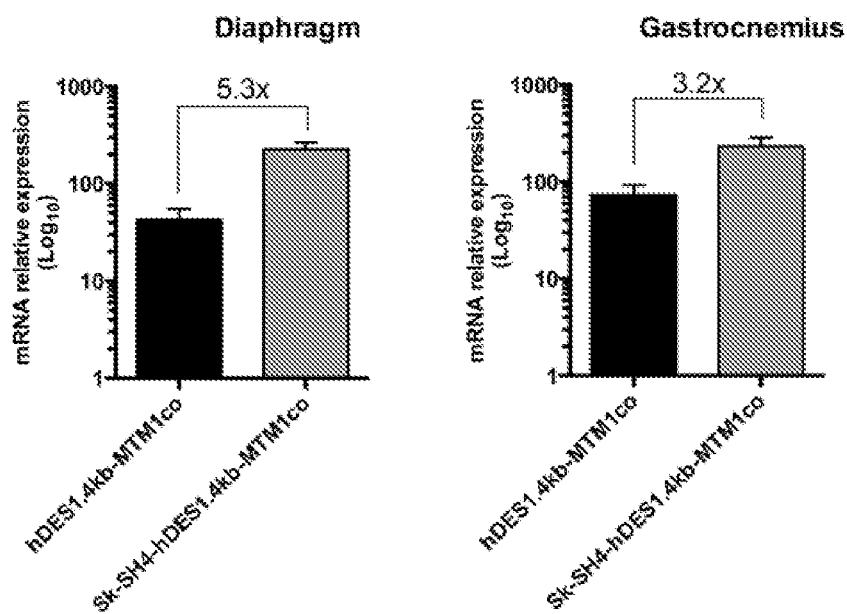
FIG. 26: A) Effect of the cis regulatory element (SK-SH4) on the mRNA expression of human codon optimized MTM1 gene. B) Codon optimization led to an increase of 2.2 to 3.8 folds of hMTM1 protein expression in gastrocnemius and diaphragm respectively.
Figures 26, 26B:
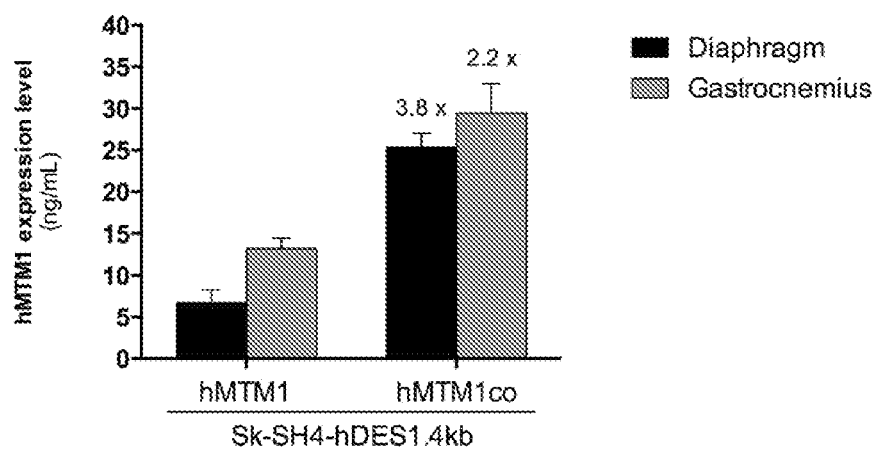

Using quantitative RT-PCR and ELISA, the expression of the hMTM1 and hMTM1co genes in diaphragm and gastrocnemius of CB.17-SCID mice injected with the pAAVss-hDES1.4 kb-MVM-hMTM1-SynthpA (referred to as "hDES1.4 kb-hMTM1co" in FIG. 26), pAAVss-SkSH4-hDES1.4 kb-MVM-hMTM1-SynthpA (referred to as "Sk-SH4-hDES1.4 kb-hMTM1" in FIG. 26) (SEQ ID NO: 67) and pAAVss-SkSH4-hDES1.4 kb-MVM-hMTM1co-SynthpA (referred to as "Sk-SH4-hDES1.4 kb-(h)MTM1co" in FIG. 26) (SEQ ID NO: 68) construct was assessed. The results show that Sk-SH4 can increase the hMTM1co mRNA expression up to 5.3 times (FIG. 26a). Furthermore, FIG. 26b shows that codon-optimized hMTM1 sequence can improve the translation efficiency resulting in 2- to 4-fold higher hMTM1 protein expression in diaphragm and gastrocnemius of CB.17-SCID mice, compared to non-optimized.

Example 14: In Vivo Comparison of Specific Combinations of Muscle-Specific Regulatory Elements and Promoters AAV vectors comprising the muscle-specific regulatory element Sk-SH4 or CSk-SH5 were generated according to the protocol described in Example 2. Briefly, the muscle-specific regulatory element Sk-SH4 (SEQ ID NO: 10) or CSk-SH5 (SEQ ID NO: 5) was synthesized by conventional oligonucleotide synthesis. The Sk-SH4 was cloned upstream of the SPc5-12 promoter (SEQ ID NO: 53) in the context of the AAV vector backbone of AAVsc-SPc5-12-MVM-Luc, upstream of the human desmin 1.4 kb promoter (SEQ ID NO:48) in the context of the AAV vector backbone of AAVsc-hDes1.4 kb-MVM-Luc, or upstream of the murine desmin promoter (SEQ ID NO:16) in the context of the AAV vector backbone of AAVsc-mDes-MVM-Luc. Similarly, the CSk-SH5 was cloned upstream of the SPc5-12 promoter (SEQ ID NO: 53) in the context of the AAV vector backbone of AAVsc-SPc5-12-MVM-Luc or upstream of the murine desmin promoter (SEQ ID NO:16) in the context of the AAV vector backbone of AAVsc-mDes-MVM-Luc. The AAV vector backbones also contained a polyadenylation site (pA) (SEQ ID NO:46). The generated constructs were designated as pAAVss-SkSH4-hDES1.4 kb-Luc2 (SEQ ID NO: 69), pAAVss-SkSH4-mDES-Luc2, pAAVss-SkSH4-SPc5-12-Luc2, AAVss-CSkSH5-SPc5-12-Luc2 (SEQ ID NO: 70) and pAAVss-CSkSH5-mDES-Luc2. pAAVss-CSkSH5-SPc5-12_GTRM-Luc2 (SEQ ID NO:107)

Adult CB17/IcrTac/Prkdcscid mice were intravenously injected with the different vectors (n=5) at a dose of $1 \times 10^{10}$ vg/mouse.

Mice were sacrificed at two weeks and four weeks after injection of the vectors and the different muscle types (biceps, diaphragm, gastrocnemius, heart, quadriceps, tibialis and triceps) were isolated and quantified using bioluminescence imaging as described in Keyaerts M1, Caveliers V, Lahoutte T. Trends Mol Med. 2012 March; 18(3):164-72. doi: 10.1016/j.molmed.2012.01.005. Epub 2012 Feb. 8. Bioluminescence imaging: looking beyond the light.

Results

Figures 27, 27E:
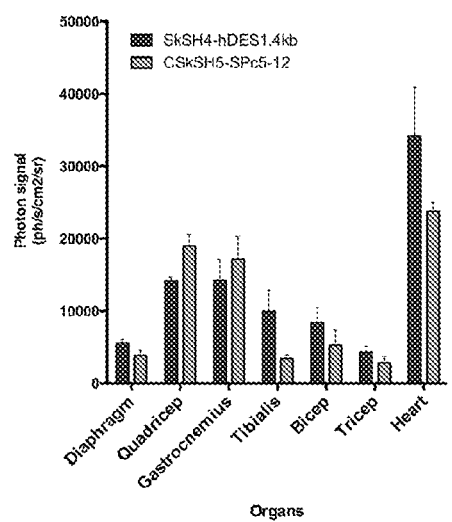
FIG. 27: In vivo comparison of different combinations of muscle specific regulatory elements and promoters. A) comparison of the luciferase expression induced by SkSH4-hDES1.4 kb and SkSH4-SPc5-12, B) comparison of the luciferase expression induced by SkSH4-mDes and CSkSH5-mDes, C) comparison of the luciferase expression induced by CSkSH5-mDes and CSkSH5-SPc5-12, D) comparison of the luciferase expression induced by SkSH4-SPc5-12 and CSkSH5-SPc5-12 and E) comparison of the luciferase expression induced by SkSH4-hDES1.4 kb and CSkSH5-SPc5-12, in skeletal muscles and heart.

FIG. 27 A-B shows that the combination of the muscle-specific regulatory element Sk-SH4 with either the human 1.4 kb DES or mouse DES promoter leads to an increased level of luciferase expression in the skeletal muscle and heart when compared to the luciferase expression level induced by the combination of Sk-SH4 with the SPc5-12 promoter or by the combination of CSk-SH5 with the mouse DES promoter. On the other hand, FIGS. 27 C-E show that the combination of the muscle-specific regulatory element CSk-SH5 with the SPc5-12 promoter leads to an increased level of luciferase expression in the skeletal muscle and heart when compared to the luciferase expression level induced by the combination of CSk-SH5 with the mDES promoter and also when compared to the luciferase expression level induced by the combination of Sk-SH4 with the SPc5-12 promoter.

Overall, these results show that, although it appears that all combinations of the muscle-specific regulatory element Sk-SH4 or CSk-SH5 and the SPc5-12 or DES promoter could elevate the expression level in skeletal muscle and heart, certain combinations of a specific promoter used in conjunction with a specific muscle-specific regulatory element lead to a more robust expression than others.

The invention claimed is:

1. A method for gene therapy for the treatment of Pompe disease comprising intravenously administering to a subject an effective amount of
   a) an adeno-associated viral vector comprising a nucleic acid expression cassette comprising at least one nucleic acid regulatory element for enhancing muscle-specific gene expression, operably linked to a promoter and a transgene encoding alpha-glucosidase (GAA), wherein said nucleic acid regulatory element comprises the sequence set forth in SEQ ID NO:10, or a functional fragment of SEQ ID NO:10, wherein said functional fragment comprises a nucleotide sequence selected from the group consisting of SEQ ID NO:37, SEQ ID NO:38, SEQ ID NO:39, SEQ ID NO:40 and SEQ ID NO:41; or
   b) a pharmaceutical composition comprising the vector according to a) and a pharmaceutically acceptable carrier.

2. The method according to claim 1, wherein the promoter is a muscle-specific promoter.

3. The method according to claim 1, wherein the promoter is a promoter from the desmin (DES) gene or the SPc5-12 promoter.

4. The method according to claim 1, wherein the promoter is the human DES 1.0 kb promoter having SEQ ID NO:47, the human DES 1.4 kb promoter having SEQ ID NO:48 or the SPc5-12 promoter having SEQ ID NO:53.

5. A method of treating a subject requiring restoration of GAA expression or increase of GAA expression comprising intraveneously administering to said subject an effective amount of
   a) an adeno-associated viral vector comprising a nucleic acid expression cassette comprising at least one nucleic acid regulatory element for enhancing muscle-specific gene expression, operably linked to a promoter and a GAA transgene, wherein said nucleic acid regulatory element comprises the sequence set forth in SEQ ID NO:10, or a functional fragment of SEQ ID NO:10, wherein said functional fragment comprises a nucleotide sequence selected from the group consisting of SEQ ID NO:37, SEQ ID NO:38, SEQ ID NO:39, SEQ ID NO:40 and SEQ ID NO:41; or
   b) a pharmaceutical composition comprising the vector of a) and a pharmaceutically acceptable carrier.

6. The method according to claim 5, wherein said subject is suffering from Pompe disease.

7. The method according to claim 5 wherein said GAA transgene is the codon-optimised GAA gene defined by SEQ ID NO:50.

* * * * *